US009895066B2

(12) United States Patent
Krauss et al.

(10) Patent No.: US 9,895,066 B2
(45) Date of Patent: Feb. 20, 2018

(54) AUTOMATED INTERPRETIVE MEDICAL CARE SYSTEM AND METHODOLOGY

(71) Applicants: ORIDION MEDICAL 1987 LTD., Jerusalem (IL); CHILDREN'S MEDICAL CENTER CORPORATION, Boston, MA (US)

(72) Inventors: Baruch Shlomo Krauss, Brookline, MA (US); Ephraim Carlebach, Raanana (IL)

(*) Notice: Subject to any disclaimer, the term of this patent is extended or adjusted under 35 U.S.C. 154(b) by 489 days.

(21) Appl. No.: 14/447,205

(22) Filed: Jul. 30, 2014

(65) Prior Publication Data
US 2014/0343440 A1 Nov. 20, 2014

Related U.S. Application Data

(63) Continuation of application No. 14/146,556, filed on Jan. 2, 2014, which is a continuation of application (Continued)

(51) Int. Cl.
 *A61B 5/02* (2006.01)
 *A61B 5/0205* (2006.01)
 (Continued)

(52) U.S. Cl.
 CPC .......... *A61B 5/0205* (2013.01); *A61B 5/0006* (2013.01); *A61B 5/0022* (2013.01); (Continued)

(58) Field of Classification Search
 CPC ....... A61B 5/022; A61B 5/024; A61B 5/1455; A61B 5/14553; A61B 2560/0431; (Continued)

(56) References Cited

U.S. PATENT DOCUMENTS 4,440,177 A  4/1984 Anderson
4,796,639 A  1/1989 Snow
(Continued)

FOREIGN PATENT DOCUMENTS

DE  2812379  9/1979
EP  0602734  6/1994
(Continued)

OTHER PUBLICATIONS

Goldberg et al., (1990) Colorimetric end-tidal carbon dioxide monitoring for tracheal intubation. Anesth Analg 70(2): 191-4.
(Continued)

*Primary Examiner* — Navin Natnithithadha
*Assistant Examiner* — Eric Messersmith

(57) ABSTRACT

Improved apparatus and methods for monitoring, diagnosing and treating at least one medical respiratory condition of a patient are provided, including a medical data input interface adapted to provide at least one medical parameter relating at least to the respiration of the patient, and a medical parameter interpretation functionality (104, 110) adapted to receive the at least one medical parameter relating at least to the respiration (102) of the patient and to provide at least one output indication (112) relating to a degree of severity of at least one medical condition indicated by the at least one medical parameter.

8 Claims, 71 Drawing Sheets

Related U.S. Application Data

No. 12/213,619, filed on Jun. 23, 2008, now Pat. No. 8,679,029, which is a continuation of application No. 10/433,760, filed as application No. PCT/IL01/01127 on Dec. 6, 2001, now Pat. No. 8,147,419.

(60) Provisional application No. 60/251,829, filed on Dec. 7, 2000, provisional application No. 60/251,828, filed on Dec. 7, 2000.

(51) Int. Cl.
| | |
|---|---|
| *A61B 5/0402* | (2006.01) |
| *A61B 5/0476* | (2006.01) |
| *A61B 5/08* | (2006.01) |
| *A61B 5/083* | (2006.01) |
| *A61B 5/00* | (2006.01) |
| *G06F 19/00* | (2018.01) |
| *G06Q 50/22* | (2018.01) |
| *A61B 5/022* | (2006.01) |
| *A61B 5/024* | (2006.01) |
| *A61B 5/1455* | (2006.01) |
| *A61B 5/021* | (2006.01) |

(52) U.S. Cl.
CPC .......... *A61B 5/0402* (2013.01); *A61B 5/0476* (2013.01); *A61B 5/08* (2013.01); *A61B 5/082* (2013.01); *A61B 5/0836* (2013.01); *A61B 5/14552* (2013.01); *A61B 5/411* (2013.01); *A61B 5/6835* (2013.01); *A61B 5/7264* (2013.01); *A61B 5/7275* (2013.01); *A61B 5/7282* (2013.01); *A61B 5/746* (2013.01); *A61B 5/7425* (2013.01); *G06F 19/3406* (2013.01); *G06Q 50/22* (2013.01); *A61B 5/021* (2013.01); *A61B 5/022* (2013.01); *A61B 5/024* (2013.01); *A61B 5/02438* (2013.01); *A61B 5/0816* (2013.01); *A61B 5/1455* (2013.01); *A61B 5/14553* (2013.01); *A61B 2560/0431* (2013.01); *A61B 2560/0437* (2013.01)

(58) Field of Classification Search
CPC .......... A61B 2560/0437; A61B 5/0816; A61B 5/02438; A61B 5/021; A61B 5/0205; A61B 5/0402; A61B 5/0476; A61B 5/08; A61B 5/0836; A61B 5/411; A61B 5/7282; A61B 5/7264; A61B 5/7275; A61B 5/746; A61B 5/6835; A61B 5/7425; A61B 5/0006; A61B 5/14552; A61B 5/082; A61B 5/00; G06F 19/3406
See application file for complete search history.

(56) References Cited

U.S. PATENT DOCUMENTS

| | | | |
|---|---|---|---|
| 4,803,625 A | | 2/1989 | Fu |
| 4,913,160 A | | 4/1990 | John |
| 4,994,666 A | | 2/1991 | Higgison |
| 5,004,975 A | | 4/1991 | Jordan |
| 5,026,974 A | | 6/1991 | Franklin |
| 5,046,491 A | | 9/1991 | Derrick |
| 5,124,952 A | | 6/1992 | Knize |
| 5,165,270 A | | 11/1992 | Sansalone |
| 5,172,698 A | | 12/1992 | Stanko |
| 5,173,880 A | | 12/1992 | Duren |
| 5,228,449 A | * | 7/1993 | Christ ............... A61B 5/02433 379/38 |
| 5,291,879 A | | 3/1994 | Babb |
| 5,331,549 A | | 7/1994 | Crawford, Jr. |
| 5,355,390 A | | 10/1994 | Yamamoto |
| 5,360,003 A | | 11/1994 | Capistrano |
| 5,371,462 A | | 12/1994 | Hedengren |
| 5,447,165 A | | 9/1995 | Gustafsson |
| 5,467,777 A | | 11/1995 | Farwell |
| 5,518,002 A | | 5/1996 | Wolf |
| 5,651,095 A | | 7/1997 | Ogden |
| 5,655,540 A | | 8/1997 | Seegobin |
| 5,661,887 A | | 9/1997 | Byrne |
| 5,673,702 A | | 10/1997 | Albrecht |
| 5,678,562 A | | 10/1997 | Sellers |
| 5,687,717 A | | 11/1997 | Halpern |
| 5,837,897 A | | 11/1998 | Jones |
| 5,885,248 A | * | 3/1999 | Denton ............ A61M 16/0078 604/100.03 |
| 5,912,656 A | | 6/1999 | Tham |
| 5,916,163 A | | 6/1999 | Panescu |
| 5,921,920 A | | 7/1999 | Marshall |
| 5,954,664 A | | 9/1999 | Seegobin |
| 5,960,403 A | | 9/1999 | Brown |
| 5,971,934 A | | 10/1999 | Scherer |
| 5,975,081 A | | 11/1999 | Hood |
| 5,983,178 A | | 11/1999 | Naito |
| 5,995,448 A | | 11/1999 | Krehbiel |
| 6,002,723 A | | 12/1999 | Chethik |
| 6,047,203 A | | 4/2000 | Sackner |
| 6,102,856 A | * | 8/2000 | Groff ................. A61B 5/02055 128/903 |
| 6,117,073 A | * | 9/2000 | Jones .................... G06F 19/327 600/300 |
| 6,159,147 A | | 12/2000 | Lichter |
| 6,174,283 B1 | * | 1/2001 | Nevo ................... A61B 5/0205 600/301 |
| 6,190,327 B1 | | 2/2001 | Isaacson |
| 6,195,576 B1 | | 2/2001 | John |
| 6,221,012 B1 | | 4/2001 | Maschke |
| 6,223,073 B1 | | 4/2001 | Seegobin |
| 6,223,126 B1 | | 4/2001 | Neff |
| 6,236,963 B1 | | 5/2001 | Naito |
| 6,283,923 B1 | | 9/2001 | Finkelstein |
| 6,299,581 B1 | | 10/2001 | Rapoport |
| 6,309,360 B1 | | 10/2001 | Mault |
| 6,337,629 B1 | * | 1/2002 | Bader ................. A61B 5/0205 340/575 |
| 6,375,614 B1 | | 4/2002 | Braun |
| 6,398,728 B1 | | 6/2002 | Bardy |
| 6,402,691 B1 | | 6/2002 | Peddicord |
| 6,428,483 B1 | | 8/2002 | Carlebach |
| 6,585,661 B1 | | 7/2003 | Hunt |
| 6,609,016 B1 | | 8/2003 | Lynn |
| 6,648,833 B2 | | 11/2003 | Hampton |
| 6,662,032 B1 | | 12/2003 | Gavish |
| 2002/0007127 A1 | | 1/2002 | Sullivan |
| 2002/0082513 A1 | | 6/2002 | Ennen |
| 2002/0169367 A1 | | 11/2002 | Bardy |
| 2002/0183644 A1 | | 12/2002 | Levendowski |
| 2003/0216660 A1 | | 11/2003 | Ben-Oren |

FOREIGN PATENT DOCUMENTS

| | | |
|---|---|---|
| EP | 0699414 | 3/1996 |
| EP | 0978256 | 2/2000 |
| JP | 10091884 | 4/1998 |
| WO | 98/34537 | 8/1998 |
| WO | 99/62403 | 12/1999 |

OTHER PUBLICATIONS

Ward and Yealy (1998) End-tidal carbon dioxide monitoring in emergency medicine, Part 1: Basic principles. Acad Emerg Med 5(6): 628-36.

Ward and Yealy (1998) End-tidal carbon dioxide monitoring in emergency medicine, Part 2: Clinical applications. Acad Emerg Med 5(6): 637-46.

Dang and Breen, Ambulatory Capnography, RT: for Decision Makers in Respiratory Care—Jun./Jul. 1998.

Hans et al., Respiratory Sounds, Advances Beyond the Stethoscope, Am J Respir Crit Care Med 156: 974-987 (1997).

(56) References Cited

OTHER PUBLICATIONS

Katz, Steven H., et al., "Misplaced endotracheal tubes by paramedics in an urban emergency medical services system." Annals of emergency medicine, Jan. 2001, vol. 37, No. 1, pp. 32-37, 62-64.
Larsen, R. J. and Marx, M. L. (Eds.) An introduction to mathematical statistics and its applications. Third edition 2005 pp. 242, 264, 274, 278, 282-284, 286, 699.
Van Genderingen H. R. et al., "Computer assisted capnogram analysis." J Clin Monit 3(3): 194-200 (1987).
Weinger, M. B. and Brimm, J. E. (1987) End-tidal carbon dioxide as a measure of arterial carbon dioxide during intermitted mandatory ventilation. J Clin Monit 3(2): 73-74.
Yaron et al., "Utility of the expiratory capnogram in the assessment of bronchospasm." Ann Emerg Med 28(4): 403-407 (1996).
You et al., "Expiatory Capnography in asthma.", European Respiration Journal 7: 318-323 (1994).
Murphy et al., (1997) Guidelines for the Diagnosis and Management of Asthma. Jul. 1997, NIH Publication No. 97-4051.

\* cited by examiner

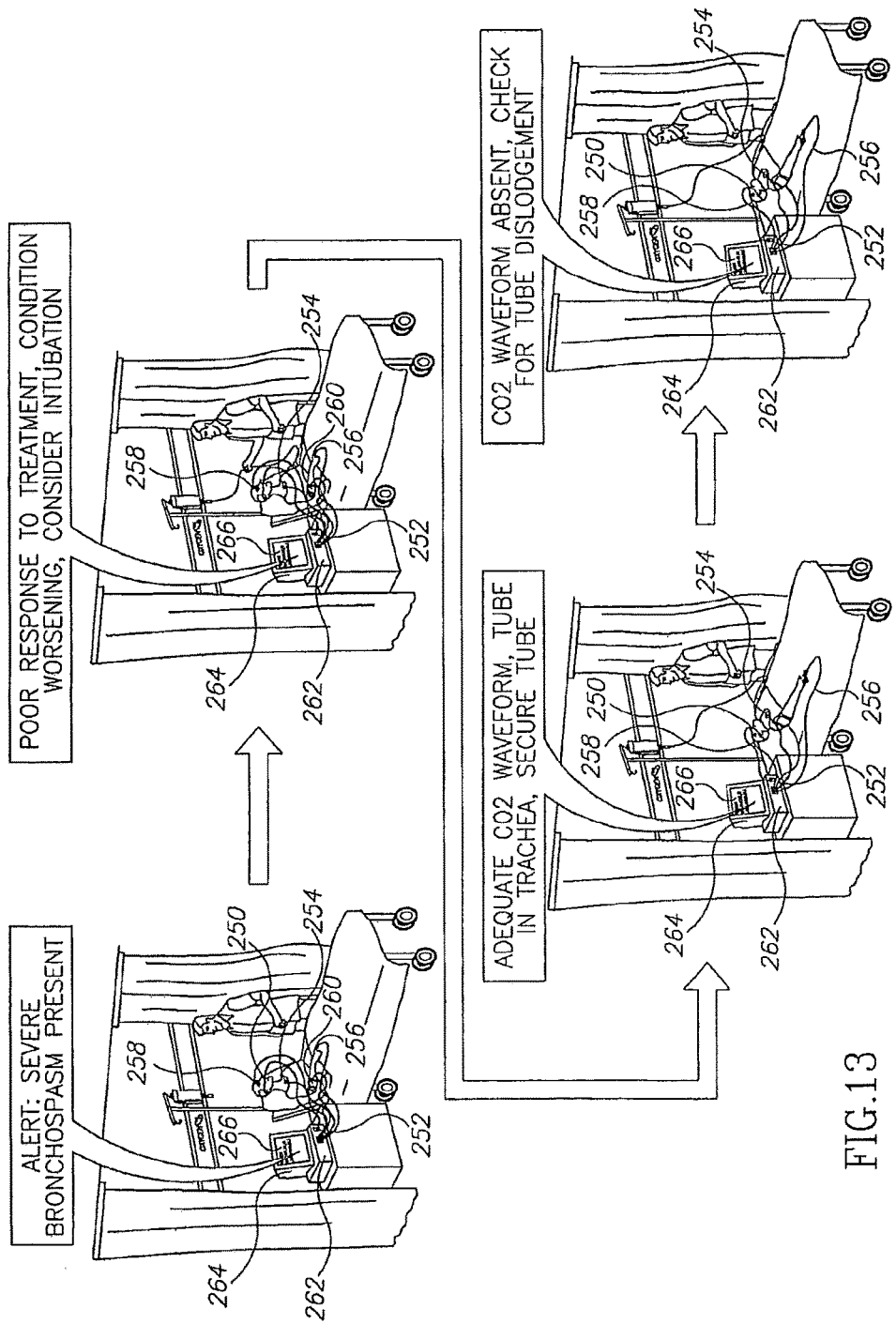

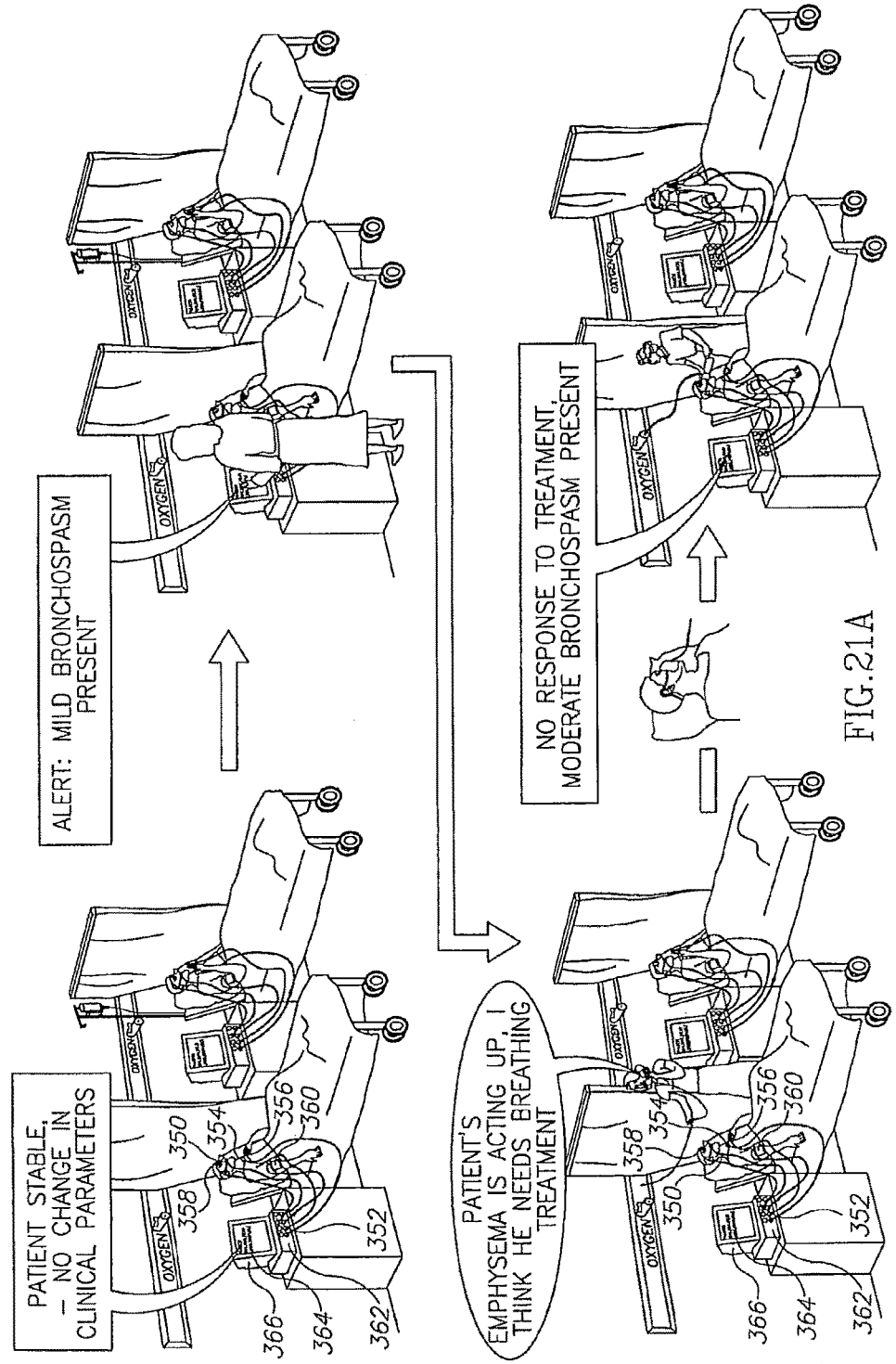

Fig. 26B

IF CAP-FEV1<50% FOR MOST OR ALL FOUR POST-TREATMENT MEASUREMENTS, THEN DISPLAY MESSAGE "POOR RESPONSE TO TREATMENT: CONSIDER ADMISSION TO HOSPITAL INTENSIVE CARE."

AUTOMATED INTERPRETIVE MEDICAL CARE SYSTEM AND METHODOLOGY

REFERENCE TO CO-PENDING APPLICATIONS

This application is a Continuation Application of U.S. patent application Ser.No. 14/146,556, filed Jan. 2, 2014 (published as U.S. Publication No. 20140135640), which is a Continuation Application of U.S. patent application Ser. No. 12/213,619, filed Jun. 23, 2008 (now U.S. Pat. No. 8,679,029), which is a Continuation Application of U.S. patent application Ser. No. 10/433,760 filed on Jun. 10, 2004 (now U.S. Pat. No. 8,147,419), which is a U.S. National phase of PCT Application No. PCT/IL01/01127, filed Dec. 6, 2001 which claims priority of U.S. Provisional Application Ser. No. 60/251,828 filed Dec. 7, 2000 and U.S. Provisional Application Ser. No. 60/251,829 filed Dec. 7, 2000, all of which are hereby incorporated in their entirety by reference.

FIELD OF THE INVENTION

The present invention relates to the use of respiratory information in automated medical status assessment.

BACKGROUND OF THE INVENTION

The following U.S. patent and publication are believed to represent the current state of the art: U.S. Pat. No. 4,440,177 to Anderson et al, describes a respiratory analyzer system. Reference is also made to NIH publication on. 97-4051 entitled "Guidelines for the Diagnosis and Management of Asthma" pp 108-109, 1991.

The disclosures of all references mentioned above and throughout the present specification are hereby incorporated herein by reference.

SUMMARY OF THE INVENTION

The present invention seeks to provide improved methods and apparatus for monitoring, diagnosing and treating at least one medical respiratory condition.

There is thus provided in accordance with a preferred embodiment of the present invention, a system employing at least one parameter relating at least to respiration of a patient for providing an indication relating to at least one medical condition, the system including:

a medical data input interface adapted to provide the at least one medical parameter relating at least to respiration of the patient, and a medical parameter interpretation functionality receiving the at least one medical parameter relating at least to respiration of the patient and providing the at least one output indication relating to a degree of severity of at least one medical condition indicated by the at least one medical parameter.

There is thus also provided in accordance with another preferred embodiment of the present invention, a system employing at least one parameter relating at least to respiration of a patient for providing at least one indication relating to at least one medical condition, the system including:

a mobile platform, and a medical care facility suitable for use by an operator other than a medical doctor, the medical care facility including:

a medical data input interface providing the at least one medical parameter regarding a patient, and a medical parameter interpretation functionality receiving the at least one medical parameter regarding the patient and providing the at least one output indication relating to a degree of severity of the at least one medical condition indicated by the at least one medical parameter.

There is thus further provided in accordance with another preferred embodiment of the present invention, a system employing at least one parameter relating at least to respiration of a patient for providing at least one indication relating to at least one medical condition, the system including:

a medical data input interface providing the at least one medical parameter regarding a patient, a medical parameter interpretation functionality receiving the at least one medical parameter regarding the patient and providing the at least one output indication, and a treatment control functionality for controlling the provision of at least one treatment to a patient in response to the at least one output indication.

There is thus further provided in accordance with yet another preferred embodiment of the present invention, a system employing at least one parameter relating at least to respiration of a patient for providing at least one indication relating to at least one medical condition, the system including:

a mobile platform, and a medical care facility suitable for use by an operator other than a medical doctor, the medical care facility including:

a medical data input interface providing the at least one medical parameter regarding a patient, a medical parameter interpretation functionality receiving the at least one medical parameter regarding the patient and providing the at least one output indication, and a treatment control functionality for controlling the provision of at least one treatment to a patient in response to the at least one output indication.

There is thus also provided in accordance with another preferred embodiment of the present invention, a system employing at least two parameters relating at least to respiration of a patient for providing at least one indication relating to at least one medical condition, the system including:

a medical data input interface providing at least two medical parameters regarding a patient, and a medical parameter interpretation functionality receiving the at least two medical parameters regarding the patient and providing the at least one output indication relating to at least one medical condition indicated by the at least two medical parameters.

There is thus yet further provided in accordance with another preferred embodiment of the present invention, a system employing at least two parameters relating at least to respiration of a patient for providing at least one indication relating to at least one medical condition, the system including:

a mobile platform, and a medical care facility suitable for use by an operator other than a medical doctor the medical care facility including:

a medical data input interface providing at least two medical parameters regarding a patient, and a medical parameter interpretation functionality receiving the at least two medical parameters regarding the patient and providing the at least one output indication relating to at least one medical condition indicated by the at least two medical parameters.

There is thus also provided in accordance with another preferred embodiment of the present invention, a system employing a plurality of parameters relating at least to respiration of a patient for providing a plurality of indications relating to at least one medical condition, the system including:

a medical data input interface providing the plurality of medical parameters regarding a patient, a medical parameter interpretation functionality receiving the plurality of medical parameters regarding the patient and providing the plurality of output indications, and a medical treatment control functionality for controlling the provision of at least one treatment to a patient in response to changes in the relationship between the output indications.

There is thus further provided in accordance with yet another preferred embodiment of the present invention, a system employing a plurality of parameters relating at least to respiration of a patient for providing a plurality of indications relating to at least one medical condition, the system including:

a mobile platform, and a medical care facility suitable for use by an operator other than a medical doctor, the medical care facility including:

a medical data input interface providing a plurality of medical parameters regarding a patient, a medical parameter interpretation functionality receiving the plurality of medical parameters regarding the patient and providing the plurality of output indications, and a medical treatment control functionality for controlling the provision of at least one treatment to a patient in response to changes in the relationship between the output indications.

There is thus further provided in accordance with another preferred embodiment of the present invention, a system employing a plurality of parameters relating at least to respiration of a patient for providing an indication relating to at least one medical condition, the system including:

a medical data input interface providing the plurality of medical parameters regarding a patient, and a medical parameter response functionality receiving the plurality of medical parameters regarding the patient and providing an output indication based on the relationship between the medical parameters.

There is thus yet further provided in accordance with another preferred embodiment of the present invention, a system employing a plurality of parameters relating at least to respiration of a patient for providing an indication relating to at least one medical condition, the system including:

a mobile platform, and a medical care facility suitable for use by an operator other than a medical doctor, the medical care facility including:

a medical data input interface providing the plurality of medical parameters regarding a patient, and a medical parameter response functionality receiving the plurality of medical parameters regarding the patient and providing an output indication based on the relationship between the medical parameters.

There is thus additionally provided in accordance with another preferred embodiment of the present invention, a system employing a plurality of parameters relating at least to respiration of a patient for providing an indication relating to at least one medical condition, the system including:

a medical data input interface providing the plurality of medical parameters regarding a patient, and a medical treatment control functionality receiving the plurality of medical parameters regarding the patient and controlling at least one treatment based on a relationship between the medical parameters.

There is thus further provided in accordance with another preferred embodiment of the present invention, a system employing a plurality of parameters relating at least to respiration of a patient for providing an indication relating to at least one medical condition, the system including:

a mobile platform, and a medical care facility suitable for use by an operator other than a medical doctor, the medical care facility including:

a medical data input interface providing the plurality of medical parameters regarding a patient, and a medical treatment control functionality receiving the plurality of medical parameters regarding the patient and controlling at least one treatment based on a relationship between the medical parameters.

There is thus also provided in accordance with another preferred embodiment of the present invention, a system employing a plurality of parameters relating at least to respiration of a patient for providing an indication relating to at least one medical condition, the system including:

a medical data input interface providing the plurality of medical parameters regarding a patient, and a medical parameter response functionality receiving the plurality of medical parameters regarding the patient and providing an output indication relating to a degree of severity of at least one medical condition indicated by the plurality of medical parameters.

There is thus also provided in accordance with another preferred embodiment of the present invention, a system employing a plurality of parameters relating at least to respiration of a patient for providing an indication relating to at least one medical condition, the system including:

a mobile platform, and a medical care facility suitable for use by an operator other than a medical doctor, the medical care facility including:

a medical data input interface providing the plurality of medical parameters regarding a patient, and a medical parameter response functionality receiving the plurality of medical parameters regarding the patient and providing an output indication relating to a degree of severity of at least one medical condition indicated by the plurality of medical parameters.

There is thus further provided in accordance with another preferred embodiment of the present invention, an emergency medical transport facility including:

a mobile platform, and a medical care system suitable for use by an operator other than a medical doctor, the medical care system including:

a medical data input interface providing at least one medical parameter regarding a patient, and a medical parameter interpretation functionality receiving the at least one medical parameter regarding the patient and providing an output indication relating to a degree of severity of at least one medical condition indicated by the at least one medical parameter.

There is thus also provided in accordance with another preferred embodiment of the present invention, a system employing at least one parameter relating at least to respiration of a patient for providing an indication relating to at least one medical condition, the system including:

a medical data input interface adapted to provide the at least one medical parameter relating at least to respiration of the patient, and a medical parameter interpretation functionality receiving the at least one medical parameter regarding the patient, and wherein the at least one medical parameter interpretation functionality includes:

a medical condition diagnosis functionality for diagnosing the presence of the at least one medical condition, and a medical condition severity functionality indicating the degree of severity of the at least one medical condition.

There is thus further provided in accordance with another preferred embodiment of the present invention, a system employing at least one parameter relating at least to respiration of a patient for providing an indication relating to at least one medical condition, the system including:

a mobile platform, and a medical care facility suitable for use by an operator other than a medical doctor, the medical care facility including:

a medical data input interface providing the at least one medical parameter regarding a patient, and a medical parameter interpretation functionality receiving the at least one medical parameter regarding the patient and wherein the at least one medical parameter interpretation functionality includes:

a medical condition diagnosis functionality for diagnosing the presence of the at least one medical condition, and a medical condition severity functionality indicating the degree of severity of the at least one medical condition.

There is thus also provided in accordance with another preferred embodiment of the present invention, a system employing at least one parameter relating at least to respiration of a patient for providing an indication relating to at least one medical condition, the system including:

a medical data input interface adapted to provide the at least one medical parameter relating at least to respiration of the patient, and a medical parameter interpretation functionality receiving the at least one medical parameter regarding the patient, and wherein the at least one medical parameter interpretation functionality includes:

a medical condition diagnosis functionality for diagnosing the presence of the at least one medical condition, and a medical condition severity functionality indicating the degree of severity of the at least one medical condition, and, a treatment control functionality for controlling the provision of at least one treatment to the patient in response to the degree of severity.

There is thus further provided in accordance with another preferred embodiment of the present invention, a system employing at least one parameter relating at least to respiration of a patient for providing an indication relating to at least one medical condition, the system including:

a mobile platform, and a medical care facility suitable for use by an operator other than a medical doctor, the medical care facility including:

a medical data input interface providing the at least one medical parameter regarding a patient, and a medical parameter interpretation functionality receiving the at least one medical parameter regarding the patient and wherein the at least one medical parameter interpretation functionality includes:

a medical condition diagnosis functionality for diagnosing the presence of the at least one medical condition, and a medical condition severity functionality indicating the degree of severity of the at least one medical condition, and, a treatment control functionality for controlling the provision of at least one treatment to the patient in response to the degree of severity.

There is thus also provided in accordance with another preferred embodiment of the present invention, an emergency medical transport methodology including:

transporting a patient on a mobile platform, interfacing the patient with a medical data interface which provides at least one medical parameter of the patient, and inputting the medical parameter to a medical parameter interpretation functionality, which interprets the at least one medical parameter and provides an output indication relating to a degree of severity of the at least one medical condition.

There is thus also provided in accordance with another preferred embodiment of the present invention, a method of determining the degree of severity of at least one medical condition of a patient, the condition being associated with at least one medical parameter, including the steps of:

interfacing the patient with a medical data interface which provides at least one medical parameter of the patient, and inputting the medical parameter to a medical parameter interpretation functionality, which interprets the at least one medical parameter and provides an output indication relating to a degree of severity of the at least one medical condition.

There is thus also provided in accordance with another preferred embodiment of the present invention, a method of controlling the provision of at least one treatment to a patient for at least one medical condition including the steps of:

interfacing the patient with a medical data interface which provides at least one medical parameter of the patient, inputting the at least one medical parameter to a medical parameter interpretation functionality, which interprets the at least one medical parameter and provides an output indication, and controlling the provision of the at least one treatment in response to the output indication.

There is thus further provided in accordance with another preferred embodiment of the present invention, a method of providing an output indication relating to at least one medical condition indicated by at least two medical parameters, including the steps of:

interfacing the patient with a medical data interface which provides at least two medical parameters of the patient, inputting the at least two medical parameters to a medical parameter interpretation functionality, which interprets the at least two medical parameters and provides an output indication of the at least one medical condition.

There is thus also provided in accordance with another preferred embodiment of the present invention, a method of controlling the provision of at least one treatment for at least one medical condition to a patient including the steps of:

interfacing the patient with a medical data interface which provides a plurality of medical parameters of the patient, inputting the medical parameters to a medical parameter interpretation functionality, which interprets the medical parameters and provides a plurality of output indications, and controlling the provision of the at least one treatment in response to changes in the relationship between the output indications.

There is thus further provided in accordance with another preferred embodiment of the present invention, a method of providing an output indication regarding the clinical state for at least one medical condition of a patient, including the steps of:

interfacing the patient with a medical data interface which provides a plurality of medical parameters regarding the patient, and inputting the plurality of medical parameters to a medical parameter interpretation functionality, which provides an output indication based on the relationship between the medical parameters.

There is thus additionally provided in accordance with another preferred embodiment of the present invention, a method of controlling the provision of at least one treatment to a patient for at least one medical condition including the steps of;

interfacing the patient with a medical data interface which provides a plurality of medical parameters of the patient, inputting the medical parameters to a medical parameter interpretation functionality, interpreting the medical parameters by the medical parameter interpretation functionality, providing a plurality of output indications by the medical parameter interpretation functionality, and inputting the output indications to a medical treatment control unit, which controls the at least one treatment in response to the relationship between the medical parameters.

There is thus also provided in accordance with another preferred embodiment of the present invention, a method of providing an output indication relating to a degree of severity of at least one medical condition of a patient including the steps of:

interfacing the patient with a medical data interface which provides a plurality of medical parameters regarding the patient, and inputting the medical parameters to a medical parameter interpretation functionality, interpreting the medical parameters by the medical parameter interpretation functionality, providing a plurality of output indications by the medical parameter interpretation functionality, and inputting the output indications to a medical parameter response unit which provides a response relating to a degree of severity of the at least one medical condition indicated by the plurality of medical parameters.

There is thus also provided in accordance with another preferred embodiment of the present invention, a method of determining the degree of severity of at least one medical condition of a patient, the condition being associated with at least one medical parameter, including the steps of:

interfacing the patient with a medical data interface which provides at least one medical parameter of the patient, inputting the medical parameter to a medical parameter interpretation functionality, which interprets the at least one medical parameter and provides an output indication relating to a degree of severity of the at least one medical condition, and medically treating the patient in accordance with the output indication.

There is thus further provided in accordance with another preferred embodiment of the present invention, a medical care methodology employing at least one parameter relating at least to respiration for providing an indication relating to at least one medical condition, the method including:

(i) monitoring the at least one parameter relating at least to respiration of a patient over a period of time by means of at least one monitoring device so as to provide at least one monitoring output, (ii) processing the at least one monitoring output so as to provide at least one corresponding processing output by means of a processor, (iii) displaying a first indication of the patient on a display responsive to the at least one corresponding processing output, (iv) medically treating the patient in accordance with the indication, (v) repeating the monitoring step (i) and processing step (ii), subsequent to the treatment so as to provide a difference in the at least one monitoring parameter, (vi) processing the difference in the at least one at least one monitoring parameter so as to provide at least one corresponding processing output of the difference, and, (vii) displaying a second indication of the patient on a display responsive to the at least one corresponding processing output of the difference.

There is thus yet further provided in accordance with another preferred embodiment of the present invention, a method of controlling the provision of at least one treatment to a patient for at least one medical condition including the steps of:

interfacing the patient with a medical data interface which provides at least one medical parameter of the patient, inputting the at least one medical parameter to a medical parameter interpretation functionality, which interprets the at least one medical parameter and provides an output indication, and controlling the provision of the at least one treatment in response to the output indication.

There is thus also provided in accordance with another preferred embodiment of the present invention, a method of controlling the provision of at least one treatment for at least one medical condition to a patient including the steps of:

interfacing the patient with a medical data interface which provides a plurality of medical parameters of the patient, inputting the medical parameters to a medical parameter interpretation functionality, which interprets the medical parameters and provides a plurality of output indications, controlling the provision of the at least one treatment in response to changes in the relationship between the output indications, and providing an update in a status of the patient responsive to the output indications.

There is thus further provided in accordance with another preferred embodiment of the present invention, a method of providing an output indication regarding the clinical state for at least one medical condition of a patient, including the steps of:

interfacing the patient with a medical data interface which provides a plurality of medical parameters regarding the patient, inputting the plurality of medical parameters to a medical parameter interpretation functionality, which provides the output indication based on the relationship between the medical parameters, and providing a treatment recommendation by means of a treatment recommendation functionality.

There is thus further provided in accordance with another preferred embodiment of the present invention, a method of controlling the provision of at least one treatment to a patient for at least one medical condition including the steps of:

interfacing the patient with a medical data interface which provides a plurality of medical parameters of the patient, inputting the medical parameters to a medical parameter interpretation functionality, which interprets the medical parameters and provides a plurality of output indications, inputting the output indications to a medical treatment control unit, which controls the at least one treatment in response to the relationship between the medical parameters, and providing an update in a status of the patient responsive to the relationship between the medical parameters.

There is thus yet further provided in accordance with another preferred embodiment of the present invention, a method of providing an output indication relating to a degree of severity of at least one medical condition of a patient including the steps of:

interfacing the patient with a medical data interface which provides a plurality of medical parameters regarding the patient, and inputting the medical parameters to a medical parameter interpretation functionality, which interprets the medical parameters and provides a plurality of output indications, inputting the output indications to a medical parameter response unit which provides a response relating to a degree of severity of the at least one medical condition indicated by the plurality of medical parameters, and controlling the provision of at least one treatment in response to the degree of severity.

There is thus also provided in accordance with another preferred embodiment of the present invention, a computer software product for determining the degree of severity of at least one medical condition of a patient, the condition being associated with at least one medical parameter, including a computer-readable medium in which program instructions are stored, which instructions, when read by a computer, cause the computer to:

interface the patient with a medical data interface which provides at least one medical parameter of the patient, and input the medical parameter to a medical parameter interpretation functionality, which interprets the at least one medical parameter and provides an output indication relating to a degree of severity of the at least one medical condition.

There is thus further provided in accordance with another preferred embodiment of the present invention, a computer software product for controlling the provision of at least one treatment to a patient including a computer-readable medium in which program instructions are stored, which instructions, when read by a computer, cause the computer to:

interface the patient with a medical data interface which provides at least one medical parameter of the patient, input the medical parameter to a medical parameter interpretation functionality, which interprets the at least one medical parameter and provides an output indication, and control the provision of the at least one treatment in response to the output indication.

There is thus further provided in accordance with another preferred embodiment of the present invention, a computer software product for providing an output indication relating to at least one medical condition of a patient indicated by at least two medical parameters, including a computer-readable medium in which program instructions are stored, which instructions, when read by a computer, cause the computer to:

interface the patient with a medical data interface which provides at least two medical parameters of the patient, input the at least two medical parameters to a medical parameter interpretation functionality, which interprets the at least two medical parameters and provides an output indication of the at least one medical condition.

There is thus further provided in accordance with another preferred embodiment of the present invention, a computer software product for controlling the provision of at least one treatment to a patient, including a computer-readable medium in which program instructions are stored, which instructions, when read by a computer, cause the computer to:

interface the patient with a medical data interface which provides a plurality of medical parameters of the patient, input the medical parameters to a medical parameter interpretation functionality, which interprets the medical parameters and provides a plurality of output indications, and control the provision of the at least one treatment in response to changes in the relationship between the output indications.

There is thus also provided in accordance with another preferred embodiment of the present invention, a computer software product for providing an output indication regarding the clinical state of a patient, including a computer-readable medium in which program instructions are stored, which instructions, when read by a computer, cause the computer to:

interface the patient with a medical data interface which provides a plurality of medical parameters regarding the patient, and input the medical parameters to a medical parameter response unit, which providing the output indication based on the relationship between the medical parameters.

There is thus further provided in accordance with another preferred embodiment of the present invention, a computer software product for controlling the provision of at least one treatment to a patient, including a computer-readable medium in which program instructions are stored, which instructions, when read by a computer, cause the computer to:

interface the patient with a medical data interface which provides a plurality of medical parameters of the patient, input the medical parameters to a medical treatment control unit, which controls the at least one treatment in response to the relationship between the medical parameters.

There is thus additionally provided in accordance with another preferred embodiment of the present invention, a computer software product for providing an output indication relating to a degree of severity of at least one medical condition of a patient including a computer-readable medium in which program instructions are stored, which instructions, when read by a computer, cause the computer to:

interface the patient with a medical data interface which provides a plurality of medical parameters regarding the patient, and input the medical parameters to a medical parameter response unit which provides an output indication relating to a degree of severity of the at least one medical condition indicated by the plurality of medical parameters.

There is thus also provided in accordance with another preferred embodiment of the present invention, a computer software product for relating at least to respiration of a patient for providing an indication relating to at least one medical condition, including a computer-readable medium in which program instructions are stored, which instructions, when read by a computer, cause the computer to:

provide the at least one medical parameter relating at least to respiration of the patient by means of a medical data input interface, and receive the at least one medical parameter regarding the patient by means of a medical parameter interpretation functionality, and, provide an output indication relating to a degree of severity of at least one medical condition indicated by the at least one medical parameter.

There is thus also provided in accordance with another preferred embodiment of the present invention, a computer software product for providing an indication relating to at least one medical condition, including a computer-readable medium in which program instructions are stored, which instructions, when read by a computer, cause the computer to:

(i) monitor at least one parameter relating at least to respiration of a patient over a period of time by means of at least one monitoring device so as to provide at least one monitoring output, (ii) process the at least one monitoring output so as to provide at least one corresponding processing output by means of a processor, (iii) display a first indication of the patient on a display responsive to the at least one corresponding processing output, (iv) medical treating the patient in accordance with the indication, (v) repeat the monitoring step (i) and processing step (ii), subsequent to the treatment so as to provide a difference in the at least one monitoring parameter, (vi) process the difference in the at least one at least one monitoring parameter so as to provide at least one corresponding processing output of the difference, and, (vii) display a second indication of the patient on a display responsive to the at least one corresponding processing output of the difference.

There is thus also provided in accordance with another preferred embodiment of the present invention, a computer software product for controlling the provision of at least one treatment to a patient for at least one medical condition including a computer-readable medium in which program instructions are stored, which instructions, when read by a computer, cause the computer to:

interface the patient with a medical data interface which provides at least one medical parameter of the patient, input the at least one medical parameter to a medical parameter interpretation functionality, which interprets the at least one medical parameter and provides an output indication, and control the provision of the at least one treatment in response to the output indication.

Also, in accordance with a preferred embodiment of the present invention, there is provided a system wherein the data input interface includes at least one monitoring device operative to continuously monitor the at least one medical parameter.

Additionally, in accordance with a preferred embodiment of the present invention, there is provided a system wherein the data input interface includes at least one monitoring device operative to continuously monitor the at least two medical parameters.

Further, in accordance with a preferred embodiment of the present invention, there is provided a system wherein the data input interface includes at least one monitoring device operative to continuously monitor the plurality of medical parameters.

Preferably, the at least one monitoring device includes a capnograph.

Additionally, in accordance with a preferred embodiment of the present invention, there is provided a system wherein the at least one monitoring device is operative to collect a sample of expired air from the patient.

Also, in accordance with a preferred embodiment of the present invention, there is provided a system wherein the at least one monitoring device includes at least one of the following:

an electrocardiogram (ECG) monitoring device,
a blood pressure monitoring device,
an electroencephalogram (EEG) monitoring device,
an NI blood pressure monitoring device,
a respiratory rate monitoring device,
a heart rate monitoring device,
a systemic perfusion monitoring device, and
an exhaled air monitoring device.

Further, in accordance with a preferred embodiment of the present invention, there is provided a system wherein the at least one monitoring device is operative to monitor at least one of:

an expired air carbon dioxide concentration, and
an expired air carbon dioxide profile parameter.

Yet further, in accordance with a preferred embodiment of the present invention, there is provided a system wherein the at least one monitoring device is operative to monitor at least one of the following waveforms:

a carbon dioxide waveform (capnogram),
an EEG waveform, and
an ECG waveform.

Additionally, in accordance with a preferred embodiment of the present invention, there is provided a system wherein the at least one monitoring device is adapted to digitize at least one of the waveforms.

Additionally, in accordance with a preferred embodiment of the present invention, there is provided a system wherein at least one of:

the at least one monitoring device, and
the medical parameter interpretation functionality,
is further operative to provide at least one of the following measurements:

a slope of the increase in the carbon dioxide concentration,
a run of time taken to reach 80% maximum exhaled $CO_2$ concentration, and
an angle of rise to 80% maximum exhaled $CO_2$ concentration.

Also, in accordance with a preferred embodiment of the present invention, there is provided a system wherein at least one of:

the at least one monitoring device, and
the medical parameter interpretation functionality,
is further operative to a value of CAP-FEV1.

Furthermore, in accordance with a preferred embodiment of the present invention, there is provided a system wherein the medical parameter interpretation functionality is further operative to provide an alert responsive to a measure of CAP-FEV1 being less than 50% of an expected value.

Moreover, in accordance with a preferred embodiment of the present invention, there is provided a system wherein the medical parameter interpretation functionality is further operative to provide an alert responsive to the run being greater than 0.3 seconds and the slope being less than 100 mm Hg/sec.

Additionally, in accordance with a preferred embodiment of the present invention, there is provided a system wherein the medical parameter interpretation functionality is further operative to provide an indication of at least one of:

defective functioning of the monitoring device, and,
defective placing of the monitoring device,
responsive to a value of at least one of the measurements.

Also, in accordance with a preferred embodiment of the present invention, there is provided a system wherein the at least one medical parameter includes at least one of:
  an expired air carbon dioxide concentration, and
  an expired air carbon dioxide profile parameter.

Also, in accordance with a preferred embodiment of the present invention, there is provided a system wherein the at least one medical parameter includes at least one of:
  a visual parameter,
  a breathing parameter,
  an oxygen parameter,
  an ECG parameter,
  a heart function parameter,
  a neurological parameter,
  a blood pressure parameter, and
  an EEG parameter.

Additionally, in accordance with a preferred embodiment of the present invention, there is provided a system wherein the at least two medical parameters include at least one of:
  a visual parameter,
  a breathing parameter,
  an oxygen parameter,
  an ECG parameter,
  a heart function parameter,
  a neurological parameter,
  a blood pressure parameter, and
  an EEG parameter.

Also, in accordance with a preferred embodiment of the present invention, there is provided a system wherein the plurality of medical parameters includes at least one of:
  a visual parameter,
  a breathing parameter,
  an oxygen parameter,
  an ECG parameter,
  a heart function parameter,
  a neurological parameter,
  a blood pressure parameter, and
  an EEG parameter.

Also, the visual parameter includes a visual appearance of the patient.

Additionally, the breathing parameter includes at least one of:
  a respiratory rate of the patient,
  an FEV value, and
  an FVC value.

Furthermore, the oxygen parameter includes at least one of:
  $PO_2$, and
  $SPO_2$ Preferably, the ECG parameter includes at least one of:
  a QRS parameter, and
  an ST segment.

Typically, the heart function parameter includes a heart rate parameter.

Generally, the neurological function parameter includes a reflex parameter.

Also, the blood pressure parameter includes at least one of:
  a blood pressure measurement, and
  a systolic:diastolic ratio.

Furthermore, in accordance with a preferred embodiment of the present invention, there is provided a system wherein the medical parameter interpretation functionality is operative to provide an indication of the patient's status being within a normal range if at least one of the following requirements is fulfilled:
  a) the blood pressure values are within the normal range,
  b) the respiratory rate is normal,
  c) $CO_2$ run is less than or equal to 0.3 sec,
  d) $CO_2$ slope is more than or equal to 100 mm Hg/sec,
  e) $SPO_2$ is greater or equal to than 95%, and
  f) $ETCO_2$ is less than or equal to 45 mm Hg.

Additionally, in accordance with a preferred embodiment of the present invention, there is provided a system wherein the medical parameter response functionality is operative to provide an output indication responsive to a deviation from any one of the following requirements:
  a) the blood pressure values are within the normal range,
  b) the respiratory rate is normal,
  c) $CO_2$ run is less than or equal to 0.3 sec,
  d) $CO_2$ slope is more than or equal to 100 mm Hg/sec,
  e) $SPO_2$ is greater or equal to than 95%, and
  f) $ETCO_2$ is less than or equal to 45 mm Hg.

Also, in accordance with a preferred embodiment of the present invention, there is provided a system wherein the medical treatment control functionality is operative to provide a treatment to the patient responsive to a deviation from any one of these requirements:
  a) the blood pressure values are within the normal range,
  b) the respiratory rate is normal,
  c) $CO_2$ run is less than or equal to 0.3 sec,
  d) $CO_2$ slope is more than or equal to 100 mm Hg/sec,
  e) $SPO_2$ is greater or equal to than 95%, and
  f) $ETCO_2$ is less than or equal to 45 mm Hg.

Additionally, in accordance with a preferred embodiment of the present invention, there is provided a system wherein the medical parameter interpretation functionality is operative to provide an indication of the patient's status being within a normal range if all of the following requirements are fulfilled:
  a) the blood pressure values are within the normal range,
  b) the respiratory rate is normal,
  c) $CO_2$ run is less than or equal to 0.3 sec,
  d) $CO_2$ slope is more than or equal to 100 mm Hg/sec,
  e) $SPO_2$ is greater or equal to than 95%, and
  f) $ETCO_2$ is less than or equal to 45 mm Hg.

Additionally, in accordance with a preferred embodiment of the present invention, there is provided a system wherein the medical parameter interpretation functionality includes:
  a medical condition diagnosis functionality for diagnosing the presence of the at least one medical condition, and
  a medical condition severity indication functionality for indicating the degree of severity of the at least one medical condition.

Also, in accordance with a preferred embodiment of the present invention, there is provided a system wherein the medical parameter interpretation functionality is operative to provide an indication of the patient's status being outside the normal range if any of the requirements are not fulfilled.

Furthermore, in accordance with a preferred embodiment of the present invention, there is provided a system wherein the medical condition severity functionality is operative to provide an indication of the degree of severity of the at least one medical condition responsive to a degree of deviation of from at least one of the requirements.

Additionally, in accordance with a preferred embodiment of the present invention, there is provided a system wherein the medical condition diagnosis functionality is operative to diagnose a respiratory disorder.

Moreover, in accordance with a preferred embodiment of the present invention, there is provided a system wherein the medical condition diagnosis functionality is further operative to provide a diagnosis of a respiratory disorder responsive to any of the requirements not being fulfilled.

Also, in accordance with a preferred embodiment of the present invention, there is provided a system wherein the medical condition diagnosis functionality is further operative to provide a diagnosis of a severity of the respiratory disorder responsive to a quantitative measure of deviation of at least one parameter from at least one of the requirements.

Additionally, in accordance with a preferred embodiment of the present invention, there is provided a system wherein the respiratory disorder includes at least one of:
 a restrictive lung disease,
 bronchospasm,
 asthma,
 bronchitis,
 emphysema,
 a respiratory failure,
 fibrosis, and
 an upper airway obstructive disease.

Furthermore, in accordance with a preferred embodiment of the present invention, there is provided a system wherein the medical condition diagnosis functionality is operative to provide a diagnosis of the restrictive lung disease responsive to at least one of the following cases:
 the run is greater or equal to 0.3 sec, or
 the slope is less than or equal to 100 mm Hg/sec.

Additionally, in accordance with a preferred embodiment of the present invention, there is provided a system wherein the medical condition diagnosis functionality is operative to provide a diagnosis of the obstructive lung disease responsive to at least one of the following cases:
 the run is less than 0.3 sec, or
 the slope is more than 100 nm Hg/sec.

Further, in accordance with a preferred embodiment of the present invention, there is provided a system wherein the medical condition diagnosis functionality is further operative to provide a diagnosis of a heart disorder responsive to any of the requirements not being fulfilled.

Yet further, in accordance with a preferred embodiment of the present invention, there is provided a system wherein the medical condition diagnosis functionality is further operative to provide a diagnosis of a heart failure if the following requirements are fulfilled:
 CAP-FEV1 is less than or equal to a 40:10 point ratio,
 a normal CAP-FEV1/FVC ratio,
 $CO_2$ run is less than 0.3 sec, and
 $CO_2$ slope is more than 100 mm Hg/sec.

Additionally, in accordance with a preferred embodiment of the present invention, there is provided a system wherein the medical condition diagnosis functionality is further operative to provide a diagnosis of a severity of the heart disorder responsive to a quantitative measure of a deviation from any of the requirements.

Moreover, in accordance with a preferred embodiment of the present invention, there is provided a system wherein the medical parameter interpretation functionality is operative to provide a recommendation to perform at least one of the following treatments responsive to the indication:
 intubation of the patient,
 hospitalization of the patient,
 treat the patient with medication, and
 transfer of the patient to an intensive care unit.

Further, in accordance with a preferred embodiment of the present invention, there is provided a system wherein the medical parameter interpretation functionality is operative to provide the at least one output indication responsive to a pattern of changes in the at least one medical parameter over time.

Furthermore, in accordance with a preferred embodiment of the present invention, there is provided a system wherein the medical parameter interpretation functionality is further operative to provide an output indication responsive to a pattern of changes in the degree of severity of the at least one medical condition over time.

Yet further, in accordance with a preferred embodiment of the present invention, there is provided a system wherein the medical parameter interpretation functionality is operative to provide the plurality of output indications responsive to a pattern of changes in the plurality of medical parameters over time.

Still further, in accordance with a preferred embodiment of the present invention, there is provided a system wherein the medical parameter interpretation functionality is further operative to provide the plurality of output indications responsive to a pattern of changes in the degree of severity of the at least one medical condition over time.

Further, in accordance with a preferred embodiment of the present invention, there is provided a system which also includes a treatment recommendation functionality.

Furthermore, in accordance with a preferred embodiment of the present invention, there is provided a system wherein the treatment recommendation functionality is operative to recommend treatment responsive to the location of the patient.

Further, in accordance with a preferred embodiment of the present invention, there is provided a system wherein the treatment recommendation functionality is operative to recommend treatment responsive to a change in at least one of the following:
 a change in the run,
 a change in the $ETCO_2$,
 a change in the slope,
 a change in the angle of rise of $CO_2$, and
 a change in the $SPO_2$.

Yet further, in accordance with a preferred embodiment of the present invention, there is provided a system wherein the treatment recommendation functionality is responsive to a pattern of changes in the degree of severity of the at least one medical condition over time.

Still further, in accordance with a preferred embodiment of the present invention, there is provided a system wherein the treatment recommendation functionality is operative to provide an alert if at least one of the following requirements is fulfilled:
 a change in the run of more than 0.1 s,
 a change in the slope is more negative than −15 mm Hg/sec, and
 a change in the $SPO_2$ is more negative than −5%.

Further, in accordance with a preferred embodiment of the present invention, there is provided a system wherein the treatment recommendation functionality is operative to provide a recommendation for at least one of the following treatments responsive to at least one of the requirements:
 intubation of the patient,
 hospitalization of the patient,
 treat the patient with intravenous medication, and
 transfer of the patient to an intensive care unit.

Further, in accordance with a preferred embodiment of the present invention, there is provided a system wherein the treatment recommendation functionality is operative to provide a recommendation to perform at least one of:
 continue monitoring, and
 continue treating the patient if at least one of the following conditions is fulfilled:

a change in the run is less negative or equal to −0.1 s but less positive or equal to 0.1 s, a change in the slope is less negative or equal to −15 Hg/sec, but less positive or equal to +15 mm Hg/sec, and a change in the $SPO_2$ is less negative or equal to −5%, but less positive or equal to +5%.

Further, in accordance with a preferred embodiment of the present invention, there is provided a system wherein the treatment recommendation functionality is operative to perform at least one of the following:

provide a message indicative of an improvement in the patient's status, and recommend discontinuing a treatment procedure, if at least one of the following conditions is fulfilled:

a change in the run is more negative than −0.1 s, a change in the slope is more positive than +15 mm Hg/sec, and a change in the $SPO_2$ is more positive than 5%.

Also, in accordance with a preferred embodiment of the present invention, there is provided a system wherein the treatment recommendation functionality is operative to provide a recommendation to continue monitoring the patient responsive to the pattern of changes indicating at least one of:

a deterioration in the status of the patient, and, a non-significant change in the status of the patient.

Additionally, in accordance with a preferred embodiment of the present invention, there is provided a system wherein the treatment recommendation functionality is operative to provide a recommendation to stop monitoring the patient responsive to a pattern of changes indicating an improvement in the status of the patient.

Further, in accordance with a preferred embodiment of the present invention, there is provided a system wherein the treatment recommendation functionality is additionally responsive to information regarding other treatment received by the patient.

Also, in accordance with a preferred embodiment of the present invention, there is provided a system including a treatment control functionality for controlling the provision of at least one treatment to a patient.

Further, in accordance with a preferred embodiment of the present invention, there is provided a system wherein the at least one treatment includes at least one of:

intubation of the patient, hospitalization of the patient, treat the patient with medication, and transfer of the patient to an intensive care unit.

Yet further, in accordance with a preferred embodiment of the present invention, there is provided a system wherein the treatment control functionality is responsive to a pattern of changes in the at least one medical parameter over time.

Also, in accordance with a preferred embodiment of the present invention, there is provided a system wherein the treatment control functionality is responsive to a pattern of changes in the degree of severity of the at least one medical condition over time.

Further, in accordance with a preferred embodiment of the present invention, there is provided a system wherein the treatment control functionality is additionally responsive to information regarding other treatment received by the patient.

Still further, in accordance with a preferred embodiment of the present invention, there is provided a system wherein the treatment control functionality controls the provision of the at least one treatment to the patient in response to changes in the at least output indication over time.

Further, in accordance with a preferred embodiment of the present invention, there is provided a system wherein the at least one medical parameter includes a plurality of medical parameters.

Furthermore, in accordance with a preferred embodiment of the present invention, there is provided a system wherein at least two medical parameters include a plurality of medical parameters.

Additionally, in accordance with a preferred embodiment of the present invention, there is provided a system wherein the plurality of medical parameters includes at least two of $CO_2$, ECG, $SPO_2$, $PO_2$, NIBP and spirometry parameters.

Further, in accordance with a preferred embodiment of the present invention, there is provided a system wherein the output indication relating to a degree of severity of at least one medical condition is determined at least partially by changes in the at least one medical parameter.

Furthermore, in accordance with a preferred embodiment of the present invention, there is provided a system wherein the at least one medical parameter includes a plurality of medical parameters.

Also, the at least one medical parameter preferably includes a plurality of medical parameters.

Yet further, in accordance with a preferred embodiment of the present invention, there is provided a system and also including a transmitter functionality adapted to convey the output indication to a remote location.

Further, in accordance with a preferred embodiment of the present invention, there is provided a system further operative to provide a treatment responsive to at least one of:

the output indication, and the remote location.

Further, in accordance with a preferred embodiment of the present invention, there is provided an emergency medical transport facility and wherein the medical parameter interpretation functionality includes:

a medical condition diagnosis functionality for diagnosing the presence of the at least one medical condition, and a medical condition severity functionality indicating the degree of severity of the at least one medical condition.

Furthermore, in accordance with a preferred embodiment of the present invention, there is provided an emergency medical transport facility wherein the medical parameter interpretation functionality provides an output indication responsive to a pattern of changes in the at least one medical parameter over time.

Furthermore, in accordance with a preferred embodiment of the present invention, there is provided an emergency medical transport facility wherein the medical parameter interpretation functionality provides an output indication responsive to a pattern of changes in the degree of severity of the at least one medical condition over time.

Additionally, in accordance with a preferred embodiment of the present invention, there is provided an emergency medical transport facility also including treatment recommendation functionality.

Furthermore, in accordance with a preferred embodiment of the present invention, there is provided an emergency medical transport facility wherein the treatment recommendation functionality is responsive to a pattern of changes in the at least one medical parameter over time.

Also, in accordance with a preferred embodiment of the present invention, there is provided an emergency medical transport facility wherein the treatment recommendation functionality is responsive to a pattern of changes in the degree of severity of the at least one medical condition over time.

Additionally, in accordance with a preferred embodiment of the present invention, there is provided an emergency medical transport facility wherein the treatment recommendation functionality is additionally responsive to information regarding other treatment received by the patient.

Moreover, in accordance with a preferred embodiment of the present invention, there is provided an emergency medical transport facility which includes a treatment control functionality for controlling the provision of at least one treatment to a patient.

Furthermore, in accordance with a preferred embodiment of the present invention, there is provided an emergency medical transport facility wherein the treatment control functionality is responsive to a pattern of changes in the at least one medical parameter over time.

Further, in accordance with a preferred embodiment of the present invention, there is provided an emergency medical transport facility wherein the treatment control functionality is responsive to a pattern of changes in the degree of severity of the at least one medical condition over time.

Also, in accordance with a preferred embodiment of the present invention, there is provided an emergency medical transport facility wherein the treatment control functionality is additionally responsive to information regarding other treatment received by the patient.

Furthermore, in accordance with a preferred embodiment of the present invention, there is provided an emergency medical transport facility wherein the at least one medical parameter includes a plurality of medical parameters.

Additionally, in accordance with a preferred embodiment of the present invention, there is provided an emergency medical transport facility wherein the plurality of medical parameters includes at least two of $CO_2$, ECG, $SPO_2$, $PO_2$, NIBP, EEG and spirometry parameters.

Further, in accordance with a preferred embodiment of the present invention, there is provided an emergency medical transport facility wherein the output indication relating to a degree of severity of at least one medical condition is determined at least partially by changes in at least one medical parameter.

Yet further, in accordance with a preferred embodiment of the present invention, there is provided an emergency medical transport facility which also includes a transmitter functionality for conveying the output indication to a remote location.

Also, in accordance with a preferred embodiment of the present invention, there is provided an emergency medical transport facility wherein the treatment control functionality controls the provision of the at least one treatment to a patient in response to changes in the output indication over time.

Also, in accordance with a preferred embodiment of the present invention, there is provided a method wherein the at least one medical parameter includes at least one of:
 an expired air carbon dioxide concentration, and
 an expired air carbon dioxide profile parameter.

Additionally, in accordance with a preferred embodiment of the present invention, there is provided a method wherein the at least two medical parameters include at least one of:
 an expired air carbon dioxide concentration, and
 an expired air carbon dioxide profile parameter.

Furthermore, in accordance with a preferred embodiment of the present invention, there is provided a method wherein the plurality of parameters includes at least one of:
 an expired air carbon dioxide concentration, and
 an expired air carbon dioxide profile parameter.

Also, in accordance with a preferred embodiment of the present invention, there is provided a method wherein interfacing the patient includes monitoring the patient by means of at least one of:
 a monitoring device, and
 the medical parameter interpretation functionality.

Additionally, in accordance with a preferred embodiment of the present invention, there is provided a method wherein monitoring the patient includes monitoring by means of at least one of the following:
 an electrocardiogram (ECG) monitoring device,
 a blood pressure monitoring device,
 an electroencephalogram (EEG) monitoring device,
 an NI blood pressure monitoring device,
 a respiratory rate monitoring device,
 a heart rate monitoring device,
 a methodic perfusion monitoring device, and
 an exhaled air monitoring device.

Also, in accordance with a preferred embodiment of the present invention, there is provided a method wherein monitoring includes monitoring at least one of the following waveforms:
 a carbon dioxide waveform (capnogram),
 an EEG waveform, and
 an ECG waveform.

Additionally, in accordance with a preferred embodiment of the present invention, there is provided a method wherein the monitoring includes analyzing a sample of expired air from the patient by a capnograph.

Also, in accordance with a preferred embodiment of the present invention, there is provided a method wherein analyzing the sample includes digitizing at least one of the waveforms.

Further, in accordance with a preferred embodiment of the present invention, there is provided a method wherein monitoring the patient includes providing at least one of the following measurements:
 a slope of the increase in the carbon dioxide concentration,
 a run of time taken to reach 80% maximum exhaled $CO_2$ concentration, and
 an angle of rise to 80% maximum exhaled $CO_2$ concentration.

Also, in accordance with a preferred embodiment of the present invention, there is provided a method wherein providing the output includes indicating at least one of:
 defective functioning of the monitoring device, and,
 defective placing of the monitoring device,
 responsive to a value of at least one of the measurements.

Additionally, in accordance with a preferred embodiment of the present invention, there is provided a method wherein monitoring the patient includes providing a value of CAP-FEV1.

Also, in accordance with a preferred embodiment of the present invention, there is provided a method including providing an alert responsive to a measure of CAP-FEV1 being less than 50% of an expected value.

Additionally, in accordance with a preferred embodiment of the present invention, there is provided a method wherein analyzing the sample includes providing responsive to at least one of:
 the run being greater than 0.3 seconds, or
 the slope being less than 100 mm Hg/sec.

Also, in accordance with a preferred embodiment of the present invention, there is provided a method wherein the at least one medical parameter includes at least one of:

a visual parameter,
a breathing parameter,
an oxygen parameter,
an ECG parameter,
a heart function parameter,
a neurological parameter,
a blood pressure parameter, and
an EEG parameter.

Additionally, in accordance with a preferred embodiment of the present invention, there is provided a method wherein the at least two medical parameters include at least one of:
a visual parameter,
a breathing parameter,
an oxygen parameter,
an ECG parameter,
a heart function parameter,
a neurological parameter,
a blood pressure parameter, and
an EEG parameter.

Furthermore, in accordance with a preferred embodiment of the present invention, there is provided a method wherein the plurality of medical parameters include at least one of:
a visual parameter,
a breathing parameter,
an oxygen parameter,
an ECG parameter,
a heart function parameter,
a neurological parameter,
a blood pressure parameter, and
an EEG parameter.

Also, in accordance with a preferred embodiment of the present invention, there is provided a method further including providing an indication of a status of the patient as being within a normal range if at least one of the following requirements is fulfilled:
a) the blood pressure values are within the normal range,
b) the respiratory rate is normal,
c) $CO_2$ run is less than or equal to 0.3 sec,
d) $CO_2$ slope is more than or equal to 100 mm Hg/sec,
e) $SPO_2$ is greater or equal to than 95%, and
f) $ETCO_2$ is less than or equal to 45 mm Hg.

Additionally, in accordance with a preferred embodiment of the present invention, there is provided a method wherein providing the indication of the patient's status being within the normal range if all of the following requirements are fulfilled:
a) the blood pressure values are within the normal range,
b) the respiratory rate is normal,
c) $CO_2$ run is less than or equal to 0.3 sec,
d) $CO_2$ slope is more than or equal to 100 mm Hg/sec,
e) $SPO_2$ is greater or equal to than 95%, and
f) $ETCO_2$ is less than or equal to 45 mm Hg.

Furthermore, in accordance with a preferred embodiment of the present invention, there is provided a method including:
diagnosing a presence of the at least one medical condition by a medical condition diagnosis functionality, and
indicating a degree of severity of the at least one medical condition by a medical condition severity indication functionality Yet further, in accordance with a preferred embodiment of the present invention, there is provided a method including providing an indication of the patient's status being outside the normal range if any of the requirements are not fulfilled.

Also, in accordance with a preferred embodiment of the present invention, there is provided a method wherein including indicating the degree of severity of the at least one medical condition responsive to a degree of deviation from of any of the requirements.

Additionally, in accordance with a preferred embodiment of the present invention, there is provided a method wherein diagnosing the presence of the at least one medical condition includes diagnosing a respiratory disorder.

Furthermore, in accordance with a preferred embodiment of the present invention, there is provided a method wherein diagnosing, the respiratory disorder includes providing a diagnosis of a severity of the respiratory disorder responsive to a quantitative measure of deviation from at least one of the requirements.

Also, in accordance with a preferred embodiment of the present invention, there is provided a method wherein the respiratory disorder includes at least one of:
a restrictive lung disease,
bronchospasm,
asthma,
bronchitis,
emphysema,
a respiratory failure,
fibrosis, and
an upper airway obstructive disease.

Additionally, in accordance with a preferred embodiment of the present invention, there is provided a method wherein indicating the degree of severity includes providing a diagnosis of the restrictive lung disease responsive to at least one of the following cases:
the run is greater than 0.3 sec, or
the slope is less than 100 mm Hg/sec.

Also, in accordance with a preferred embodiment of the present invention, there is provided a method wherein indicating the degree of severity includes providing a diagnosis of the obstructive lung disease responsive to at least one of the following cases:
the run is less than or equal to 0.3 sec, or
the slope is more than or equal to 100 mm Hg/sec.

Further, in accordance with a preferred embodiment of the present invention, there is provided a method wherein providing the indication includes providing a diagnosis of a heart disorder responsive to any of the requirements not being fulfilled.

Additionally, in accordance with a preferred embodiment of the present invention, there is provided a method including providing a diagnosis of a heart failure if the following conditions are fulfilled:
CAP-FEV1 is less than or equal to a 40:10 point ratio,
a normal CAP-FEV1/FVC ratio,
$CO_2$ run is less than or equal to 0.3 sec, and
$CO_2$ slope is more than or equal to 100 mm Hg/sec.

Also, in accordance with a preferred embodiment of the present invention, there is provided a method wherein providing an indication includes providing a diagnosis of a severity of the heart disorder.

Furthermore, in accordance with a preferred embodiment of the present invention, there is provided a method wherein providing an output indication includes providing a plurality of output indications.

Also, in accordance with a preferred embodiment of the present invention, there is provided a method wherein providing a plurality of output indications includes providing at least one recommendation to perform at least one of the following treatments:
intubation of the patient,
hospitalization of the patient,
treat the patient with medication, and
transfer of the patient to an intensive care unit.

Typically the visual parameter includes a visual appearance of the patient. Generally the breathing parameter includes at least one of:
a respiratory rate of the patient,
an FEV value, and
an FVC value.

Normally, the oxygen parameter includes at least one of:
$PO_2$, and
$SPO_2$.

Generally, the ECG parameter includes at least one of:
a QRS parameter, and
an ST segment.

Preferably, the heart function parameter includes a heart rate parameter.

Typically, the neurological function parameter includes a reflex parameter.

Also, in accordance with a preferred embodiment of the present invention, there is provided a method wherein the blood pressure parameter includes at least one of:
a blood pressure measurement, and
a systolic:diastolic ratio.

Furthermore, in accordance with a preferred embodiment of the present invention, there is provided a method including providing the output indication responsive to a pattern of changes in the at least one medical parameter over time.

Also, in accordance with a preferred embodiment of the present invention, there is provided a method wherein the output indication is responsive to a pattern of changes in the at least two medical parameters over time.

Additionally, in accordance with a preferred embodiment of the present invention, there is provided a method providing the output indication responsive to a pattern of changes in the plurality of medical parameters over time.

Also, in accordance with a preferred embodiment of the present invention, there is provided a method including providing an output indication responsive to a pattern of changes in the degree of severity of the at least one medical condition over time.

Further, in accordance with a preferred embodiment of the present invention, there is provided a method including providing a treatment recommendation by means of a treatment recommendation functionality.

Also, in accordance with a preferred embodiment of the present invention, there is provided a method wherein providing the treatment recommendation is responsive to a pattern of changes of at least one medical parameter over time.

Additionally, in accordance with a preferred embodiment of the present invention, there is provided a method wherein providing the treatment recommendation is responsive to the location of the patient.

Furthermore, in accordance with a preferred embodiment of the present invention, there is provided a method wherein the pattern of changes includes a change in at least one of the following:
a change in a run,
a change in an $ETCO_2$,
a change in a slope,
a change in an angle of rise of $CO_2$, and
a change in an $SPO_2$.

Also, in accordance with a preferred embodiment of the present invention, there is provided a method wherein providing the treatment recommendation is responsive to a pattern of changes in the degree of severity of the at least one medical condition over time.

Additionally, in accordance with a preferred embodiment of the present invention, there is provided a method wherein providing the treatment recommendation includes providing an alert if at least one of the following conditions is fulfilled:
a change in the run of more than 0.1 s,
a change in the slope is more negative than −15 mm Hg/sec, and
a change in the $SPO_2$ is more negative than −5%.

Also, in accordance with a preferred embodiment of the present invention, there is provided a method wherein providing the treatment recommendation includes providing a recommendation for at least one of the following treatments:
intubation of the patient,
hospitalization of the patient,
treat the patient with intravenous medication, and
transfer of the patient to an intensive care unit.

Additionally, in accordance with a preferred embodiment of the present invention, there is provided a method wherein providing the treatment includes providing a recommendation to perform at least one of:
continue monitoring the patient, and
continue treating the patient,
provided at least one of the following conditions is fulfilled:
a change in the run is less negative or equal to −0.1 s but less positive or equal to 0.1 s,
a change in the slope is less negative or equal to −15, Hg/sec, but less positive or equal to +15 mm Hg/sec, and
a change in the $SPO_2$ is less negative or equal to −5%, but less positive or equal to +5%.

Further, in accordance with a preferred embodiment of the present invention, there is provided a method wherein providing the treatment includes at least one of the following:
providing a message indicative of an improvement in the patient's status, and
recommending discontinuing a treatment procedure, if at least one of the following conditions is fulfilled:
a change in the run is more negative than −0.1 s,
a change in the slope is more positive than +15 mm Hg/sec, and
a change in the $SPO_2$ is more positive than 5%.

Also, in accordance with a preferred embodiment of the present invention, there is provided a method wherein providing the treatment includes providing a recommendation to continue monitoring the patient responsive to the pattern of changes indicating at least one of:
a deterioration in the status of the patient, and,
a non-significant change in the status of the patient.

Additionally, in accordance with a preferred embodiment of the present invention, there is provided a method wherein providing the treatment includes providing a recommendation to stop monitoring the patient responsive to the pattern of changes indicating an improvement in the status of the patient.

Also, in accordance with a preferred embodiment of the present invention, there is provided a method including providing at least one of the following treatments to the patient:
intubation of the patient,
hospitalization of the patient,
treat the patient with medication, and
transfer of the patient to an intensive care unit.

Additionally, in accordance with a preferred embodiment of the present invention, there is provided a method wherein controlling the provision of at least one treatment includes responding to a pattern of changes in the degree of severity of the at least one medical condition over time.

Further, in accordance with a preferred embodiment of the present invention, there is provided a method wherein the treatment control functionality is additionally responds to information regarding other treatment received by the patient.

Also, in accordance with a preferred embodiment of the present invention, there is provided a method wherein the at least one medical parameter includes a plurality of parameters.

Additionally, in accordance with a preferred embodiment of the present invention, there is provided a method wherein the at least two medical parameters include a plurality of parameters.

Further, in accordance with a preferred embodiment of the present invention, there is provided a method wherein the plurality of medical parameters includes at least two of $CO_2$, ECG, $SPO_2$, $PO_2$, NIBP and spirometry parameters.

Also, in accordance with a preferred embodiment of the present invention, there is provided a method wherein the output indication relating to the degree of severity of the at least one medical condition is determined at least partially by changes in the at least one medical parameter.

Additionally, in accordance with a preferred embodiment of the present invention, there is provided a method including conveying the output indication to a remote location by means of a transmitter functionality.

Also, in accordance with a preferred embodiment of the present invention, there is provided a method including conveying the plurality of output indications to a remote location by means of a transmitter functionality.

Also, in accordance with a preferred embodiment of the present invention, there is provided a method wherein the treatment control functionality controls the provision of the at least one treatment to a patient in response to changes in the output indication over time.

Also, in accordance with a preferred embodiment of the present invention, there is provided an emergency medical transport methodology wherein interpreting the at least one medical parameter includes:
  diagnosing the presence of at least one medical condition by means of a medical condition diagnosis functionality, and
  indicating the degree of severity of the at least one medical condition by means of a medical condition severity functionality.

Additionally, in accordance with a preferred embodiment of the present invention, there is provided an emergency medical transport methodology including providing an output indication responsive to a pattern of changes in the at least one medical parameter over time by means of the medical parameter interpretation functionality.

Additionally, in accordance with a preferred embodiment of the present invention, there is provided an emergency medical transport methodology including providing an output indication responsive to a pattern of changes in the degree of severity of the at least one medical condition over time.

Also, in accordance with a preferred embodiment of the present invention, there is provided an emergency medical transport methodology including providing a treatment recommendation by means of a treatment recommendation functionality.

Additionally, in accordance with a preferred embodiment of the present invention, there is provided an emergency medical transport methodology wherein the treatment recommendation functionality is responsive to a pattern of changes in the at least one medical parameter over time.

Also, in accordance with a preferred embodiment of the present invention, there is provided an emergency medical transport methodology wherein the treatment recommendation functionality is responsive to a pattern of changes in the degree of severity of the at least one medical condition over time.

Further, in accordance with a preferred embodiment of the present invention, there is provided an emergency medical transport methodology wherein the treatment recommendation functionality is additionally responsive to information regarding other treatment received by the patient.

Also, in accordance with a preferred embodiment of the present invention, there is provided an emergency medical transport methodology wherein including treatment control functionality for controlling the provision of at least one treatment to the patient.

Additionally, in accordance with a preferred embodiment of the present invention, there is provided an emergency medical transport methodology wherein the treatment control functionality is responsive to a pattern of changes in the at least one medical parameter over time.

Also, in accordance with a preferred embodiment of the present invention, there is provided an emergency medical transport methodology wherein the treatment control functionality is responsive to a pattern of changes in the degree of severity of the at least one medical condition over time.

Furthermore, in accordance with a preferred embodiment of the present invention, there is provided an emergency medical transport methodology wherein the treatment control functionality is additionally responsive to information regarding other treatment received by the patient.

Also, in accordance with a preferred embodiment of the present invention, there is provided an emergency medical transport methodology wherein the at least one medical parameter includes a plurality of medical parameters.

Additionally, in accordance with a preferred embodiment of the present invention, there is provided an emergency medical transport methodology wherein the plurality of medical parameters includes at least two of $CO_2$, ECG, $SPO_2$, $PO_2$, NIBP, EEG and spirometry parameters.

Further, in accordance with a preferred embodiment of the present invention, there is provided an emergency medical transport methodology wherein the output indication relating to a degree of severity of at least one medical condition is determined at least partially by changes in at least one medical parameter.

Yet further, in accordance with a preferred embodiment of the present invention, there is provided an emergency medical transport methodology including a transmitter functionality for conveying the output indication to a remote location.

Also, in accordance with a preferred embodiment of the present invention, there is provided an emergency medical transport methodology wherein the treatment control functionality controls the provision of the at least one treatment to a patient in response to changes in the output indication over time.

Additionally, in accordance with a preferred embodiment of the present invention, there is provided an emergency medical transport methodology wherein the treatment control functionality controls the provision of the at least one treatment to a patient in response to the location of the patient.

1. BRIEF DESCRIPTION OF THE DRAWINGS

The present invention will be understood and appreciated more fully from the following detailed description, taken in conjunction with the drawings in which:

FIG. 13 is a simplified pictorial illustration of an automatic medical diagnostic and treatment system and methodology in an ambulance environment for detecting the presence and severity of bronchospasm, gauging the response to treatment and recommending disposition of mechanically ventilated patients;

FIGS. 21A and 21B are simplified pictorial illustrations of an automatic medical diagnostic and treatment system and methodology operative in a hospital environment for monitoring intubation status of a patient in a second clinical scenario;

FIGS. 26A and 26B are flowcharts illustrating operation of the embodiment of FIGS. 25A and 25B, FIGS. 27A and 27B are simplified pictorial illustrations of an automatic medical diagnostic and treatment system and methodology in an ambulance environment for detecting the presence and severity of bronchospasm from an allergic reaction, gauging the response to treatment and recommending disposition;

2. DETAILED DESCRIPTION OF PREFERRED EMBODIMENTS

Figure 1A:
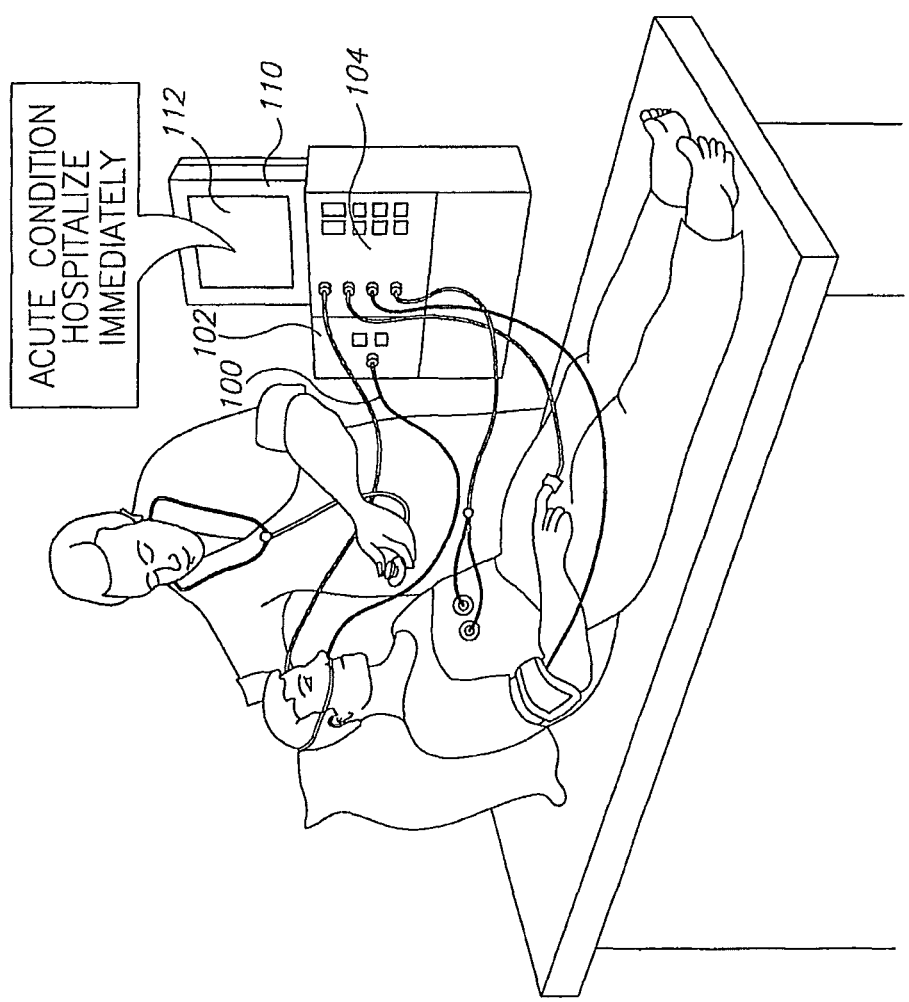
FIGS. 1A, 1B and 1C are simplified pictorial illustrations showing a medical care system and methodology employing at least one parameter relating at least to respiration for automatically providing an output indication relating to at least one medical condition in accordance with a preferred embodiment of the present invention in three different types of care environments.
Figure 1B:
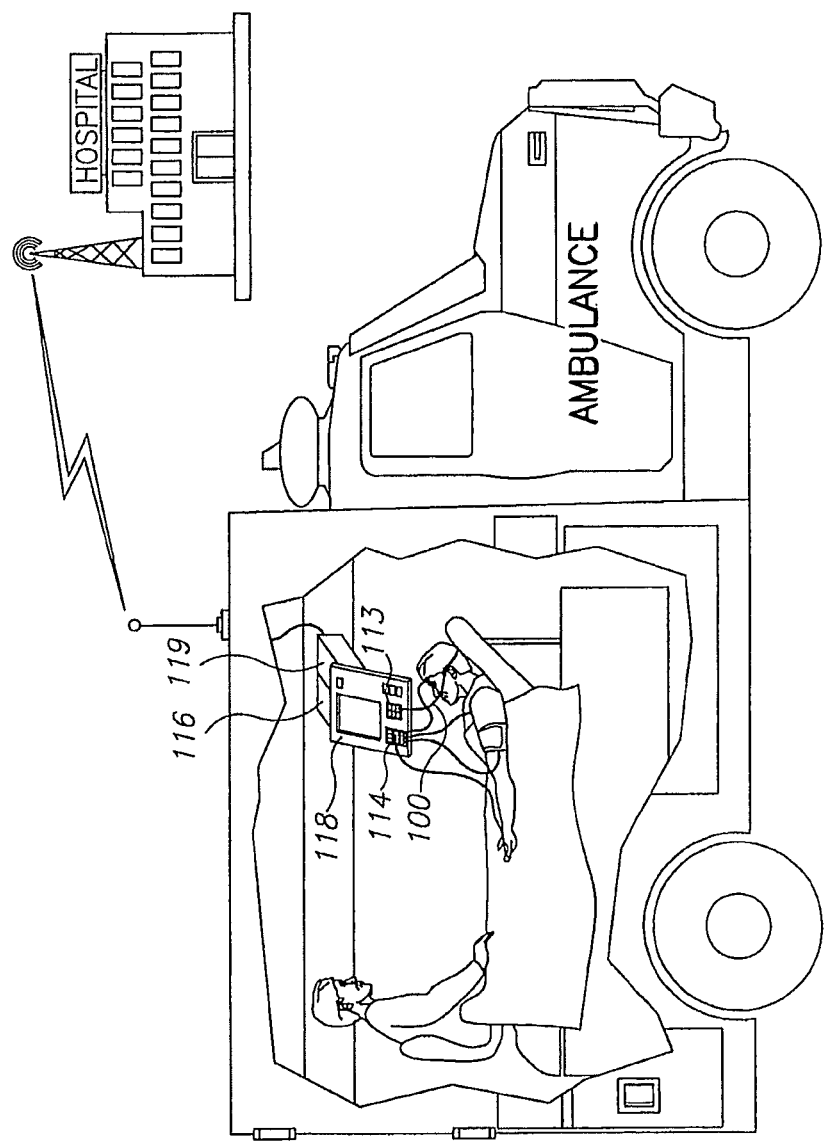
Figure 1C:
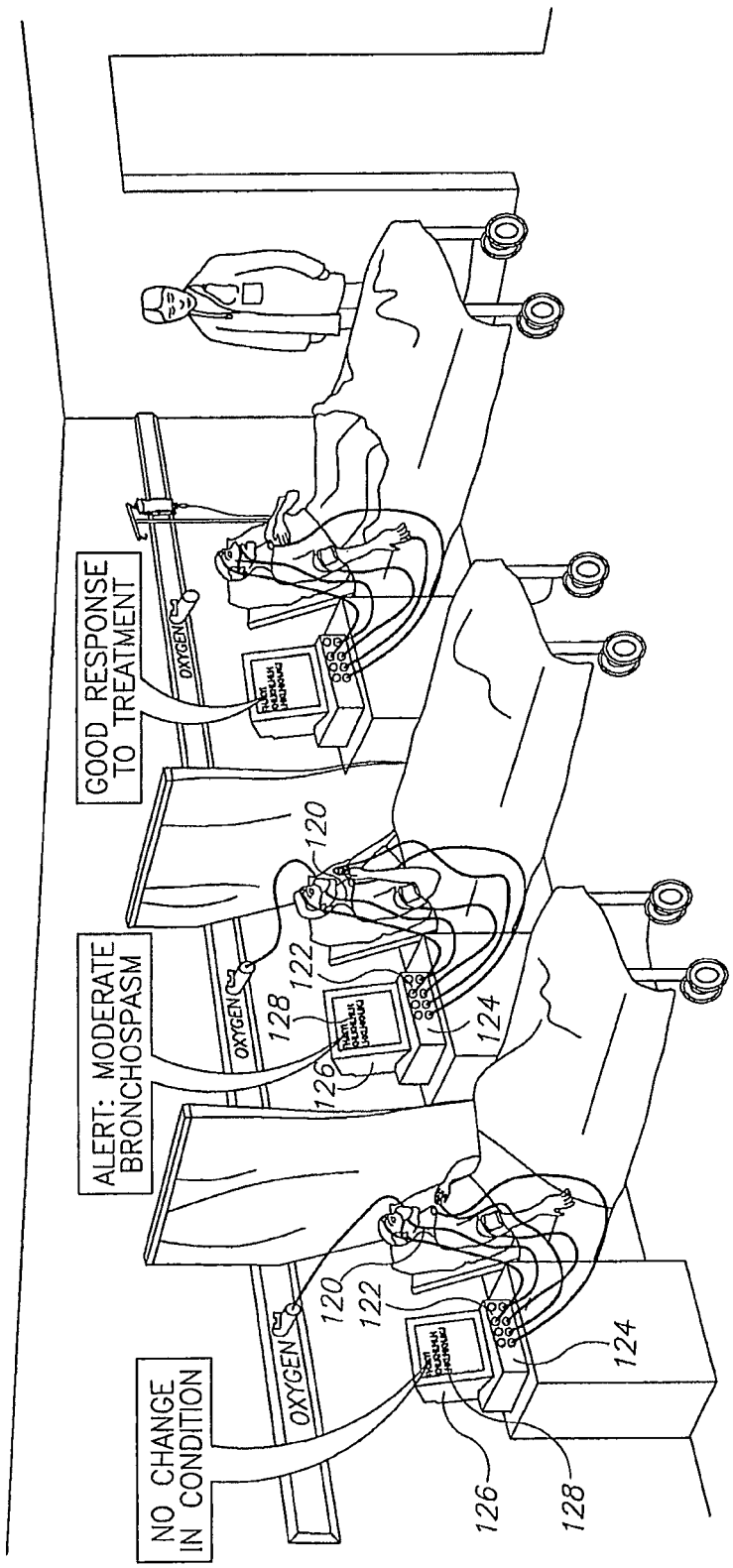

Reference is now made to FIGS. 1A, 1B and 1C, which are simplified pictorial illustrations showing a medical care system and methodology employing at least one parameter relating at least to respiration for automatically providing an output indication relating to at least one medical condition in accordance with a preferred embodiment of the present invention in three different types of care environments.

Turning to FIG. 1A, it is seen that in an out of hospital environment, such as a doctor's office or other ambulatory care facility, various patient physiologic activities are sensed and measured, including respiratory physiologic activities, preferably via an oral airway adapter and/or a nasal or nasal/oral cannula 100, such as a Model Nasal FilterLine Adult XS 04461, $O_2/CO_2$ Nasal FilterLine Adult 007141, or Smart CapnoLine Adult (Oral/nasal FilterLine) 007414, commercially available from Oridion Ltd., of Jerusalem Israel, typically coupled with a capnograph 102, such as a Microcap®, commercially available from Oridion Ltd., of Jerusalem Israel. Other patient physiologic activities relating to cardiac function (e.g. electrocardiogram (ECG)), cerebral perfusion (e.g. CEREBRAL OXIMETRY), oxygenation (e.g. pulse oximetry) and systemic circulation (e.g. . . . blood pressure (NIBP)), may also be sensed and measured by suitable instrumentation 104.

The outputs of the capnograph 102 and possibly of additional instrumentation 104 are preferably supplied to a suitably programmed automatic diagnostic and treatment computer 110, which typically analyzes the respiration parameter output of the capnograph 102, and also typically has an associated display 112, the display being at least one of a visual display, such as a computer screen, a virtual display, or a printed form of a display. Optionally further physiologic activities are outputted from capnograph 102 and instrumentation 104, and provided as outputs via computer 110 and display 112, which preferably contain diagnostic statements, which preferably characterize the type and severity of a medical condition, as well as treatment recommendations.

Turning to FIG. 1B, it is seen that in an ambulance environment, various patient physiologic activities are sensed and measured, including respiratory physiologic activities, preferably via an oral airway adapter and/or a nasal or nasal/oral cannula 100, such as a such as a Nasal FilterLine Adult XS 04461, $O_2/CO_2$ Nasal FilterLine Adult 007141, or Smart CapnoLine Adult (Oral/nasal FilterLine) 007414, commercially available from Oridion Ltd., of Jerusalem Israel, typically coupled with a capnograph 113, such as a Microcap®, commercially available from Oridion Ltd., of Jerusalem Israel. Other patient physiologic activities relating to cardiac function (e.g. ECG), cerebral perfusion (e.g. CEREBRAL OXIMETRY), oxygenation (e.g. pulse oximetry) and systemic circulation (e.g. NIBP), may also be sensed and measured by suitable instrumentation 114.

The outputs of the capnograph 113 and possibly of additional instrumentation 114 are preferably supplied to a suitably programmed automatic diagnostic and treatment computer 116, having an associated display 118, which typically analyzes the respiration parameter output of the capnograph 113 and possibly other parameters and provides an output which preferably contains diagnostic statements, which preferably characterize the type and severity of a medical condition, as well as treatment recommendations.

Preferably some or all of the outputs of computer 116 are transmitted in a wireless manner by a transmitter 119, such as via radio or a cellular telephone link, preferably to a dispatch center or patient receiving facility.

Turning to FIG. 1C, it is seen that in a hospital environment, such as an emergency department, medical ward or intensive care unit (ICU), various patient physiologic activities are sensed and measured, including respiratory physiologic activities, preferably via an oral airway adapter and/or a nasal or nasal/oral cannula 120, such as a Nasal FilterLine Adult XS 04461, $O_2/CO_2$ Nasal FilterLine Adult 007141, or Smart CapnoLine Adult (Oral/nasal FilterLine) 007414, commercially available from Oridion Ltd., of Jerusalem Israel, typically coupled with a capnograph 122, such as a Microcap®, commercially available from Oridion Ltd., of Jerusalem Israel. Other patient physiologic activities relating to cardiac function (e.g. ECG), cerebral perfusion (e.g. CEREBRAL OXIMETRY), oxygenation (e.g. pulse oximetry) and systemic circulation (e.g. NIBP), may also be sensed and measured by suitable instrumentation 124.

The outputs of the capnograph 122 and possibly of additional instrumentation 124 are preferably supplied to a suitably programmed automatic diagnostic and treatment computer 126 at the patient's bedside and/or at a central monitoring station, having an associated display 128, which typically continuously analyzes the respiration parameter output of the capnograph 122 and possibly other parameters and provides an output which preferably contains diagnostic statements, which preferably characterize the type and severity of a medical condition, as well as treatment recommendations.

Figure 2:
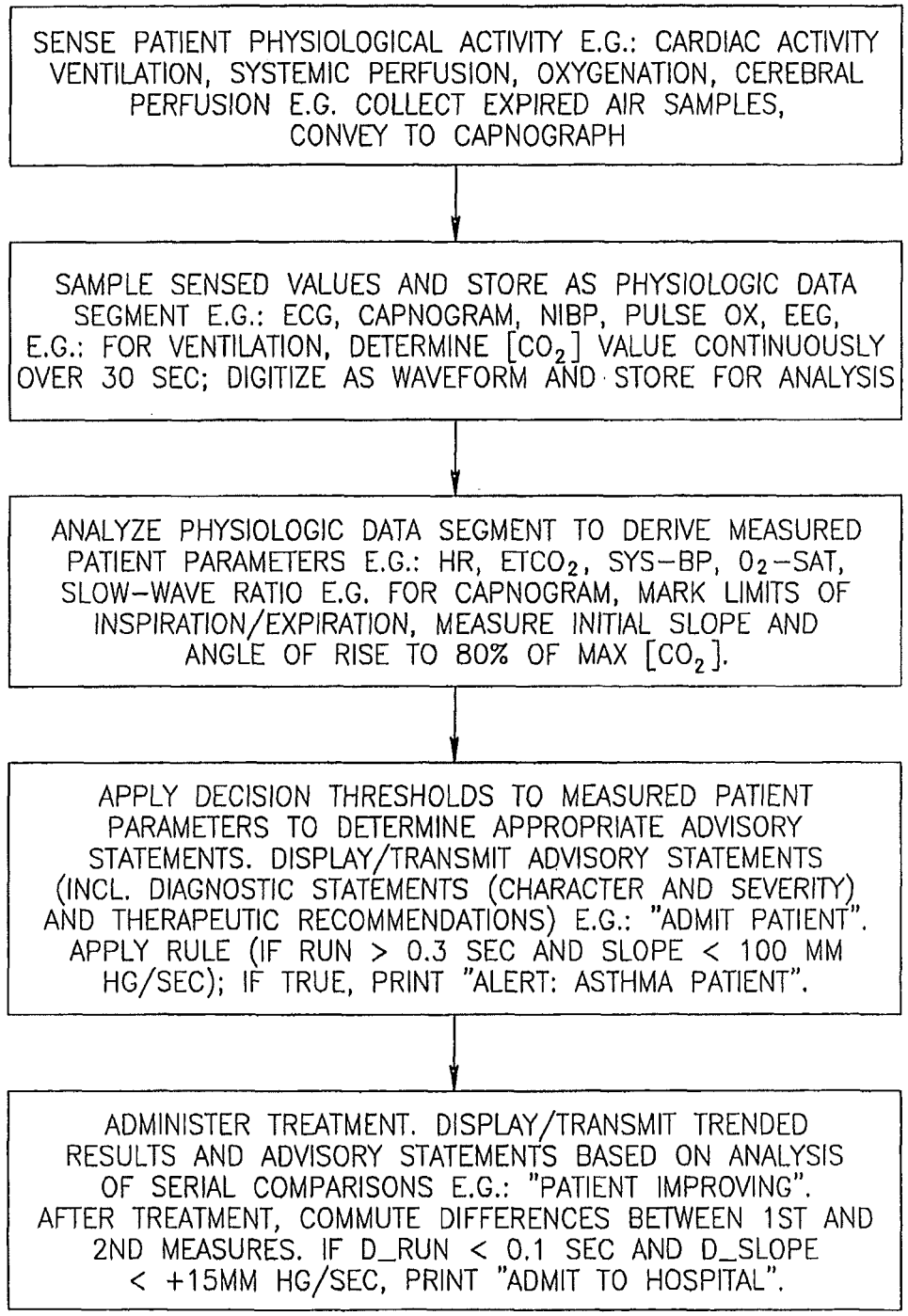
FIG. 2 is a flowchart illustrating operation of the embodiments of FIGS. 1A-1C.

Reference is now made to FIG. 2, which is a flowchart illustrating operation of the embodiments of FIGS. 1A-1C.

In a sensing stage, the patient's physiologic activity preferably is monitored by collecting an expired air sample via cannula 100, and conveying the sample to an analyzer, integrally part of a capnograph, such as capnograph 102 (FIG. 1A), 113 (FIG. 1B), and 122 (FIG. 1C). Simultaneously, some of the patient's other physiological parameters may be sensed, sampled and monitored employing suitable instrumentation 104 (FIG. 1A), 114 (FIG. 1B), and 124 (FIG. 1C). These parameters include, but are not limited to, cardiac activity, ventilation and systemic and cerebral perfusion, and oxygenation parameters.

Data including the parameters monitored and sampled by, for example, instrumentation 104 are relayed to computer 110. The measured patient parameters are analyzed by computer 110 and advisory statements, preferably including at least one of diagnostic statements as to the character and severity of a medical condition and therapeutic recommendations may be displayed on a display 112, or transmitted to a remote location. Changes in the measured patient parameters are recorded over time by computer 110 and the resulting trends may be displayed on display 112 or transmitted. The trends may also be employed for generating trend based advisory statements, preferably including at least one of diagnostic statements as to the character and severity of a medical condition and therapeutic recommendations.

Typically, the exhaled carbon dioxide of the patient is measured continuously over thirty seconds by capnograph 102. Additionally or altetively, patient may be measured for shorter or longer durations. The end tidal value of the exhaled carbon dioxide ($ETCO_2$) profile is digitized as a waveform and may be stored for analysis in the memory of suitably programmed automatic diagnostic and treatment computer 110. Additionally or altetively, the waveform may be stored and analyzed by other means, Thereafter, in an analyzing stage, the measured patient parameters, such as the limits of inspiration and expiration are delineated and/or marked on computer 110. The initial slope in the increase of the exhaled carbon dioxide concentration up to 80% of the maximum (henceforth designated as "slope") and angle of rise up to 80% of the maximum carbon dioxide exhaled are measured.

In a rule application step, the following rules defining the patient status preferably are applied by computer 110, for example, to the $CO_2$ profile measured by capnograph 102:

If:
a) the time duration to reach 80% of the maximum $CO_2$ concentration (designated henceforth as "run" or "$CO_2$ run") is greater than 0.3 seconds; and,
b) the slope of the increase in concentration of $CO_2$ is less than 100 mm Hg/sec (designated henceforth as "slope" or "$CO_2$ slope");
then: an alert signal such as "ALERT: BRONCHOSPASM PRESENT" or "ALERT: ASTHMA PATIENT" is displayed on display 112 associated with computer 110.

If the patient is an asthma patient according to the definition of the previous step, then the patient receives the appropriate treatment. Thereafter, a second set of exhaled carbon dioxide profile measurements are taken by capnograph 102, and the differences between the initial measurements and these second set of measurements are computed by computer 110. The following decision rule is preferably applied:

If:
a) the difference in the run is less than 0.1 sec; and
b) the difference in the slope is less than +15 mm Hg/sec;
then,
a message is displayed on display 112 such as "ADMIT PATIENT TO HOSPITAL". Additionally or altetively, further tests may be performed for checking the severity of the patient's condition as are described hereinbelow.

If the patient is not yet in hospital, as is portrayed in FIGS. 1A and 1B, then a typical message is "ADMIT TO HOSPITAL". Whereas, if the patient is already in the hospital environment (FIG. 1C), a typical message is "PATIENT REQUIRES URGENT TREATMENT BY PHYSICIAN." Additionally or altetively, further tests may be performed for checking the severity of the patient's condition as are described hereinbelow.

If the values of the difference in the run and the difference in the slope are beyond those of the decision rule, then another message may be displayed such as "PATIENT IMPROVING" on display 112.

Figure 3:
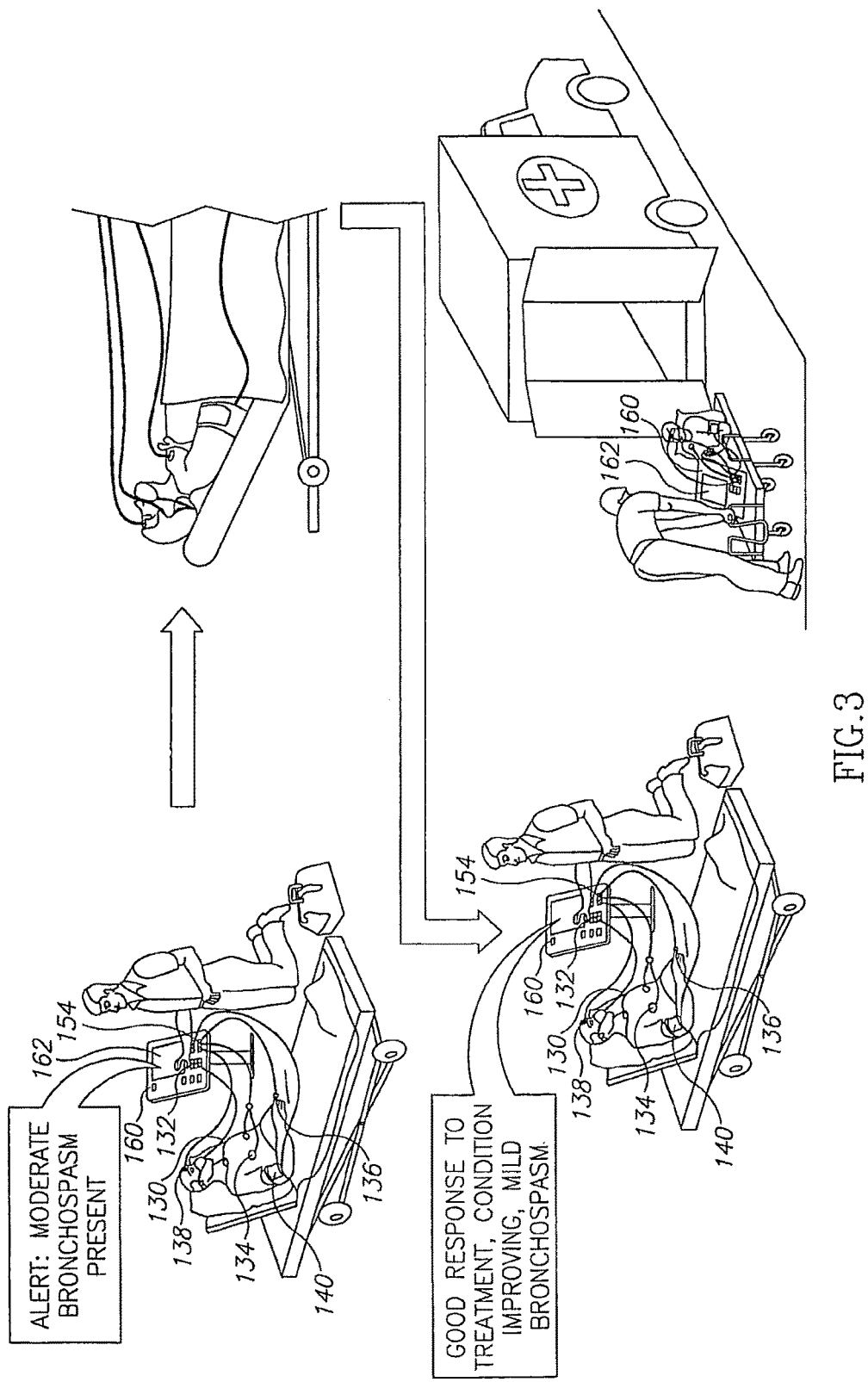
FIG. 3 is a simplified pictorial illustration of an automatic medical diagnostic and treatment system and methodology in an on-scene environment for detecting the presence and severity of bronchospasm, gauging the response to treatment and recommending disposition of a spontaneously breathing patient.

Reference is now made to FIG. 3, which is a simplified pictorial illustration of an automatic medical diagnostic and treatment system and methodology in an on-scene environment for detecting the presence and severity of bronchospasm, gauging the response to treatment and recommending disposition of the patient. As seen in FIG. 3, in an on scene environment, such as at a patients home, after a patient calls EMS after having sensed shortness of breath, various patient physiologic activities are sensed and measured, including respiratory physiologic activities, preferably via an oral airway adapter and/or a nasal or nasal/oral cannula 130, such as a Model Nasal FilterLine Adult XS 04461, $O_2/CO_2$ Nasal FilterLine Adult 007141, or Smart CapnoLine Adult (Oral/nasal FilterLine) 007414, commercially available from Oridion Ltd., of Jerusalem Israel, typically coupled with a capnograph 132, such as a Microcap®, commercially available from Oridion Ltd., of Jerusalem Israel. Other patient physiologic activities relating to cardiac function (e.g. ECG), systemic oxygenation (e.g. pulse oximetry), cerebral oxygenation (e.g. cerebral oximetry) and systemic circulation (e.g. NIBP), typically sensed by means of chest electrodes 134, a finger sensor 136, a forehead/scalp sensor 138, cannula 130 and a blood pressure cuff (sphygmomanometer) 140 respectively, may also be sensed and measured by suitable instrumentation 154.

The outputs of the capnograph 132 and preferably of additional instrumentation 154 are preferably supplied to a suitably programmed automatic diagnostic and treatment computer 144, having an associated display 146, which typically analyzes the respiration parameter output of the capnograph 132, and preferably other physiologic activities and provides an output which preferably contains a diagnostic statement, here "ALERT: MODERATE BRONCHOSPASM PRESENT". The severity of the patient's condition is defined by measured parameters as described hereinbelow.

The patient is preferably given breathing treatment, such as a beta agonist nebulizer treatment and following such treatment and/or in the course thereof, the physiologic activities of the patient continue to be monitored. This monitoring is employed by computer 160 to indicate the response to the breathing treatment and the current status of the bronchospasm condition. The patient is then transferred to an ambulance.

Figure 4:
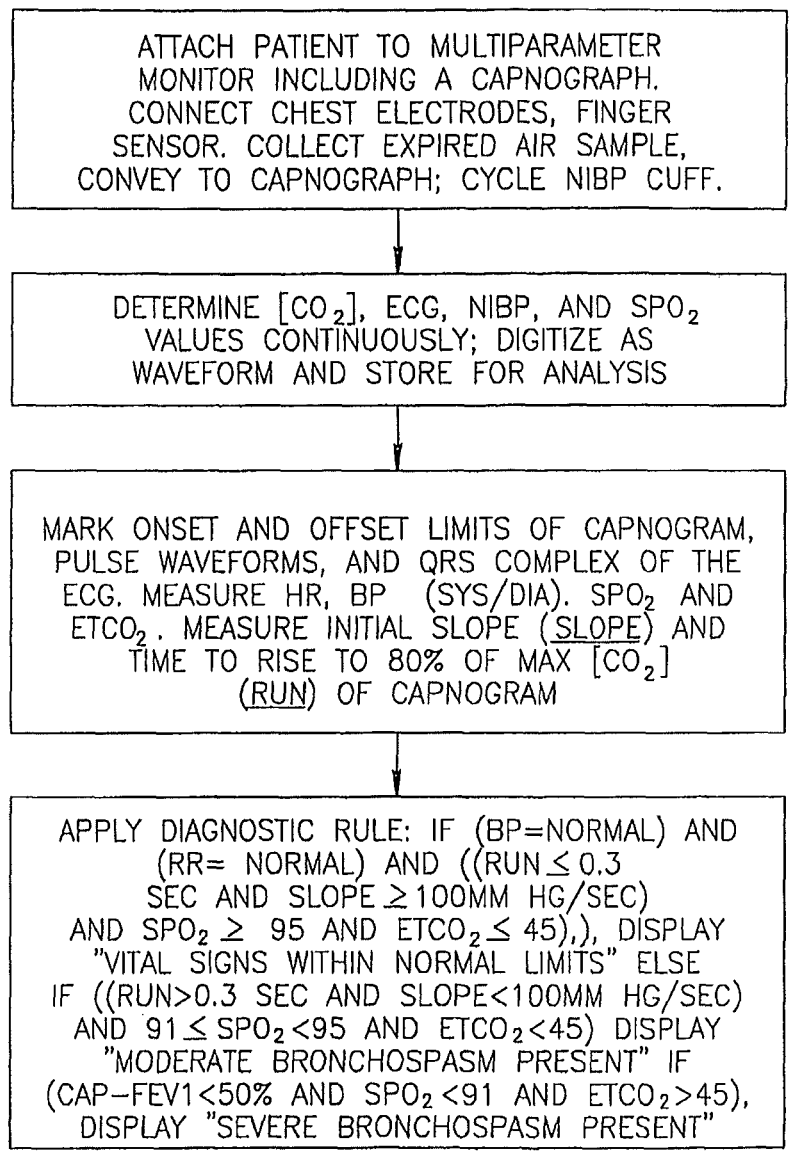
FIG. 4 is a flowchart illustrating operation of the embodiment of FIG. 3.

Reference is now made additionally to FIG. 4, which illustrates the operation of the system and methodology of the system of the present invention in the context of FIG. 3. The patient previously attached to a multi-parameter monitor including a capnograph 132 and suitable instrumentation 154, by means of cannula 130 and preferably also by means of chest electrodes 134, finger sensor 136, forehead sensor 138 and blood pressure cuff 140, is monitored continuously for at least thirty seconds. Neurological status of the patient is acquired by any suitable technique, including visual and electroencephalograph (EEG) monitoring. Values of $CO_2$ concentration, ECG, NIBP and the $SPO_2$ (the percent saturation of the hemoglobin molecule with oxygen) in units of % saturation (designated as % SAT herein), are continuously monitored, and carbon dioxide waveforms are preferably digitized as a capnogram 169 and together with other waveforms are stored in computer 144.

At least one expired air sample is collected and conveyed for analysis by capnograph 132. The following gold standards of base pulmonary function measures are as follows: FEV1 is defined as the Forced Expiratory Volume over 1 second, and is a measure of flow. FVC is the Forced Vital Capacity and is a measure of volume. The character ratio is FEV1/FVC. This is the ratio of flow to volume: markedly less than 1 in bronchospasm and close to a value of 1 in patients of normal status and those with restrictive disease.

Severity of a pulmonary disease may preferably be defined by FEV 1: Reduced flow and/or volume over the first second, as compared to normal. This applies to both obstructive and restrictive disorders.

Forced expiratory volume (FEV) values are preferably determined employing a correlation from at least one capnographic measurement, and are denoted herein as CAP-FEV or CAP-FEV1 (measured over one second). The severity criteria is assessed from the capnogram using a measure that we refer to as Cap-FEV1, to emphasize it's relation to the gold-standard FEV1 and it's derivation from the Capnogram. The area under capnogram 169 is measured over the first second. This, the CAP-FEV1 is computed as (SUM $[CO_2]$ (First second)) or, at 40 Hz device sampling rate, (SUM (n=0:40). $[CO_2]$n). The units are "% of expected value", or "%". Additionally or altetively, the CAP-FEV1 may be determined by standard spirometry techniques known in the art-as is FEV1.

The capnographic analysis preferably includes molecular correlation spectroscopy (MSC), but may also be performed employing infrared analysis. The outputs of the capnograph 132 and possibly of additional instrumentation 154 are preferably supplied to suitably programmed automatic diagnostic and treatment computer 144, having associated display 146, which typically analyzes the respiration parameter output of the capnograph 132.

In an analyzing step, computer 144 marks the onset and offset limits of a capnogram 169, pulse waveforms, and the QRS complex (of the ECG). The actual parameters measured include, but are not limited to heart rate (HR), BP, the systolic to diastolic ratio (SYS/DIA). $SPO_2$, AND $ETCO_2$. The slope of $CO_2$ (mm Hg/sec), and $CO_2$ "run", of the capnogram 132, measured to 80% of maximum $CO_2$ concentration, are calculated by computer 144.

Following each treatment, computer 144 computes the differences between consecutive measurements of the various patient parameters. Thereafter, in a diagnostic rule application step, the following diagnostic rules are preferably applied to the measured parameters by computer 144:

1). If:
a) the blood pressure values are within the normal range;
b) the respiratory rate is normal;
c) $CO_2$ run is less than or equal to 0.3 sec;
d) $CO_2$ slope is more than or equal to 100 mm Hg/sec;
e) $SPO_2$ is greater or equal to than 95% SAT; and
f) $ETCO_2$ is less than or equal to. 45 mm Hg;
then,
display 146 shows the message "VITAL SIGNS WITHIN NORMAL LIMITS."

2) In contrast, if:
a) $CO_2$ run is greater than 0.3 sec;
b) $CO_2$ slope is less than 100 mm Hg/sec;
c) $SPO_2$ is more than or equal to 91% SAT but less than 95% SAT; and
d) $ETCO_2$ is less than 45 mm Hg;
then,
the message "MODERATE BRONCHOSPASM PRESENT" is displayed on display 146;

3) If the parameters measured are yet further removed from the acceptable range, such as if:
a) CAP-FEV1 (forced expiratory volume in one second) is less than 50%;
b) $SPO_2$ is less than 92% SAT; and
c) $ETCO_2$ (end tidal value of the exhaled carbon dioxide) is greater than 45 mm Hg;
then,
a message such as "SEVERE BRONCHOSPASM PRESENT" is displayed on display 146.

It should be understood from this example that the severity of the a respiratory disorder, whether restrictive or obstructive, may be determined by CAP-FEV 1 measurements. The use of the capnographic measurements for diagnosis of whether the respiratory disorder is restrictive or obstructive is described in FIG. 30 hereinbelow. Similarly, the ratio CAP-FEV1/FVC (forced vital capacity) may be applied to diagnose whether the patient is suffering from a restrictive or obstructive breathing disorder as is described hereinabove.

Figure 5:
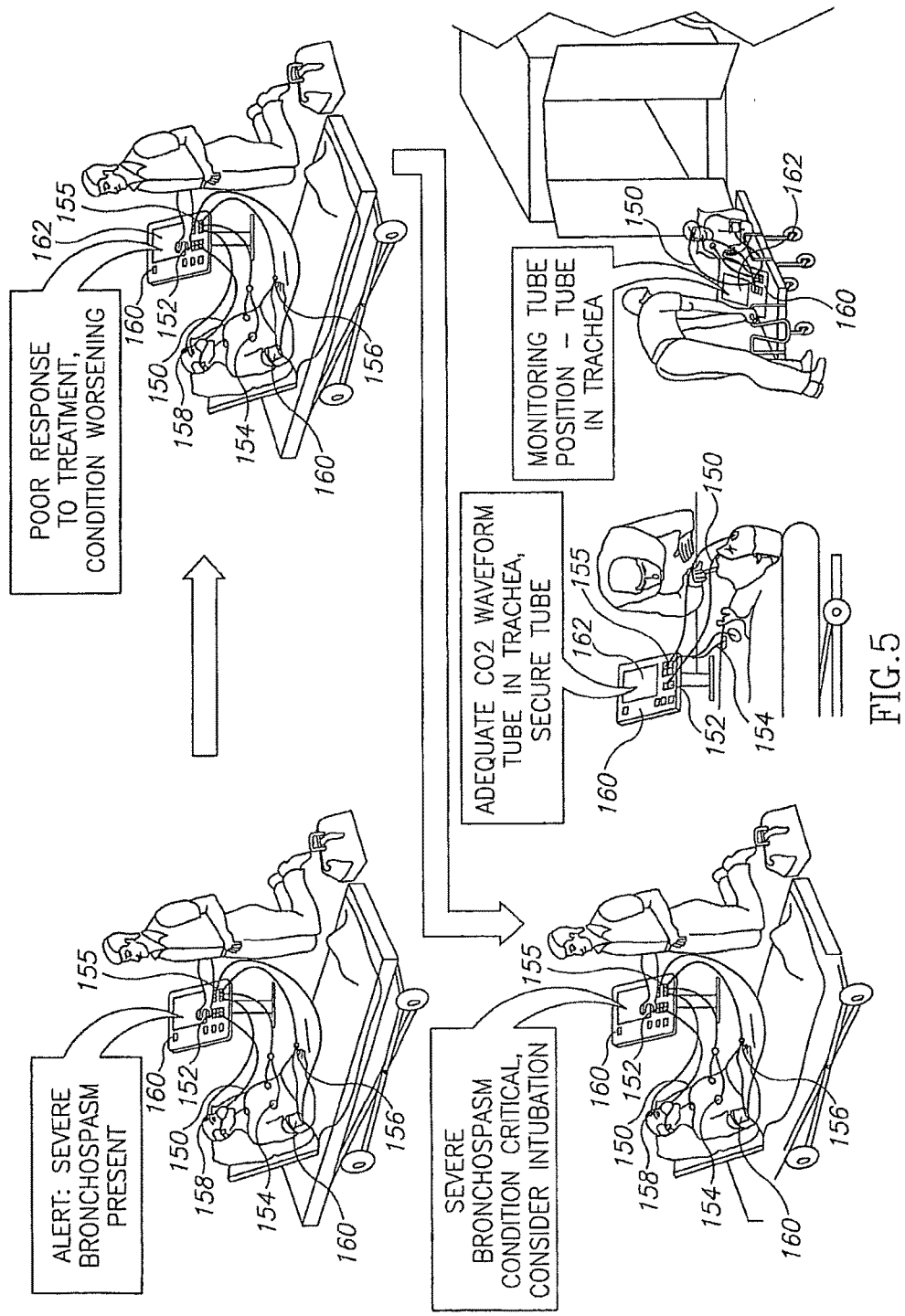
FIG. 5 is a simplified pictorial illustration of an automatic medical diagnostic and treatment system and methodology in an on-scene environment for detecting the presence and severity of bronchospasm, gauging the response to treatment and recommending disposition of mechanically ventilated patients.

Reference is now made to FIG. 5, which is also a simplified pictorial illustration of an automatic medical diagnostic and treatment system and methodology in an on-scene environment for detecting the presence and severity of bronchospasm, gauging the response to treatment and recommending disposition of the patient. As seen in FIG. 5 and similarly to that described hereinabove with reference to FIG. 3, in an on scene environment, such as at a patient's home, after a patient calls EMS after having sensed shortness of breath, various patient physiologic activities are sensed and measured, including respiratory physiologic activities, preferably via an oral airway adapter and/or a nasal or nasal/oral cannula 150, such as a Model Nasal FilterLine Adult XS 04461, $O_2/CO_2$ Nasal FilterLine Adult 007141, or Smart CapnoLine Adult (Oral/nasal FilterLine)

007414, commercially available from Oridion Ltd., of Jerusalem Israel, typically coupled with a capnograph 152, such as a Microcap®, commercially available from Oridion Ltd., of Jerusalem Israel. Other patient physiologic activities relating to cardiac function (e.g. ECG), systemic oxygenation. (e.g. pulse oximetry), cerebral oxygenation (e.g. cerebral oximetry) and systemic circulation (e.g. NIBP), typically sensed by means of chest electrodes 154, a finger sensor 156, a forehead/scalp sensor 158 and a blood pressure cuff 160 respectively, and may also be sensed and measured by suitable instrumentation 154.

The outputs of the capnograph 152 and preferably of additional instrumentation 154 are preferably supplied to a suitably programmed automatic diagnostic and treatment computer 160, having an associated display 162, which typically analyzes the respiration parameter output of the capnograph 152 and preferably other physiologic activities and provides an output which preferably contains a diagnostic statement, here "ALERT: SEVERE BRONCHOSPASM PRESENT".

The patient is given breathing treatment, such as a beta agonist nebulizer treatment and following such treatment and/or in the course thereof, the physiologic activities of the patient continue to be monitored. This monitoring is employed by computer 160 to indicate the response to the breathing treatment and the current status of the bronchospasm condition. In the scenario of FIG. 3, the patient fails to respond sufficiently to the breathing treatment and this is indicated by a status statement, here "POOR RESPONSE TO TREATMENT, CONDITION CRITICAL". A treatment recommendation may also be provided, such as "CONSIDER INTUBATION".

Intubation is performed and correct intubation tube placement is confirmed by continuing monitoring of the physiologic activities of the patient. A status statement, here: "ADEQUATE $CO_2$ WAVEFORM-TUBE IN TRACHEA" and a treatment recommendation, here "SECURE TUBE" appear.

The patient is then transferred to an ambulance. While the physiologic activities of the patient continue to be monitored and serve to confirm continued proper placement of the intubation tube in the trachea. A status statement, here "TUBE IN TRACHEA" appears. Typically, the position of the tube is continuously monitored by computer 160, and a status statement "MONITORING TUBE POSITION" appears on display 162.

Figure 6A:
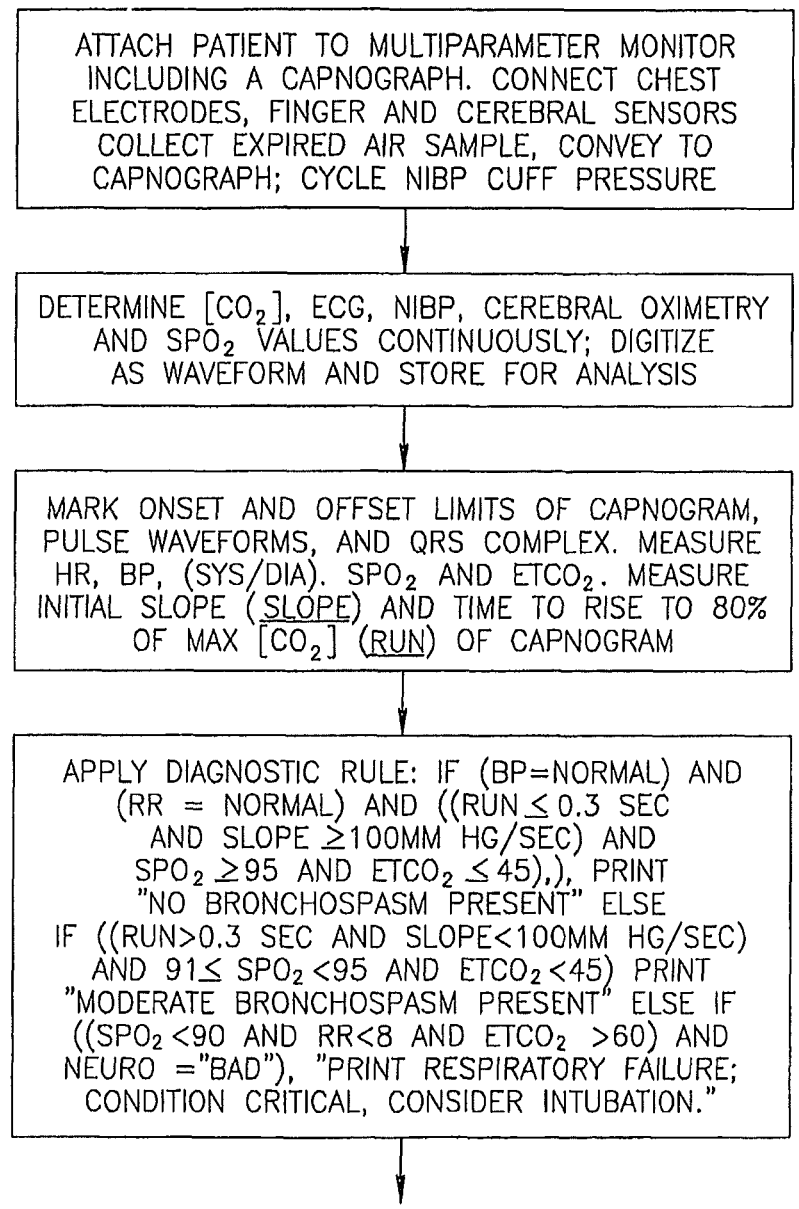
FIGS. 6A and 6B are flowcharts illustrating operation of the embodiment of FIG. 5.
Figure 6B:
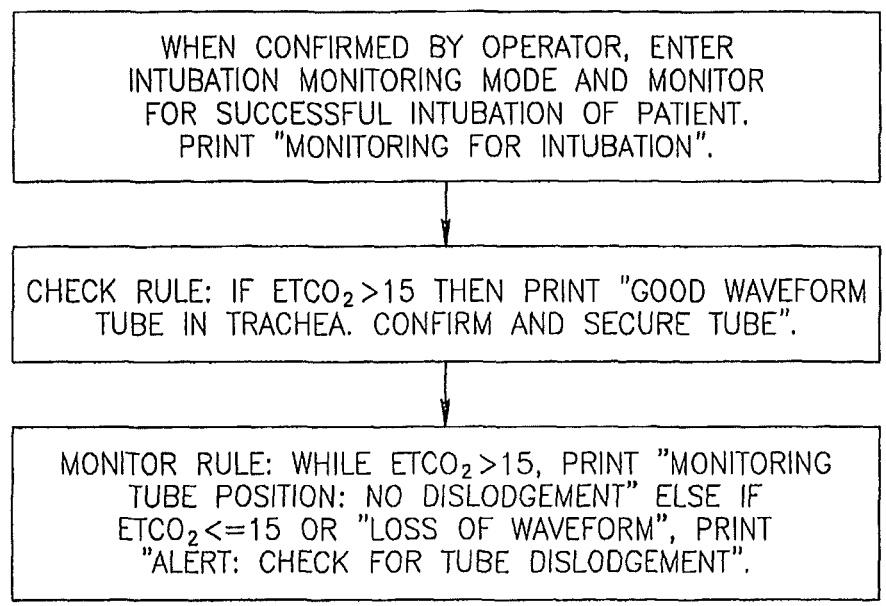

Reference is now made additionally to FIGS. 6A and 6B, which illustrate the operation of the system and methodology of the system of the present invention in the context of FIG. 5. In a monitoring step, the patient, attached to a multi-parameter monitor including a capnograph 152 and instrumentation 154, by means of cannula 150 and preferably also by means of chest electrodes 164, finger sensor 166, forehead/scalp sensor 158 and blood pressure cuff 168, is monitored. Neurological status of the patient is acquired by any suitable technique.

At least one expired air sample is collected and conveyed to capnograph 152. Further measurements of ECG and blood pressure are monitored by standard techniques, employing chest electrodes 164 and blood pressure cuff 168 respectively. The actual parameters measured include, but are not limited to heart rate, blood pressure $ETCO_2$ and $SPO_2$ (SYS/DIA). $SPO_2$, NIBP, and cerebral oximetry values, and these parameters are measured and/or determined continuously by techniques as detailed hereinabove. These parameter values are typically digitized as waveforms and are further stored for analysis by computer 160.

In an analyzing step, the onset and offset limits of capnograph 152, pulse waveforms, and the QRS complex (ECG) measured by additional instrumentation 154, are delineated and marked by computer 160. The limits of the capnogram, the pulse waveform and QRS onset and offset are determined and recorded in computer 160. The slope of the capnogram (mm Hg/sec), and the run and thereof is measured to 80% of maximum $CO_2$ concentration are calculated by computer 160.

Thereafter, in a diagnostic rule application step, the following diagnostic rules are applied to the measured parameters by computer 160:

1. if:
   a) the blood pressure values are within the normal range;
   b) respiratory rate is normal;
   c) $CO_2$ run is less than or equal to 0.3 sec;
   d) $CO_2$ slope is more than or equal to 100 mm Hg/sec;
   e) $SPO_2$ is greater than or equal to 95% SAT; and
   f) $ETCO_2$ is less than or equal to 45 mm Hg;
   then,
   computer 160 displays a message "NO BRONCHOSPASM PRESENT" on display 162.

2) In contrast, if:
   a) $CO_2$ run is greater than 0.3 sec;
   b) $CO_2$ slope is less than 100 mm Hg/sec;
   c) $SPO_2$ is more than or equal to 91% SAT, but less than 95% SAT; and
   d) $ETCO_2$ is less than 45 mm Hg;
   then,
   computer 160 provides the message "MODERATE BRONCHOSPASM PRESENT" on display 162.

3) If the parameters measured are yet further removed from the acceptable range, such as if:
   a) CAP-FEV1 is less than 50%;
   b) $SPO_2$ is more than or equal to 90% SAT, but is less than 91% SAT; and
   c) $ETCO_2$ is greater than 45 mm Hg, but less than or equal to 60 mm Hg;
   then,
   computer 160 provides a message "SEVERE BRONCHOSPASM PRESENT" on display 162.

4. If the parameters measured are still yet further removed from the acceptable range, such as if:
   a) $SPO_2$ is less than 90% SAT;
   b) the respiratory rate is less than 8 per minute;
   c) $ETCO_2$ is greater than 60 mm Hg; and
   d) the neurological parameters are poor;
   then,
   computer 160 issues a message on display 162 stating "RESPIRATORY FAILURE; CONDITION CRITICAL; CONSIDER INTUBATION".

Subsequently, in an intubation stage, a standard intubation procedure is followed, as is described hereinabove in FIG. 5. Thereafter, an operator, typically a physician or paramedic, confirms that the intubation monitoring mode has been activated, and the patient is monitored for a successful outcome of the intubation. Thereafter, computer 160 displays a message stating "MONITORING FOR INTUBTION" on display 162.

The next step entails a checking procedure, wherein the $ETCO_2$ value is measured by capnograph 152.

The following checking rule is preferably applied.

1) If:
   a) the $ETCO_2$ value is more than 15;
   then,
   a display is provided by computer 160 stating "GOOD WAVEFORM, TUBE IN TRACHEA, CONFIRM AND SECURE TUBE" on display 162.

Thereafter, the $ETCO_2$ value is measured again by capnograph 152, and recorded by computer 160. The following monitoring rules are preferably applied.

1). If:
   a) the $ETCO_2$ value is more than 15 mm Hg;
   then,
   a message is displayed by computer 160 on display 162 stating "MONITORING TUBE IN POSITION: NO DISLODGEMENT."

2) Whereas, if:
   a) the $ETCO_2$ value is less than or equal to 15 mm Hg; or
   b) there is a loss in the tracking of the waveform by capnograph 152;
   then,
   a message is displayed by computer 160 stating "ALERT: CHECK FOR TUBE DISLODGEMENT" on display 162.

Figure 7:
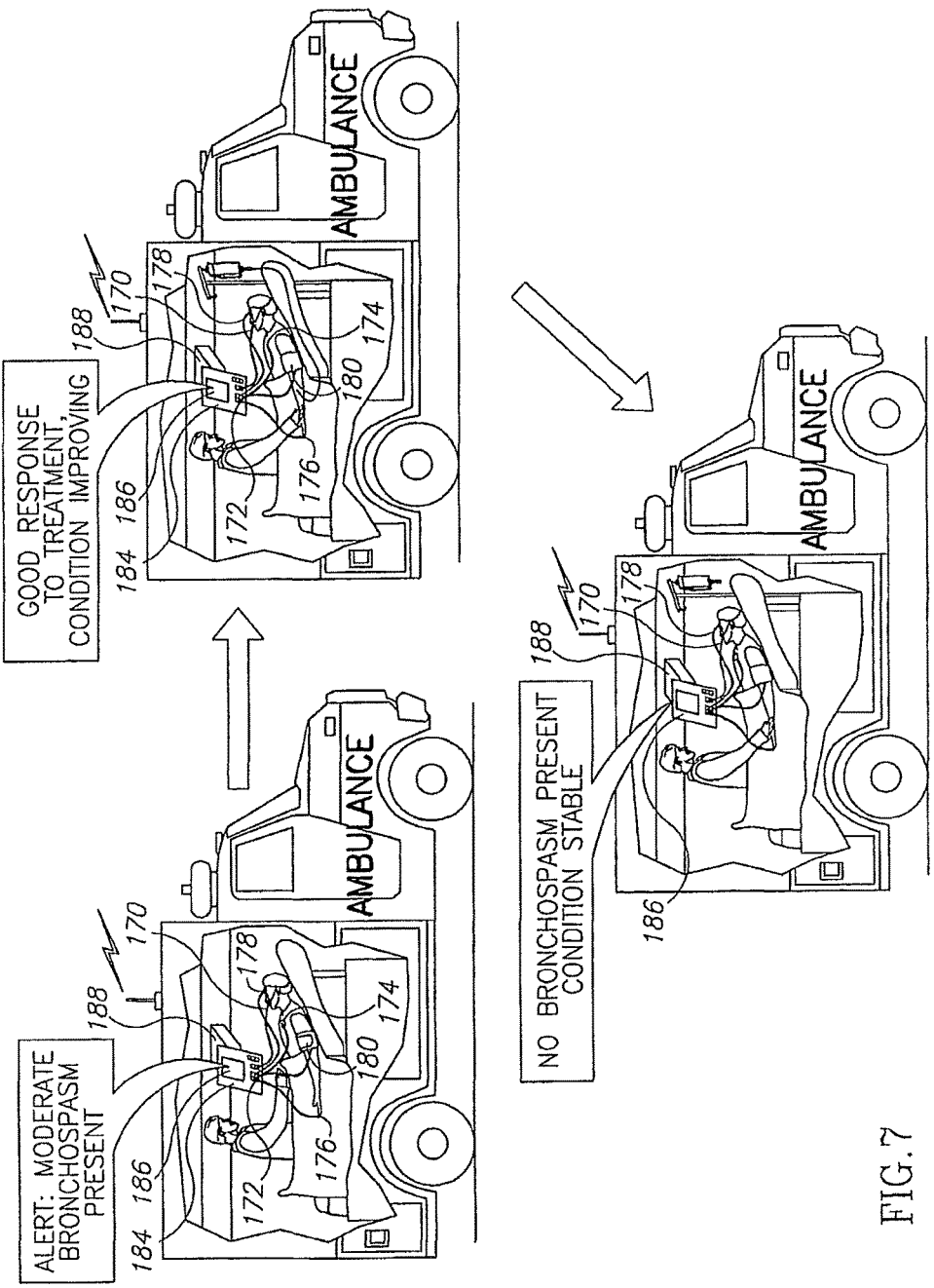
FIG. 7 is a simplified pictorial illustration of an automatic medical diagnostic and treatment system and methodology in an ambulance environment for detecting the presence and severity of bronchospasm, gauging the response to treatment and recommending disposition of spontaneously breathing patients.

Reference is now made FIG. 7, which is a simplified pictorial illustration of an automatic medical diagnostic and treatment system and methodology in an ambulance environment for detecting the presence and severity of bronchospasm, gauging the response to treatment and recommending disposition of spontaneously breathing patients. As seen in FIG. 7, in an ambulance environment, various patient physiologic activities are sensed and measured, including respiratory physiologic activities, preferably via an oral airway adapter and/or a nasal or nasal/oral cannula 170, such as a Model Nasal FilterLine Adult XS 04461, $O_2/CO_2$ Nasal FilterLine Adult 007141, or Smart CapnoLine Adult (Oral/nasal FilterLine) 007414, commercially available from Oridion Ltd., of Jerusalem Israel, typically coupled with a capnograph 172, such as a Microcap®, commercially available from Oridion Ltd., of Jerusalem Israel. Other patient physiologic activities relating to cardiac function (e.g. ECG), systemic oxygenation (e.g. pulse oximetry), cerebral oxygenation (e.g. cerebral oximetry) and systemic circulation (e.g. NIBP), typically sensed by means of chest electrodes 174, a finger sensor 176, a forehead/scalp sensor 178 and a blood pressure cuff 180 respectively, may be received and analyzed by additional instrumentation 182.

The outputs of the capnograph 172 and possibly of additional instrumentation 182 are preferably supplied to a suitably programmed automatic diagnostic and treatment computer 184, having an associated display 186, which typically analyzes the respiration parameter output of the capnograph 172 and possibly other parameters and provides an output which preferably contains a diagnostic statement, here "ALERT: MODERATE BRONCHOSPASM PRESENT". A breathing treatment is administered after which a diagnostic statement which indicates the patient status and the severity of the respiratory condition is preferably presented, here "GOOD RESPONSE TO TREATMENT, CONDITION IMPROVING". Additional breathing treatment is typically administered after which a diagnostic statement which indicates the current patient status and the severity of the respiratory condition is preferably presented, here "NO BRONCHOSPASM PRESENT, CONDITION STABLE".

Preferably, response to treatment statements as well as disposition recommendations may be appended to patient status statements, here "RAPID RESPONSE TO TREATMENT, CONDITION REMAINS STABLE, DISCHARGE TO HOME LIKELY".

Preferably some or all of the outputs of computer 184 are transmitted in a wireless manner by a transmitter 188, such as via radio or a cellular telephone link, preferably to a dispatch center or patient receiving facility.

Figure 8A:
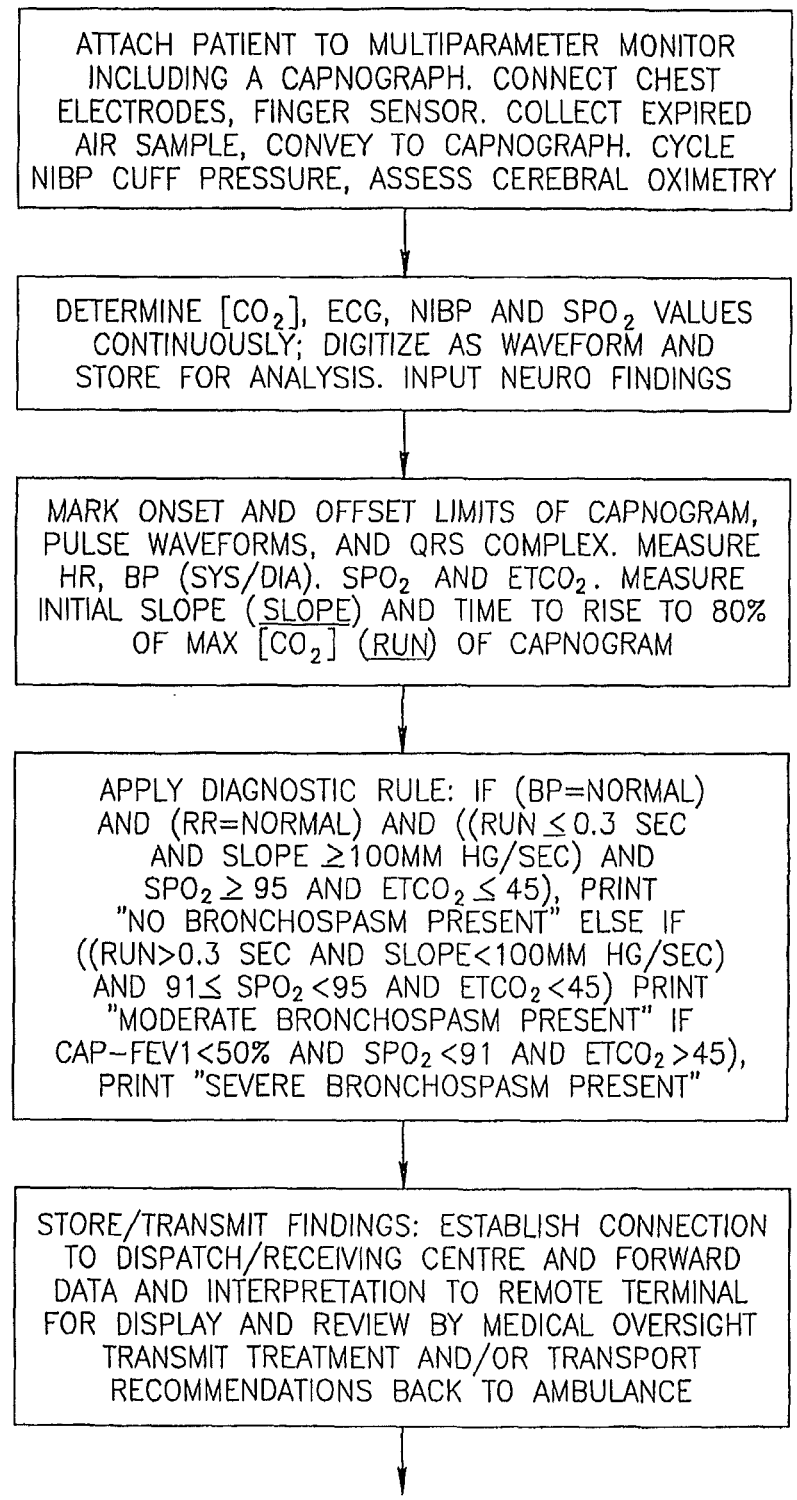
FIGS. 8A and 8B are flowcharts illustrating operation of the embodiment of FIG. 7.
Figure 8B:
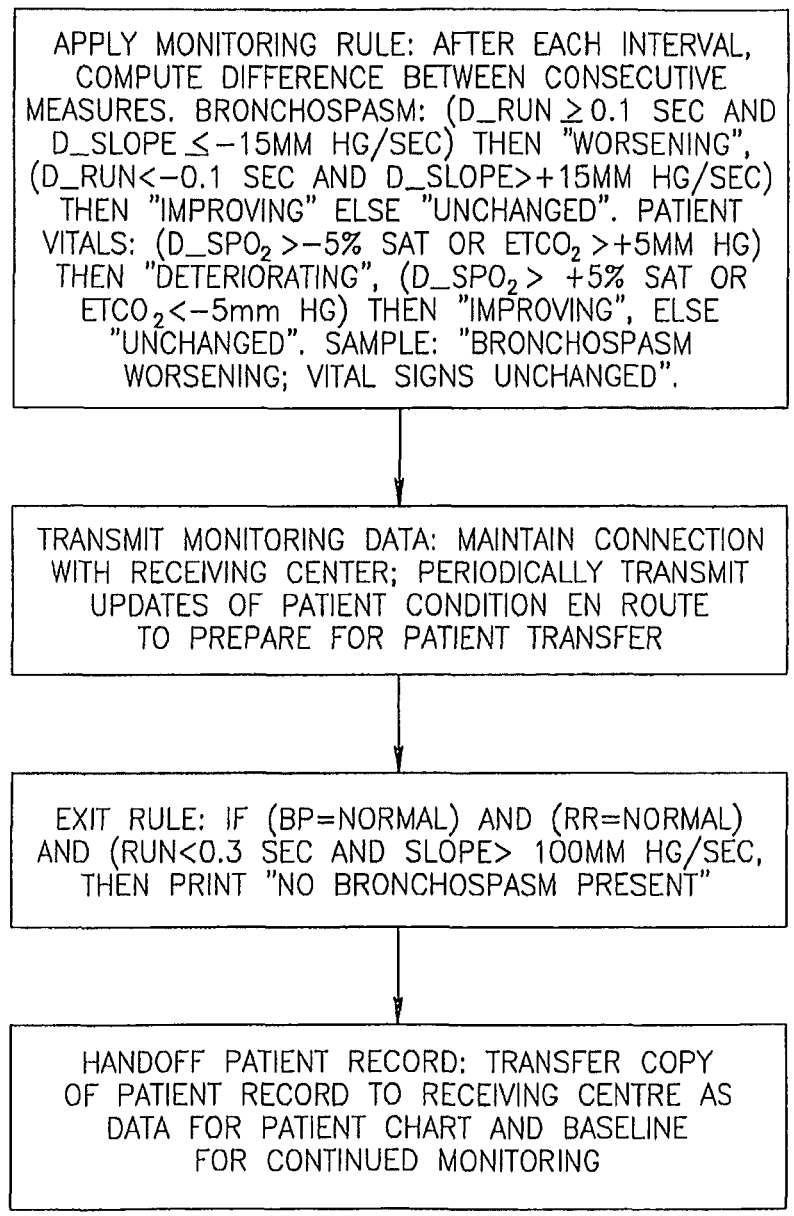

Reference is now made additionally to FIGS. 8A and 8B, which illustrate the operation of the system and methodology of the system of the present invention in the context of FIG. 7. In a monitoring step, the patient in an ambulance environment, attached to a multi-parameter monitor including capnograph 172, by means of cannula 170 and preferably also by means of chest electrodes 174, finger sensor 176, scalp/forehead sensor 178 and blood pressure cuff 178, is monitored continuously. Neurological status of the patient is acquired by any suitable technique. Values of the $CO_2$ concentration monitored by capnograph 172, and ECG, NIBP, cerebral oximetry and $SPO_2$ values, monitored by additional instrumentation 182 are supplied to computer 184, and are typically measured continuously over a period of 30 seconds, by techniques as detailed hereinabove. The parameter data may be digitized as waveforms and are further stored for analysis by computer 184. Thereafter, the limits of the capnogram, the pulse waveform and QRS onset and offset are determined by computer 184. The heart rate, blood pressure $ETCO_2$ and $SPO_2$ values are measured. The initial slope of the capnogram and the run, monitored by capnograph 172, are calculated by computer 184. Additionally, neurological findings, monitored by means of an EEG are inputted to computer 184.

In an analyzing step, the onset and offset limits of the capnogram, pulse waveforms, and the QRS complex (ECG) are marked by computer 184.

Following each treatment, the differences between consecutive measurements of the various patient parameters are evaluated by computer 184. After each treatment, in a diagnostic rule application step, the following diagnostic rules are preferably applied to the measured parameters by computer 184:

I) If:
   a) the blood pressure values are within the normal range;
   b) the respiratory rate is normal;
   c) $CO_2$ run is less than or equal to 0.3 sec;
   d) $CO_2$ slope is more than or equal to 100 mm Hg/sec;
   e) $SPO_2$ is greater than or equal to 95% SAT; and
   f) $ETCO_2$ is less than or equal to 45 mm Hg;
   then,
   display 162 shows the message "NO BRONCHOSPASM PRESENT"

2) In contrast, if:
   a) $CO_2$ run is greater than 0.3 sec;
   b) $CO_2$ slope is less than 100 mm Hg/sec;
   c) $SPO_2$ is more than or equal to 91% SAT less than 95% SAT; and
   d) $ETCO_2$ is less than 45 mm Hg;
   then,
   the message "MODERATE BRONCHOSPASM PRESENT" is displayed on display 186.

3) If the parameters measured are yet further removed from the acceptable range, such as if:
   a) CAP-FEV1 is less than 50%;
   b) $SPO_2$ is less than 92% SAT; and
   c) $ETCO_2$ is greater than 45 mm Hg;
   then,
   a message such as "SEVERE BRONCHOSPASM PRESENT" is displayed on display 186.

The findings of the last stage are stored by computer 184 and/or transmitted to a dispatch/receiving center, typically located at a hospital or medical center [ref. no]. A connection is established with the dispatch/receiving center [ref. no], and the data is forwarded thereto. A medical supervisor typically watches display of the received data, and consequentially transmits the recommended treatment and/or transport recommendations back to the ambulance.

After each time interval, the difference between consecutive measures of each parameter are calculated by computer 184: Thereafter, the following monitoring rules are preferably applied to the measured parameters by computer 184.

1) If
 a) the difference in the run values is greater than +0.1 sec; and
 b) the difference in the slope is more negative than −15 mm Hg/sec;
 then,
 computer 184 displays on display 186 "BRONCHOSPASM WORSENING".

2) If:
 a) the difference in the run values is more negative than −0.1 sec; and
 b) the difference in the slope is more than +15 mm Hg/sec; then,
 computer 184 displays on display 186 "BRONCHOSPASM IMPROVING".

3) If:
 a) the difference in the slope is more than or equal to −15 mm Hg/sec and less than or equal to +15 mm Hg/sec;
 then,
 computer 184 displays on display 186 "UNCHANGED".

The change in patient's vital functional activities, including $SPO_2$ and $ETCO_2$, over the time interval are calculated by computer 184, 4) If
 a) the decrease in $SPO_2$ is more than −5% SAT; or
 b) the increase in the $ETCO_2$ is more than +5 mm Hg;
 then,
 computer 184 displays on display 186 "VITAL SIGNS DETERIORATING."

5) If:
 a) the increase in $SPO_2$ is greater than +5% SAT; or
 b) the decrease in the $ETCO_2$ is less than −5 mm Hg; then,
 computer 184 displays on display 186 "VITAL SIGNS IMPROVING".

6) If:
 a) the change in $SPO_2$ is greater than or equal to −5% SAT, but less than or equal to +5%; or
 b) the change in the $ETCO_2$ is more than or equal to −5 mm Hg, or less than or equal to +5 mm Hg;
 then.
 computer 184 displays on display 186 "VITAL SIGNS UNCHANGED."

Computer 184 preferably combines the results of these monitoring rules to display an integrated display 186 such as "BRONCHOSPASM WORSENING; VITAL SIGNS UNCHANGED."

Thereafter, in a transmission stage, the connection with the receiving center is maintained. The receiving center periodically receives updates of the patient's condition, who is in the ambulance en route to the hospital, in order to prepare in the most fitting and efficient transfer of the patient upon arrival to the hospital.

Following the transmission stage, the following exit rules are preferably applied to the measured parameters by computer 184:

1) If
 a) the blood pressure values are within normal limits;
 b) the respiratory rate is within normal limits;
 c) the value of the $CO_2$ run is less than 0.3 seconds; and
 d) the $CO_2$ slope is greater than 100 mm Hg/sec;
 then,
 Computer 184 preferably displays on display 186 "NO BRONCHOSPASM PRESENT".

If the patient's record complies with this exit rule, then a copy of the patient's record is handed off from computer 184 to the receiving center, for example, in the form of a chart. Typically, the receiving center stores this chart, so that it may be used as a baseline for continued monitoring of the patient.

Figure 9:
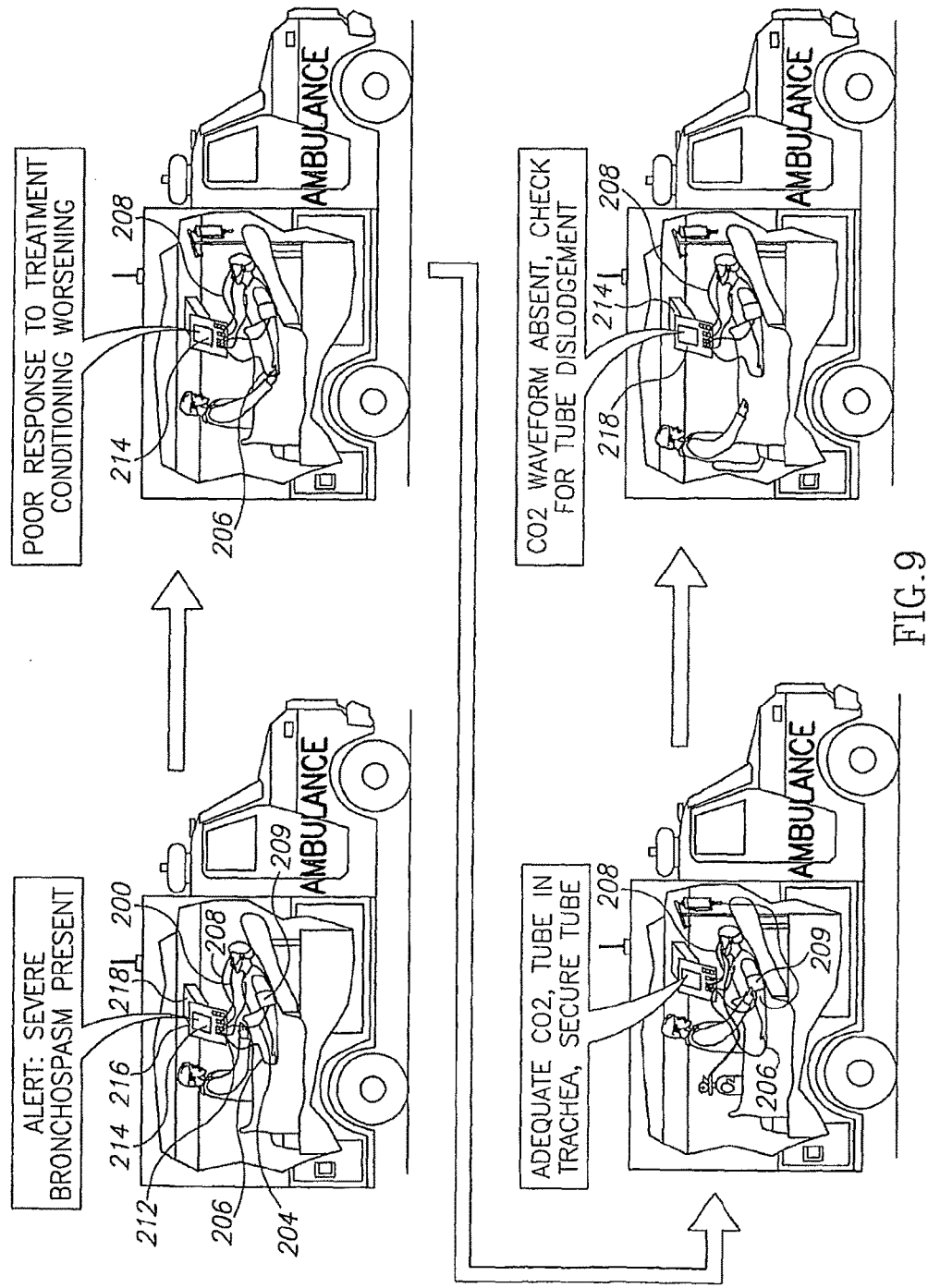
FIG. 9 is a simplified pictorial illustration of an automatic medical diagnostic and treatment system and methodology in an ambulance environment for detecting the presence and severity of bronchospasm, gauging the response to treatment and recommending disposition of mechanically ventilated patients.

Reference is now made to FIG. 9, which is a simplified pictorial illustration of an automatic medical diagnostic and treatment system and methodology in an ambulance environment for detecting the presence and severity of bronchospasm, gauging the response to treatment and recommending disposition of mechanically ventilated patients. As seen in FIG. 9 and similarly to that described hereinabove with reference to FIG. 5, in an ambulance environment various patient physiologic activities are sensed and measured, including respiratory physiologic activities, preferably via an oral airway adapter and/or a nasal or nasal/oral cannula 200, such as a Model Nasal FilterLine Adult XS 04461, $O_2/CO_2$ Nasal FilterLine Adult 007141, or Smart CapnoLine Adult (Oral/nasal FilterLine) 007414, commercially available from Oridion Ltd., of Jerusalem Israel, typically coupled with a capnograph 202, such as a Microcap®, commercially available from Oridion Ltd., of Jerusalem Israel. Other patient physiologic activities relating to cardiac function (e.g. ECG), systemic oxygenation (e.g. pulse oximetry), cerebral oxygenation (e.g. cerebral oximetry) and systemic circulation (e.g. NIBP), typically sensed by means of chest electrodes 204, a finger sensor 206, a forehead/scalp sensor 208 and a blood pressure cuff 209 respectively, may also be sensed and measured by suitable instrumentation 210. Other patient physiologic activities relating to cardiac function (e.g. ECG), cerebral perfusion (e.g. CEREBRAL OXIMETRY), oxygenation (e.g. pulse oximetry) and systemic circulation (e.g. NIBP), may also be sensed and measured by suitable instrumentation 212

The outputs of the capnograph 202 and preferably of additional instrumentation 212 are preferably supplied to a suitably programmed automatic diagnostic and treatment computer 214 having an associated display 216, which typically analyzes the respiration parameter output of the capnograph 202 and preferably other physiologic activities and provides an output which preferably contains a diagnostic statement, here "ALERT: SEVERE BRONCHOSPASM PRESENT".

The patient is given breathing treatment, such as a beta agonist nebulizer treatment and following such treatment and/or in the course thereof, the physiologic activities of the patient continue to be monitored. This monitoring is employed by computer 214 to indicate the response to the breathing treatment and the current status of the patient condition. In the scenario of FIG. 9, the patient fails to respond sufficiently to the breathing treatment and this is indicated by a status change statement, here "POOR RESPONSE TO TREATMENT, CONDITION WORSENING". A treatment recommendation may also be provided, such as "CONSIDER INTUBATION".

Intubation is performed and correct initial tube placement is confirmed followed by continuous monitoring of the physiologic activities of the patient, which indicate current tube position. Where intubation is successful, a status statement, here: "ADEQUATE CO2 WAVEFORM-TUBE IN TRACHEA" and a treatment recommendation, here "SECURE TUBE" appear. Where intubation is not successful, a status statement, here: "NO CO2 WAVEFORM-TUBE IN ESOPHAGUS" and a treatment recommendation, here "REINTUBATE" appear.

Following successful intubation, continuous monitoring may provide a status statement such as "ADEQUATE CO2 WAVEFORM-TUBE IN TRACHEA-NO DISLOGEMENT" may appear. If tube dislodgment occurs at any time following intubation-, a status statement appears, here "CO2 WAVEFORM ABSENT" preferably accompanied by a treatment recommendation, here "CHECK FOR TUBE DISLOGEMENT".

Preferably some or all of the outputs of computer 214 are transmitted in a wireless manner by a transmitter 218, such as via radio or a cellular telephone link, preferably to a dispatch center or patient receiving facility.

Figure 10A:
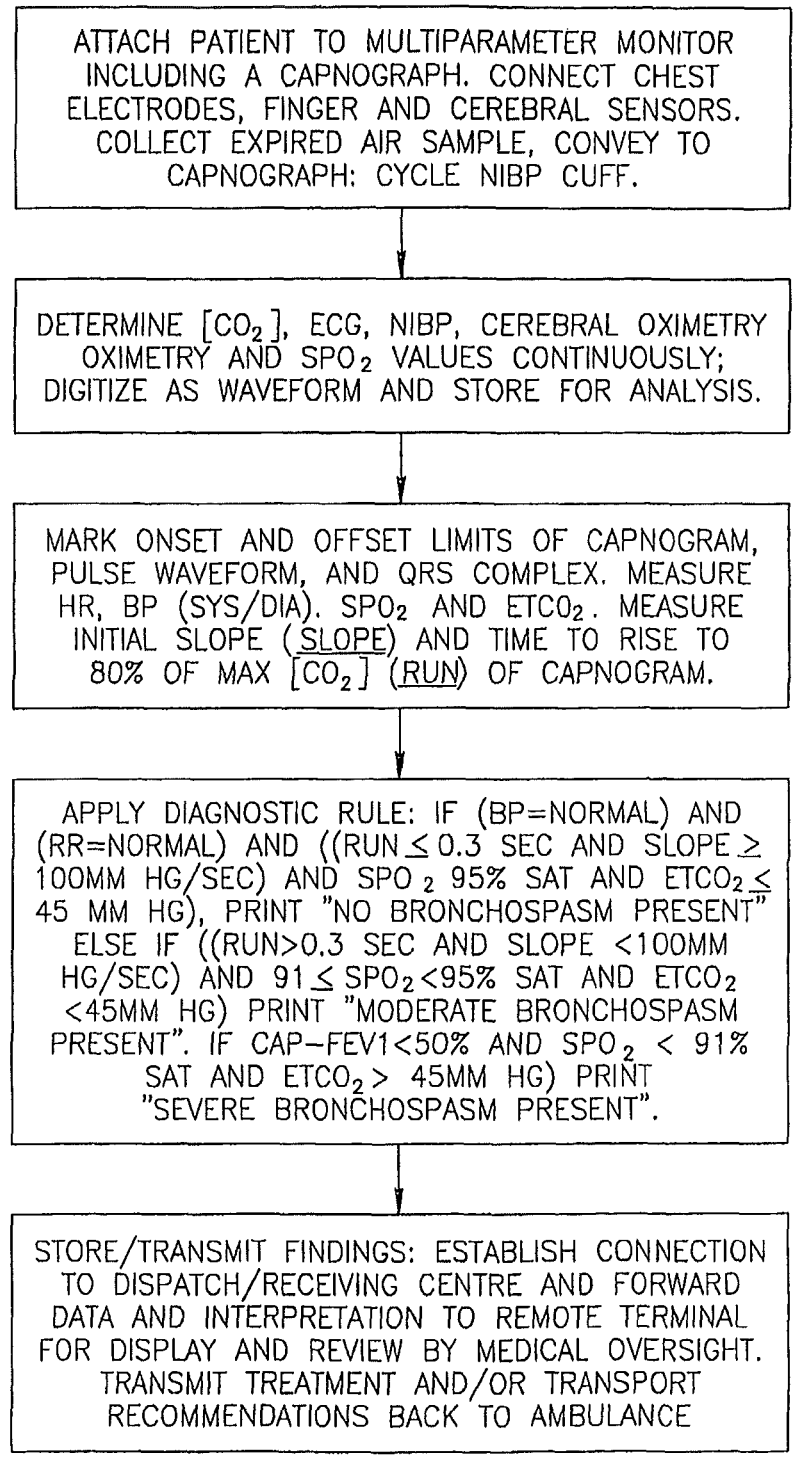
FIGS. 10A, 10B and 10C are a flowcharts illustrating operation of the embodiment of FIG. 9.
Figure 10B:
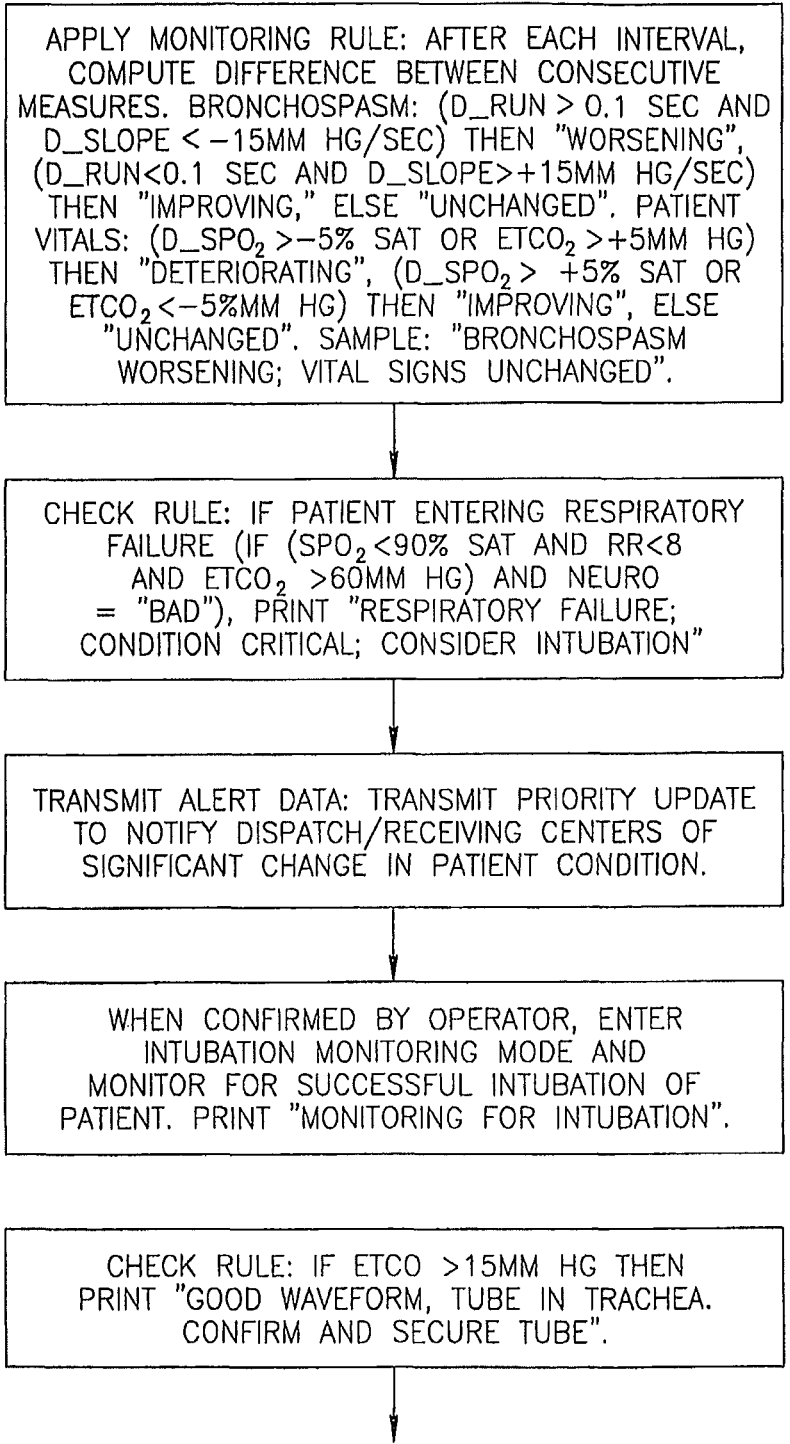
Figure 10C:
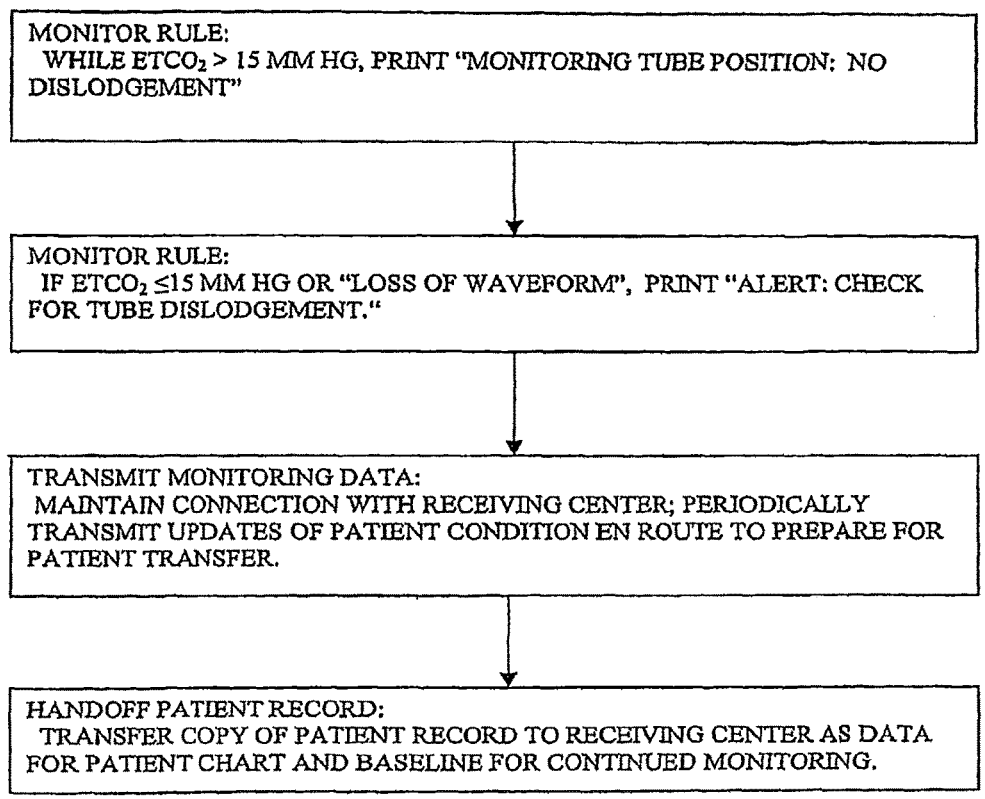

Reference is now made additionally to FIGS. 10A-10C, which illustrate the operation of the system and methodology of the system of the present invention in the context of FIG. 9.

In a monitoring step, the patient in an ambulance environment, attached to a multi-parameter monitor including capnograph 202 and instrumentation 212, by means of cannula 200 and preferably also by means of chest electrodes 204, finger sensor 206, scalp/forehead sensor 208 and blood pressure cuff 209, is monitored continuously. Neurological status of the patient is acquired by any suitable technique. Values of the $CO_2$ concentration monitored by capnograph 202, and ECG, NIBP, cerebral oximetry and $SPO_2$ values, monitored by additional instrumentation 212 are supplied to computer 214, and are typically measured continuously over a period of 30 seconds, by techniques as detailed hereinabove. The parameter data may be digitized as waveforms and are further stored for analysis by computer 214. Thereafter, the onset and offset limits of the capnogram, the pulse waveform and QRS onset and offset are determined by computer 214. The heart rate, blood pressure $ETCO_2$ and $SPO_2$ values are measured. The initial slope of the capnogram and the run, monitored by capnograph 202, are calculated by computer 214. Additionally, neurological findings, monitored by means of an EEG are inputted to computer 214.

Following each treatment, the differences between consecutive measurements of the various patient parameters are evaluated by computer 214. After each treatment, in a diagnostic rule application step, the following diagnostic rules are preferably applied to the measured parameters by computer 214:

1) If:
a) the blood pressure values are within the normal range;
b) the respiratory rate is normal;
c) $CO_2$ run is less than or equal to 0.3 sec;
d) $CO_2$ slope is more than or equal to 100 mm Hg/sec;
e) $SPO_2$ is greater than or equal to 95% SAT; and
f) $ETCO_2$ is less than or equal to 45 mm Hg;
then,
display 216 shows the message "NO BRONCHOSPASM PRESENT."

2) In contrast, if:
a) $CO_2$ run is greater than 0.3 sec;
b) $CO_2$ slope is less than 100 mm Hg/sec;
c) $SPO_2$ is more than or equal to 91% SAT but less than 95% SAT; and
d) $ETCO_2$ is less than 45 mm Hg;
then,
the message "MODERATE BRONCHOSPASM PRESENT" is displayed on display 216.

3) If the parameters measured are yet further removed from the acceptable range, such as if:
a) CAP-FEV1 is less than 50%;
b) $SPO_2$ is less than 91% SAT; and
c) $ETCO_2$ is greater than 45 mm Hg;
then,
a message such as "SEVERE BRONCHOSPASM PRESENT" is preferably displayed on display 216.

The findings of the last stage are stored by computer 214 and/or transmitted to a dispatch/receiving center, typically located at a hospital or medical center]. A connection is established with the dispatch/receiving center, and the data is forwarded thereto. A medical supervisor typically watches display of the received data, and consequentially transmits the recommended treatment and/or transport recommendations back to the ambulance.

After each time interval, the difference between consecutive measures of each parameter are calculated by computer 214: Thereafter, the following monitoring rules are preferably applied to the measured parameters by computer 214.

1) If:
a) the difference in the run values is greater than 0.1 sec; and
b) the difference in the slope is more negative than −15 mm Hg/sec;
then,
computer 214 displays on display 216 "BRONCHOSPASM WORSENING".

2) If
a) the difference in the run values is more negative than −0.1 sec; and
b) the difference in the slope is more positive than +15 mm Hg/sec;
then,
computer 214 displays on display 216 "BRONCHOSPASM IMPROVING".

3) If:
a) the difference in the slope is more than or equal to −15 mm Hg/sec and less than or equal to +15 mm Hg/sec;
then,
computer 214 displays on display 216 "BRONCHOSPASM UNCHANGED".

The change in patient's vital functional activities, including $SPO_2$ and $ETCO_2$, over the time interval are calculated by computer 214.

4) If:
a) the decrease in $SPO_2$ is more negative than −5% SAT; or
b) the increase in the $ETCO_2$ is more positive than +5 mm Hg;
then,
computer 214 displays on display 216 "VITAL SIGNS DETERIORATING."

5) If:
a) the change in $SPO_2$ is greater than +5% SAT; or
b) the change in the $ETCO_2$ is more negative than −5 mm Hg;
then,
computer 214 displays on display 216 "VITAL SIGNS IMPROVING".

6) If:
a) the change in $SPO_2$ is greater than or equal to −5% SAT, but less than or equal to +5% SAT; or b) the change in the $ETCO_2$ is more than or equal to −5 mm Hg, but less than or equal to +5 mm Hg;

then, computer 214 displays on display 216 "VITAL SIGNS UNCHANGED."

Computer 214 preferably combines the results of these monitoring rules to display an integrated display such as "BRONCHOSPASM WORSENING; VITAL SIGNS UNCHANGED."

In a checking rule step, the following rule is preferably applied:

1) A patient appears to be entering respiratory failure phase if:

a) the $SPO_2$ is less than 90% SAT;

b) the respiratory rate is less than 8/min;

c) $ETCO_2$ is greater than 60 mm Hg; and d) the patient's neurological symptoms are qualified as being "bad";

then, computer 214 displays "RESPIRATORY FAILURE; CONDITION CRITICAL; CONSIDER INTUBATION." on display 216.

Following this, in an alert data transmission stage, a high priority update is transmitted via transmitter 218 from computer 214 to notify the dispatch/receiving centers of the significant deterioration and change in the patient's condition.

Once these changes in the patient's condition have been confirmed by an operator, the patient is consequentially intubated according to standard techniques and capnograph 202 is activated in intubation monitoring mode by computer 214. Once the successful intubation of the patient is verified by data comparison of the patient's capnogram and standardized capnograms for incubation in computer 214, the computer displays "MONITORING FOR INTUBATION".

Thereafter, the following check rule is preferably applied to the patient's capnogram:

1. If a) $ETCO_2$ is greater than 15 mm Hg;

then, computer 214 displays "GOOD WAVEFORM, TUBE IN TRACHEA. CONFIRM AND SECURE TUBE."

In the next step, the following monitoring rules are preferably applied to the patient's capnogram:

1) If:

a) the value of $ETCO_2$ is greater than 15 mm Hg;

then, computer 214 displays "MONITORING TUBE POSITION: NO DISLODGEMENT" on display 216.

2) If:

a) the value of $ETCO_2$ is less than or equal to 15 mm Hg; or b) there is a loss of the waveform;

then, computer 214 displays "ALERT: CHECK FOR TUBE DISLODGEMENT" on display 216.

Computer 214 transmits the data monitored via transmitter 218 to the receiving center. The receiving center periodically receives updates of the patient's condition, who is in the ambulance en route to the hospital, in order to prepare in the most fitting and efficient transfer of the patient upon arrival to the hospital.

A copy of the patient's record is handed off from computer 184 via transmitter 218 to the receiving center, for example, in the form of a chart. Typically, the receiving center stores this chart, so that it may be used as a baseline for continued monitoring of the patient.

Figure 11:
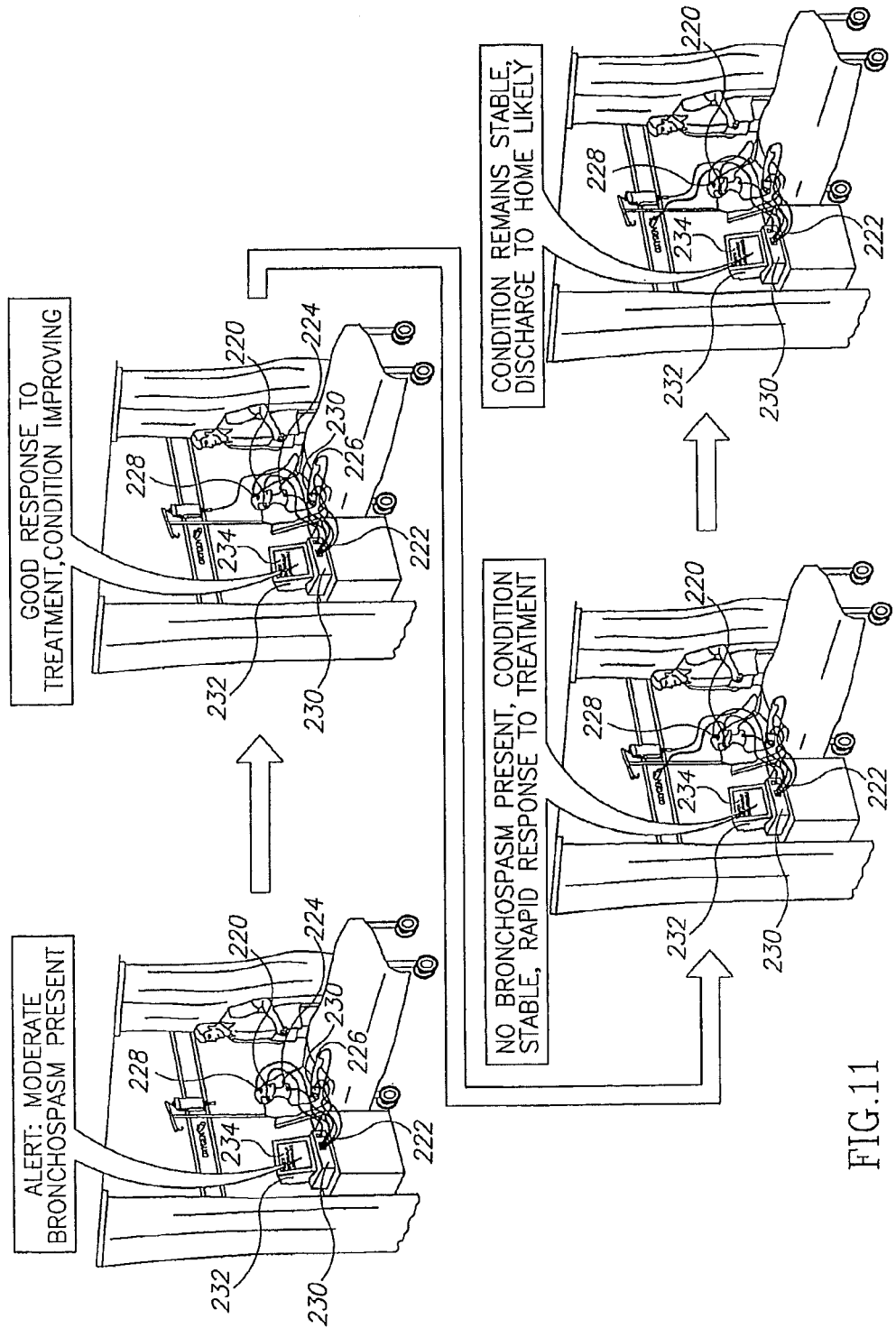
FIG. 11 is a simplified pictorial illustration of an automatic medical diagnostic and treatment system and methodology in an ambulance environment for detecting the severity of bronchospasm, gauging the response to treatment and recommending disposition of spontaneously breathing patients.

Reference is now made to FIG. 11, which is a simplified pictorial illustration of an automatic medical diagnostic and treatment system and methodology in a hospital environment, such as a medical ward, emergency department or ICU, for detecting the presence and indicating the severity of bronchospasm, gauging the response to treatment and recommending treatment and disposition of spontaneously breathing patients. As seen in FIG. 11, in a hospital environment, various patient physiologic activities are sensed and measured, including respiratory physiologic activities, preferably via an oral airway adapter and/or a nasal or nasal/oral cannula 220, such as a Model Nasal FilterLine Adult XS 04461, $O_2/CO_2$ Nasal FilterLine Adult 007141, or Smart CapnoLine Adult (Oral/nasal FilterLine) 007414, commercially available from Oridion Ltd., of Jerusalem Israel, typically coupled with a capnograph 222, such as a Microcap®, commercially available from Oridion Ltd., of Jerusalem Israel. Other patient physiologic activities relating to cardiac function (e.g. ECG), systemic oxygenation (e.g. pulse oximetry), cerebral oxygenation (e.g. cerebral oximetry) and systemic circulation (e.g. NIBP), typically sensed by means of chest electrodes 224, a finger sensor 226, a forehead/scalp sensor 228 and a blood pressure cuff 230 respectively.

The outputs of the capnograph 222 and possibly of additional instrumentation 230 are preferably supplied to a suitably programmed automatic diagnostic and treatment computer 232, having an associated display 234 which typically analyzes the respiration parameter output of the capnograph 222 and possibly other parameters and provides an output which preferably contains a diagnostic statement, here "ALERT: MODERATE BRONCHOSPASM PRESENT". A breathing treatment is administered after which a diagnostic statement which indicates the patient status and the severity of the respiratory condition is preferably presented, here "GOOD RESPONSE TO TREATMENT, CONDITION IMPROVING". Additional breathing treatment is typically administered after which a diagnostic statement which indicates the current patient status and the severity of the respiratory condition is preferably presented, here NO BRONCHOSPASM PRESENT, CONDITION STABLE".

Preferably, response to treatment statements as well as disposition recommendations may be appended to patient status statements, here "RAPID RESPONSE TO TREATMENT, CONDITION REMAINS STABLE, DISCHARGE TO HOME LIKELY".

Figure 12:
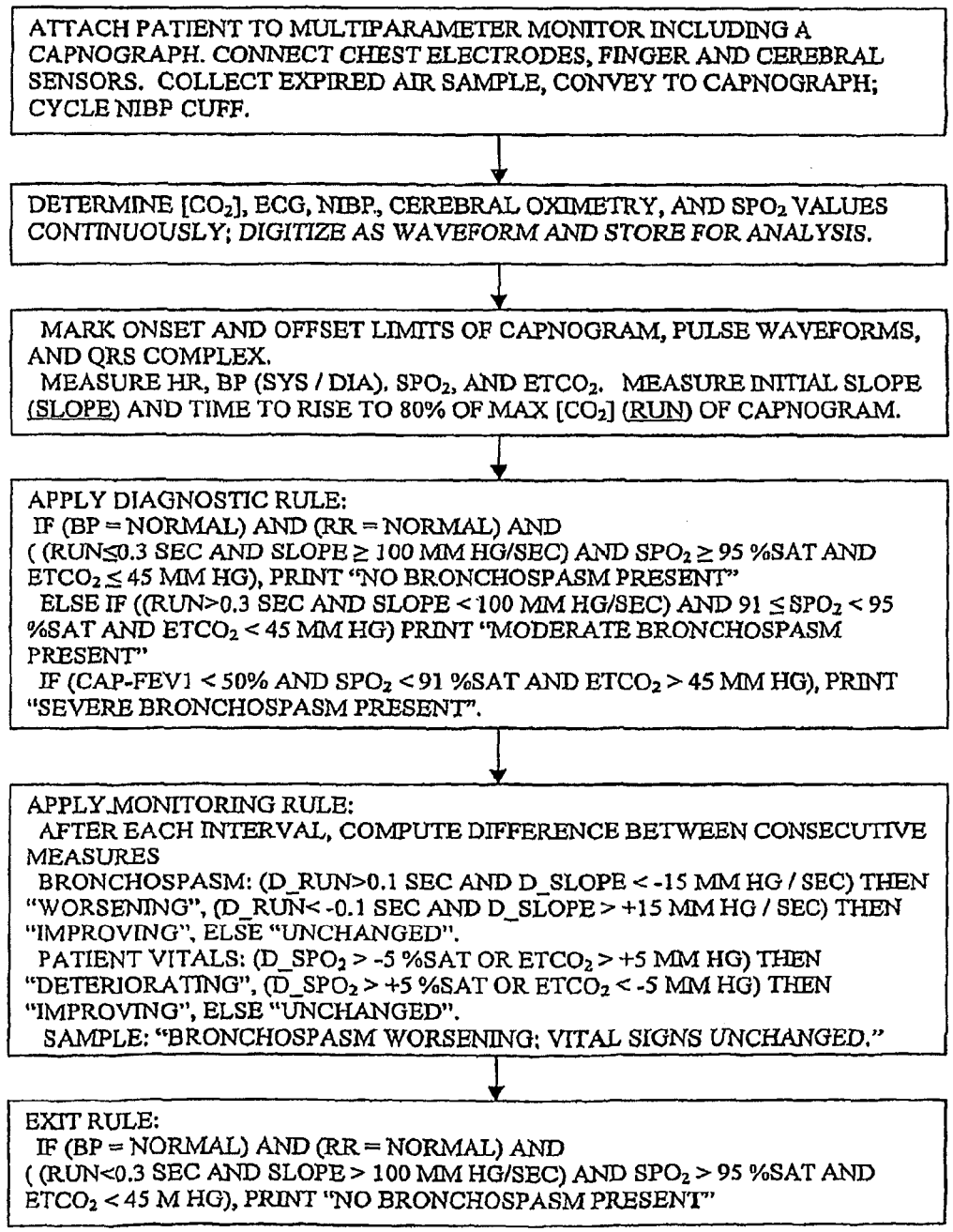
FIG. 12 is a flowchart illustrating operation of the embodiment of FIG. 11.

Reference is now made additionally to FIG. 12, which illustrates the operation of the system and methodology of the system of the present invention in the context of FIG. 11. The patient in the hospital environment, preferably attached to a multi-parameter monitor including capnograph 222 and instrumentation 230, by means of cannula 220 and preferably also by means of chest electrodes 230, finger sensor 226, scalp/forehead sensor 228 and blood pressure cuff 236, is monitored continuously. The neurological status of the patient is acquired by any suitable technique. Values of $CO_2$ concentration, ECG, NIBP and $SPO_2$ are continuously measured, typically over a period of 30 seconds, and carbon dioxide waveforms are preferably digitized as a capnogram and other waveforms and stored.

The parameter data may be digitized as waveforms and are further stored for analysis by computer 232. Thereafter, the onset and offset limits of the capnogram, the pulse waveform and QRS onset and offset are determined by computer 232. The heart rate, blood pressure $ETCO_2$ and $SPO_2$ values are measured. The initial slope of the capnogram and the run, monitored by capnograph 222, are calculated by computer 232. Additionally, neurological findings, monitored by means of an EEG are inputted to computer 232.

Following each treatment, the differences between consecutive measurements of the various patient parameters are evaluated by computer 232. After each treatment, in a diagnostic rule application step, the following diagnostic rules are preferably applied to the measured parameters by computer 234:

1) If:
a) the blood pressure values are within the normal range;
b) the respiratory rate is normal;
c) $CO_2$ run is less than or equal to 0.3 sec;
d) $CO_2$ slope is more than or equal to 100 mm Hg/sec;
e) $SPO_2$ is greater than or equal to 95% SAT; and
f) $ETCO_2$ is less than or equal to 45 mm Hg;
then,
display 234 shows the message "VITAL SIGNS WITHIN NORMAL LIMITS."

2) In contrast, if:
a) $CO_2$ run is greater than 0.3 sec;
b) $CO_2$ slope is less than 100 mm Hg/sec;
c) $SPO_2$ is more than or equal to 91% SAT, but less than 95% SAT; and
d) $ETCO_2$ is less than 45 mm Hg;
then,
the message "MODERATE BRONCHOSPASM PRESENT" is displayed on display 234.

3) If the parameters measured are yet further removed from the acceptable range, such as if:
a) CAP-FEV1 is less than 50%;
b) $SPO_2$ is less than 92% SAT; and
c) $ETCO_2$ is greater than 45 mm Hg;
then,
a message such as "SEVERE BRONCHOSPASM PRESENT" is displayed on display 234.

The findings of the last stage are stored by computer 232 and/or transmitted to a dispatch/receiving center, typically located at a hospital or medical center. A connection is established with the dispatch/receiving center, and the data is forwarded thereto. A medical supervisor typically watches display of the received data, and consequentially transmits the recommended treatment and/or transport recommendations back to the hospital.

After each time interval, the difference between consecutive measures of each parameter are calculated by computer 232. Thereafter, the following monitoring rules are preferably applied to the measured parameters by computer 232.

1) If:
a) the difference in the run values is greater than 0.1 sec; and
b) the difference in the slope is less than -15 mm Hg/sec;
then,
computer 232 displays on display 234 "BRONCHOSPASM WORSENING".

2) If:
a) the difference in the run values is more negative than -0.1 sec; and
b) the difference in the slope is more than +15 mm Hg/sec;
then,
computer 232 displays on display 234 "BRONCHOSPASM IMPROVING".

3) If:
a) the difference in the slope is greater than or equal to -15 mm Hg/sec, but less than or equal to +15 mm Hg/sec; and a) the difference in the run values is greater or equal to -0.1 sec; but less than or equal to +0.1 sec;
then,
computer 232 displays on display 234 "BRONCHOSPASM UNCHANGED".

The change in patient's vital functional activities, including $SPO_2$ and $ETCO_2$, over the time interval are calculated by computer 232.

4) If:
a) the change in $SPO_2$ is greater than -5% SAT; or
b) the change in the $ETCO_2$ is more than +5 mm Hg;
then,
computer 232 displays on display 234 "VITAL SIGNS DETERIORATING."

5) If:
a) the change in $SPO_2$ is greater than +5% SAT; or
b) the change in the $ETCO_2$ is less than -5 mm Hg;
then,
computer 232 displays on display 234 "VITAL SIGNS IMPROVING".

6) If:
a) the change in $SPO_2$ is greater than or equal to -5% SAT, and less than or equal to +5% SAT; or
b) the change in the $ETCO_2$ is more than or equal to -5 mm Hg, but less than or equal to +5 mm Hg;
then,
computer 232 displays on display 234 "VITAL SIGNS UNCHANGED."

Computer 232 preferably combines the results of these monitoring rules to display an integrated display 234 such as "BRONCHOSPASM WORSENING; VITAL SIGNS UNCHANGED."

Following the monitoring stage, the following exit rules are preferably applied to the measured parameters of the patient by computer 232:

1) If:
a) the blood pressure values are within normal limits;
b) the respiratory rate is within normal limits;
c) the value of the $CO_2$ run is less than 0.3 seconds;
d) the $CO_2$ slope is greater than 100 mm Hg/sec; and
e) $ETCO_2$ is less than 45 mm Hg;
then,
Computer 232 preferably displays on display 234 "NO BRONCHOSPASM PRESENT"

(If the patient's record complies with this exit rule, then a copy of the patient's record is handed off from computer 232 to the receiving center, for example, in the form of a chart. Typically, the receiving center stores this chart, so that it may be used as a baseline for continued monitoring of the patient).

Reference is now made to FIG. 13, which is a simplified pictorial illustration of an automatic medical diagnostic and treatment system and methodology in an ambulance environment for detecting the presence and severity of bronchospasm, gauging the response to treatment and recommending disposition of mechanically ventilated patients. As seen in FIG. 13 and similarly to that described hereinabove with reference to FIGS. 5 and 9, in a hospital environment, such as a medical ward, emergency department or ICU, various patient physiologic activities are sensed and measured, including respiratory physiologic activities, preferably via an oral airway adapter and/or a nasal or nasal/oral cannula 250, such as a Model Nasal FilterLine Adult XS 04461, $O_2/CO_2$ Nasal FilterLine Adult 007141, or Smart CapnoLine Adult (Oral/nasal FilterLine) 007414, commercially available from Oridion Ltd., of Jerusalem Israel, typically coupled with a capnograph 252, such as a Microcap®, commercially available from Oridion Ltd., of Jerusalem Israel. Other patient physiologic activities relating to cardiac function (e.g. ECG), systemic oxygenation (e.g. pulse oximetry), cerebral oxygenation (e.g. cerebral oximetry) and systemic circulation (e.g. NIBP), typically sensed by means of chest electrodes 254, a finger sensor 256, a forehead/scalp sensor 258 and a blood pressure cuff 260 respectively, may also be sensed and measured by suitable instrumentation 262.

The outputs of the capnograph 252 and preferably of additional instrumentation 262 are preferably supplied to a suitably programmed automatic diagnostic and treatment computer 264 having an associated display 266, which typically analyzes the respiration parameter output of the capnograph 252 and preferably other physiologic activities and provides an output which preferably contains a diagnostic statement, here "ALERT: SEVERE BRONCHOSPASM PRESENT".

The patient is given breathing treatment, such as a beta agonist nebulizer treatment and following such treatment and/or in the course thereof, the physiologic activities of the patient continue to be monitored. This monitoring is employed by computer 264 to indicate the response to the breathing treatment and the current status of the patient condition. In the scenario of FIG. 13, the patient fails to respond sufficiently to the breathing treatment and this is indicated by a status change statement, here "POOR RESPONSE TO TREATMENT, CONDITION WORSENING". A treatment recommendation may also be provided, such as "CONSIDER INTUBATION".

Intubation is performed and correct initial tube placement is confirmed followed by continuous monitoring of the physiologic activities of the patient, which indicate current tube position. Where intubation is successful, a status statement, here: "ADEQUATE CO2 WAVEFORM-TUBE IN TRACHEA" and a treatment recommendation, here "SECURE TUBE" appear. Where intubation is not successful, a status statement, here: "NO CO2 WAVEFORM-TUBE IN ESOPHAGUS" and a treatment recommendation, here "REINTUBATE" appear.

Following successful intubation, continuous monitoring may provide a status statement such as "ADEQUATE CO2 WAVEFORM-TUBE IN TRACHEA-NO DISLOGEMENT" may appear. If tube dislodgment occurs at any time following intubation, a status statement appears, here "CO2 WAVEFORM ABSENT" preferably accompanied by a treatment recommendation, here "CHECK FOR TUBE DISLOGEMENT".

Preferably some or all of the outputs of computer 262 are transmitted in a wireless manner by a transmitter 268, such as via radio or a cellular telephone link, preferably to a dispatch center or patient receiving facility.

Figure 14A:
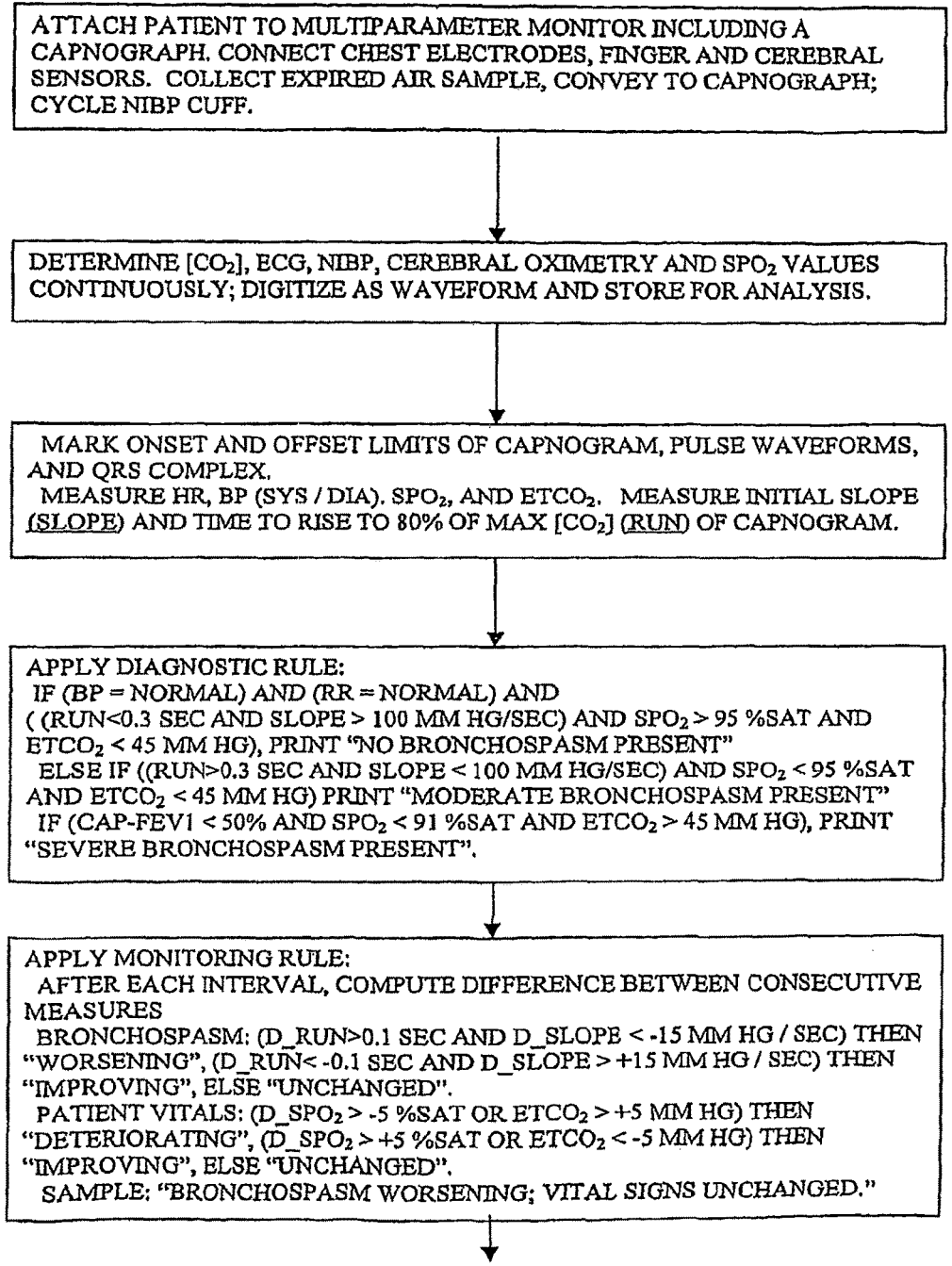
FIGS. 14A and 14B are flowcharts illustrating operation of the embodiment of FIG. 13.
Figure 14B:
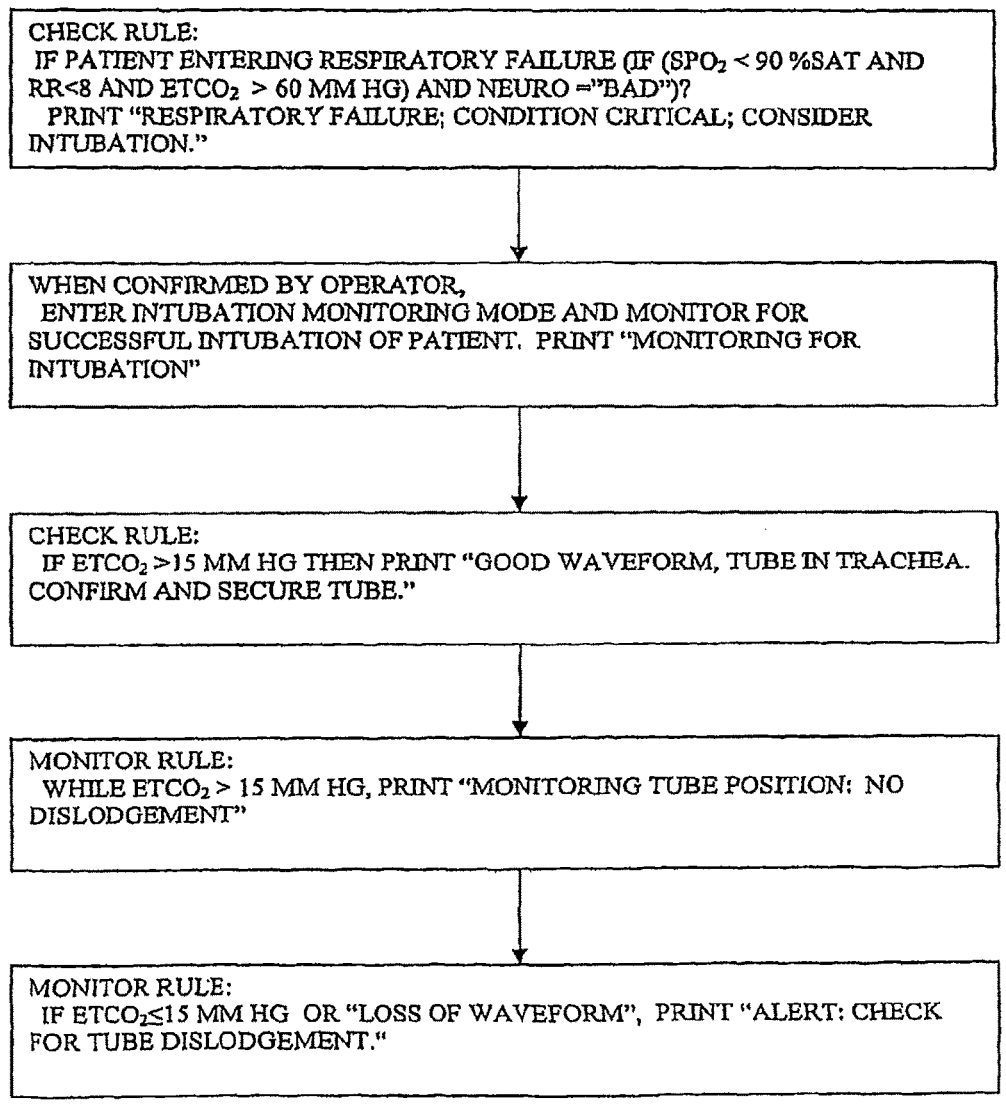

Reference is now made additionally to FIGS. 14A and 14B, which illustrate the operation of the system and methodology of the system of the present invention in the context of FIG. 13.

The patient in the hospital environment, preferably attached to a multi-parameter monitor including capnograph 252 and instrumentation 262, by means of cannula 250 and preferably also by means of chest electrodes 254, finger sensor 256, scalp/forehead sensor 258 and blood pressure cuff 260, is monitored continuously. The neurological status of the patient is acquired by any suitable technique. Values of $CO_2$ concentration, ECG, NIBP and $SPO_2$ are continuously measured, typically over a period of 30 seconds, and carbon dioxide waveforms are preferably digitized as a capnogram and other waveforms and stored by computer 264.

Thereafter, the onset and offset limits of the capnogram, the pulse waveform and QRS onset and offset are determined by computer 264. The heart rate, blood pressure $ETCO_2$ and $SPO_2$ values are measured. The initial slope of the capnogram and the run, monitored by capnograph 252, are calculated by computer 264. Additionally, neurological findings, monitored by means of an EEG are inputted to computer 264.

Following each treatment, the differences between consecutive measurements of the various patient parameters are evaluated by computer 264. After each treatment, in a diagnostic rule application step, the following diagnostic rules are preferably applied to the measured parameters by computer 264:

1) If:
a) the blood pressure values are within the normal range;
b) the respiratory rate is normal;
c) $CO_2$ run is less than or equal to 0.3 sec;
d) $CO_2$ slope is more than or equal to 100 mm Hg/sec;
e) $SPO_2$ is greater than or equal to 95% SAT; and
f) $ETCO_2$ is less than or equal to 45 mm, Hg;
then,
display 266 shows the message "VITAL SIGNS WITHIN NORMAL LIMITS."

2) In contrast, if:
a) $CO_2$ run is greater than 0.3 sec;
b) $CO_2$ slope is less than 100 mm Hg/sec;
c) $SPO_2$ is greater than or equal to 91% SAT, but less than 95% SAT; and
d) $ETCO_2$ is less than 45 mm Hg;
then,
the message "MODERATE BRONCHOSPASM PRESENT" is displayed on display 266.

3) If the parameters measured are yet further removed from the acceptable range, such as if:
a) CAP-FEV1 is less than 50%;
b) $SPO_2$ is less than 91% SAT; and
c) $ETCO_2$ is greater than 45 mm Hg;
then,
a message such as "SEVERE BRONCHOSPASM PRESENT" is displayed on display 266.

The findings of the last stage are stored by computer 264 and/or transmitted by transmitter 268 to a dispatch/receiving center, typically located at a hospital or medical center. A connection is established with the dispatch/receiving center [ref. no], and the data is forwarded thereto. A medical supervisor typically watches display of the received data, and consequentially transmits the recommended treatment and/or transport recommendations back to the hospital.

After each time interval, the difference between consecutive measures of each parameter are calculated by computer 264: Thereafter, the following monitoring rules are preferably applied to the measured parameters by computer 264.

1) If
a) the difference in the run values is greater than +0.1 sec; and
b) the difference in the slope is more negative than −15 mm Hg/sec;
then,
computer 264 displays on display 266 "BRONCHOSPASM WORSENING".

2) If:
a) the difference in the run values is more negative than −0.1 sec; and b) the difference in the slope is more positive than +15 mm Hg/sec;
then,
computer 264 displays on display 266 "BRONCHOSPASM IMPROVING".
3) If:
a) the difference in the run values is greater or equal to −0.1 sec but less than or equal to +0.1 sec; or
b) the difference in the slope is more than or equal to −15 mm Hg/sec but less than or equal to +15 mm Hg/sec;
then,
computer 264 displays on display 266 "BRONCHOSPASM UNCHANGED".
The change in patient's vital functional activities, including $SPO_2$ and $ETCO_2$, over the time interval are calculated by computer 264.
4) If:
a) the change in $SPO_2$ is greater than −5% SAT; or
b) the change in the $ETCO_2$ is more than +5 mm Hg;
then,
computer 264 displays on display 266 "VITAL SIGNS DETERIORATING."
5) If:
a) the change in $SPO_2$ is greater than +5% SAT; or
b) the change in the $ETCO_2$ is less than −5 mm Hg;
then,
computer 264 displays on display 266 "VITAL SIGNS IMPROVING".
6) If:
a) the change in $SPO_2$ is greater than or equal to −5% SAT, but less than or equal to +5% SAT; or
b) the change in the $ETCO_2$ is more than or equal to −5 mm Hg, but less than or equal to +5 mm Hg;
then,
computer 264 displays on display 266 "VITAL SIGNS UNCHANGED."
Computer 264 preferably combines the results of these monitoring rules to display an integrated display 266 such as "BRONCHOSPASM WORSENING; VITAL SIGNS UNCHANGED."
In a checking rule step, the following rule is preferably applied:
1) A patient appears to be entering respiratory failure phase if:
a) the $SPO_2$ is less than 90% SAT;
b) the respiratory rate is less than 8/min;
c) $ETCO_2$ is greater than 60 mm Hg; and
d) the patient's neurological symptoms are qualified as being "bad";
then,
computer 264 displays "RESPIRATORY FAILURE; CONDITION CRITICAL; CONSIDER INTUBATION." on display 266.
Once these changes in the patient's condition have been confirmed by an operator, the patient is consequentially intubated according to standard techniques and capnograph 252 is activated in intubation monitoring mode by computer 264. Once the successful intubation of the patient is verified by data comparison of the patient's capnogram and standardized capnograms for intubation in computer 264, the computer displays "MONITORING FOR INTUBATION".
Thereafter, the following check rule is preferably applied to the patient's capnogram:
1. If:
a) $ETCO_2$ is greater than 15 mm Hg;
then,
computer 264 displays "GOOD WAVEFORM, TUBE IN TRACHEA. CONFIRM AND SECURE TUBE."

Figure 15:
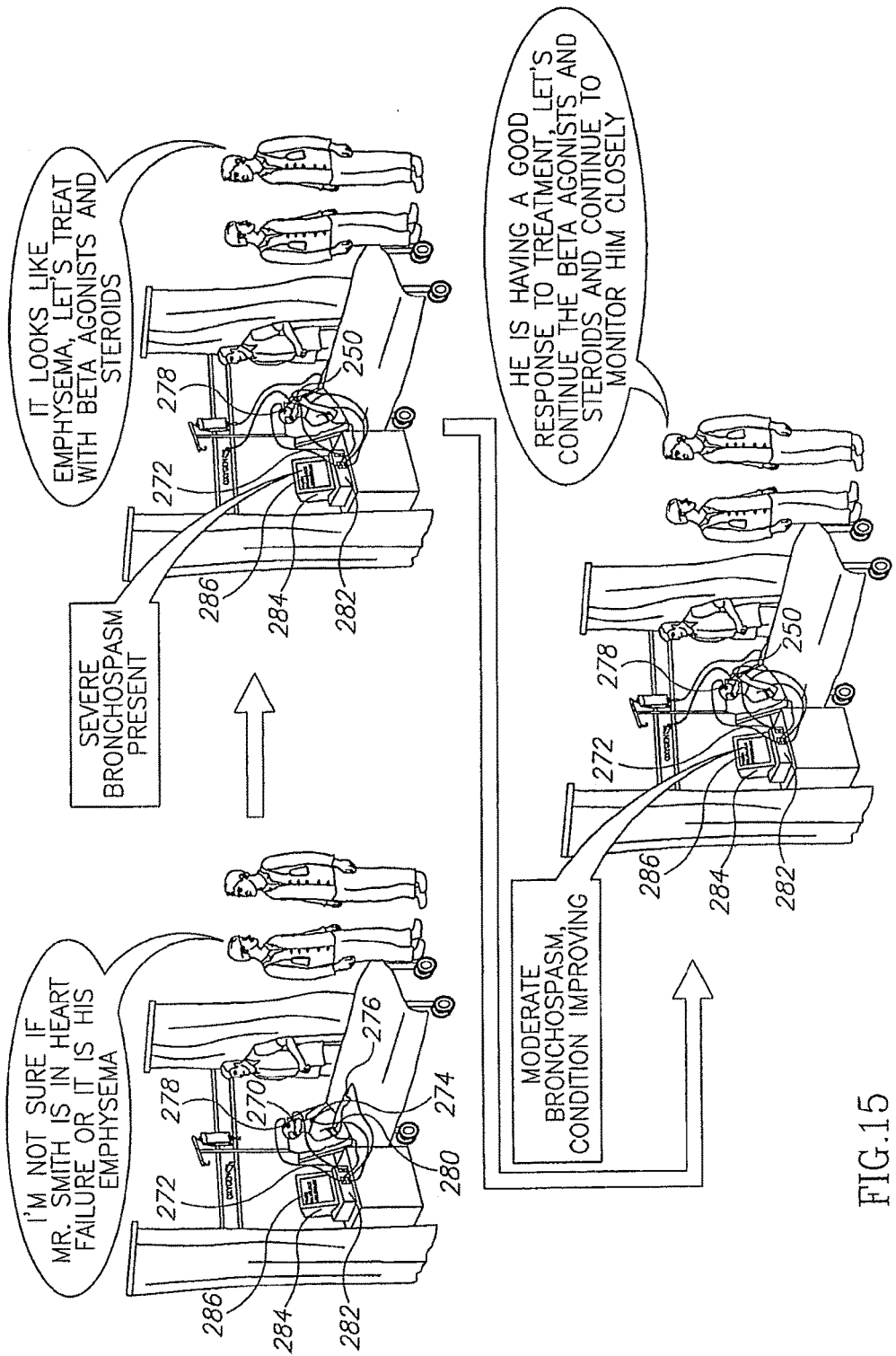
FIG. 15 is a simplified pictorial illustration of an automatic medical diagnostic and treatment system and methodology operative in a hospital environment for distinguishing between heart failure and emphysema, where emphysema is present.
Figure 16A:
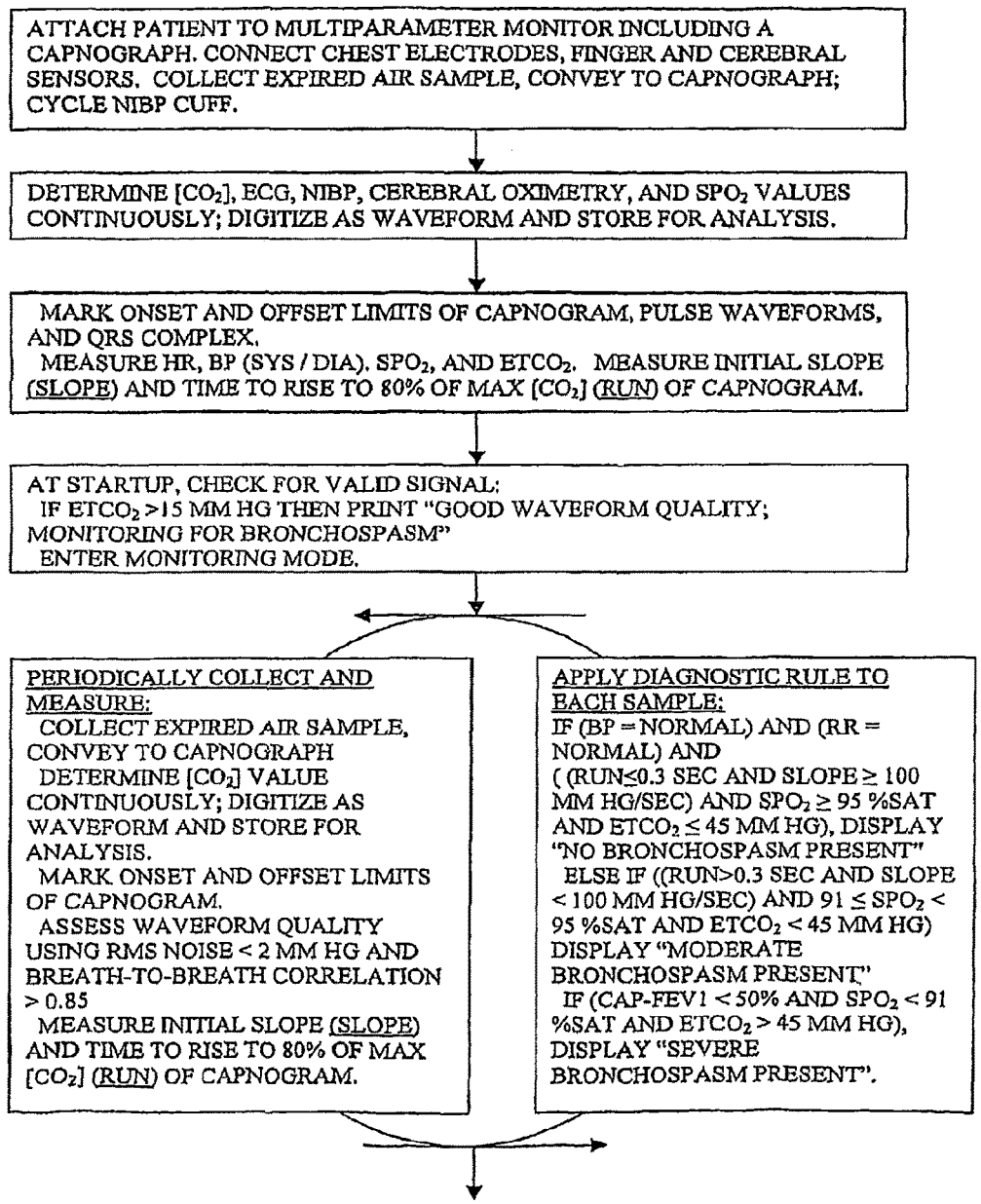
FIGS. 16A and 16B are flowcharts illustrating operation of the embodiment of FIG. 15.
Figure 16B:
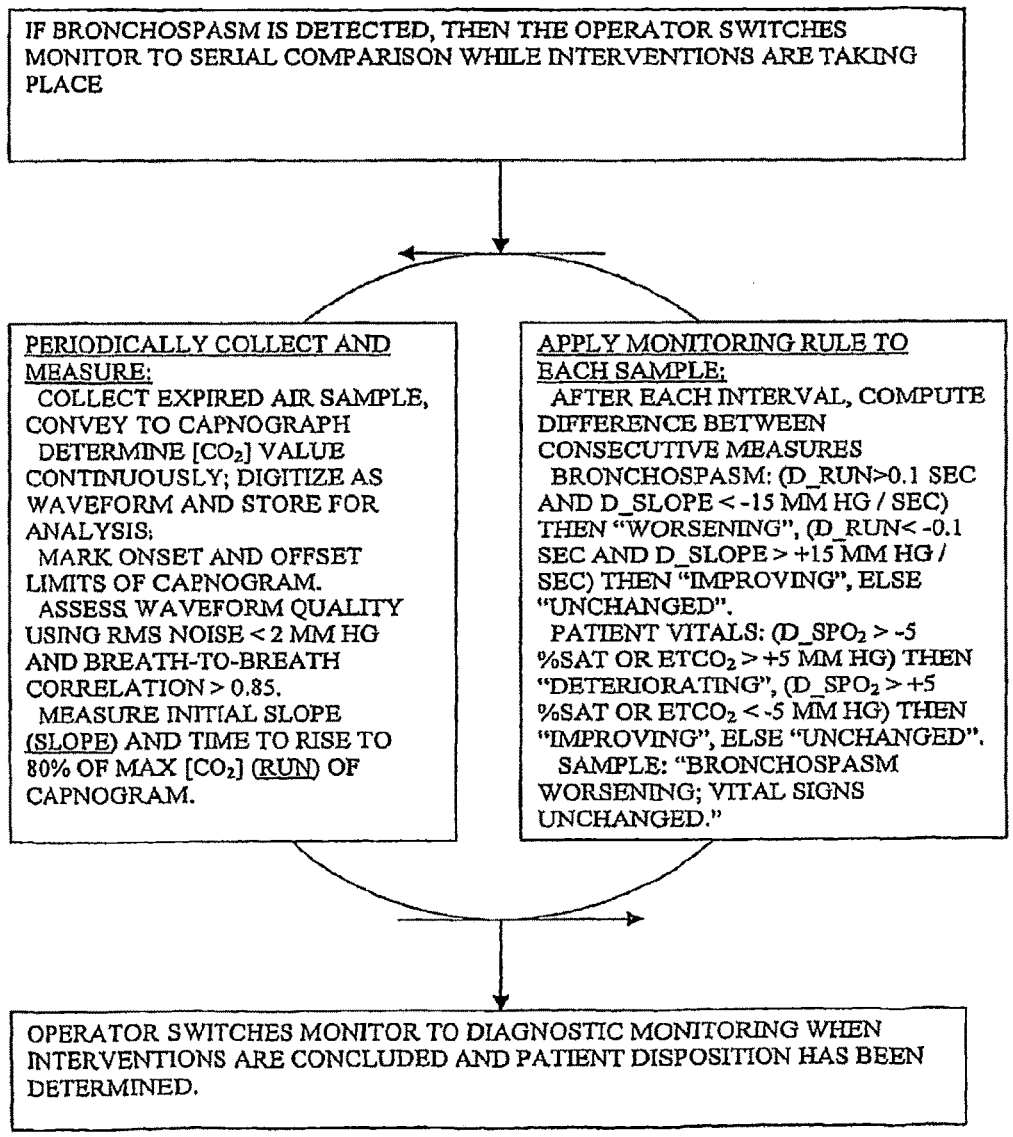

In the next step, the following monitoring rules are preferably applied to the patient's capnogram:
1) If:
a) the value of $ETCO_2$ is greater than 15 mm Hg;
then,
computer 266 displays "MONITORING TUBE POSITION: NO DISLODGEMENT" on display 268.
2) If:
a) the value of $ETCO_2$ is less than or equal to 15 mm Hg; or
b) there is a loss of the waveform;
then,
computer 264 displays "ALERT: CHECK FOR TUBE DISLODGEMENT" on display 266.
Reference is now made to FIG. 15, which is a simplified pictorial illustration of an automatic medical diagnostic and treatment system and methodology in a hospital environment operative for distinguishing between heart failure and emphysema in a situation where a hospital patient becomes short of breath. As seen in FIG. 15, in a hospital environment, various patient physiologic activities are sensed and measured, including respiratory physiologic activities, preferably via an oral airway adapter and/or a nasal or nasal/oral cannula 270, such as a Model Nasal FilterLine Adult XS 04461, $O_2/CO_2$ Nasal FilterLine Adult 007141, or Smart CapnoLine Adult (Oral/nasal FilterLine) 007414, commercially available from Oridion Ltd., of Jerusalem Israel, typically coupled with a capnograph 272, such as a Microcap, commercially available from Oridion Ltd., of Jerusalem Israel. Other patient physiologic activities relating to cardiac function (e.g. ECG), systemic oxygenation (e.g. pulse oximetry), cerebral oxygenation (e.g. cerebral oximetry) and systemic circulation (e.g. NIBP), typically sensed by means of chest electrodes 274, a finger sensor 276, a forehead/scalp sensor 278 and a blood pressure cuff 280 respectively, may also be sensed and measured by suitable instrumentation 282.
The outputs of the capnograph 272 and possibly of additional instrumentation 282 are preferably supplied to a suitably programmed automatic diagnostic and treatment computer 284, having an associated display 286 which typically analyzes the respiration parameter output of the capnograph 272 and possibly other parameters and provides an output which preferably contains a diagnostic statement, here "SEVERE BRONCHOSPASM PRESENT". This diagnostic statement would suggest treatment for emphysema rather than for heart failure. Breathing treatment is administered after which a diagnostic statement which indicates the patient status and the severity of the respiratory condition is preferably presented, here "MODERATE BRONCHOSPASM, CONDITION IMPROVING"
Reference is now made additionally to FIGS. 16A and 16B, which illustrates the operation of the system and methodology of the system of the present invention in the context of FIG. 15. FIGS. 16A and 16B illustrate the utility of using the capnograph in both diagnostic and monitoring modes as an aid to diagnosis and monitoring respectively.
The patient in the hospital environment, preferably attached to a multi-parameter monitor including capnograph 272 and the suitable instrumentation, by means of cannula 270 and preferably also by means of chest electrodes 274, finger sensor 276, forehead/scalp sensor 278 and blood pressure cuff 280, is monitored continuously. The neurological status of the patient is acquired by any suitable technique. Values of $CO_2$ concentration, ECG, NIBP and $SPO_2$ are continuously measured, typically over a period of 30 seconds, and carbon dioxide waveforms are preferably digitized as a capnogram and other waveforms and stored on computer 284

In the above exemplified scenario (FIG. 15), the medical team initially do not know whether the patient's symptoms are indicative of a breathing-related medical problem, such as emphysema, or from a heart related medical problem, such as heart failure. The following methodology assists and enables the medical team to reach the correct diagnosis. In contrast, in FIG. 11 above, there were no indications that the patient's diagnosis could include a heart-related episode.

Thereafter, the onset and offset limits of the capnogram, the pulse waveform and QRS onset and offset are determined by computer 284. The initial slope of the capnogram and the run are determined and stored in computer 284;

At a startup stage, computer 284 checks to verify that a valid signal is received from capnograph 272. In a case where the signal is indicative of there being obstructive lung disease, due to the sluggish run time for example or an acute angled initial slope, then the mode of monitoring on capnograph 272 is shifted to its bronchospastic monitoring mode.

In a monitoring rule stage, the following rule is preferably applied to the values of the end tidal value of exhaled carbon dioxide:

1) If:
a) $ETCO_2$ is greater than 15 mm Hg;
then,
computer 284 displays on display 286 "GOOD WAVEFORM QUALITY; CRITERIA FOR BRONCHOSPASM MET: STARTING MONITORING".

Thereafter a cycle of alteting I) sampling step (data collection and measurement) and II) diagnostic rule application to the previous sample step I) is initiated.

I) Sampling Step
a) A sample of expired air is taken and conveyed from cannula 270 to capnograph 272.
b) The carbon dioxide concentration is measured continuously by capnograph 272 as a capnogram.
c) The capnogram is digitized as waveform and store for analysis by computer 284.
d) Computer 284 marks onset and offset limits of the capnogram.
e) The waveform quality of the capnogram is assessed by employing the criteria that an acceptable quality is defined by:
  i) the root mean square (rms) of the noise of the waveform must be less than 2 mm Hg; and
  ii) the breath-to-breath correlation must be greater than 0.85.
f) The slope and the run are determined by computer 284.

II) Diagnostic Rule Application Step

In a diagnostic rule application step, the following diagnostic rules are preferably applied to the measured parameters of I) Sampling step by computer 284:

1) If:
a) the blood pressure values are within the normal range;
b) the respiratory rate is normal;
c) $CO_2$ run is less than or equal to 0.3 sec;
d) $CO_2$ slope is more than or equal to 100 mm Hg/sec;
e) $SPO_2$ is greater than or equal to 95% SAT; and
f) $ETCO_2$ is less than or equal to 45 mm Hg;
then,
display 286 shows the message "NO BROCHOSPASM PRESENT."

2) In contrast, if
a) $CO_2$ run is greater than 0.3 sec;
b) $CO_2$ slope is less than 100 mm Hg/sec;
c) $SPO_2$ is greater than or equal to 91% SAT, but less than 95% SAT; and
d) $ETCO_2$ is less than 45 mm Hg;
then,
the message "MODERATE BRONCHOSPASM PRESENT" is displayed on display 286.

3) If the parameters measured are yet further removed from the acceptable range, such as if:
a) CAP-FEV1 is less than 50%;
b) $SPO_2$ is less than 91% SAT; and
c) $ETCO_2$ is greater than 45 mm Hg;
then,
a message such as "SEVERE BRONCHOSPASM PRESENT" is displayed on display 286.

At any one of the diagnostic rule application steps, it may be verified that the patient is suffering from bronchospasm. Once bronchospasm is verified, the operator switches capnograph 272 to a serial comparison mode. The medical team applies the appropriate interventions to the patient to treat the bronchospasm.

Thereafter, a cycle of alteting I) sampling step (data collection and measurement) and II) monitoring rule application step to the previous sample step I) is initiated.

I) Sampling Step
a) A sample of expired air is taken and conveyed from cannula 270 to capnograph 272.
b) The carbon dioxide concentration is measured continuously by capnograph 272 as a capnogram.
c) The capnogram is digitized as waveform and store for analysis by computer 284.
d) Computer 284 marks onset and offset limits of the capnogram.
e) The waveform quality of the capnogram is assessed by employing the criteria that an acceptable quality is defined by:
  i) the root mean square (rms) of the noise of the waveform must be less than 2 mm Hg; and
  ii) the breath-to-breath correlation must be greater than 0.85.
f) The slope and the run are determined by computer 284.

II) Monitoring Rule Application Step

After each time interval, the difference between consecutive measures of each parameter are calculated by computer 284: Thereafter, the following monitoring rules are preferably applied to the measured parameters by computer 284.

1) If:
a) the difference in the run values is greater than 0.1 sec; and
b) the difference in the slope is less than −15 mm Hg/sec;
then,
computer 284 displays on display 286 "BRONCHOSPASM WORSENING".

2) If:
a) the difference in the run values is more negative than −0.1 sec; and
b) the difference in the slope is more than +15 mm Hg/sec;
then,
computer 284 displays on display 286 "BRONCHOSPASM IMPROVING"

If:
a) the difference in the run is more than or equal to −0.1 sec, but is less than or equal to 0.1 sec; or b) the difference in the slope is more than or equal to −15 mm Hg/sec and less than or equal to +15 mm Hg/sec;
then,
computer 284 displays on display 286 "BRONCHOSPASM UNCHANGED".

The change in patient's vital functional activities, including $SPO_2$ and $ETCO_2$, over the time interval are calculated by computer 284.

4) If:
a) the change in $SPO_2$ is more negative than −5% SAT; or
b) the change in the $ETCO_2$ is more than +5 mm Hg;
then,
computer 284 displays on display 286 "VITAL SIGNS DETERIORATING."

5) If:
a) the change in $SPO_2$ is greater than +5% SAT; or
b) the change in the $ETCO_2$ is less than −5 mm Hg;
then,
computer 284 displays on display 286 "VITAL SIGNS IMPROVING".

6) If:
a) the change in $SPO_2$ is greater than or equal to −5% SAT, but less than or equal to +5% SAT; or
b) the change in the $ETCO_2$ is more than or equal to −5 mm Hg, but less than or equal to +5 mm Hg;
then,
computer 284 displays on display 286 "VITAL SIGNS UNCHANGED."

Computer 284 preferably combines the results of these monitoring rules to display an integrated display 286 such as "BRONCHOSPASM WORSENING; VITAL SIGNS UNCHANGED."

Once the medical interventions have concluded and the patient's disposition has been determined, the operator switches the capnograph back to its diagnostic mode.

Figure 17:
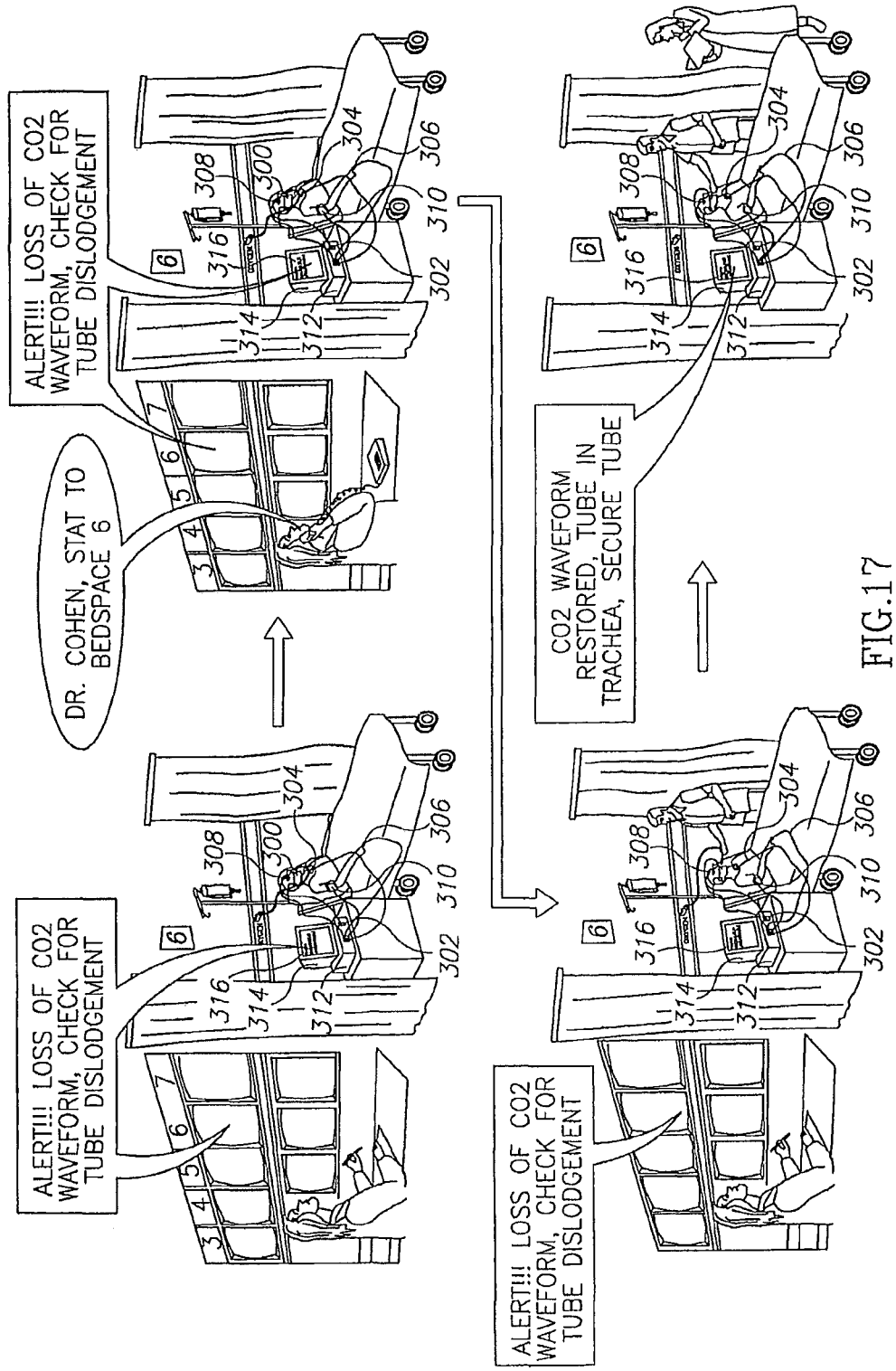
FIG. 17 is a simplified pictorial illustration of an automatic medical diagnostic and treatment system and methodology operative in a hospital environment for monitoring intubation status of a patient.

Reference is now made to FIG. 17, which is a simplified pictorial illustration of an automatic medical diagnostic and treatment system and methodology in a hospital environment, operative for continuously monitoring correct tube position in an intubated patient. As seen in FIG. 17, in a hospital environment, various patient physiologic activities are sensed and measured, including respiratory physiologic activities, preferably via an oral airway adapter and/or a nasal or nasal/oral cannula 300, such as a Model Nasal FilterLine Adult XS 04461, $O_2/CO_2$ Nasal FilterLine Adult 007141, or Smart CapnoLine Adult (Oral/nasal FilterLine) 007414, commercially available from Oridion Ltd., of Jerusalem Israel, typically coupled with a capnograph 302, such as a Microcap®, commercially available from Oridion Ltd., of Jerusalem Israel. Other patient physiologic activities relating to cardiac function (e.g. ECG), systemic oxygenation (e.g. pulse oximetry), cerebral oxygenation (e.g. cerebral oximetry) and systemic circulation (e.g. NIBP), typically sensed by means of chest electrodes 304, a finger sensor 306, a forehead/scalp sensor 308 and a blood pressure cuff 310 respectively, may also be sensed and measured by suitable instrumentation 312.

The outputs of the capnograph 302 and possibly of additional instrumentation 312 are preferably supplied to a suitably programmed automatic diagnostic and treatment computer 314, having an associated display 316 which typically analyzes the respiration parameter output of the capnograph 302 and possibly other parameters and provides an output which preferably contains a diagnostic statement, here "ALERT !!! LOSS OF $CO_2$ WAVEFORM" preferably accompanied by a treatment recommendation, here CHECK FOR TUBE DISLODGEMENT". Following re-intubation, a revised diagnostic statement, here "$CO_2$ WAVEFORM RESTORED, TUBE IN TRACHEA", preferably accompanied by a treatment recommendation, here "SECURE TUBE" appears.

Figure 18:
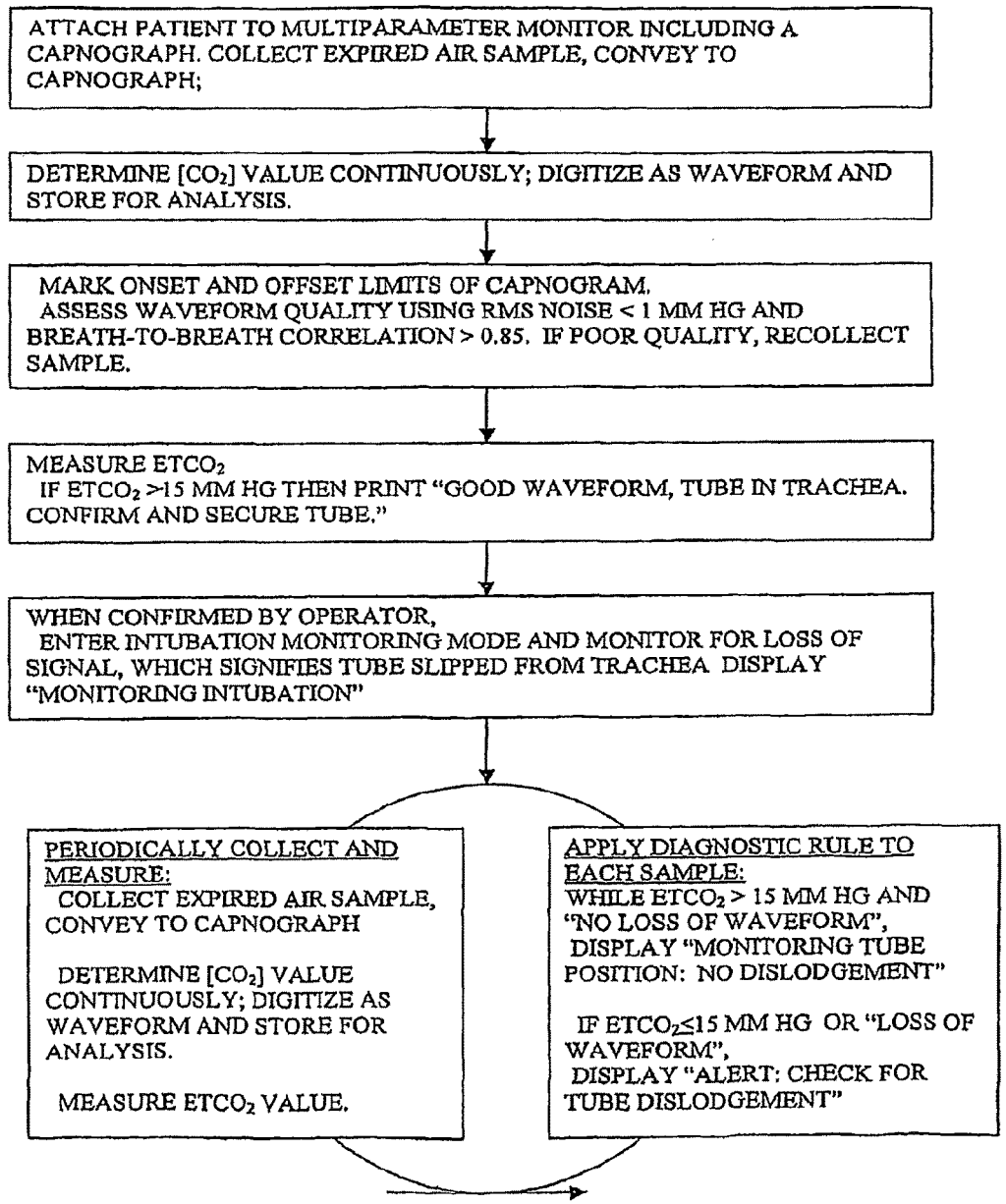
FIG. 18 is a flowchart illustrating operation of the embodiment of FIG. 17.

Reference is now made additionally to FIG. 18, which illustrates the operation of the system and methodology of the system of the present invention in the context of FIG. 17.

The patient in the hospital environment, preferably attached to a multi-parameter monitor including capnograph 302 and instrumentation 312, by means of cannula 200 and preferably also by means of chest electrodes 304, finger sensor 306, forehead/scalp sensor 308 and blood pressure cuff 310, is monitored continuously. The neurological status of the patient is acquired by any suitable technique. Expired air is collected via cannula 300 and is conveyed to the capnograph 302.

Values of $CO_2$ concentration, ECG, NIBP and $SPO_2$ are continuously measured, typically over a period of 30 seconds, and carbon dioxide waveforms are preferably digitized as a capnogram and together with other waveforms are stored on computer 314.

The onset and offset limits of the patient's capnogram from capnograph 302 are delineated by computer 314.

The waveform quality of the capnogram is assessed by employing the criteria that an acceptable quality is defined by:

i) the root mean square (rms) of the noise of the waveform must be less than 1 mm Hg; and ii) the breath-to-breath correlation must be greater than 0.85.

If the quality is unacceptable, further samples are collected until a sample of acceptable quality, according to the above two criteria, is taken.

The next step entails a checking procedure, wherein the $ETCO_2$ value is measured by capnograph 302.

The following checking rule is preferably applied.

1) If:
a) the $ETCO_2$ value is more than 15 mm Hg;
then,
a display is provided by computer 314 stating "GOOD WAVEFORM, TUBE IN TRACHEA, CONFIRM AND SECURE TUBE" on display 316.

If the intubation is successful, the operator confirms this, by for example, entering the relevant code into computer 314, and capnograph 302 is then entered into an intubation monitoring mode. The patient is monitored continuously. Thus, computer 314 displays "MONITORING INTUBATION" on display 316.

If there is a loss of the signal from capnograph 302, it may be indicative that the cannula tube 300 has slipped away from the patient's trachea In such a case, the computer preferably displays "ALERT: CHECK FOR TUBE DISLODGEMENT".

Thereafter a cycle of alteting I) sampling step (data collection and measurement) and II) diagnostic rule application to the previous sample step I) is initiated.

I) Sampling Step

In this sampling step, an exhaled air sample from cannula 300 is periodically collected, conveyed and measured by capnograph 302. The carbon dioxide concentration value is determined continuously by capnograph 302. Computer 314 digitizes the capnograph signals as a waveform and store the waveform for analysis.

Thereafter, the $ETCO_2$ value is determined.

II) Diagnostic Rule Application Step.

The following diagnostic rules are applied to each sample:

1) If:

a) The value of $ETCO_2$ is greater or equal to 15 mm Hg; and b) There is no loss in the waveform from capnograph 302; then, computer 314 displays "MONITORING TUBE POSITION: NO DISLODGMENT" on display 316.

2) If:

a) The value of $ETCO_2$ is less than or equal to 15 mm Hg; or b) There is a loss in the waveform from capnograph 302; then, computer 314 displays "ALERT: CHECK FOR TUBE DISLODGMENT" on display 316.

This cycle typically proceeds until the patient monitoring is halted by the medical team or operator.

Figure 19:
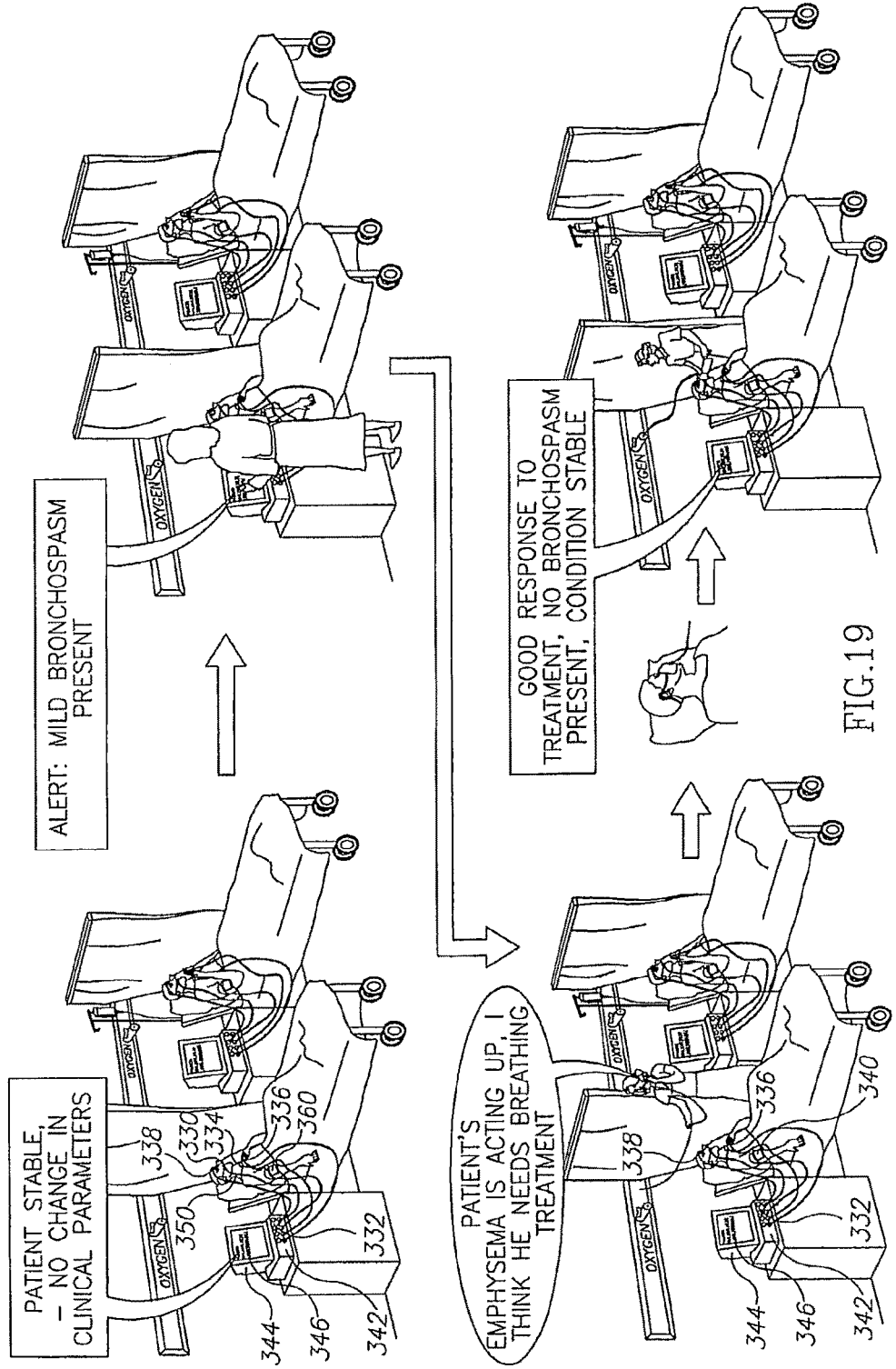
FIG. 19 is a simplified pictorial illustration of an automatic medical diagnostic and treatment system and methodology operative in a hospital environment for monitoring respiratory status of a patient in a first clinical scenario.

Reference is now made to FIG. 19, which is a simplified pictorial illustration of an automatic medical diagnostic and treatment system and methodology, operative in a hospital environment, for continuously monitoring the respiratory status of a spontaneously breathing patient in first operational scenario. As seen in FIG. 19, in a hospital environment, various patient physiologic activities are sensed and measured, including respiratory physiologic activities, preferably via an oral airway adapter and/or a nasal or nasal/oral cannula 330, such as a Model Nasal FilterLine Adult XS 04461, $O_2/CO_2$ Nasal FilterLine Adult 007141, or Smart CapnoLine Adult (Oral/nasal FilterLine) 007414, commercially available from Oridion Ltd., of Jerusalem Israel, typically coupled with a capnograph 332, such as a Microcap®, commercially available from Oridion Ltd., of Jerusalem Israel. Other patient physiologic activities relating to cardiac function (e.g. ECG), systemic oxygenation (e.g. pulse oximetry), cerebral oxygenation (e.g. cerebral oximetry) and systemic circulation (e.g. NIBP), typically sensed by means of chest electrodes 334, a finger sensor 336, a forehead/scalp sensor 338 and a blood pressure cuff 340 respectively, may also be sensed and measured by suitable instrumentation 342.

The outputs of the capnograph 332 and possibly of additional instrumentation 342 are preferably supplied to a suitably programmed automatic diagnostic and treatment computer 344, having an associated display 346 which typically analyzes the respiration parameter output of the capnograph 332 and possibly other parameters and provides an output which preferably contains a diagnostic statement, here "PATIENT STABLE-NO CHANGE IN CLINICAL PARAMETERS. If a change occurs in the patient respiratory status, a diagnostic statement, here "ALERT: MILD BRONCHOSPASM PRESENT" appears on the display 346, indicating to medical personnel that a bronchospastic condition is present. Following administration of breathing treatment, an updated diagnostic statement appears, here "GOOD RESPONSE TO TREATMENT, NO BRONCHOSPASM PRESENT".

Figure 20:
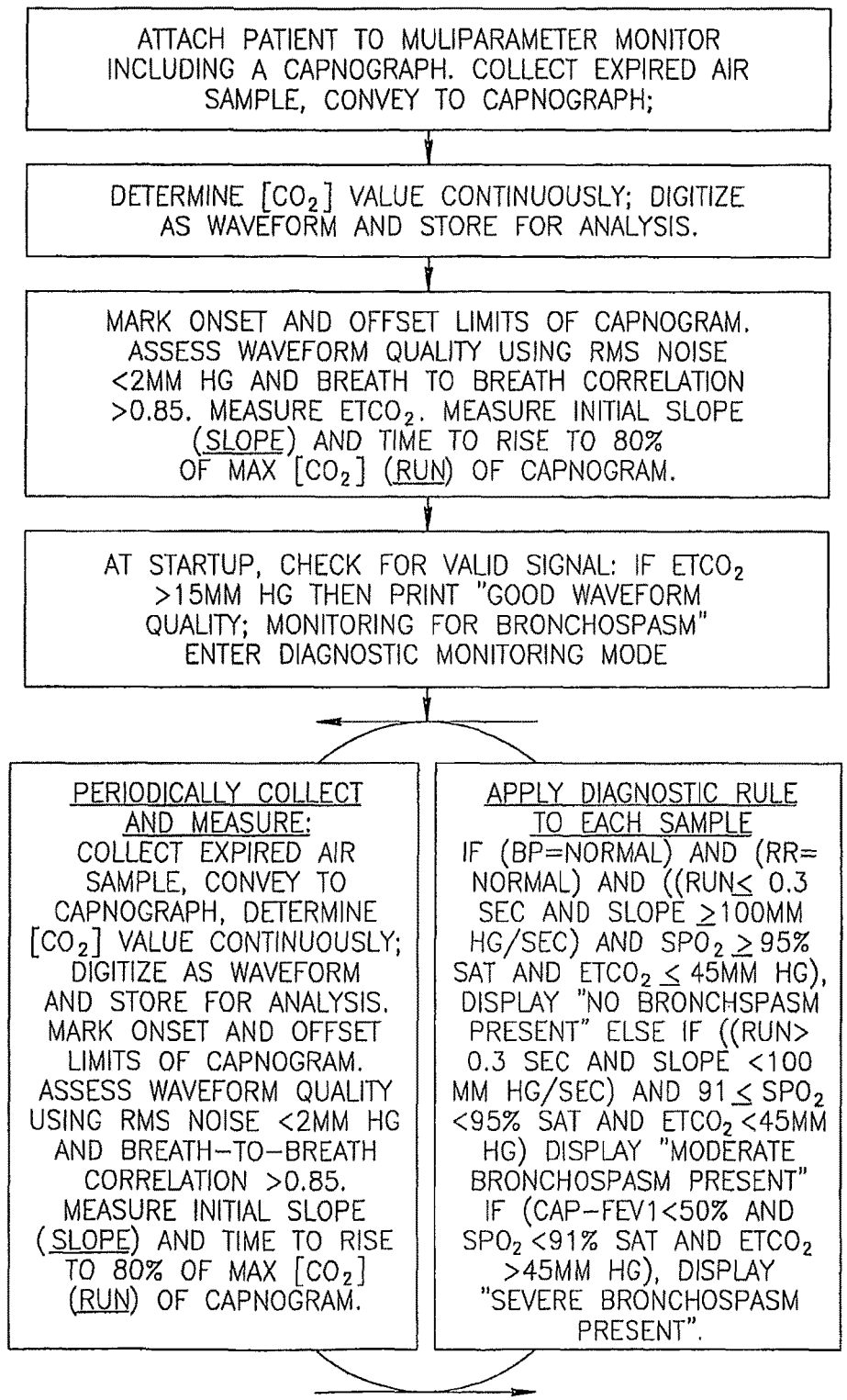
FIG. 20 is a flowchart illustrating operation of the embodiment of FIG. 19.

Reference is now made additionally to FIG. 20, which illustrates the operation of the system and methodology of the system of the present invention in the context of FIG. 19.

The patient in the hospital environment, preferably attached to a multi-parameter monitor including capnograph 332 and instrumentation 342, by means of cannula 330 and preferably also by means of chest electrodes 334, finger sensor 336," forehead/scalp sensor 338 and blood pressure cuff 340, is monitored continuously. The neurological status of the patient is acquired by any suitable technique. Expired air is collected via cannula 300 and is conveyed to the capnograph 332.

Values of $CO_2$ concentration, ECG, NIBP and $SPO_2$ are continuously measured, typically over a period of 30 seconds, and carbon dioxide waveforms are preferably digitized as a capnogram and together with other waveforms are stored on computer 344.

The onset and offset limits of the patient's capnogram from capnograph 332 are delineated by computer 344.

The waveform quality of the capnogram is assessed by employing the criteria that an acceptable quality is defined by:

i) the root mean square (rms) of the noise of the waveform must be less than 2 mm Hg; and ii) the breath-to-breath correlation must be greater than 0.85.

If the quality is unacceptable, further samples are collected until a sample of acceptable quality, according to the above two criteria, is taken.

The next step entails a checking procedure, wherein the $ETCO_2$ value is measured by capnograph 332. The slope and run values of the capnogram from capnograph 332 are determined by computer 344.

At startup, the following checking rule is preferably applied.

1) If a) the $ETCO_2$ value is more than 15 mm Hg;

then, a display is provided by computer 344 stating "GOOD WAVEFORM, QUALITY: MONITORING FOR BRONCHOSPASM".

If the monitoring is successful, the operator confirms this, by for example, entering the relevant code into computer 344, and capnograph 332 is then entered into a diagnostic monitoring mode. The patient is monitored continuously by capnograph 332.

Thereafter a cycle of alteting I) sampling step (data collection and measurement) and II) diagnostic rule application to the previous sample step I) is initiated.

I) Sampling Step a) A sample of expired air is taken and conveyed from cannula 330 to capnograph 332.

b) The carbon dioxide concentration is measured continuously by capnograph 332 as a capnogram.

c) The capnogram is digitized as waveform and store for analysis by computer 344.

d) Computer 344 marks onset and offset limits of the capnogram.

e) The waveform quality of the capnogram is assessed by employing the criteria that an acceptable quality is defined by:

i) the root mean square (rms) of the noise of the waveform must be less than 2 mm Hg; and ii) the breath-to-breath correlation must be greater than 0.85.

f) The slope and the run are determined by computer 344.

II) Diagnostic Rule Application Step

In a diagnostic rule application step, the following diagnostic rules are preferably applied to the measured parameters of I) Sampling step by computer 344:

1) If:

a) the blood pressure values are within the normal range;

b) the respiratory rate is normal;

c) $CO_2$ run is less than or equal to 0.3 sec;

d) $CO_2$ slope is more than or equal to 100 mm Hg/sec;

e) $SPO_2$ is greater than or equal to 95% SAT; and f) $ETCO_2$ is less than or equal to 45 mm Hg; then, display 346 shows the message "NO BRONCHOSPASM PRESENT."

2) In contrast, if:

a) $CO_2$ run is greater than 0.3 sec;

b) $CO_2$ slope is less than 100 mm Hg/sec;

c) $SPO_2$ is greater or equal to 91% SAT, but less than 95% SAT; and d) $ETCO_2$ is less than 45 mm Hg;

then, the message "MODERATE BRONCHOSPASM PRESENT" is displayed on display 346. The patient then receives suitable breathing treatment as is shown in FIG. 19 hereinabove.

3) If the parameters measured are yet further removed from the acceptable range, such as if:

a) CAP-FEV1 is less than 50%;

b) $SPO_2$ is less than 91% SAT; and c) $ETCO_2$ is greater than 45 mm Hg;

then, a message such as "SEVERE BRONCHOSPASM PRESENT" is displayed on display 346.

Figure 21B:
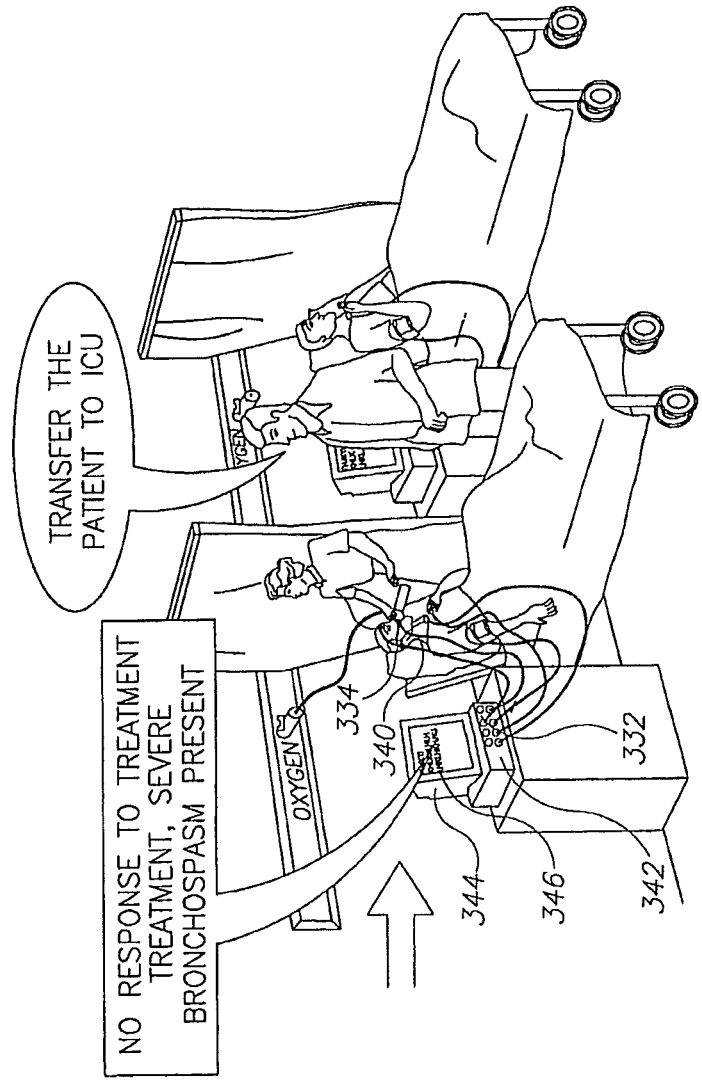

Reference is now made to FIGS. 21A and 21B, which are simplified pictorial illustrations of an automatic medical diagnostic and treatment system and methodology, operative in a hospital environment, for continuously monitoring the respiratory status of a spontaneously breathing patient in a second clinical scenario.

As seen in FIGS. 21A and 21B, in a hospital environment, various patient physiologic activities are sensed and measured, including respiratory physiologic activities, preferably via an oral airway adapter and/or a nasal or nasal/oral cannula 350, such as a Model Nasal FilterLine Adult XS 04461, $O_2/CO_2$ Nasal FilterLine Adult 007141, or Smart CapnoLine Adult (Oral/nasal FilterLine) 007414, commercially available from Oridion Ltd., of Jerusalem Israel, typically coupled with a capnograph 352, such as a Microcap®, commercially available from Oridion Ltd., of Jerusalem Israel. Other patient physiologic activities relating to cardiac function (e.g. ECG), systemic oxygenation (e.g.; pulse oximetry), cerebral oxygenation (e.g. cerebral oximetry) and systemic circulation (e.g. NIBP), typically sensed by means of chest electrodes 354, a finger sensor 356, a forehead/scalp sensor 358 and a blood pressure cuff 360 respectively, may also be sensed and measured by suitable instrumentation 362.

The outputs of the capnograph 352 and possibly of additional instrumentation 362 are preferably supplied to a suitably programmed automatic diagnostic and treatment computer 364, having an associated display 366 which typically analyzes the respiration parameter output of the capnograph 352 and possibly other parameters and provides an output which preferably contains a diagnostic statement, here "PATIENT STABLE-NO CHANGE IN CLINICAL PARAMETERS. If a change occurs in the patient respiratory status, a diagnostic statement, here "ALERT: MILD BRONCHOSPASM PRESENT" appears on the display 346, indicating to medical personnel that a bronchospastic condition is present. Following administration of breathing treatment, an updated diagnostic statement appears, here "NO RESPONSE TO TREATMENT, MODERATE BRONCHOSPASM PRESENT". Additional breathing treatment is administered and thereafter an updated diagnostic statement appears, here "NO RESPONSE TO TREATMENT, SEVERE BRONCHOSPASM PRESENT", which may prompt the physician to transfer the patient to the ICU.

Figure 22A:
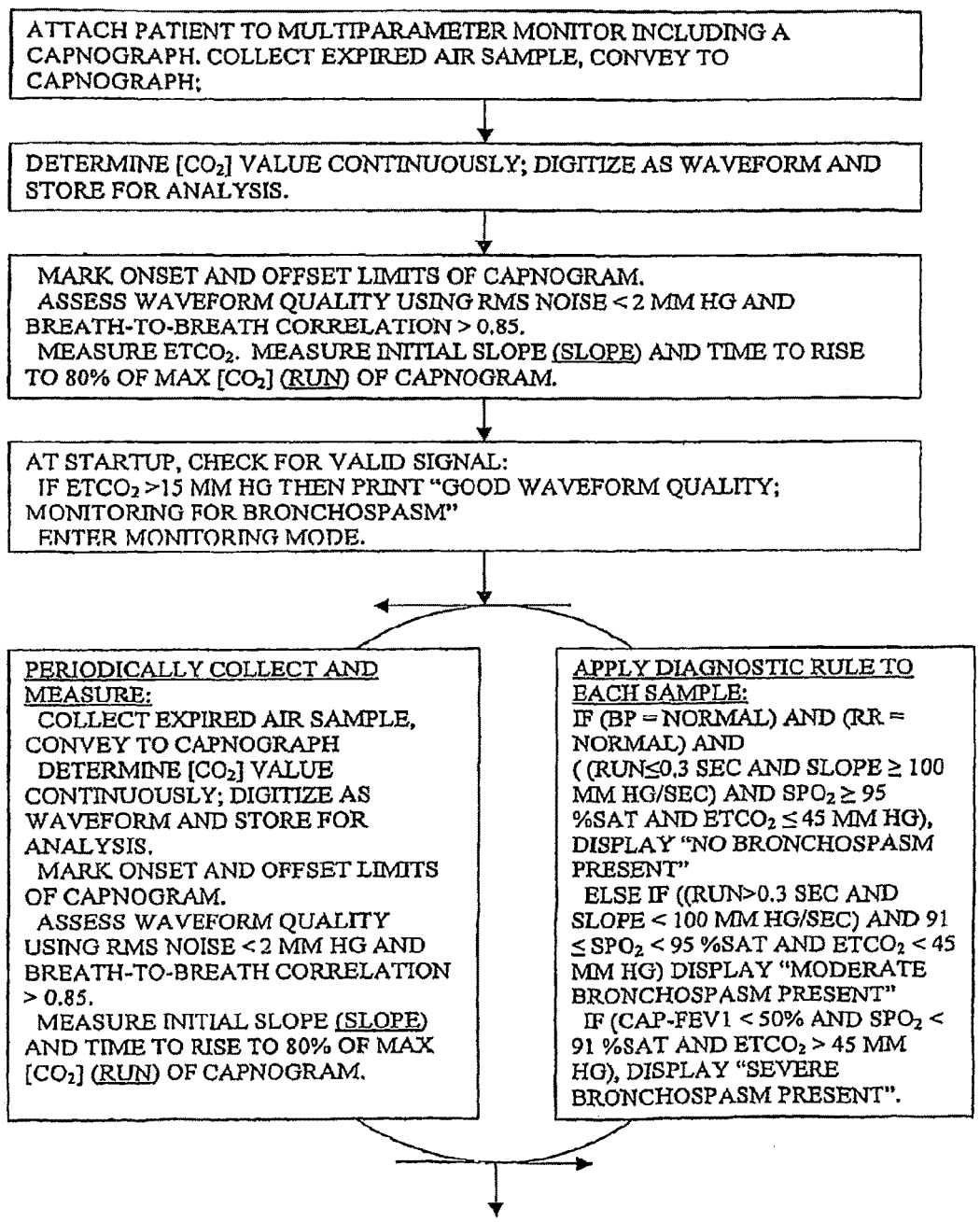
FIGS. 22A, 22B and 22C are flowcharts illustrating operation of the embodiment of FIGS. 21A and 21B.
Figure 22B:
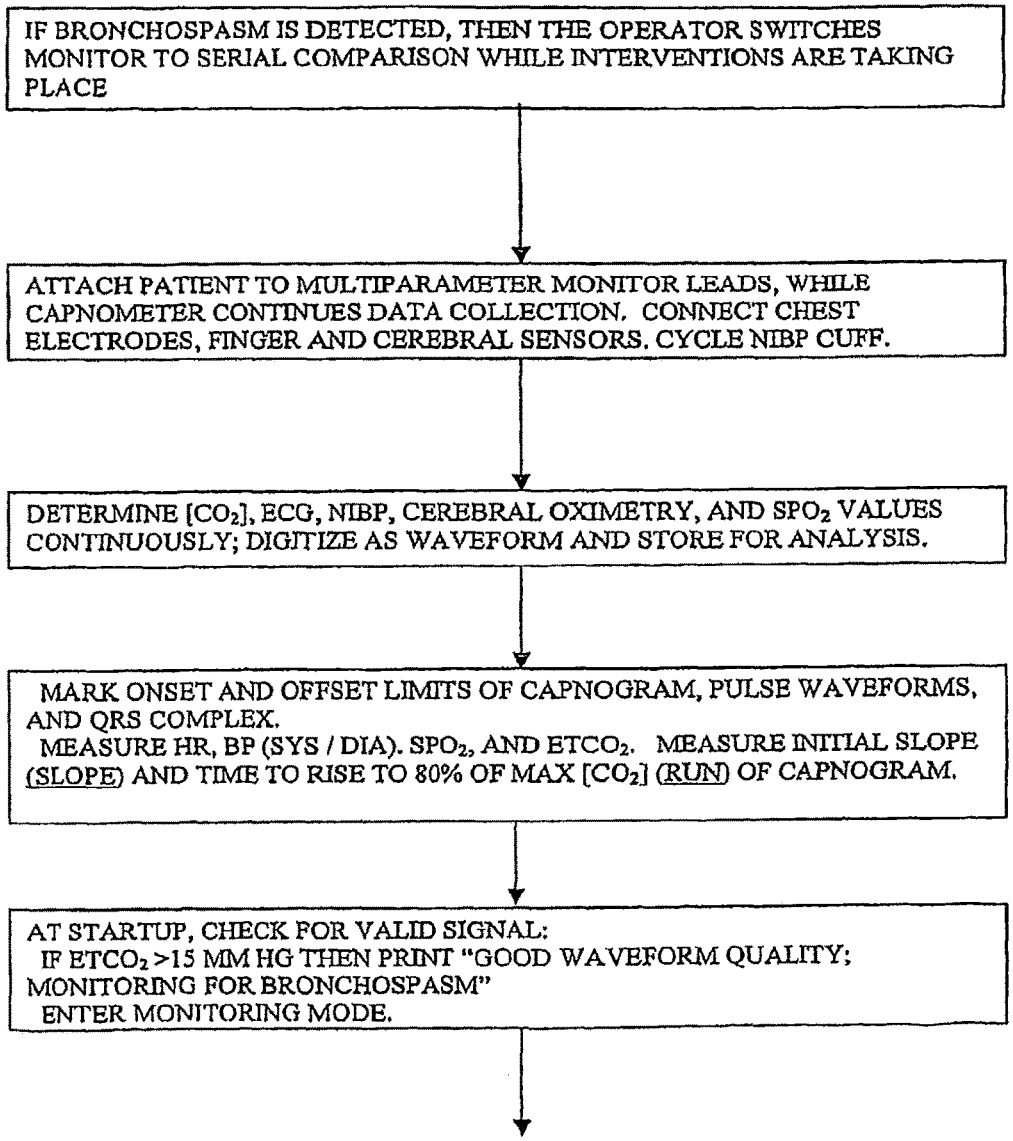
Figure 22C:
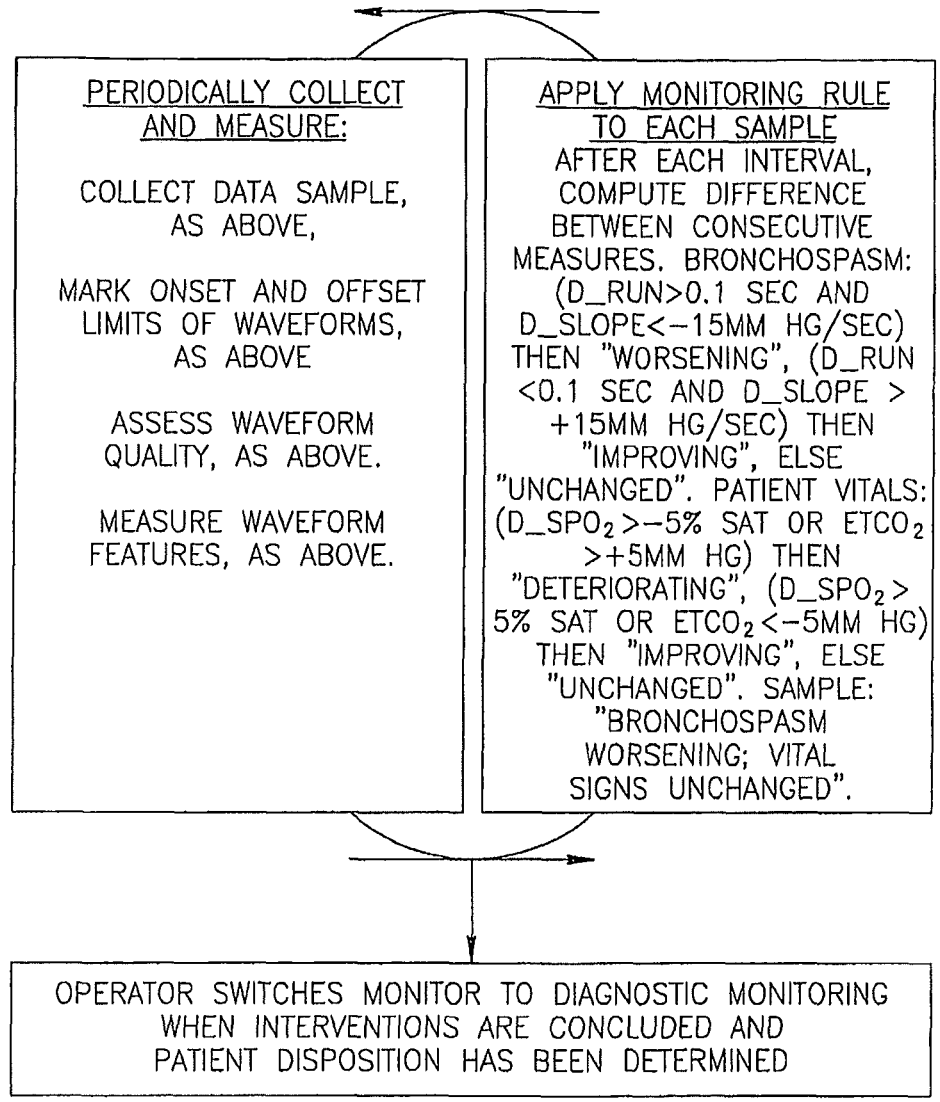

Reference is now made additionally to FIGS. 22A-22C, which illustrates the operation of the system and methodology of the system of the present invention in the context of FIGS. 21A and 21B.

The patient in the hospital environment, preferably attached to a multi-parameter monitor including capnograph 352, is monitored continuously for at least 30 seconds. Expired air is collected via cannula 350 and is conveyed to the capnograph 352.

Values of the $CO_2$ concentration is continuously measured, typically over a period of 30 seconds, and carbon dioxide waveforms are preferably digitized as a capnogram and together with other waveforms are stored on computer 364.

The onset and offset limits of the patient's capnogram from capnograph 352 are delineated by computer 364.

The waveform quality of the capnogram is assessed by employing the criteria that an acceptable quality is defined by:

i) the root mean square (rms) of the noise of the waveform must be less than 2 mm Hg; and ii) the breath-to-breath correlation must be greater than 0.85.

If the quality is unacceptable, further samples are collected until a sample of acceptable quality, according to the above two criteria, is taken.

The next step entails a checking procedure, wherein the $ETCO_2$ value is measured by capnograph 352. The slope and run values of the capnogram from capnograph 352 are determined by computer 364.

At startup, the following checking rule is preferably applied.

1) If:

a) the $ETCO_2$ value is more than 15 mm Hg;

then, a display is provided by computer 364 stating "GOOD WAVEFORM, QUALITY: MONITORING FOR BRONCHOSPASM".

If the monitoring is successful, the operator confirms this, by for example, entering the relevant code into computer 364, and capnograph 352 is then entered into a diagnostic monitoring mode. The patient is monitored continuously by capnograph 352.

Thereafter a cycle of alteting I) sampling step (data collection and measurement) and II) diagnostic rule application to the previous sample step I) is initiated.

I) Sampling Step a) A sample of expired air is taken and conveyed from cannula 350 to capnograph 352.

b) The carbon dioxide concentration is measured continuously by capnograph 352 as a capnogram.

c) The capnogram is digitized as waveform and store for analysis by computer 364.

d) Computer 364 marks onset and offset limits of the capnogram.

e) The waveform quality of the capnogram is assessed by employing the criteria that an acceptable quality is defined by:

i) the root mean square (rms) of the noise of the waveform must be less than 2 mm Hg; and ii) the breath-to-breath correlation must be greater than 0.85.

f) The slope and the run are determined by computer 364.

II) Diagnostic Rule Application Step

In a diagnostic rule application step, the following diagnostic rules are preferably applied to the measured parameters of I) Sampling step by computer 364:

1) If:
a) the blood pressure values are within the normal range;
b) the respiratory rate is normal;
c) $CO_2$ run is less than or equal to 0.3 sec;
d) $CO_2$ slope is more than or equal to 100 mm Hg/sec;
e) $SPO_2$ is greater than or equal to 95% SAT; and
f) $ETCO_2$ is less than 45 mm Hg;
then,
display 366 shows the message "NO BRONCHOSPASM PRESENT."

2) In contrast, if:
a) $CO_2$ run is greater than 0.3 sec;
b) $CO_2$ slope is less than 100 mm Hg/sec;
c) $SPO_2$ is greater than or equal to 91% SAT, but less than 95% SAT; and
d) $ETCO_2$ is less than 45 mm Hg;
then,
the message "MODERATE BRONCHOSPASM PRESENT" is displayed on display 366.

3) If the parameters measured are yet further removed from the acceptable range, such as if:
a) CAP-FEV1 is less than 50%;
b) $SPO_2$ is less than 91% SAT; and
c) $ETCO_2$ is greater than 45 mm Hg;
then,
a message such as "SEVERE BRONCHOSPASM PRESENT" is displayed on display 366.

At any one of the diagnostic rule application steps, it may be verified that the patient is suffering from bronchospasm. Once bronchospasm is verified, the operator switches capnograph 352 to a serial comparison mode. The medical team applies the appropriate interventions to the patient to treat the bronchospasm.

The patient is attached multi-parameter monitor leads and instrumentation 362, by means of cannula 350 and preferably also by means of chest electrodes 354, finger sensor 356, forehead/scalp sensor 358 and blood pressure cuff 360, is monitored continuously. The neurological status of the patient is acquired by any suitable technique.

Values of the $CO_2$ concentration monitored by capnograph 352, and ECG, NIBP, cerebral oximetry and $SPO_2$ values, monitored by additional instrumentation 362 are supplied to computer 364, and are typically measured continuously over a period of 30 seconds, by techniques as detailed hereinabove. The parameter data may be digitized as waveforms and are further stored for analysis by computer 364. Thereafter, the limits of the capnogram, the pulse waveform and QRS onset and offset are determined by computer 364.

The next step entails a checking procedure, wherein the $ETCO_2$ value is measured by capnograph 352. The initial slope of the capnogram and the run, monitored by capnograph 352, are calculated by computer 364.

At startup, the following checking rule is preferably applied.

1) If:
a) the $ETCO_2$ value is more than 15 mm Hg;
then,
a display is provided by computer 344 stating "GOOD WAVEFORM, QUALITY: MONITORING FOR BRONCHOSPASM".

If the monitoring is successful, the operator confirms this, by for example, entering the relevant code into computer 364, and capnograph 352 is then entered into a diagnostic monitoring mode. The patient is monitored continuously by capnograph 352.

Thereafter, a cycle of alteting I) sampling step (data collection and measurement) and II) monitoring rule application step to the previous sample step I) is initiated.

I) Sampling Step
a) A sample of expired air is taken and conveyed from cannula 350 to capnograph 352.
b) The carbon dioxide concentration is measured continuously by capnograph 352 as a capnogram.
c) The capnogram is digitized as waveform and store for analysis by computer 364.
d) Computer 364 marks onset and offset limits of the capnogram.
e) The waveform quality of the capnogram is assessed by employing the criteria that an acceptable quality is defined by:
i) the root mean square (rms) of the noise of the waveform must be less than 2 mm Hg; and
ii) the breath-to-breath correlation must be greater than 0.85.
f) The slope and the run are determined by computer 364.

II) Monitoring Rule Application Step

After each time interval, the difference between consecutive measures of each parameter are calculated by computer 364: Thereafter, the following monitoring rules are preferably applied to the measured parameters by computer 364.

1) If:
a) the difference in the run values is greater than +0.1 sec; and
b) the difference in the slope is more negative than −15 mm Hg/sec;
then,
computer 364 displays on display 366 "BRONCHOSPASM WORSENING".

2) If:
a) the difference in the run values is more negative than −0.1 sec; and
b) the difference in the slope is more than +15 mm Hg/sec;
then,
computer 364 displays on display 366 "BRONCHOSPASM IMPROVING".

3) If:
a) the difference in the run values is equal to or greater than −0.1 sec, but less than or equal to +0.1 sec; or
b) the difference in the slope is more than or equal to −15 mm Hg but less than or equal to +15 mm Hg/sec;
then,
computer 364 displays on display 366 "BRONCHOSPASM UNCHANGED".

The change in patient's vital functional activities, including $SPO_2$ and $ETCO_2$, over the time interval are calculated by computer 364.

4 If:
a) the decrease in $SPO_2$ is more than −5% SAT; or
b) the increase in the $ETCO_2$ is more than 5 mm Hg;
then,
computer 364 displays on display 366 "VITAL SIGNS DETERIORATING."

5) If:
a) the increase in $SPO_2$ is more than 5% SAT; or
b) the decrease in the $ETCO_2$ is greater than −5 mm Hg;
then,
computer 364 displays on display 366 "VITAL SIGNS IMPROVING".

6) If:
a) the change in SPO$_2$ is greater than or equal to −5% SAT but less than or equal to +5% SAT; or
b) the change in the ETCO$_2$ is more than or equal to −5 mm Hg or less than or equal to +5 mm Hg;
then,
computer 364 displays on display 366 "VITAL SIGNS UNCHANGED".

Computer 364 preferably combines the results of these monitoring rules to display an integrated display 366 such as "BRONCHOSPASM WORSENING; VITAL SIGNS UNCHANGED."

Once the medical interventions have concluded and the patient's disposition has been determined, the operator switches the capnograph back to its diagnostic mode.

Figure 23A:
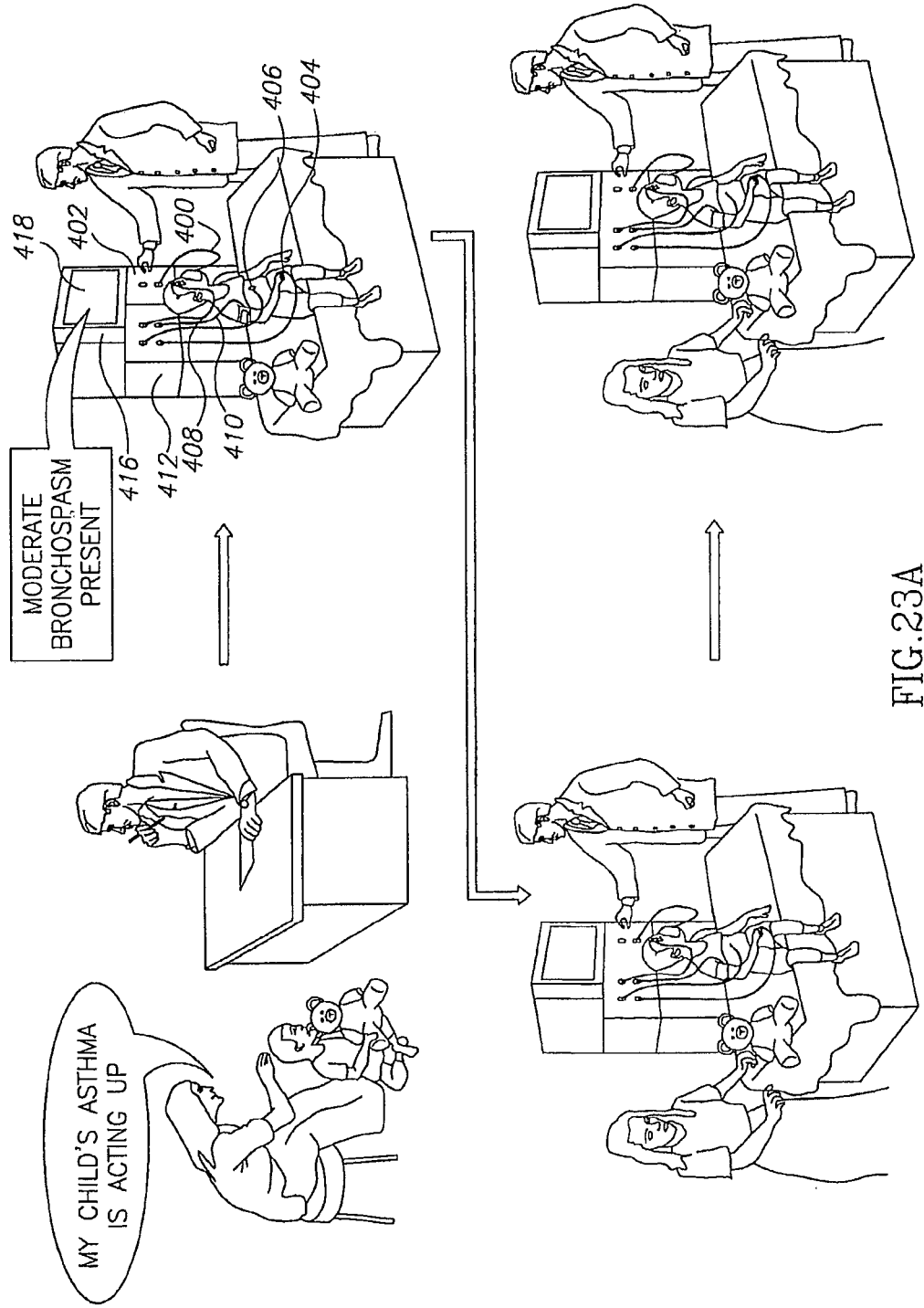
FIGS. 23A and 23B are simplified pictorial illustrations of a diagnostic and treatment system and methodology operative in a physician's office environment for detecting the presence and severity of bronchospasm, gauging the response to treatment and recommending disposition of a spontaneously breathing patient in a first clinical scenario.
Figure 23B:
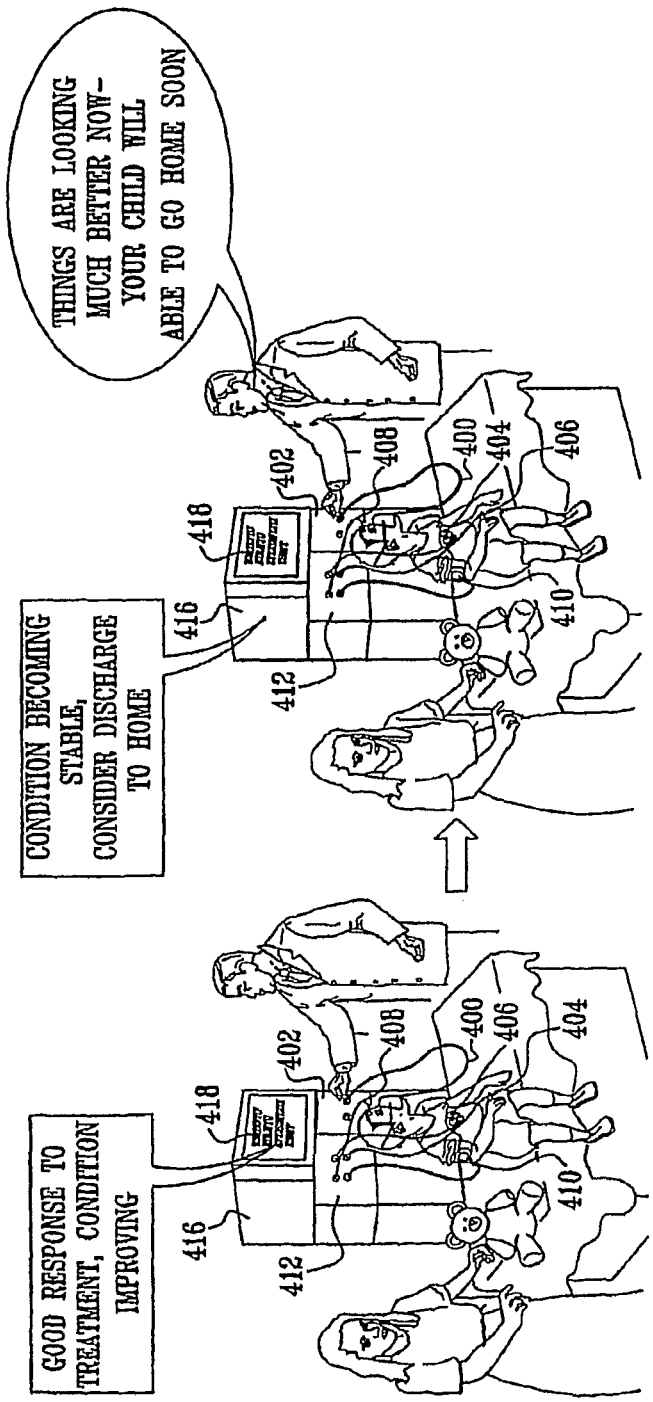

Reference is now made to FIGS. 23A and 23B, which are simplified pictorial illustrations of an automatic medical diagnostic and treatment system and methodology operative in a physician's office environment for detecting the presence and severity of bronchospasm, gauging the response to treatment and recommending disposition of a spontaneously breathing patient in a first clinical scenario. As seen in FIGS. 23A and 23B, a child having an asthma attack is brought to a physician's office. Various patient physiologic activities are sensed and measured, including respiratory physiologic activities, preferably via an oral airway adapter and/or a nasal or nasal/oral cannula 400, such as a Model Nasal FilterLine Adult XS 04461, 02/CO$_2$ Nasal FilterLine Adult 007141, or Smart CapnoLine Adult (Oral/nasal FilterLine) 007414, commercially available from Oridion Ltd., of Jerusalem Israel, typically coupled with a capnograph 402, such as a Microcap, commercially available from Oridion Ltd., of Jerusalem Israel. Other patient physiologic activities relating to cardiac function (e.g. ECG), systemic oxygenation (e.g. pulse oximetry), cerebral oxygenation (e.g. cerebral oximetry) and systemic circulation (e.g. NIBP), typically sensed by means of chest electrodes 404, a finger sensor 406, a forehead/scalp sensor 408 and a blood pressure cuff 410 respectively, may also be sensed and measured by suitable instrumentation 412.

The outputs of the capnograph 402 and preferably of additional instrumentation 404 are preferably supplied to a suitably programmed automatic diagnostic and treatment computer 416 having an associated display 418, which typically analyzes the respiration parameter output of the capnograph 402 and preferably other physiologic activities and provides an output which preferably contains a diagnostic statement, here "MODERATE BRONCHOSPASM PRESENT".

The patient is given breathing treatments, such as beta agonist nebulizer treatments and following such treatments and/or in the course thereof, the physiologic activities of the patient continue to be monitored. This monitoring is employed by computer 160 to indicate the response to the breathing treatments and the current status of the bronchospasm condition. When the breathing treatments are successful, a status message, here "GOOD RESPONSE TO TREATMENT", is presented accompanied by a disposition recommendation, here "CONSIDER DISCHARGE TO HOME" and the physician may allow the child to return home after the treatment.

Figure 24A:
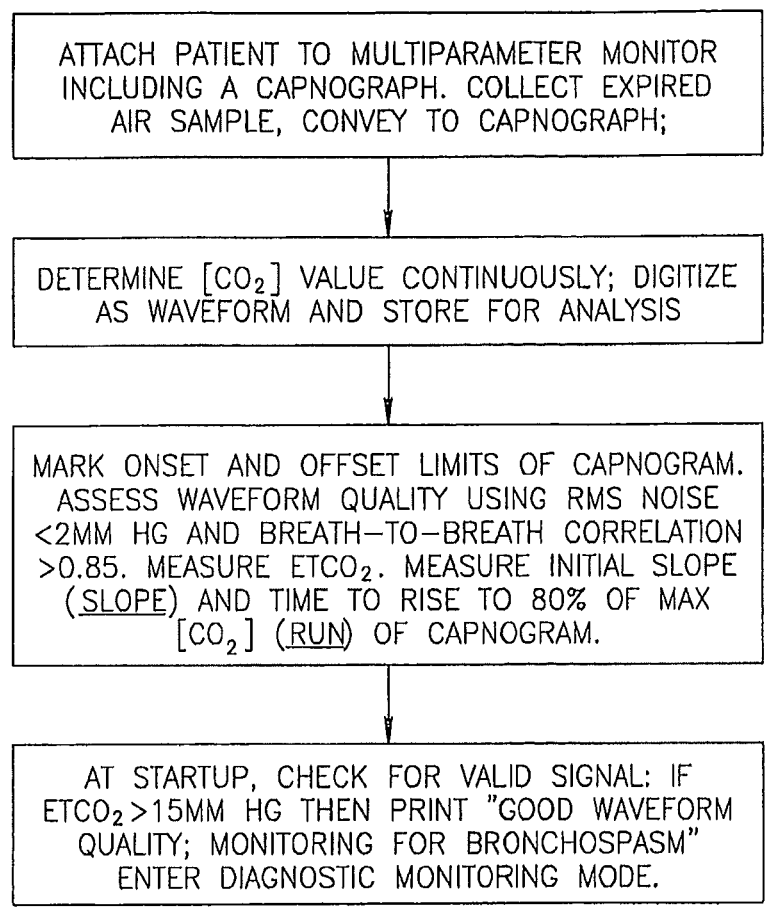
FIGS. 24A and 24B are flowcharts illustrating operation of the embodiment of FIGS. 23A and 23B.
Figure 24B:
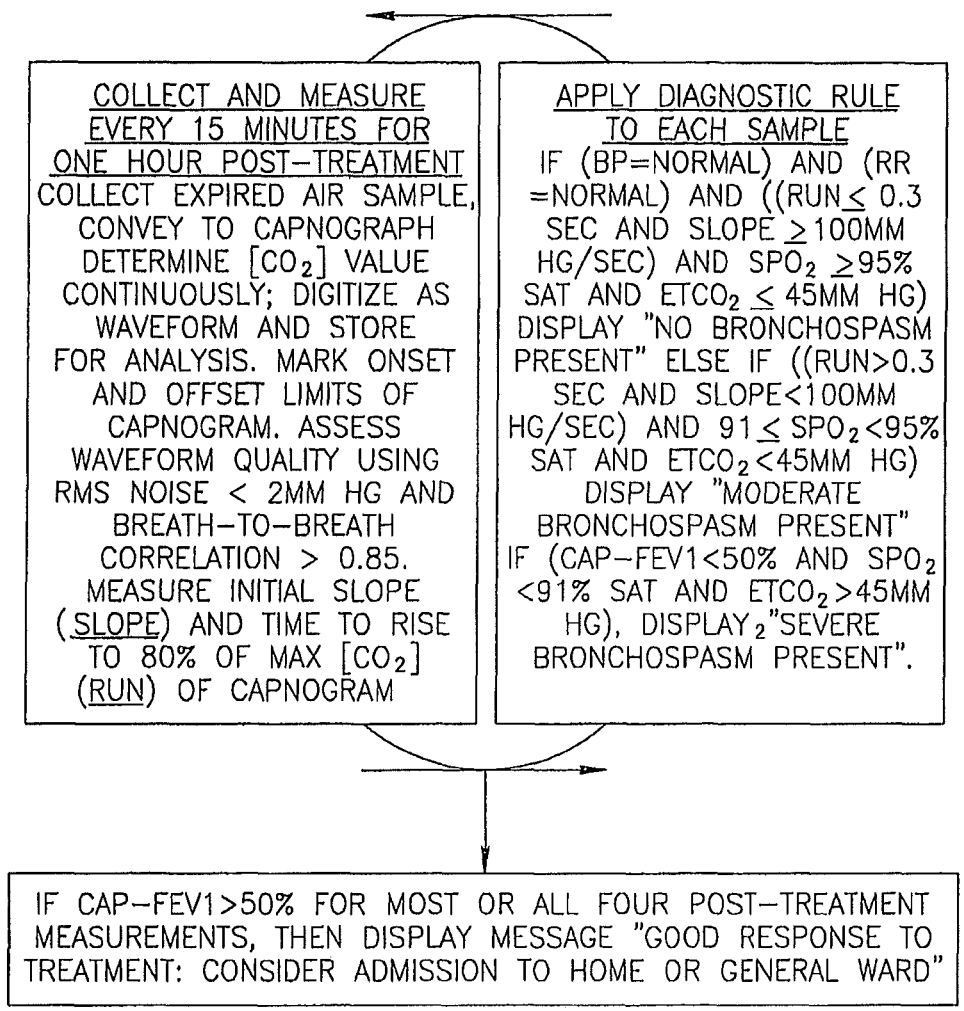

Reference is now made additionally to FIGS. 24A and 24B, which illustrate the operation of the system and methodology of the system of the present invention in the context of FIGS. 23A and 23B.

The patient in the clinical environment, preferably attached to a multi-parameter monitor including capnograph 402, is monitored continuously for at least 30 seconds. Expired air is collected via cannula 400 and is conveyed to the capnograph 402.

Values of the CO$_2$ concentration is continuously measured, typically over a period of 30 seconds, and carbon dioxide waveforms are preferably digitized as a capnogram and together with other waveforms are stored on computer 416.

The onset and offset limits of the patient's capnogram from capnograph 402 are delineated by computer 416.

The waveform quality of the capnogram is assessed by employing the criteria that an acceptable quality is defined by:
i) the root mean square (rms) of the noise of the waveform must be less than 2 mm Hg; and
ii) the breath-to-breath correlation must be greater than 0.85.

If the quality is unacceptable, further samples are collected until a sample of acceptable quality, according to the above two criteria, is taken.

The next step entails a checking procedure, wherein the ETCO$_2$ value is measured by capnograph 402. The slope and run values of the capnogram from capnograph 402 are determined by computer 416.

At startup, the following checking rule is preferably applied.
1) If:
a) the ETCO$_2$ value is more than 15 mm Hg;
a display is provided by computer 416 stating "GOOD WAVEFORM, QUALITY: MONITORING FOR BRONCHOSPASM".

If the monitoring is successful, the operator confirms this, by for example, entering the relevant code into computer 416, and capnograph 402 is then entered into a diagnostic monitoring mode. The patient is monitored continuously by capnograph 402.

Thereafter a cycle of alteting I) sampling step (data collection and measurement) and II) diagnostic rule application to the previous sample step I) is initiated. The sampling step is typically performed every 15 minutes for one hour after the treatment.

I) Sampling Step
a) A sample of expired air is taken and conveyed from cannula. 400 to capnograph 402.
b) The carbon dioxide concentration is measured continuously by capnograph 402 as a capnogram 417.
c) The capnogram is digitized as waveform and store for analysis by computer 416.
d) Computer 416 marks onset and offset limits of the capnogram.
e) The waveform quality of the capnogram is assessed by employing the criteria that an acceptable quality is defined by:
i) the root mean square (rms) of the noise of the waveform must be less than 2 mm Hg; and
ii) the breath-to-breath correlation must be greater than 0.85.
f) The slope and the run are determined by computer 416.

II) Diagnostic Rule Application Step
In a diagnostic rule application step, the following diagnostic rules are preferably applied to the measured parameters of I) Sampling step by computer 416:
I) If:
a) the blood pressure values are within the normal range;
b) the respiratory rate is normal;
c) CO$_2$ run is less than or equal to 0.3 sec;
d) CO$_2$ slope is more than or equal to 100 mm Hg/sec;

e) $SPO_2$ is greater than or equal to 95% SAT; and
f) $ETCO_2$ is less than or equal to 45 mm Hg;
then,
display 418 shows the message "NO BRONCHOSPASM PRESENT."
2) In contrast, if:
a) $CO_2$ run is greater than 0.3 sec;
b) $CO_2$ slope is less than 100 mm Hg/sec;
c) $SPO_2$ is more than or equal to 91% SAT, but less than 95% SAT; and
d) $ETCO_2$ is less than 45 mm Hg;
then,
the message "MODERATE BRONCHOSPASM PRESENT" is displayed on display 418.
3) If the parameters measured are yet further removed from the acceptable range, such as if:
a) CAP-FEV1 is less than 50%;
b) $SPO_2$ is less than 91% SAT; and
c) $ETCO_2$ is greater than 45 mm Hg;
then,
a message such as "SEVERE BRONCHOSPASM PRESENT" is displayed on display 418.

At any one of the diagnostic rule application steps, it may be verified that the patient is suffering from bronchospasm. Once bronchospasm is verified, the operator switches capnograph 402 to a serial comparison mode. The medical team applies the appropriate interventions to the patient to treat the bronchospasm.

The following rule is preferably applied to the capnogram by computer 416:
i) If:
a) the value of CAP-FEV1 is greater than 50%; and
b) the slope is greater or equal to 100 mm Hg/sec; and,
c) the angle of rise of the carbon dioxide concentration is greater than a predetermined value in degrees
then,
computer 416 displays a message on display 418: "GOOD RESPONSE TO TREATMENT: CONSIDER DISCHARGE HOME."

Figure 25A:
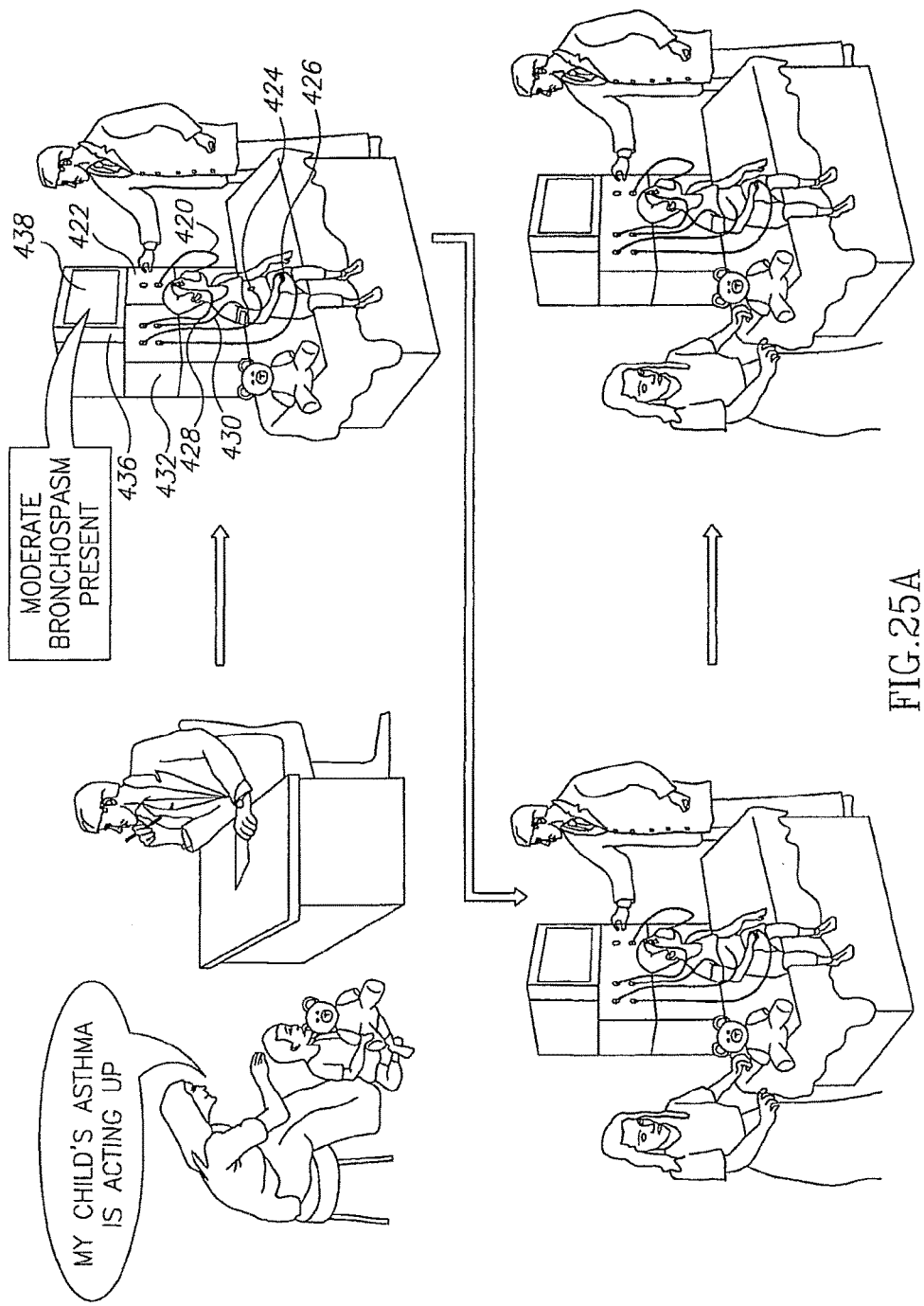
FIGS. 25A and 25B are simplified pictorial illustrations of an automatic medical diagnostic and treatment system and methodology operative in a physician's office environment for detecting the presence and severity of bronchospasm, gauging the response to treatment and recommending disposition of a spontaneously breathing patient in a second clinical scenario.
Figure 25B:
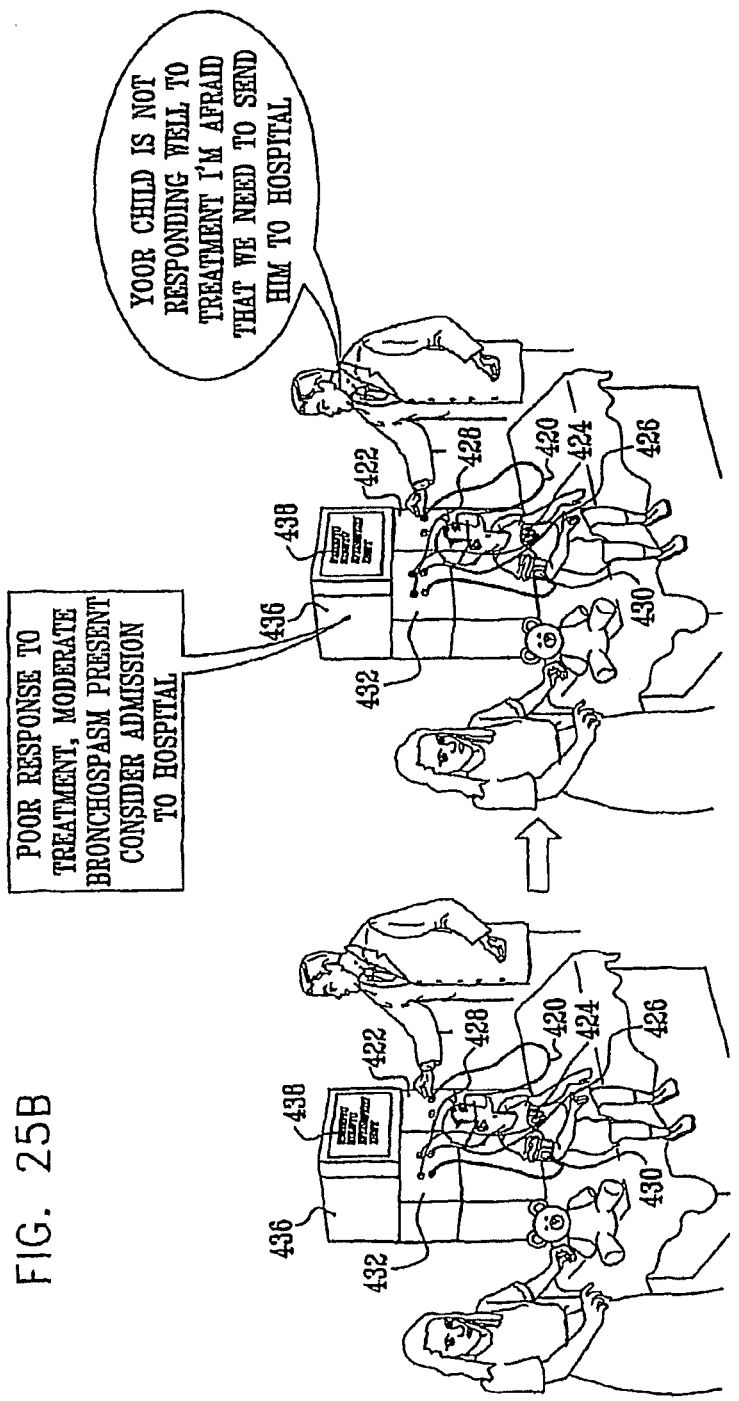

Reference is now made to FIGS. 25A and 25B, which are simplified pictorial illustrations of an automatic medical diagnostic and treatment system and methodology operative in a physician's office environment for detecting the presence and severity of bronchospasm, gauging the response to treatment and recommending disposition of a spontaneously breathing patient in a second clinical scenario. As seen in FIGS. 25A and 25B, a child having an asthma attack is brought to a physician's office. Various patient physiologic activities are sensed and measured, including respiratory physiologic activities, preferably via an oral airway adapter and/or a nasal or nasal/oral cannula 420, such as a Model Nasal FilterLine Adult XS 04461, 02/$CO_2$ Nasal FilterLine Adult 007141, or Smart CapnoLine Adult (Oral/nasal FilterLine) 007414', commercially available from Oridion Ltd., of Jerusalem Israel, typically coupled with a capnograph 422, such as a Microcap, commercially available from Oridion Ltd., of Jerusalem Israel. Other patient physiological activities relating to cardiac function (e.g. ECG), systemic oxygenation (e.g. pulse oximetry), cerebral oxygenation (e.g. cerebral oximetry) and systemic circulation (e.g. NIBP), typically sensed by means of chest electrodes 424, a finger sensor 426, a forehead/scalp sensor 428 and a blood pressure cuff 430 respectively, may also be sensed and measured by suitable instrumentation 432.

The outputs of the capnograph 422 and preferably of additional instrumentation 424 are preferably supplied to a suitably programmed automatic diagnostic and treatment computer 426 having an associated display 428, which typically analyzes the respiration parameter output of the capnograph 422 and preferably other physiologic activities and provides an output which preferably contains a diagnostic statement, here "MODERATE BRONCHOSPASM PRESENT".

The patient is given breathing treatments, such as beta agonist nebulizer treatments and following such treatments and/or in the course thereof, the physiologic activities of the patient continue to be monitored. This monitoring is employed by computer 426 to indicate the response to the breathing treatments and the current status of the bronchospasm condition. When the breathing treatments are not successful, a status message, here "POOR RESPONSE TO TREATMENT", is presented accompanied by a disposition recommendation, here "CONSIDER ADMISSION TO HOSPITAL" and the physician may send the child to the hospital.

Figure 26A:
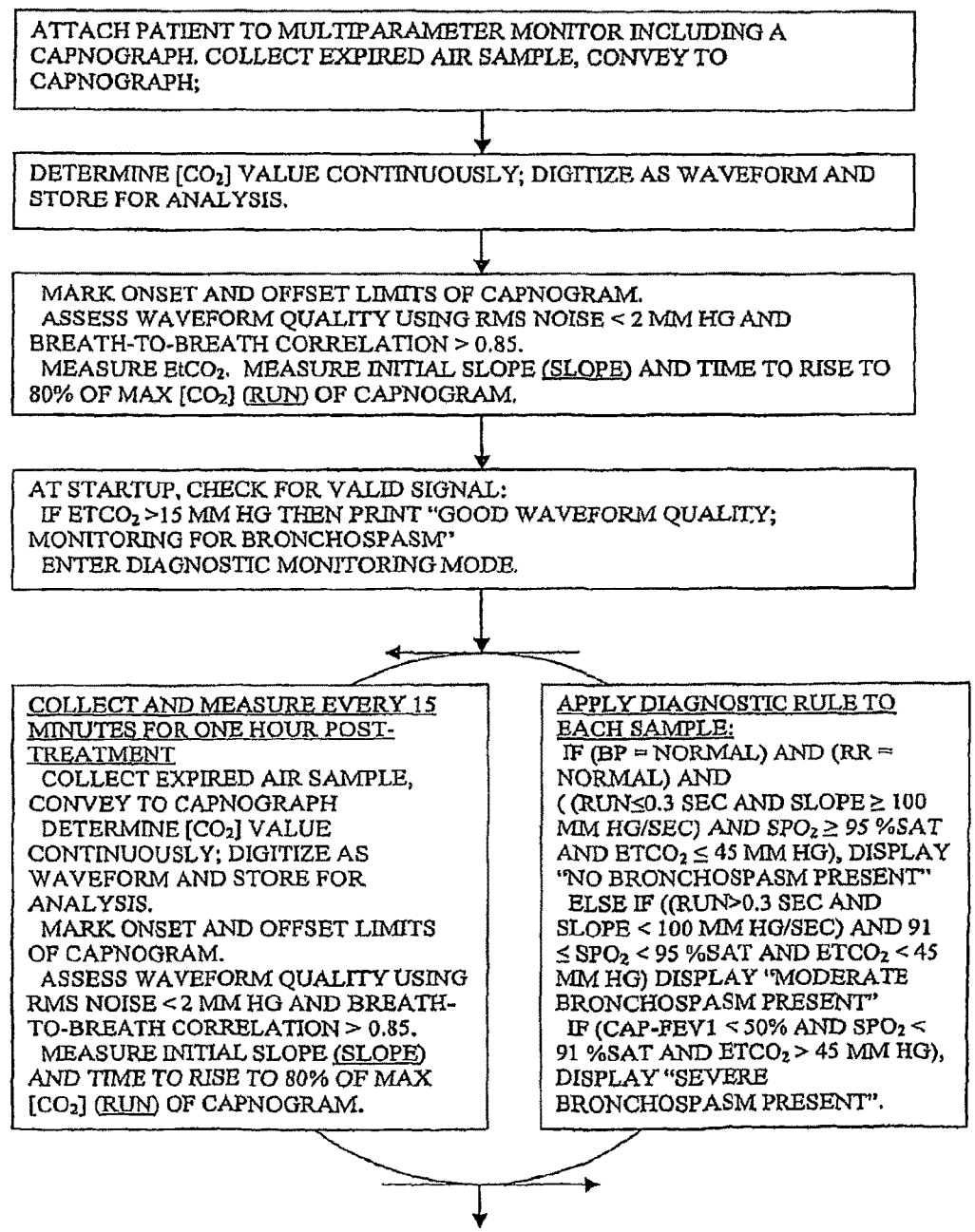

Reference is now made additionally to FIGS. 26A and 26B, which illustrate the operation of the system and methodology of the system of the present invention in the context of FIGS. 25A and 25B.

The patient in the clinical environment, preferably attached to a multi-parameter monitor including capnograph 422, is monitored continuously for at least 30 seconds. Expired air is collected via cannula 420 and is conveyed to the capnograph 422.

Values of the $CO_2$ concentration is continuously measured, typically over a period of 30 seconds, and carbon dioxide waveforms are preferably digitized as a capnogram and together with other waveforms are stored on computer 426.

The onset and offset limits of the patient's capnogram from capnograph 422 are delineated by computer 426.

The waveform quality of the capnogram is assessed by employing the criteria that an acceptable quality is defined by:
i) the root mean square (rms) of the noise of the waveform must be less than 2 mm Hg; and
ii) the breath-to-breath correlation must be greater than 0.85.

If the quality is unacceptable, further samples are collected until a sample of acceptable quality, according to the above two criteria, is taken.

The next step entails a checking procedure, wherein the $ETCO_2$ value is measured by capnograph 422. The slope and run values of the capnogram from capnograph 422 are determined by computer 426.

At startup, the following checking rule is preferably applied.
1) If:
a) the $ETCO_2$ value is more than 15 mm Hg;
a display is provided by computer 426 stating "GOOD WAVEFORM, QUALITY: MONITORING FOR BRONCHOSPASM".

If the monitoring is successful, the operator confirms this, by for example, entering the relevant code into computer 426, and capnograph 422 is then entered into a diagnostic monitoring mode. The patient is monitored continuously by capnograph 422.

Thereafter a cycle of alteting I) sampling step (data collection and measurement) and II) diagnostic rule application to the previous sample step I) is initiated. The sampling step is typically performed every 15 minutes for one hour after the treatment.

I) Sampling Step a) A sample of expired air is taken and conveyed from cannula 420 to capnograph 422.

b) The carbon dioxide concentration is measured continuously by capnograph 422 as a capnogram.

c) The capnogram is digitized as waveform and store for analysis by computer 426.

d) Computer 426 marks onset and offset limits of the capnogram.

e) The waveform quality of the capnogram is assessed by employing the criteria that an acceptable quality is defined by:

i) the root mean square (rms) of the noise of the waveform must be less than 2 mm Hg; and ii) the breath-to-breath correlation must be greater than 0.85.

f) The slope and the run are determined by computer 426.

II) Diagnostic Rule Application Step

In a diagnostic rule application step, the following diagnostic rules are preferably applied to the measured parameters of I) Sampling step by computer 426:

1) If:
a) the blood pressure values are within the normal range;
b) the respiratory rate is normal;
c) $CO_2$ run is less than or equal to 0.3 sec;
d) $CO_2$ slope is more than or equal to 100 mm Hg/sec;
e) $SPO_2$ is greater than or equal to 95% SAT; and
f) $ETCO_2$ is less than or equal to 45 mm Hg;
then,
display 428 shows the message "NO BRONCHOSPASM PRESENT."

2) In contrast, if:
a) $CO_2$ run is greater than 0.3 sec;
b) $CO_2$ slope is less than 100 mm Hg/sec;
c) $SPO_2$ is greater than or equal to 91% SAT, but less than 95% SAT; and
d) $ETCO_2$ is less than 45 mm Hg;
then,
the message "MODERATE BRONCHOSPASM PRESENT" is displayed on display 428.

3) If the parameters measured are yet further removed from the acceptable range, such as if:
a) CAP-FEV1 is less than 50%;
b) $SPO_2$ is less than 91% SAT; and
c) $ETCO_2$ is greater than 45 mm Hg;
then,
a message such as "SEVERE BRONCHOSPASM PRESENT" is displayed on display 428.

At any one of the diagnostic rule application steps, it may be verified that the patient is suffering from bronchospasm. Once bronchospasm is verified, the operator switches capnograph 422 to a serial comparison mode. The medical team applies the appropriate interventions to the patient to treat the bronchospasm.

The following rule is preferably applied to the capnogram by computer 426:

1) If:
a) the value of CAP-FEV1 is less than 50%; and
b) the slope is less than 100 mm Hg/sec; and,
c) the angle of rise of the carbon dioxide concentration is less than a predetermined value in degrees;
then,
computer 426 displays a message on display 428: "POOR RESPONSE TO TREATMENT: CONSIDER ADMISSION TO HOSPITAL INTENSIVE CARE."

Figure 27A:
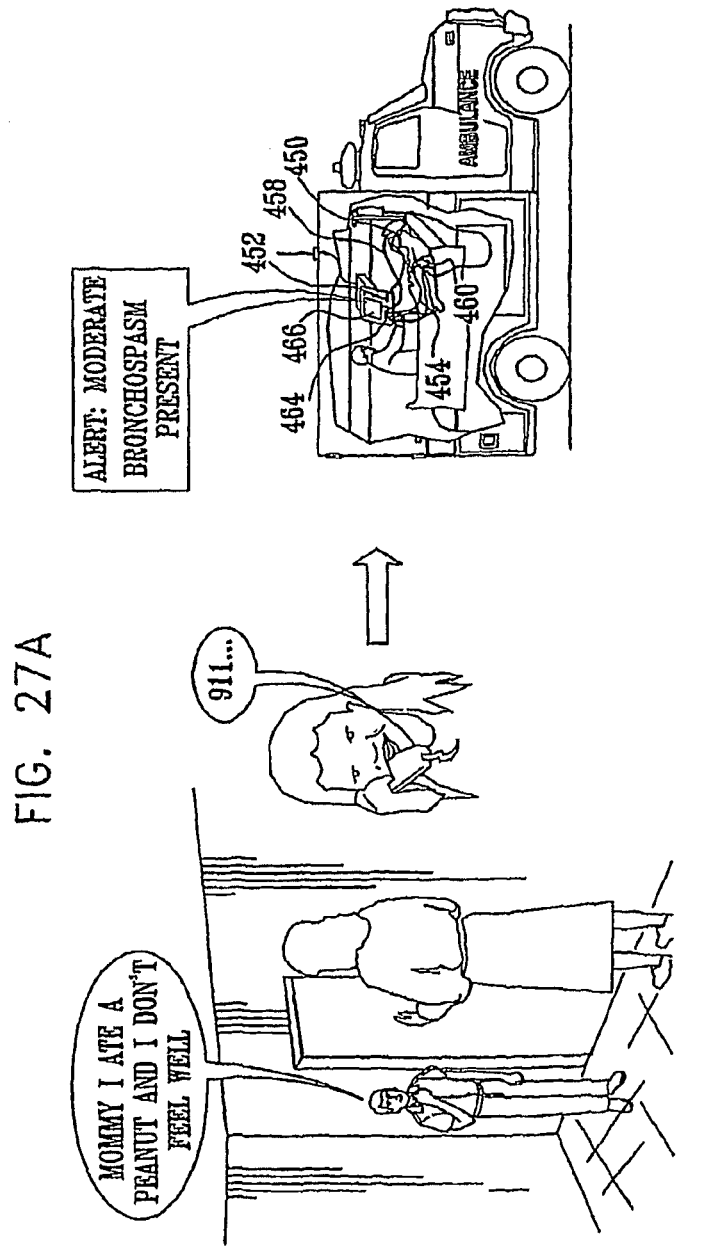
Figure 27B:
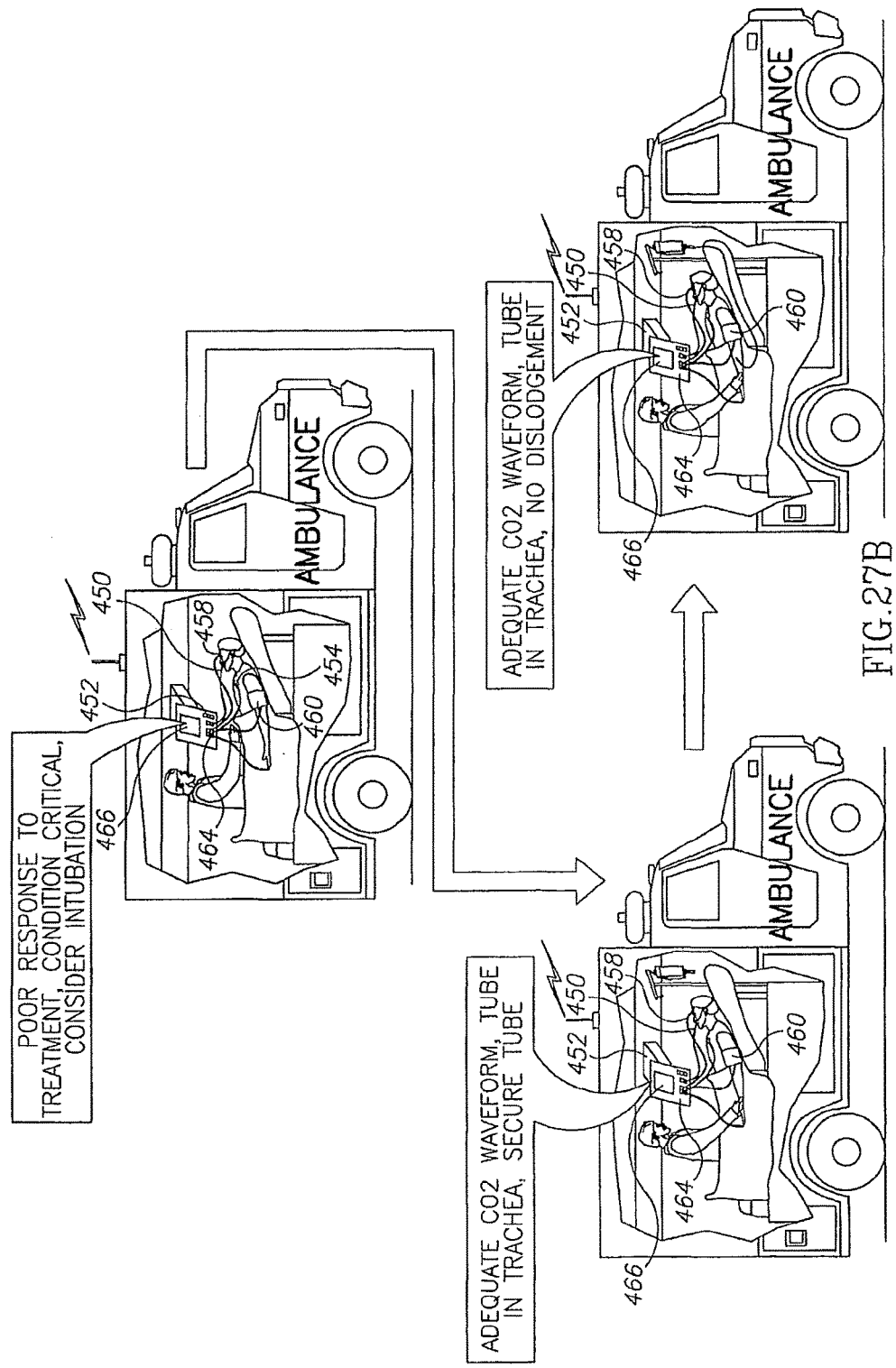

Reference is now made to FIGS. 27A and 27B, which are simplified pictorial illustrations of an automatic medical diagnostic and treatment system and methodology in an ambulance environment for detecting the presence and severity of bronchospasm from an allergic reaction, gauging the response to treatment and recommending disposition. As seen in FIGS. 27A and 27B, a child complains of difficulty breathing. The parent summons an ambulance and similarly to that described hereinabove with reference to FIG. 9, in an ambulance environment various patient physiologic activities are sensed and measured, including respiratory physiologic activities, preferably via an oral airway adapter and/or a nasal or nasal/oral cannula 450, such as a Model Nasal FilterLine Adult XS 04461, $O_2/CO_2$ Nasal FilterLine Adult 007141, or Smart CapnoLine Adult (Oral/nasal FilterLine) 007414, commercially available from Oridion Ltd., of Jerusalem Israel, typically coupled with a capnograph 452, such as a Microcap, commercially available from Oridion Ltd., of Jerusalem Israel. Other patient physiologic activities relating to cardiac function (e.g. ECG), systemic oxygenation (e.g. pulse oximetry), cerebral oxygenation (e.g. cerebral oximetry) and systemic circulation (e.g. NIBP), typically sensed by means of chest electrodes 454, a finger sensor 456, a forehead/scalp sensor 458 and a blood pressure cuff 460 respectively, may also be sensed and measured by suitable instrumentation 462. Other patient physiologic activities relating to cardiac function (e.g. ECG), cerebral perfusion (e.g. CEREBRAL OXIMETRY), oxygenation (e.g. pulse oximetry) and systemic circulation (e.g. NIBP), may also be sensed and measured by suitable instrumentation 462.

The outputs of the capnograph 452 and preferably of additional instrumentation 462 are preferably supplied to a suitably programmed automatic diagnostic and treatment computer 464 having an associated display 466, which typically analyzes the respiration parameter output of the capnograph 452 and preferably other physiologic activities and provides an output which preferably contains a diagnostic statement indicating the presence of lower airway obstruction, here "ALERT: MODERATE BRONCHOSPASM PRESENT". The presence of bronchospasm definitively indicates lower airway obstruction.

The patient is given breathing treatment, such as a beta agonist nebulizer treatment and following such treatment and/or in the course thereof, the physiologic activities of the patient continue to be monitored. This monitoring is employed by computer 464 to indicate the response to the breathing treatment and the current status of the patient condition. In the scenario of FIGS. 14A and 14B, the patient fails to respond sufficiently to the breathing treatment and this is indicated by a status change statement, here "POOR RESPONSE TO TREATMENT, CONDITION CRITICAL". A treatment recommendation may also be provided, such as "CONSIDER INTUBATION".

Intubation is performed and correct initial tube placement is confirmed followed by continuous monitoring of the physiologic activities of the patient, which indicate current tube position. In this scenario, where intubation is successful, a status statement, here: "ADEQUATE $CO_2$ WAVEFORM-TUBE IN TRACHEA" and a treatment recommendation, here "SECURE TUBE" appear.

Following successful intubation, continuous monitoring may provide a status statement such as "ADEQUATE $CO_2$ WAVEFORM-TUBE IN TRACHEA-NO DISLOGEMENT". If tube dislodgment occurs at any time following intubation, a status statement would appear, such as "$CO_2$ WAVEFORM ABSENT" preferably accompanied by a treatment recommendation, such as "CHECK FOR TUBE DISLOGEMENT".

Preferably some or all of the outputs of computer 464 are transmitted in a wireless manner by a transmitter 468, such as via radio or a cellular telephone link, preferably to a dispatch center or patient receiving facility.

Figure 28:
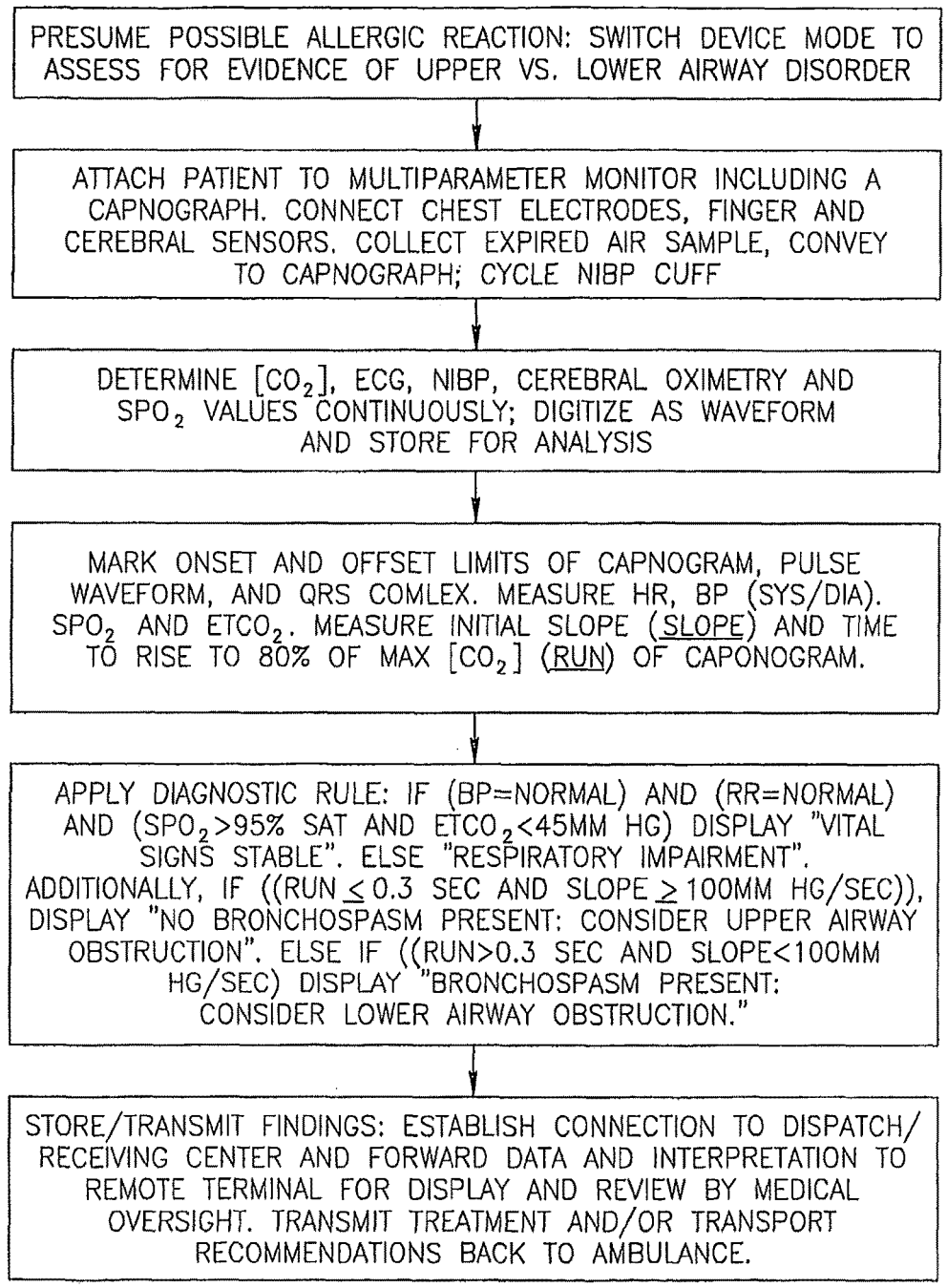
FIG. 28 is a flowchart illustrating operation of the embodiment of FIGS. 27A and 27B.

Reference is now made additionally to FIG. 28, which illustrates the operation of the system and methodology of the system of the present invention in the context of FIGS. 27A and 27B. FIG. 28 illustrates an example of the system and methodology applied to assessing whether a patient has an upper or lower airway obstruction, in the duration of the patient being transferred by ambulance.

In the scenario described in FIGS. 27A and 27B hereinabove, it is presumed that the patient may be having an allergic reaction. The operator switches capnograph 452 into an assessing mode so as to enable an assessment to be made whether and if the patient has an upper or a lower airway disorder.

The patient previously attached to a multi-parameter monitor including a capnograph 452 and suitable instrumentation 462, by means of cannula 450 and preferably also by means of chest electrodes 454, finger sensor 456, forehead sensor 458 and blood pressure cuff 460, is monitored continuously for at least thirty seconds. Neurological status of the patient is acquired by any suitable technique, including visual and electroencephalograph (EEG) monitoring. Values of $CO_2$ concentration, ECG, NIBP and (the percent saturation of the hemoglobin molecule with oxygen) $SPO_2$ are continuously monitored, and carbon dioxide waveforms are preferably digitized as a capnogram 452 and together with other waveforms are stored in computer 464.

At least one expired air sample is collected and conveyed for analysis by capnograph 452. The outputs of the capnograph 452 and possibly of additional instrumentation 462 are preferably supplied to suitably programmed automatic diagnostic and treatment computer 464, having associated display 466, which typically analyzes the respiration parameter output of the capnograph 452.

In an analyzing step, the onset and offset limits of a capnogram 469, pulse waveforms, and the QRS complex (of the ECG) are marked by computer 464. The actual parameters measured include, but are not limited to heart rate (HR), BP, the systolic to diastolic ratio (SYS/DIA). $SPO_2$, AND $ETCO_2$. The slope of $CO_2$ (mm Hg/sec), and $CO_2$ "run", of the capnogram 469, measured to 80% of maximum $CO_2$ concentration, are calculated by computer 464.

Following each treatment, the differences between consecutive measurements of the various patient parameters are computed by computer 464. Thereafter, in a diagnostic rule application step, the following diagnostic rules are preferably applied to the measured parameters by computer 464:

1) If:
a) the blood pressure values are within the normal range;
b) the respiratory rate is normal; and
c) $ETCO_2$ is less than 45 mm Hg;
then,
display 466 shows the message "VITAL SIGNS STABLE".

2) In contrast, if:
1) If:
a) the blood pressure values are not within the normal range;
b) the respiratory rate is not normal; and
c) $ETCO_2$ is more than or equal to 45 mm Hg;
then,
display 466 shows the message "RESPIRATORY IMPAIRMENT".

Additionally, the following rules may also be applied:
3) If:
a) $CO_2$ run is less than or equal to 0.3 sec; and
b) $CO_2$ slope is more than or equal to 100 mm Hg/sec;
then,
display 466 shows the message "NO BRONCHOSPASM PRESENT: CONSIDER UPPER AIRWAY OBSTRUCTION".

4) If:
a) $CO_2$ run is more than 0.3 sec;
b) $CO_2$ slope is less than 100 mm Hg/sec;
then,
display 466 shows the message "BRONCHOSPASM PRESENT: CONSIDER LOWER AIRWAY OBSTRUCTION".

The findings of the last stage are stored by computer 464 and/or transmitted via transmitter 468 to a dispatch/receiving center, typically located at a hospital or medical center. A connection is established with the dispatch/receiving center, and the data is forwarded thereto. A medical supervisor typically watches display of the received data, and consequentially transmits the recommended treatment and/or transport recommendations back to the ambulance.

After each time interval, the difference between consecutive measures of each parameter are calculated by computer 464: Thereafter, the following monitoring rules are preferably applied to the measured parameters by computer 464.

1) If:
a) the difference in the run values is greater than +0.1 sec; and
b) the difference in the slope is more negative than −15 mm Hg/sec; then,
computer 464 displays on display 466 "BRONCHOSPASM WORSENING".

2) If:
a) the difference in the run values is more negative than −0.1 sec; and
b) the difference in the slope is more positive than +15 mm Hg/sec;
then,
computer 464 displays on display 466 "BRONCHOSPASM IMPROVING".

3) If:
a) the difference in the run is greater or equal to −0.1 sec, but less than or equal to +0.1 Sec; or
b) the difference in the slope is more than or equal to −15 mm Hg/sec and less than or equal to +15 mm Hg/sec;
then,
computer 464 displays on display 466 "BRONCHOSPASM UNCHANGED".

The change in patient's vital functional activities, including $SPO_2$ and $ETCO_2$, over the time interval are calculated by computer 464.

4) If:
a) the decrease in $SPO_2$ is more negative than −5% SAT; or
b) the increase in the $ETCO_2$ is more than +5 mm Hg;
then,
computer 184 displays on display 186 "VITAL SIGNS DETERIORATING."

5) If:
a) the increase in $SPO_2$ is more than +5% SAT; or
b) the decrease in the $ETCO_2$ is more than −5 mm Hg;
then,
computer 464 displays on display 466 "VITAL SIGNS IMPROVING".

6) If:
a) the change in $SPO_2$ is greater than or equal to −5% SAT, but less than or equal to +5% SAT, or
b) the change in the $ETCO_2$ is more than or equal to −5 mm Hg, but less than or equal to +5 mm Hg;
then,
computer 464 displays on display 466 "VITAL SIGNS UNCHANGED."

Computer 464 preferably combines the results of these monitoring rules to display an integrated display 466 such as "BRONCHOSPASM WORSENING; VITAL SIGNS UNCHANGED."

In a checking rule step, the following rule is preferably applied:
1) A patient appears to be entering respiratory failure phase if:
a) the $SPO_2$ is less than 90% SAT;
b) the respiratory rate is less than 8/min;
c) $ETCO_2$ is greater than 60 mm Hg; and
d) the patient's neurological symptoms are qualified as being "bad";
then,
computer 464 displays "RESPIRATORY FAILURE; CONDITION CRITICAL; CONSIDER INTUBATION." on display 466.

Following this, in an alert data transmission stage, a high priority update is transmitted via transmitter 468 from computer 464 to notify the dispatch/receiving centers of the significant deterioration and change in the patient's condition.

Once these changes in the patient's condition have been confirmed by an operator, the patient is consequentially intubated according to standard techniques and capnograph 452 is activated in intubation monitoring mode by computer 464. Once the successful intubation of the patient is verified by data comparison of the patient's capnogram and standardized capnograms for intubation in computer 464, the computer displays "MONITORING FOR INTUBATION".

Thereafter, the following check rule is preferably applied to the patient's capnogram:
1. If:
a) $ETCO_2$ is greater than 15 mm Hg;
then
computer 464 displays "GOOD WAVEFORM, TUBE IN TRACHEA. CONFIRM AND SECURE TUBE."

In the next step, the following monitoring rules are preferably applied to the patient's capnogram:
1) If:
a) the value of $ETCO_2$ is greater than 15 mm Hg;
then,
computer 214 displays "MONITORING TUBE POSITION: NO DISLODGEMENT" on display 216.

2) If:
a) the value of $ETCO_2$ is less than or equal to 15 mm Hg; or
b) there is a loss of the waveform;
then,
computer 464 displays "ALERT: CHECK FOR TUBE DISLODGEMENT" on display 466.

Computer 464 transmits the data monitored via transmitter 468 to the receiving center. The receiving center periodically receives updates of the patient's condition, who is in the ambulance en route to the hospital, in order to prepare in the most fitting and efficient transfer of the patient upon arrival to the hospital.

A copy of the patient's record is handed off from computer 464 via transmitter 468 to the receiving center, for example, in the form of a chart. Typically, the receiving center stores this chart, so that it may be used as a baseline for continued monitoring of the patient.

Figure 29:
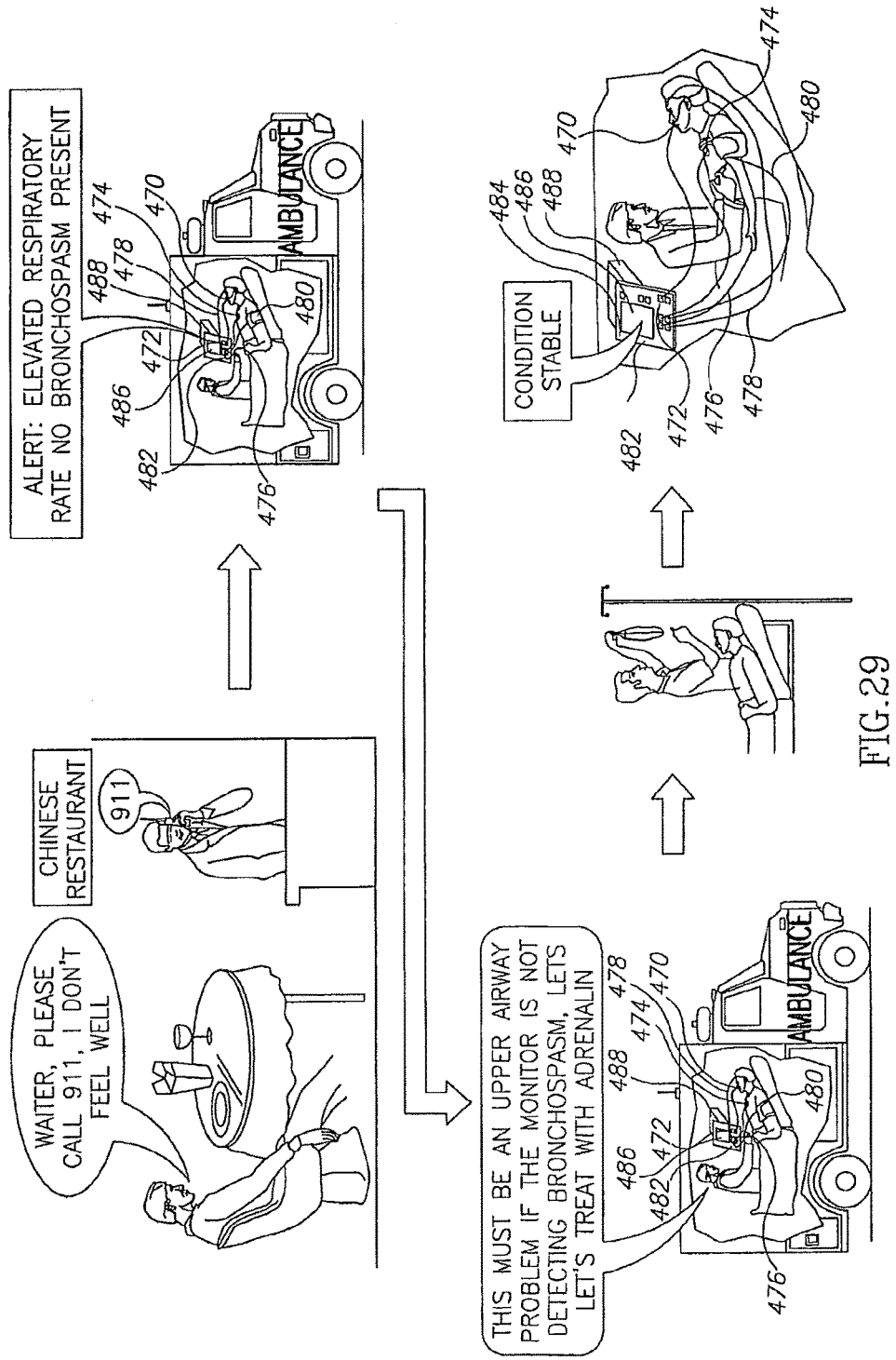
FIG. 29 is a simplified pictorial illustration of an automatic medical diagnostic and treatment system and methodology in an ambulance environment for distinguishing between upper airway obstruction and lower airway obstruction, gauging the response to treatment and recommending disposition.

Reference is now made to FIG. 29, which is a simplified pictorial illustration of an automatic medical diagnostic and treatment system and methodology in an ambulance environment for distinguishing between upper airway obstruction and lower airway obstruction, such as distinguishing between asthma and croup, bronchiolitis and croup, and allergic reactions affecting the upper or lower airways. As seen in FIG. 29, a person complains of difficulty breathing. An ambulance is summoned and similarly to that described hereinabove with reference to FIG. 17, in an ambulance environment various patient physiologic activities are sensed and measured, including respiratory physiologic activities, preferably via an oral airway adapter and/or a nasal or nasal/oral cannula 470, such as a Model Nasal FilterLine Adult XS 04461, $O_2/CO_2$Nasal FilterLine Adult 007141, or Smart CapnoLine Adult (Oral/nasal FilterLine) 007414, commercially available from Oridion Ltd., of Jerusalem Israel, typically coupled with a capnograph 472, such as a Microcap, commercially available from Oridion Ltd., of Jerusalem Israel. Other patient physiologic activities relating to cardiac function (e.g. ECG), systemic oxygenation (e.g. pulse oximetry), cerebral oxygenation (e.g. cerebral oximetry) and systemic circulation (e.g. NIBP), typically sensed by means of chest electrodes 474, a finger sensor 476, a forehead/scalp sensor 478 and a blood pressure cuff 480 respectively, may also be sensed and measured by suitable instrumentation 482. Other patient physiologic activities relating to cardiac function (e.g. ECG), cerebral perfusion (e.g. CEREBRAL OXIMETRY), oxygenation (e.g. pulse oximetry) and systemic circulation (e.g. NIBP), may also be sensed and measured by suitable instrumentation 482.

The outputs of the capnograph 472 and preferably of additional instrumentation 482 are preferably supplied to a suitably programmed automatic diagnostic and treatment computer 484 having an associated display 486, which typically analyzes the respiration parameter output of the capnograph 472 and preferably other physiologic activities and provides an output which preferably contains a diagnostic statement differentiating upper airway obstruction from lower airway obstruction, here "ELEVATED RESPIRATORY RATE. NO BRONCHOSPASM PRESENT". The absence of bronchospasm in this scenario strongly suggests upper airway obstruction.

The patient is given an intravenous or intra-muscular medication, such as adrenaline, and following such treatment and/or in the course thereof, the physiologic activities of the patient continue to be monitored. This monitoring is employed by computer 484 to indicate the response to the treatment and the current status of the patient condition. In the scenario of FIG. 29, the patient responds to the treatment and this is indicated by a status change statement, here "CONDITION STABLE". Preferably some or all of the outputs of computer 484 are transmitted in a wireless manner by a transmitter 488, such as via radio or a cellular telephone link, preferably to a dispatch center or patient receiving facility.

Figure 30:
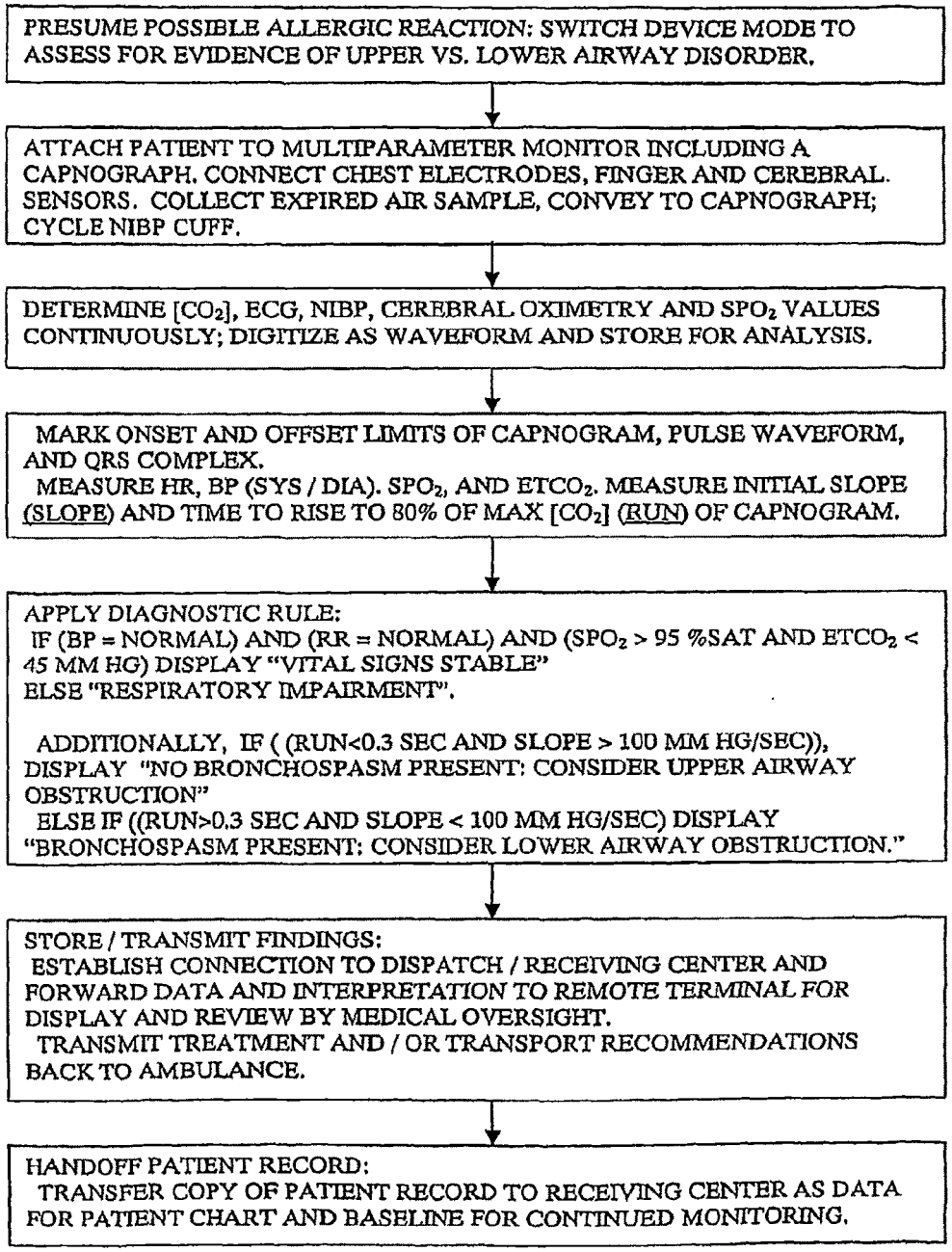
FIG. 30 is a flowchart illustrating operation of the embodiment of FIG. 29.

Reference is now made additionally to FIG. 30, which illustrates the operation of the system and methodology of the system of the present invention in the context of FIG. 29. The patient is treated in an ambulance environment as is described hereinabove in FIG. 29, and the patient is being assessed to see whether his/her upper or lower airway is obstructed. The methodology illustrates the case where an upper obstruction is found.

In the scenario described in FIG. 29 hereinabove, it is presumed that the patient may be having an allergic reaction. The operator switches capnograph 452 into an assessing mode so as to enable an assessment to be made whether and if the patient has an upper or a lower airway disorder.

The patient previously attached to a multi-parameter monitor including a capnograph 472 and suitable instrumentation 482, by means of cannula 470 and preferably also by means of chest electrodes 474, finger sensor 476, forehead sensor 478 and blood pressure cuff 480, is monitored continuously for at least thirty seconds. Neurological status of the patient is acquired by any suitable technique, including visual and electroencephalograph (EEG) monitoring. Values of $CO_2$ concentration, ECG, NIBP and $SPO_2$ are continuously monitored, and carbon dioxide waveforms are preferably digitized as a capnogram 472 and together with other waveforms are stored in computer 484.

At least one expired air sample is collected and conveyed for analysis by capnograph 472. The outputs of the capnograph 472 and possibly of additional instrumentation 482 are preferably supplied to suitably programmed automatic diagnostic and treatment computer 484, having associated display 486, which typically analyzes the respiration parameter output of the capnograph 472.

In an analyzing step, the onset and offset limits of a capnogram 489, pulse waveforms, and the QRS complex (of the ECG) are marked by computer 484. The actual parameters measured include, but are not limited to heart rate (HR), BP, the systolic to diastolic ratio (SYS/DIA). $SPO_2$, AND $ETCO_2$. The slope of $CO_2$ (mm Hg/sec), and $CO_2$ "run", of the capnogram 489, measured to 80% of maximum $CO_2$ concentration, are calculated by computer 484.

Following each treatment, the differences between consecutive measurements of the various patient parameters are computed by computer 484. Thereafter, in a diagnostic rule application step, the following diagnostic rules are preferably applied to the measured parameters by computer 484:

1) If:
a) the blood pressure values are within the normal range;
b) the respiratory rate is normal; and
c) $ETCO_2$ is less than 45 mm Hg;
then,
display 486 shows the message "VITAL SIGNS STABLE".

2) In contrast, if:
1) If:
a) the blood pressure values are not within the normal range;
b) the respiratory rate is not normal; and
c) $ETCO_2$ is more than or equal to 45 mm Hg;
then,
display 486 shows the message "RESPIRATORY IMPAIRMENT".

Additionally, the following rules may also be applied:
3) If:
a) $CO_2$ run is less than 0.3 sec;
b) $CO_2$ slope is more than 100 mm Hg/sec;
then,
display 486 shows the message "NO BRONCHOSPASM PRESENT".

4) If:
a) $CO_2$ run is more than 0.3 sec;
b) $CO_2$ slope is less than 100 mm Hg/sec;
then,
display 486 shows the message "BRONCHOSPASM PRESENT: CONSIDER LOWER AIRWAY OBSTRUCTION".

The findings of the last stage are stored by computer 484 and/or transmitted via transmitter 488 to a dispatch/receiving center, typically located at a hospital or medical center. A connection is established with the dispatch/receiving center, and the data is forwarded thereto. A medical supervisor typically watches display of the received data, and consequentially transmits the recommended treatment and/or transport recommendations back to the ambulance.

A copy of the patient's record is handed off from computer 464 via transmitter 488 to the receiving center, for example, in the form of a chart. Typically, the receiving center stores this chart, so that it may be used as a baseline for continued monitoring of the patient.

Figure 31:
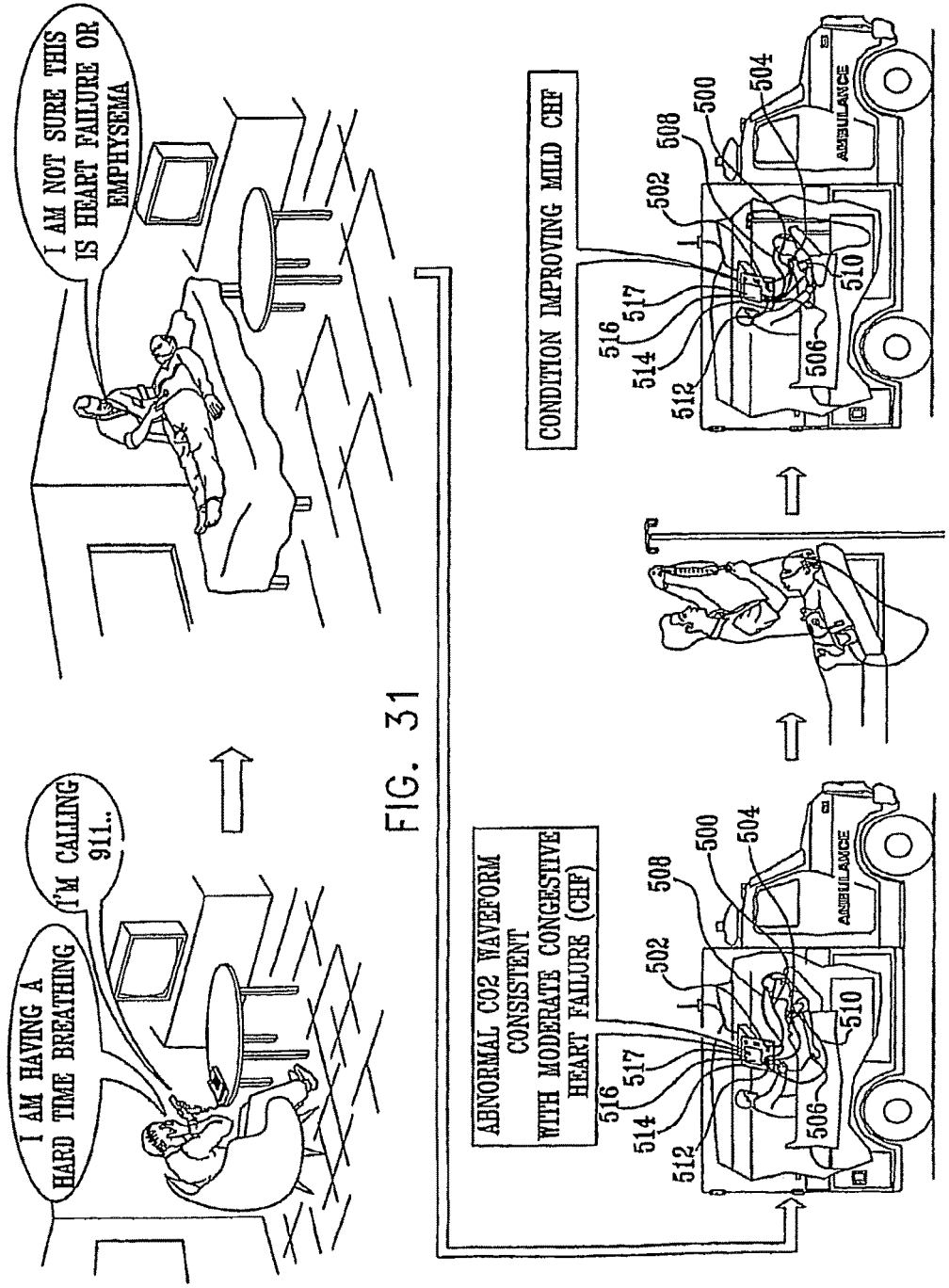
FIG. 31 is a simplified pictorial illustration of an automatic medical diagnostic and treatment system and methodology operative in a hospital environment for distinguishing between heart failure and emphysema in a scenario in which heart failure is present.

Reference is now made to FIG. 31, which is a simplified pictorial illustration of an automatic medical diagnostic and treatment system and methodology for distinguishing between heart failure and emphysema in a scenario in which heart failure is present. As seen in FIG. 31, various patient physiologic activities are sensed and measured, including respiratory physiologic activities, preferably via an oral airway adapter and/or a nasal or nasal/oral cannula 500, such as a Model Nasal FilterLine Adult XS 04461, $O_2/CO_2$ Nasal FilterLine Adult 007141, or Smart CapnoLine Adult (Oral/nasal. FilterLine) 007414, commercially available from Oridion Ltd., of Jerusalem Israel, typically coupled with a capnograph 502, such as a Microcap®, commercially available from Oridion Ltd., of Jerusalem Israel. Other patient physiologic activities relating to cardiac function (e.g. ECG), systemic oxygenation (e.g. pulse oximetry), cerebral oxygenation (e.g. cerebral oximetry) and systemic circulation (e.g. NIBP), typically sensed by means of chest electrodes 504, a finger sensor 506, a forehead/scalp sensor 508 and a blood pressure cuff 510 respectively, may also be sensed and measured by suitable instrumentation 512.

The outputs of the capnograph 502 and possibly of additional instrumentation 512 are preferably supplied to a suitably programmed automatic diagnostic and treatment computer 514, having an associated display 516 which typically analyzes the respiration parameter output of the capnograph 517 and possibly other parameters and provides an output which preferably contains a diagnostic statement differentiating heart failure from emphysema, here "ABNORMAL $CO_2$ WAVEFORM CONSISTENT WITH MODERATE CONGESTIVE HEART FAILURE".

This diagnostic statement indicates that treatment is required for heart failure rather than for emphysema. Intravenous and/or sublingual medications such as nitroglycerin, morphine and LASIX® are administered after which a diagnostic statement which indicates the patient status and the severity of the cardio-respiratory condition is preferably presented, here "MILD CONGESTIVE HEART FAILURE, CONDITION IMPROVING"

Figure 32A:
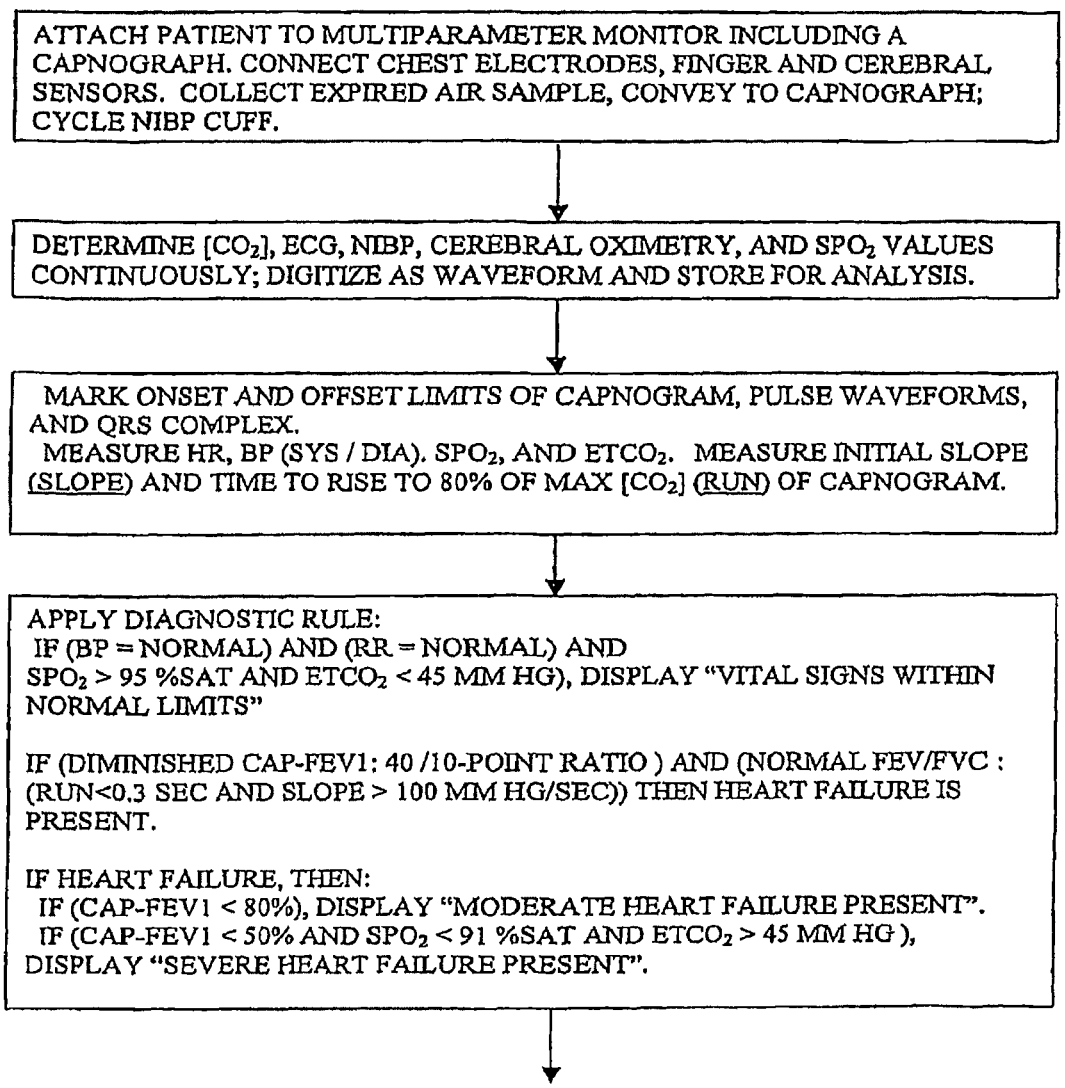
FIGS. 32A and 32B are flowcharts illustrating operation of the embodiment of FIG. 31.
Figure 32B:
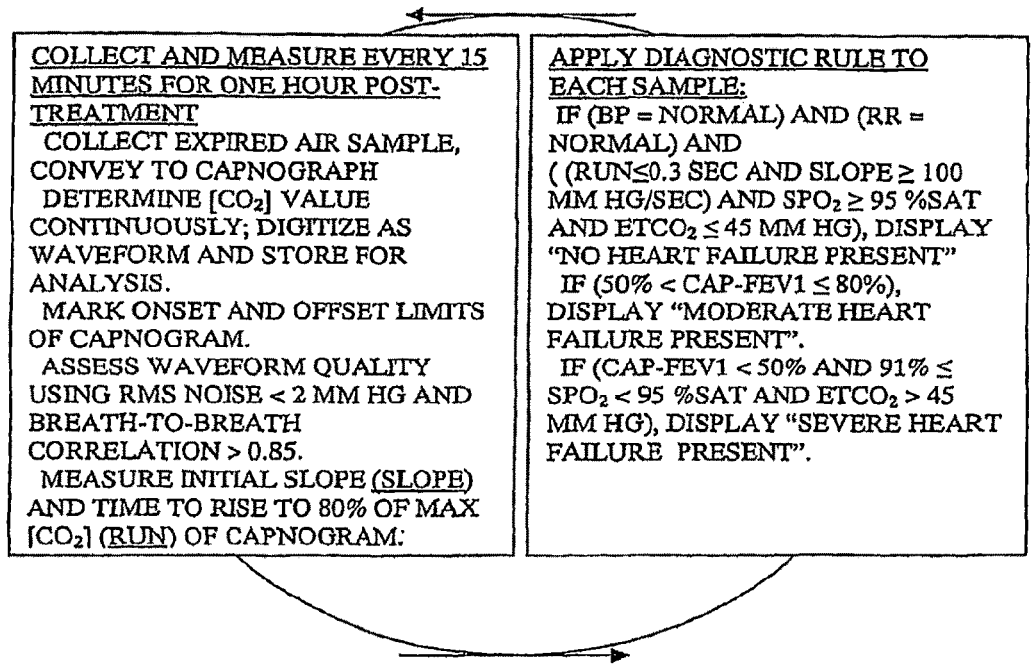

Reference is now made additionally to FIGS. 32A and 32B, which illustrate the operation of the system and methodology of the system of the present invention in the context of FIG. 31. The patient is treated in an ambulance environment as is described hereinabove in FIG. 15, and the patient is being assessed to see whether his/her upper or lower airway is obstructed. The methodology illustrates the case where an upper obstruction is found.

In the scenario described in FIG. 31 hereinabove, it is presumed that the patient may be suffering from either emphysema or a heart failure in an ambulance. It is shown hereinbelow how the patient is diagnosed as having a heart failure.

The patient, previously attached to a multi-parameter monitor including a capnograph 502 and suitable instrumentation 512, by means of cannula 500 and preferably also by means of chest electrodes 504, finger sensor 506, forehead sensor 508 and blood pressure cuff 510, is monitored continuously for at least thirty seconds. Neurological status of the patient is acquired by any suitable technique, including visual and electroencephalograph (EEG) monitoring. Values of $CO_2$ concentration, ECG, NIBP and $SPO_2$ are continuously monitored, and carbon dioxide waveforms are preferably digitized as a capnogram 517 and together with other waveforms are stored in computer 514.

At least one expired air sample is collected and conveyed for analysis by capnograph 472. The outputs of the capnograph 502 and possibly of additional instrumentation 512 are preferably supplied to suitably programmed automatic diagnostic and treatment computer 514, having associated display 516, which typically analyzes the respiration parameter output of the capnograph 502.

In an analyzing step, the onset and offset limits of a capnogram 517, pulse waveforms, and the QRS complex (of the ECG) are marked by computer 514. The actual parameters measured include, but are not limited to heart rate (HR), BP, the systolic to diastolic ratio (SYS/DIA). $SPO_2$, AND $ETCO_2$. The slope of $CO_2$ (mm Hg/sec), and $CO_2$ "run", of the capnogram 517, measured to 80% of maximum $CO_2$ concentration, are calculated by computer 514.

Following each treatment, the differences between consecutive measurements of the various patient parameters are computed by computer 514. Thereafter, in a diagnostic rule application step, the following diagnostic rules are preferably applied to the measured parameters by computer 514:

1) If:
a) the blood pressure values are within the normal range;
b) the respiratory rate is normal; and
c) $ETCO_2$ is less than 45 mm Hg;
then, display 516 shows the message "VITAL SIGNS WITHIN NORMAL LIMITS".

2) In contrast, if:
a) the value of Diminished CAP-FEV1 is a 40:10 point ratio; and,
b) Normal CAP-FEV1/FVC (FORCED VITAL CAPACITY);
c) $CO_2$ run is less than 0.3 sec;
d) $CO_2$ slope is more than 100 mm Hg/sec;
then,
display 516 shows the message "HEART FAILURE PRESENT".

Additionally, if a heart failure is present then the following rules may also be applied:

3) If:
a) the value of CAP-FEV1 is less than 80%;
then
display 516 shows the message "MODERATE HEART FAILURE PRESENT".

4) If:
a) the value of CAP-FEV1 is less than 80%,
b) the value of $SPO_2$ is less than 91% SAT; and
c) the value of $ETCO_2$ is less than 45 mm Hg;
then,
display 516 shows the message "SEVERE HEART FAILURE PRESENT".

Thereafter a cycle of alteting I) sampling step (data collection and measurement) and II) diagnostic rule application to the previous sample step I) is initiated.

I) Sampling Step
a) A sample of expired air is taken and conveyed from cannula 500 to capnograph 502.

b) The carbon dioxide concentration is measured continuously by capnograph 502 as capnogram 517.
c) The capnogram is digitized as waveform and store for analysis by computer 514.
d) Computer 514 marks onset and offset limits of the capnogram.
e) The waveform quality of the capnogram is assessed by employing the criteria that an acceptable quality is defined by:
i) the root mean square (rms) of the noise of the waveform must be less than 2 mm Hg; and
ii) the breath-to-breath correlation must be greater than 0.85.
f) The slope and the run are determined by computer 514.

II) Diagnostic Rule Application Step
In a diagnostic rule application step, the following diagnostic rules are preferably applied to the measured parameters of I) Sampling step by computer 514:

I) If:
a) the blood pressure values are within the normal range;
b) the respiratory rate is normal;
c) $CO_2$ run is less than or equal to 0.3 sec;
d) $CO_2$ slope is more than or equal to 100 mm Hg/sec;
e) $SPO_2$ is greater than or equal to 95% SAT; and
f) $ETCO_2$ is less than or equal to 45 mm Hg;
then,
display 516 shows the message "NO HEART FAILURE PRESENT."

2) If:
a) the value of CAP-FEV1 is more than 50%, but less than or equal to 80%;
and
b) the value of $SPO_2$ is greater or equal to 91% SAT but less than 95% SAT;
then
display 516 shows the message ". MODERATE HEART FAILURE PRESENT".

3) If:
a) the value of CAP-FEV1 is less than 80%;
b) the value of $SPO_2$ is less than 91% SAT; and
c) the value of $ETCO_2$ is less than 45 mm Hg;
then,
display 516 shows the message "SEVERE HEART FAILURE PRESENT".

Figure 33:
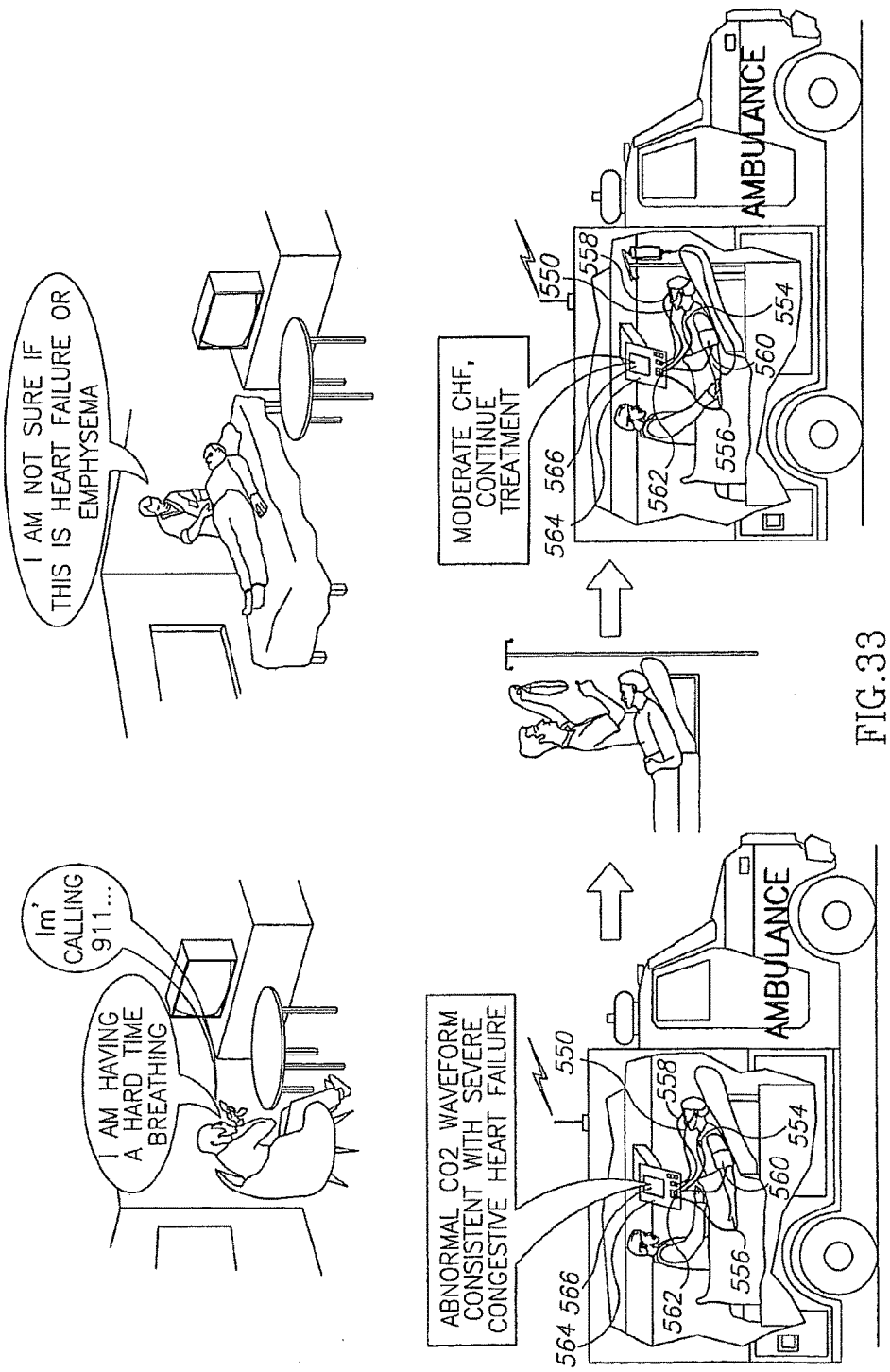
FIG. 33 is a simplified pictorial illustration of an automatic medical diagnostic and treatment system and methodology operative in a hospital environment for treating pulmonary edema.

Reference is now made to FIG. 33, which is a simplified pictorial illustration of an automatic medical diagnostic and treatment system and methodology operative in an ambulance environment for treating pulmonary edema. As seen in FIG. 33, various patient physiologic activities are sensed and measured, including respiratory physiologic activities, preferably via an oral airway adapter and/or a nasal or nasal/oral cannula 550, such as a Model Nasal FilterLine Adult XS 04461, 02/$CO_2$ Nasal FilterLine Adult 007141, or Smart CapnoLine Adult (Oral/nasal FilterLine) 007414, commercially available from Oridion Ltd., of Jerusalem Israel, typically coupled with a capnograph 552, such as a Microcap, commercially available from Oridion Ltd., of Jerusalem Israel. Other patient physiologic activities relating to cardiac function (e.g. ECG), systemic oxygenation (e.g. pulse oximetry), cerebral oxygenation (e.g. cerebral oximetry) and systemic circulation (e.g. NIBP), typically sensed by means of chest electrodes 554, a finger sensor 556, a forehead/scalp sensor 558 and a blood pressure cuff 560 respectively, may also be sensed and measured by suitable instrumentation 562.

The outputs of the capnograph 552 and possibly of additional instrumentation 562 are preferably supplied to a suitably programmed automatic diagnostic and treatment computer 564, having an associated display 566 which typically analyzes the respiration parameter output of the capnograph 552 and possibly other parameters and provides an output which preferably contains a diagnostic statement indicating the presence and severity of congestive heart failure, here "ABNORMAL $CO_2$ WAVEFORM CONSISTENT WITH SEVERE CONGESTIVE HEART FAILURE".

This diagnostic statement indicates that treatment is required for heart failure. Intravenous and/or sublingual medications such as nitroglycerin, morphine and LASIX® are administered after which a diagnostic statement which indicates the patient status and the severity of the cardio-respiratory condition is preferably presented, here "MODERATE CONGESTIVE HEART FAILURE, CONDITION IMPROVING".

Figure 34A:
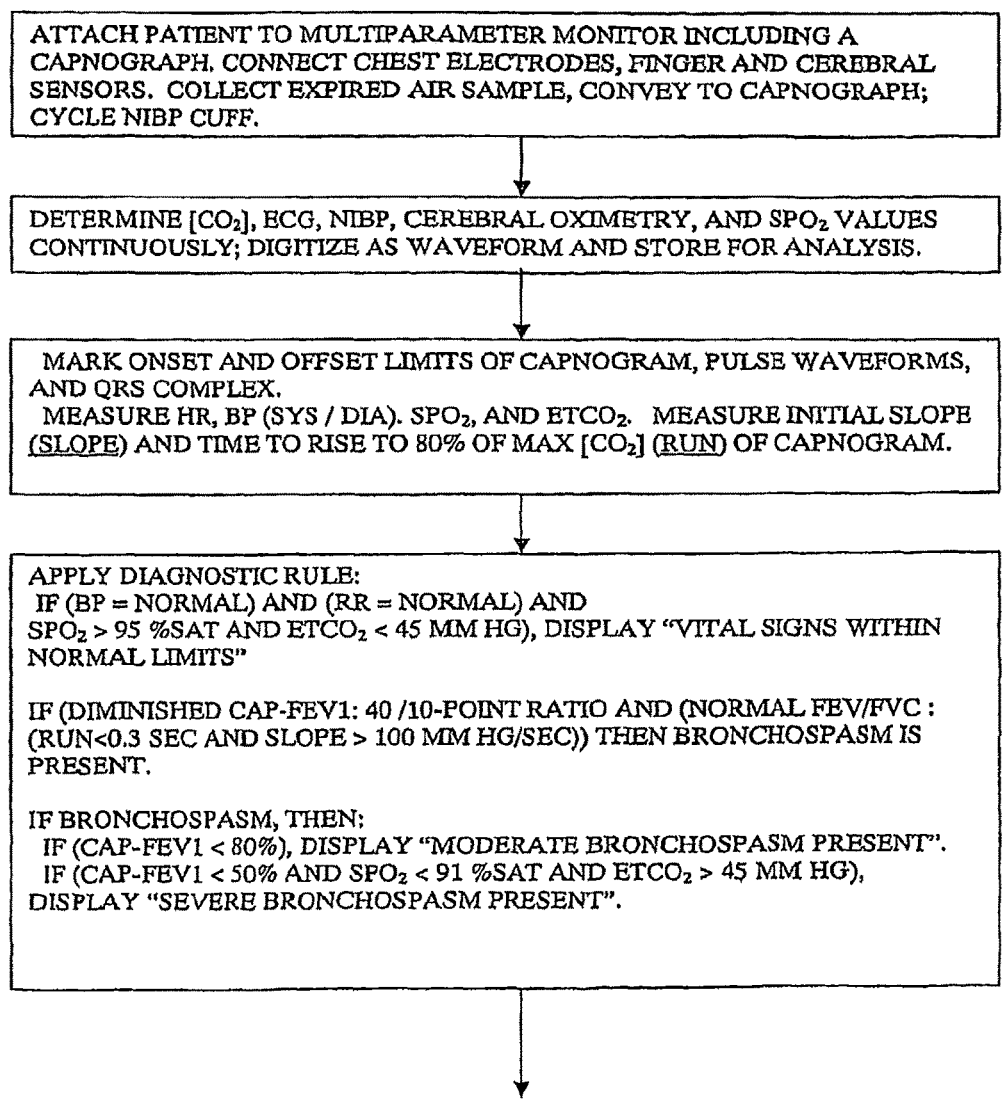
FIGS. 34A and 34B are flowcharts illustrating operation of the embodiment of FIG. 33.
Figure 34B:
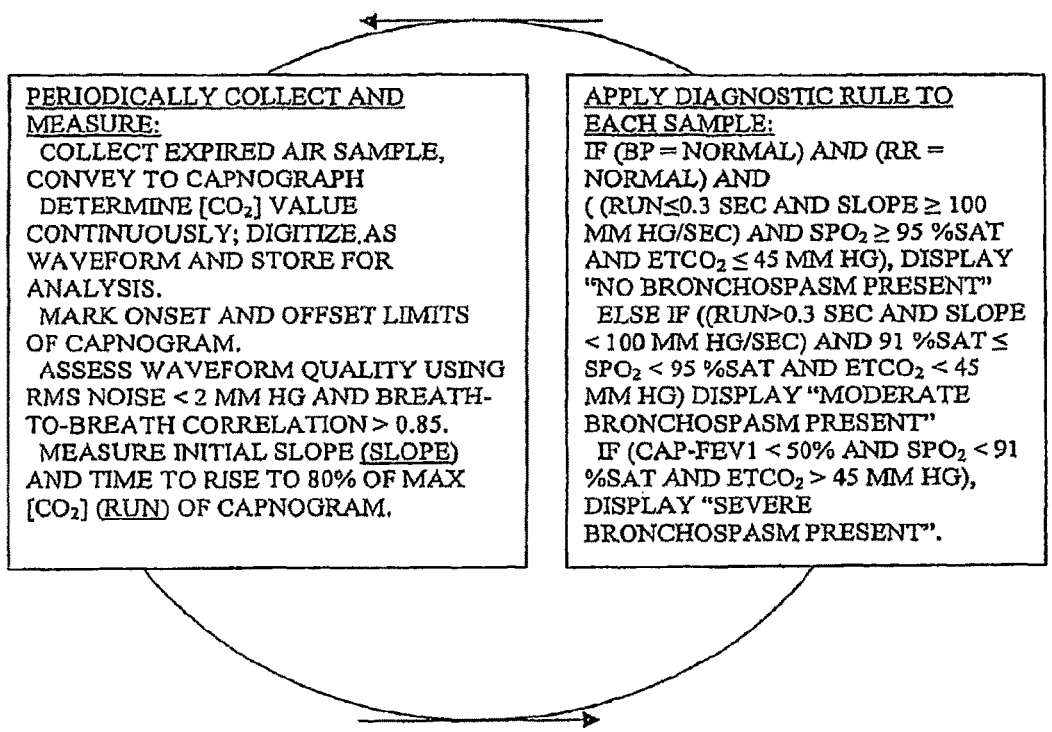

Reference is now made additionally to FIGS. 34A and 34B, which illustrate the operation of the system and methodology of the system of the present invention in the context of FIG. 33.

The patient previously attached to a multi-parameter monitor including a capnograph 552 and suitable instrumentation 562, by means of cannula 550 and preferably also by means of chest electrodes 554, finger sensor 556, forehead sensor 558 and blood pressure cuff 560, is monitored continuously for at least thirty seconds. Neurological status of the patient is acquired by any suitable technique, including visual and electroencephalograph (EEG) monitoring. Values of $CO_2$ concentration, ECG, NIBP, $SPO_2$, and cerebral oximetry are continuously monitored, and carbon dioxide waveforms are preferably digitized as a capnogram 567 and together with other waveforms are stored in computer 564.

At least one expired air sample is collected and conveyed for analysis by capnograph 552. The outputs of the capnograph 552 and possibly of additional instrumentation 562 are preferably supplied to suitably programmed automatic diagnostic and treatment computer 564, having associated display 566, which typically analyzes the respiration parameter output of the capnograph 552.

In an analyzing step, the onset and offset limits of a capnogram 567, pulse waveforms, and the QRS complex (of the ECG) are marked by computer 564. The actual parameters measured include, but are not limited to heart rate (HR), BP, the systolic to diastolic ratio (SYS/DIA). $SPO_2$, AND $ETCO_2$. The slope of $CO_2$ (mm Hg/sec), and $CO_2$ "run", of the capnogram 567, measured to 80% of maximum $CO_2$ concentration, are calculated by computer 564.

Following each treatment, the differences between consecutive measurements of the various patient parameters are computed by computer 564. Thereafter, in a diagnostic rule application step, the following diagnostic rules are preferably applied to the measured parameters by computer 564:

1) If:
a) the blood pressure values are within the normal range;
b) the respiratory rate is normal; and
c) $ETCO_2$ is less than 45 mm Hg;
then,
display 566 shows the message "VITAL SIGNS WITHIN NORMAL LIMITS".

2) In contrast, if:
a) the value of Diminished CAP-FEV1 is a 40:10 point ratio;
b) Normal CAP-FEV/FVC;
c) $CO_2$ run is less than 0.3 sec; and,
d) $CO_2$ slope is more than 100 mm Hg/sec;
then,
display 566 shows the message "BRONCHOSPASM IS PRESENT".

Additionally, if bronchospasm is present then the following rules may also be applied:

3) If:
a) the value of CAP-FEV1 is less than 80%;
then
display 566 shows the message "MODERATE BRONCHOSPASM IS PRESENT".

4) If:
a) the value of CAP-FEV1 is less than 80%;
b) the value of $SPO_2$ is less than 91% SAT; and
c) the value of $ETCO_2$ is less than 45 mm Hg;
then,
display 566 shows the message "SEVERE BRONCHOSPASM PRESENT".

Thereafter a cycle of alteting. I) sampling step (data collection and measurement) and II) diagnostic rule application to the previous sample step I) is initiated:

I) Sampling Step
a) A sample of expired air is taken and conveyed from cannula 550 to capnograph 552.
b) The carbon dioxide concentration is measured continuously by capnograph 552 as capnogram 567.
c) The capnogram is digitized as waveform and store for analysis by computer 564.
d) Computer 564 marks onset and offset limits of the capnogram.
e) The waveform quality of the capnogram is assessed by employing the criteria that an acceptable quality is defined by:
  i) the root mean square (rms) of the noise of the waveform must be less than 2 mm Hg; and
  the breath-to-breath correlation must be greater than 0.85.
f) The slope and the run are determined by computer 564.

II) Diagnostic Rule Application Step
In a diagnostic rule application step, the following diagnostic rules are preferably applied to the measured parameters of I) Sampling step by computer 564:

1) If:
a) the blood pressure values are within the normal range;
b) the respiratory rate is normal;
c) $CO_2$ run is less than or equal to 0.3 sec;
d) $CO_2$ slope is more than or equal to 100 mm Hg/sec;
e) $SPO_2$ is greater than or equal to 95% SAT; and
f) $ETCO_2$ is less than or equal to 45 mm Hg;
then,
display 566 shows the message "NO BRONCHOSPASM PRESENT."

2). In contrast, if:
a) $CO_2$ run is greater than 0.3 sec;
b) $CO_2$ slope is less than 100 mm Hg/sec;
c) $SPO_2$ is more than or equal to 91% SAT, but less than 95% SAT; and
d) $ETCO_2$ is less than 45 mm Hg;
then,
the message "MODERATE BRONCHOSPASM PRESENT" is displayed on display 566.

3) If the parameters measured are yet further removed from the acceptable range, such as if:
a) CAP-FEV1 is less than 50%;
b) $SPO_2$ is less than 91% SAT; and
c) $ETCO_2$ is greater than 45 mm Hg;
then,
a message such as "SEVERE BRONCHOSPASM PRESENT" is displayed on display 566.

At any one of the diagnostic rule application steps, it may be verified that the patient is suffering from bronchospasm. Once bronchospasm is verified, the operator switches capnograph 552 to a serial comparison mode. The medical team applies the appropriate interventions to the patient to treat the bronchospasm.

Figure 35:
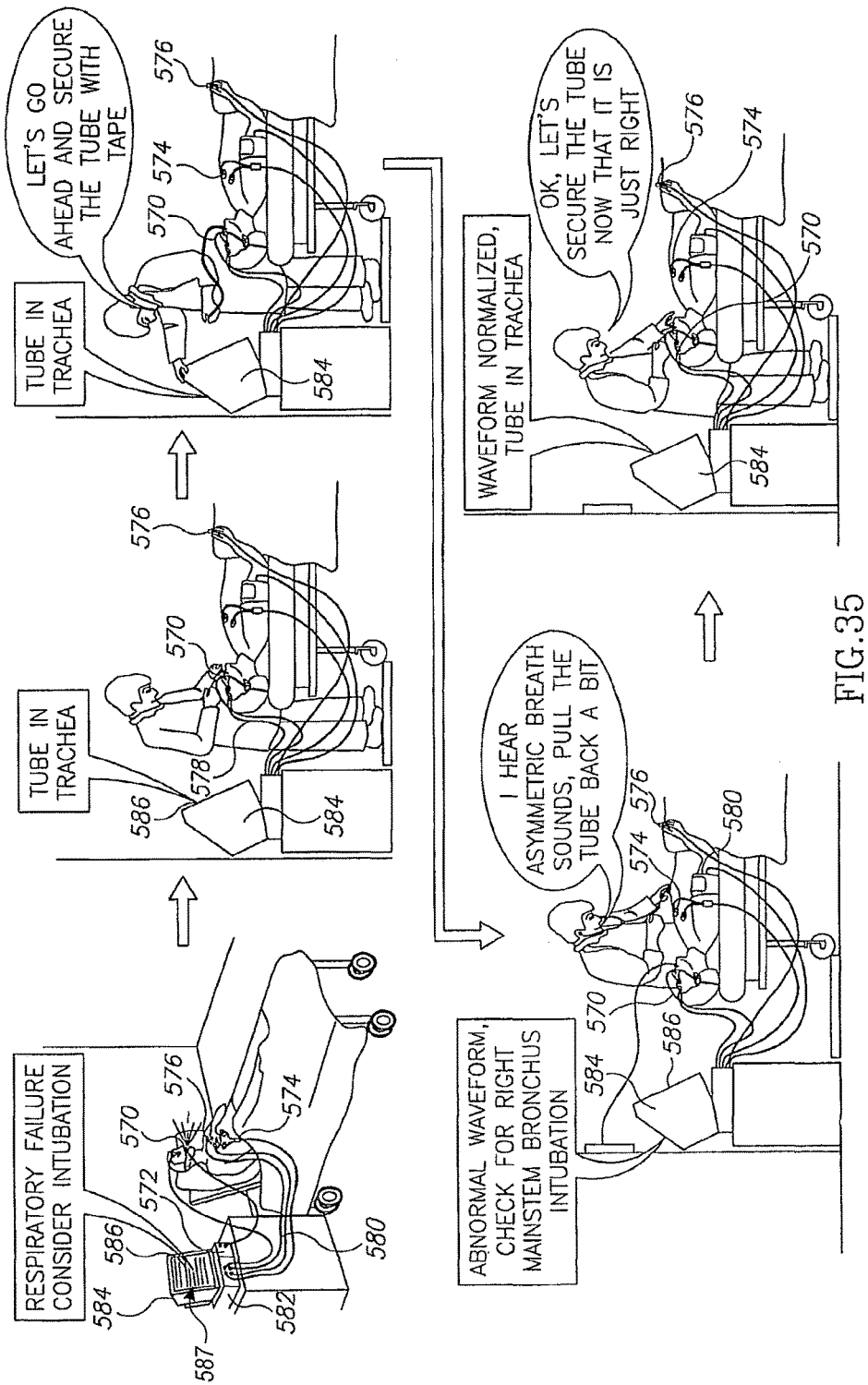
FIG. 35 is a simplified pictorial illustration of an automatic medical diagnostic and treatment system and methodology operative in a hospital environment for anesthesia monitoring.

Reference is now made to FIG. 35, which is a simplified pictorial illustration of an automatic medical diagnostic and treatment system and methodology operative in a hospital or EMS environment for diagnosing and treating respiratory failure. As seen in FIG. 35, various patient physiologic activities are sensed and measured, including respiratory physiologic activities, preferably via an oral airway adapter and/or a nasal or nasal/oral cannula 570, such as a Model Nasal FilterLine Adult XS 04461, $O_2/CO_2$ Nasal FilterLine Adult 007141, or Smart CapnoLine Adult (Oral/nasal FilterLine) 007414, commercially available from Oridion Ltd., of Jerusalem Israel, typically coupled with a capnograph 572, such as a Microcap, commercially available from Oridion Ltd., of Jerusalem Israel. Other patient physiologic activities relating to cardiac function (e.g. ECG), systemic oxygenation (e.g. pulse oximetry), cerebral oxygenation (e.g. cerebral oximetry) and systemic circulation (e.g. NIBP), typically sensed by means of chest electrodes 574, a finger sensor 576, a forehead/scalp sensor 578 and a blood pressure cuff 580 respectively, may also be sensed and measured by suitable instrumentation 582.

Following intubation of the patient and prior to securing the tube, the outputs of the capnograph 572 and possibly of additional instrumentation 582 are preferably supplied to a suitably programmed automatic diagnostic and treatment computer 584, having an associated display 586 which typically analyzes the respiration parameter output of the capnograph 572 and possibly other parameters and provides an output which preferably contains a diagnostic statement indicating proper intubation, here "TUBE IN TRACHEA".

The system determines whether characteristics of the capnograph waveform amplitude are normal. If the $CO_2$ levels as indicated by the capnograph waveform amplitude are below normal a diagnostic statement indicating right mainstem bronchus intubation is presented, here "ABNORMAL WAVEFORM, CHECK FOR RIGHT MAINSTEM BRONCHUS INTUBATION".

Following repositioning of the tube, the system provides a patient status statement, here "WAVEFORM NORMALIZED, TUBE IN TRACHEA.

Figure 36:
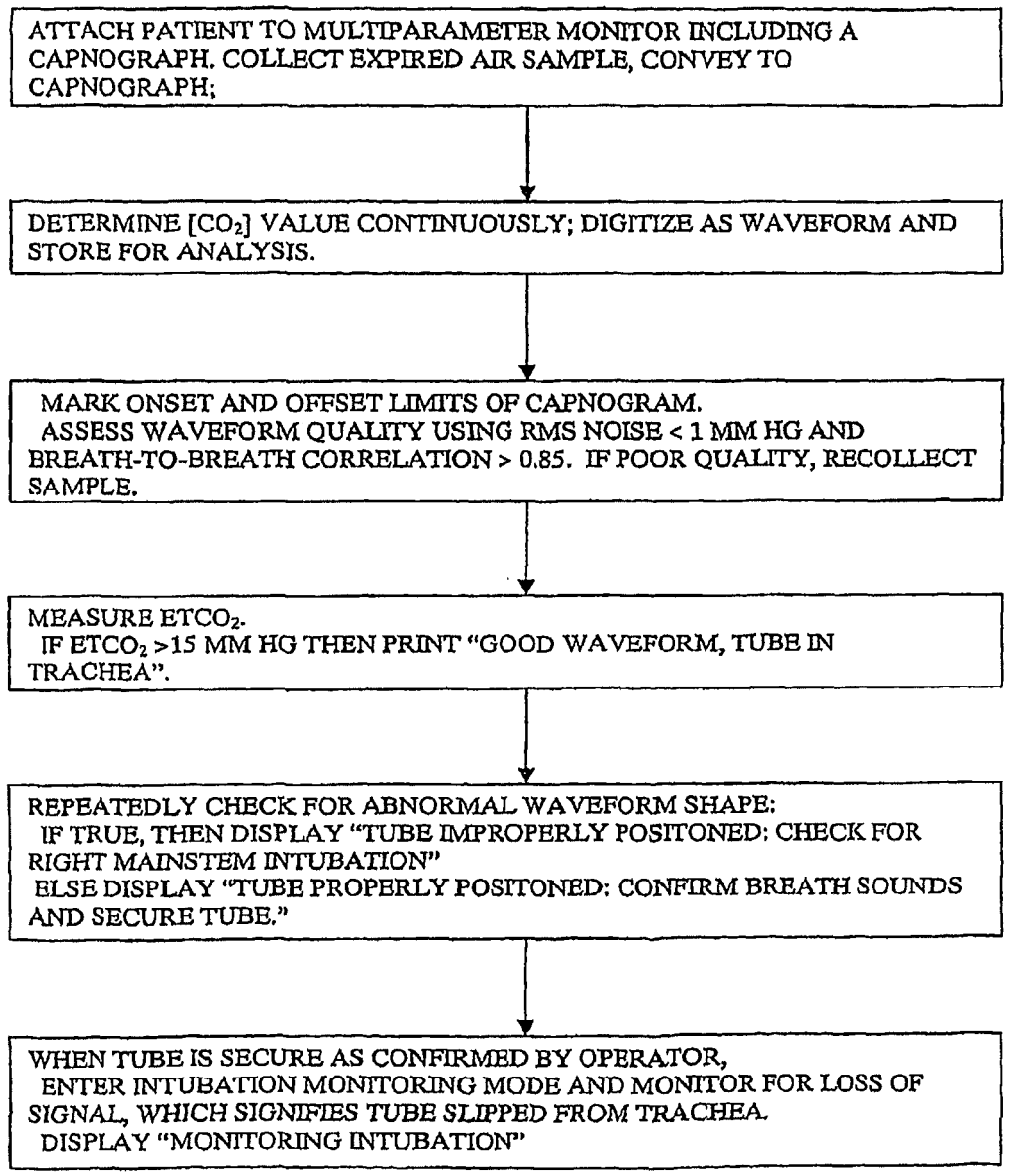
FIG. 36 is a flowchart illustrating operation of the embodiment of FIG. 35.

Reference is now made additionally to FIG. 36, which illustrates the operation of the system and methodology of the system of the present invention in the context of FIG. 35.

The patient in an ambulance, preferably attached to a multi-parameter monitor including capnograph 572, is monitored continuously for at least 30 seconds. Expired air is collected via cannula 570 and is conveyed to the capnograph 572.

Values of the $CO_2$ concentration is continuously measured, typically over a period of 30 seconds, and carbon dioxide waveforms are preferably digitized as a capnogram and together with other waveforms are stored on computer 584.

The onset and offset limits of the patient's capnogram from capnograph 572 are delineated by computer 584.

The waveform quality of the capnogram 587 is assessed by employing the criteria that an acceptable quality is defined by:

i) the root mean square (rms) of the noise of the waveform must be less than 1 mm Hg; and ii) the breath-to-breath correlation must be greater than 0.85.

If the quality is unacceptable, further samples are collected until a sample of acceptable quality, according to the above two criteria, is taken.

The next step entails a checking procedure, wherein the $ETCO_2$ value is measured by capnograph 572. The slope and run values of the capnogram from capnograph 572 are determined by computer 584.

At startup, the following checking rule is preferably applied.

1) If:

a) the $ETCO_2$ value is more than 15 mm Hg;

then, a display is provided by computer 584 stating "GOOD WAVEFORM, TUBE IN TRACHEA".

In a checking step, repeated checks for abnormal waveform shape of capnogram 587. The following rules are preferably applied to the capnogram shape:

1) if:

a) an abnormal waveform shape is observed;

then, computer 584 displays "TUBE IMPROPERLY POSITIONED: CHECK FOR RIGHT MAINSTEM INTUBATION" on display 586.

2) If a) a normal waveform shape is observed;

then, computer 584 displays "TUBE PROPERLY POSITIONED: CONFIRM BREATH SOUNDS AND SECURE TUBE" on display 586.

When tube is secure as is confirmed by an operator, the operator typically inputs a code into computer 584 to activate an intubation monitoring mode in capnograph 572. The capnogram is monitored continuously for loss of signal. Loss of signal from capnograph 572 is indicative of the tube having slipped away from the trachea. As long as there is a regular signal, computer 584 displays "MONITORING INTUBATION" on display 586.

Figure 37:
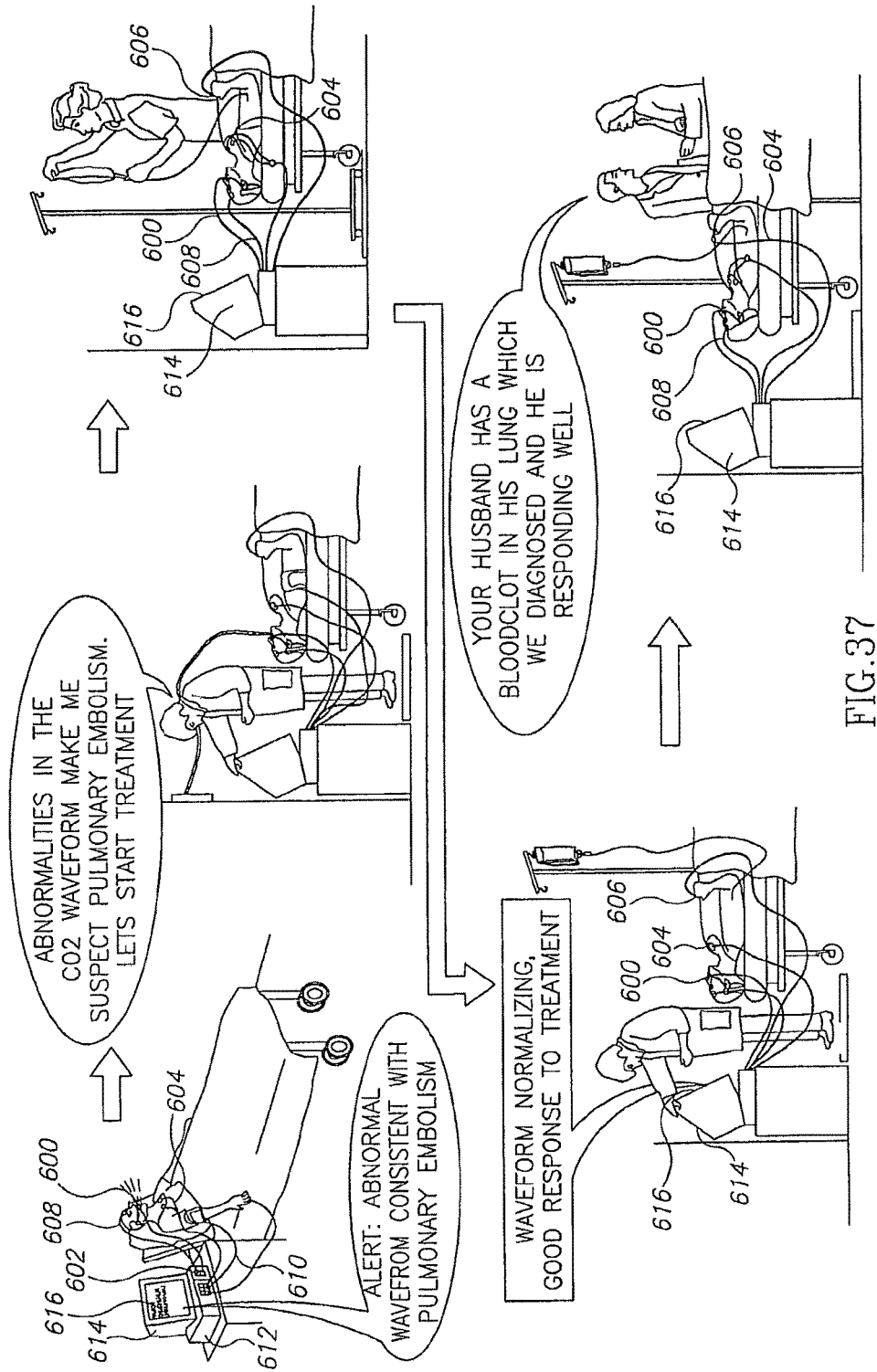
FIG. 37 is a simplified pictorial illustration of an automatic medical diagnostic and treatment system and methodology operative in a hospital environment for diagnosis and treatment of pulmonary embolism.

Reference is now made to FIG. 37, which is a simplified pictorial illustration of an automatic medical diagnostic and treatment system and methodology operative in a hospital environment for diagnosing and treating pulmonary embolism. As seen in FIG. 37, various patient physiologic activities are sensed and measured, including respiratory physiologic activities, preferably via an oral airway adapter and/or a nasal or nasal/oral cannula 600, such as a Model Nasal FilterLine Adult XS 04461, $O_2/CO_2$ Nasal FilterLine Adult 007141, or Smart CapnoLine Adult (Oral/nasal FilterLine) 007414, commercially available from Oridion Ltd., of Jerusalem Israel, typically coupled with a capnograph 602, such as a Microcap, commercially available from Oridion Ltd., of Jerusalem Israel. Other patient physiologic activities relating to cardiac function (e.g. ECG), systemic oxygenation (e.g. pulse oximetry), cerebral oxygenation (e.g. cerebral oximetry) and systemic circulation (e.g. NIBP), typically sensed by means of chest electrodes 604, a finger sensor 606, a forehead/scalp sensor 608 and a blood pressure cuff 610 respectively, may also be sensed and measured by suitable instrumentation 612.

The outputs of the capnograph 602 and possibly of additional instrumentation 612 are preferably supplied to a suitably programmed automatic diagnostic and treatment computer 614, having an associated display 616 which typically analyzes the respiration parameter output of the capnograph 602 and possibly other parameters and provides an output which preferably contains a diagnostic statement alerting hospital staff to the possible presence of pulmonary embolism. A typical such statement is "ALERT: ABNORMAL WAVEFORM CONSISTENT WITH PULMONARY EMBOLISM". Following intravenous medication for dissolving blood clots in the lungs, the system determines whether characteristics of the $CO_2$ waveform amplitude and shape are approaching normal and preferably provides a patient status statement, here "WAVEFORM NORMALIZING, GOOD RESPONSE TO TREATMENT".

Figure 38:
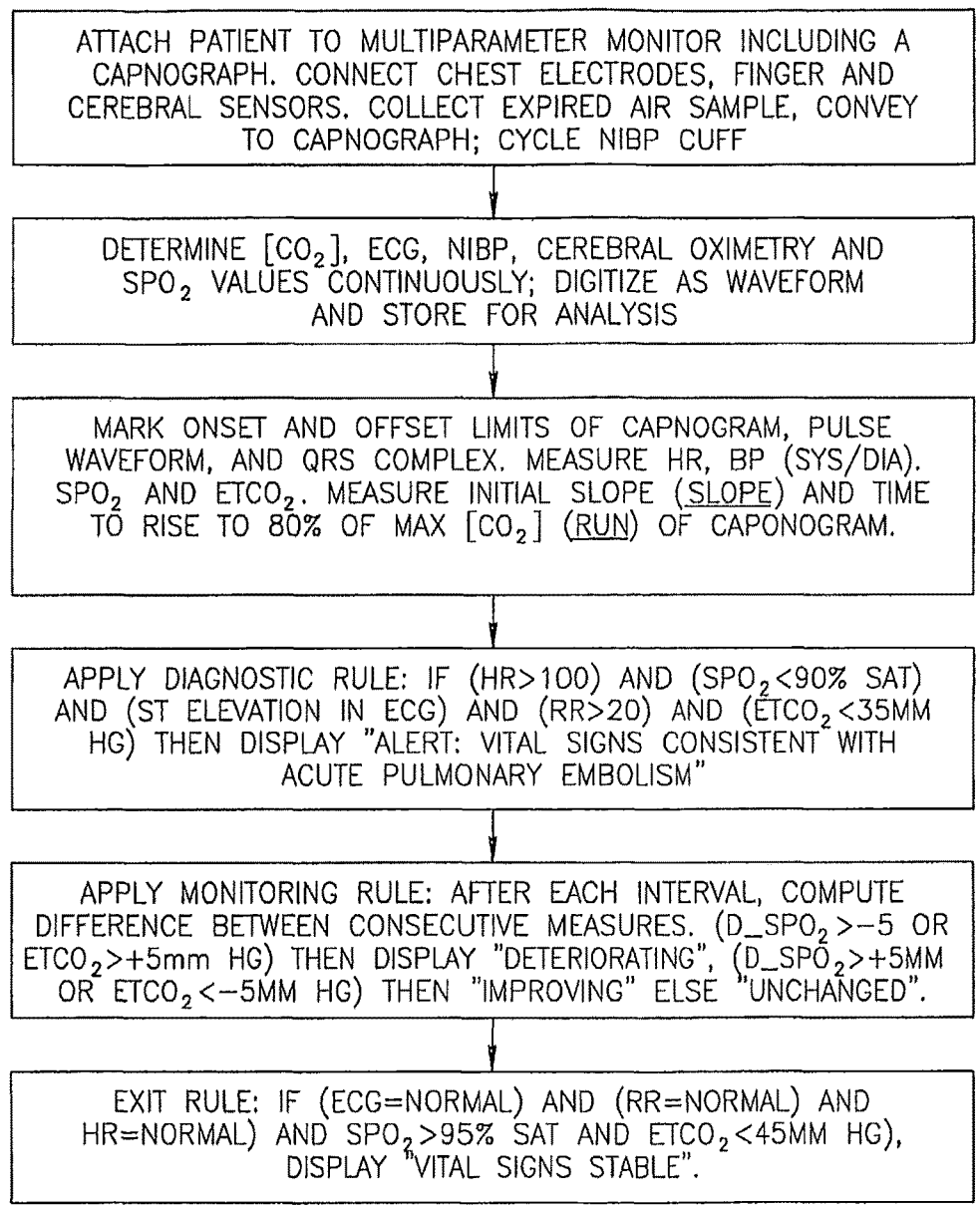
FIG. 38 is a flowchart illustrating operation of the embodiment of FIG. 37.

Reference is now made additionally to FIG. 38, which illustrates the operation of the system and methodology of the system of the present invention in the context of FIG. 37.

The patient, preferably attached to a multi-parameter monitor including capnograph 602 and instrumentation 612, by means of cannula 600 and preferably also by means of chest electrodes 604, finger sensor 606, scalp/forehead sensor 608 and blood pressure cuff 610, is monitored continuously. The neurological status of the patient is acquired by any suitable technique. Values of $CO_2$ concentration, ECG, NIBP and $SPO_2$ are continuously measured, typically over a period of 30 seconds, and carbon dioxide waveforms are preferably digitized as a capnogram 617 and other waveforms and stored by computer 614.

Thereafter, the onset and offset limits of the capnogram, the pulse waveform and QRS onset and offset are determined by computer 614. The heart rate, blood pressure $ETCO_2$ and $SPO_2$ values are measured. The initial slope of the capnogram and the run, monitored by capnograph 602, are calculated by computer 614. Additionally, neurological findings, monitored by means of an EEG are inputted to computer 614.

At various intervals, the differences between consecutive measurements of the various patient parameters are evaluated by computer 614. After each treatment, in a diagnostic rule application step, the following diagnostic rule is preferably applied to the measured parameters by computer 614:

1) If:
  a) the heart rate is greater than 100/min;
  b) the $SPO_2$ is less than 90% SAT;
  c) the $EtCO_2$ is less than 35 mm Hg;
  d) the amplitude (area under curve) of the $CO_2$ waveform is less than a predetermined value;
  e) the ECG is normal; and
  f) the respiratory rate is greater than 15/min;
  display 616 shows the message "ALERT: VITAL SIGNS CONSISTENT WITH ACUTE PULMONARY EMBOLISM".

After each time interval, the difference between consecutive measures of each parameter are calculated by computer 614: Thereafter, the following monitoring rules are preferably applied to the measured parameters by computer 614.

1) If:
  a) the decrease in the $SPO_2$ values is greater than –5% SAT; or
  b) the difference in the $ETCO_2$ slope is greater than +5 mm Hg;
  then,
  computer 614 displays on display 616 "PATIENT STATUS: DETERIORATING".

2) If:
  a) the increase in the $SPO_2$ values is greater than +5% SAT; or
  b) the difference in the $ETCO_2$ slope is more than –5 mm Hg;
  then,
  computer 614 displays on display 616 "PATIENT STATUS:IMPROVING".

3) If:
  a) the difference in the $SPO_2$ values is more positive than or equal to –5%
  SAT, but less than or equal to +5%; or
  b) the difference in the $ETCO_2$ slope greater than or equal to –5 mm Hg, but less than or equal to +5 mm Hg;
  then,
  computer 614 displays on display 616 "PATIENT STATUS:UNCHANGED".

Following the monitoring stage, the following exit rules are preferably applied to the measured parameters of the patient by computer 232:

I) If:
  a) the ECG values are within normal limits;
  b) the respiratory rate is within normal limits;
  c) the heart rate is within normal limits;
  d) the $SPO_2$ value is greater than 95% SAT; and
  e) the $ETCO_2$ value is less than 45 mm Hg;
  then,
  Computer 614 preferably displays on display 616 "VITAL SIGNS STABLE".

(If the patient's record complies with this exit rule, then a copy of the patient's record is handed-off from computer 616 to the receiving center, for example, in the form of a chart. Typically, the receiving center stores this chart, so that it may be used as a baseline for continued monitoring of the patient).

Figure 39A:
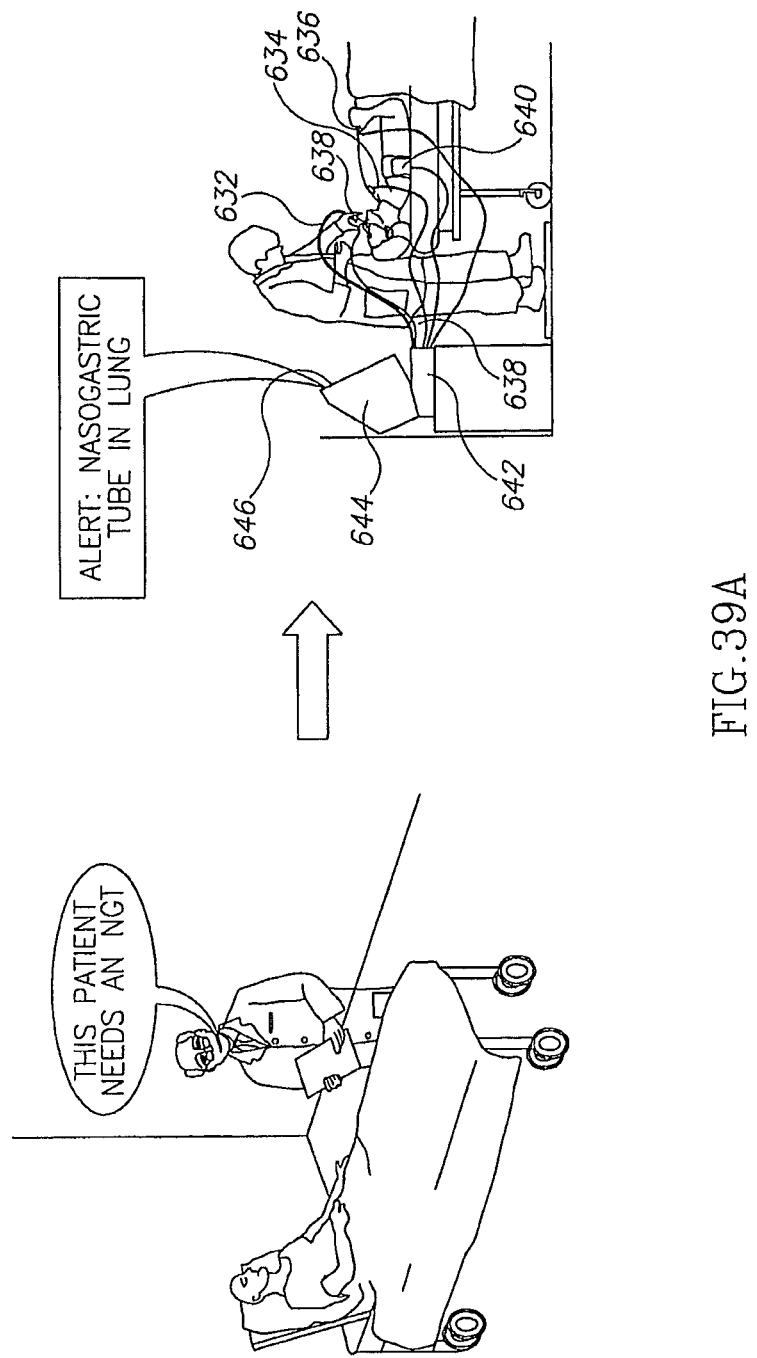
FIGS. 39A and 39B are simplified pictorial illustrations of an automatic medical diagnostic and treatment system and methodology operative in a hospital environment for determination of correct nasogastric tube placement.
Figure 39B:
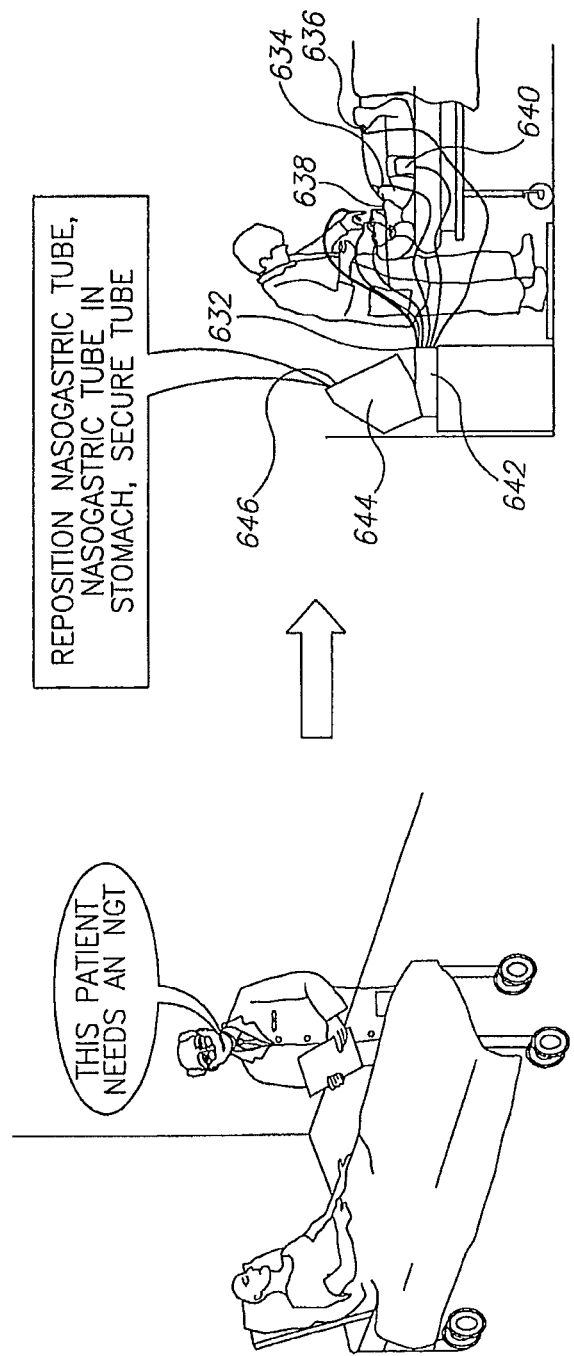

Reference is now made to FIGS. 39A and 39B, which are simplified pictorial illustrations of an automatic medical diagnostic and treatment system and methodology operative in a hospital environment for determining correct placement of a nasogastric tube in a patient. As seen in FIGS. 39A and 39B, following insertion of a nasogastric tube in a patient, various patient physiologic activities are sensed and measured, including respiratory physiologic activities, preferably via an oral airway adapter and/or a nasal or nasal/oral cannula 630, such as a Model Nasal FilterLine Adult XS 04461, $O_2/CO_2$ Nasal FilterLine Adult 007141, or Smart CapnoLine Adult (Oral/nasal FilterLine) 007414, commercially available from Oridion Ltd., of Jerusalem Israel, typically coupled with a capnograph 632, such as a Microcap, commercially available from Oridion Ltd., of Jerusalem Israel. Other patient physiologic activities relating to cardiac function (e.g. ECG), systemic oxygenation (e.g. pulse oximetry), cerebral oxygenation (e.g. cerebral oximetry) and systemic circulation (e.g. NIBP), typically sensed by means of chest electrodes 634, a finger sensor 636, a forehead/scalp sensor 638 and a blood pressure cuff 640 respectively, may also be sensed and measured by suitable instrumentation 642.

The outputs of the capnograph 632 and possibly of additional instrumentation 642 are preferably supplied to a suitably programmed automatic diagnostic and treatment computer 644, having an associated display 646 which typically analyzes the respiration parameter output of the capnograph 632 and possibly other parameters and provides an output which preferably contains a status statement alerting hospital staff to the possible misplacement of the nasogastric tube. A typical such statement is, "NASOGASTRIC (NG) TUBE IN LUNG". This status statement is preferably accompanied by a treatment recommendation: here "REPOSITION NASOGASTRIC TUBE". Following repositioning of the nasogastric tube, a status statement confirming proper placement is preferably provided, here "NASOGASTRIC TUBE 1 N STOMACH". This statement is preferably accompanied by a treatment recommendation, here "SECURE TUBE".

Figure 40:
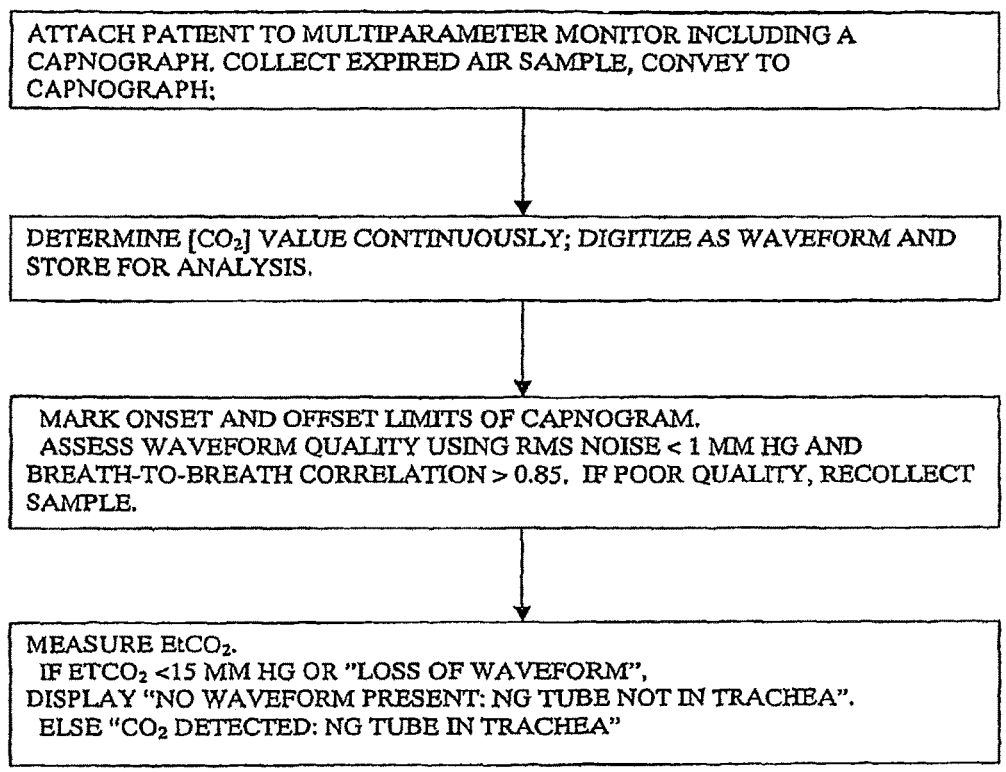
FIG. 40 is a flowchart illustrating operation of the embodiment of FIGS. 39A and 39B.

Reference is now made additionally to FIG. 40, which illustrates the operation of the system and methodology of the system of the present invention in the context of FIGS. 39A and 39B.

The patient, preferably attached to a multi-parameter monitor including capnograph—632, is monitored continuously for at least 30 seconds. Expired air is collected via cannula 630 and is conveyed to the capnograph 632.

Values of the $CO_2$ concentration is continuously measured, typically over a period of 30 seconds, and carbon dioxide waveforms are preferably digitized as a capnogram 647 and, together with other waveforms, is stored on computer 644.

The onset and offset limits of the patient's capnogram from capnograph 632 are delineated by computer 644.

The waveform quality of the capnogram 647 is assessed by employing the criteria that an acceptable quality is defined by:

i) the root mean square (rms) of the noise of the waveform must be less than 1 mm Hg; and ii) the breath-to-breath correlation must be greater than 0.85.

If the quality is unacceptable, further samples are collected until a sample of acceptable quality, according to the above two criteria, is taken.

The next step entails a checking procedure, wherein the $ETCO_2$ value is measured by capnograph 632. The slope and run values of the capnogram from capnograph 632 are determined by computer 644.

The following checking rules are preferably applied.

1) If:
a) the $ETCO_2$ value is less than or equal to 15 mm Hg; or
b) there is a loss of the waveform of capnogram 647;
then,
a display is provided by computer 644 stating "NO WAVEFORM PRESENT, NG TUBE NOT IN TRACHEA".

2) If:
a) the $ETCO_2$ value is more than or equal to 15 mm Hg; or
b) profile of exhaled gas is detected as a waveform of capnogram 647;
then,
a display is provided by computer 644 stating "$CO_2$ DETECTED, NG TUBE IN TRACHEA."

Figure 41:
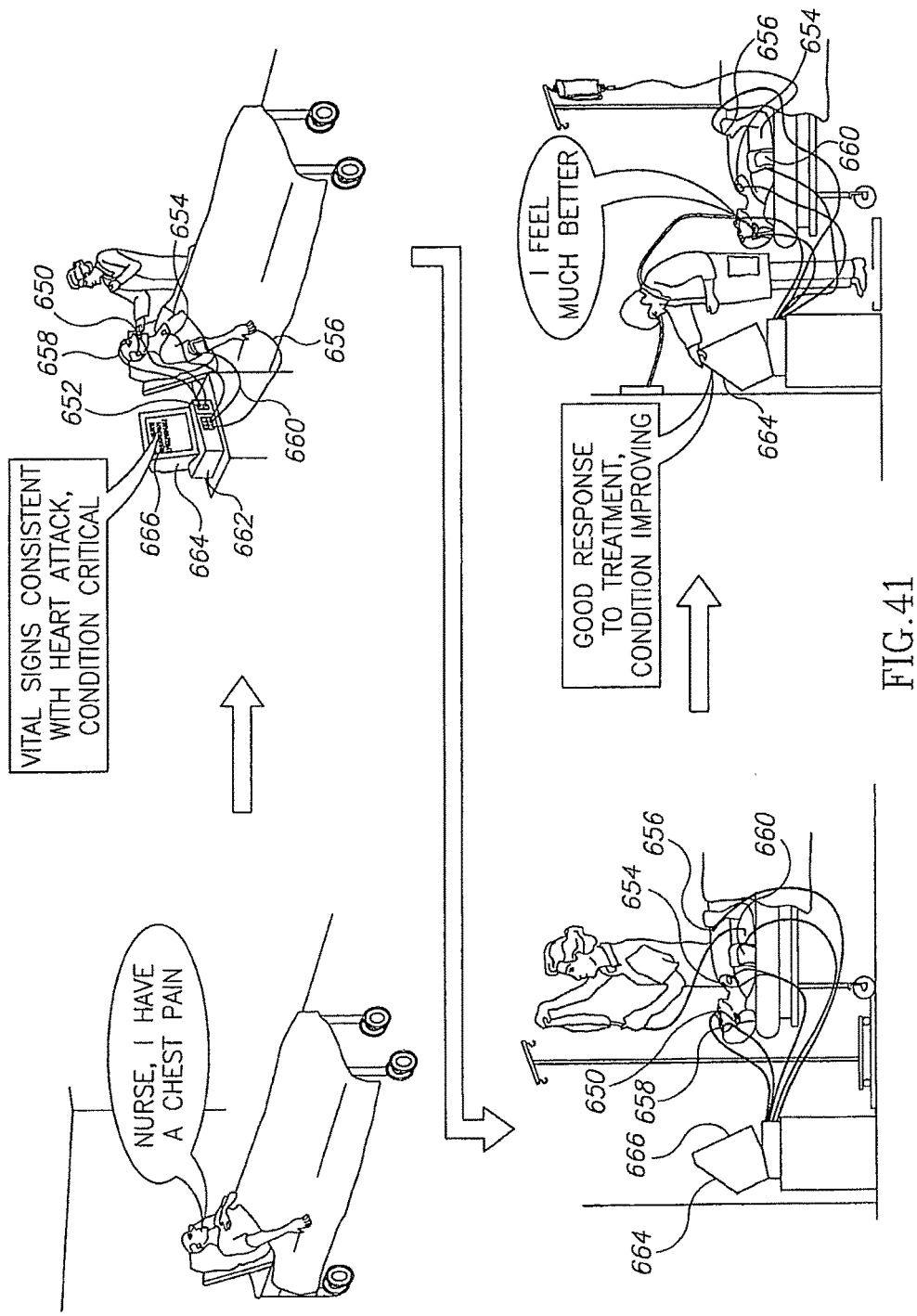
FIG. 41 is a simplified pictorial illustration of an automatic medical diagnostic and treatment system and methodology operative in a hospital environment for diagnosis and treatment of myocardial infarction.

Reference is now made to FIG. 41, which is a simplified pictorial illustration of an automatic medical diagnostic and treatment system and methodology operative in a hospital environment for determining the presence of acute myocardial infarction in a patient. As seen in FIG. 41, following a patient complaint of chest pains, various patient physiologic activities are sensed and measured, including respiratory physiologic activities, preferably via an oral airway adapter and/or a nasal or nasal/oral cannula 650, such as a Model Nasal FilterLine Adult XS 04461, $O_2/CO_2$ Nasal FilterLine Adult 007141, or Smart CapnoLine Adult (Oral/nasal-FilterLine) 007414, commercially available from Oridion Ltd., of Jerusalem Israel, typically coupled with a capnograph 652, such as a Microcap, commercially available from Oridion Ltd., of Jerusalem Israel. Other patient physiologic activities relating to cardiac function (e.g. ECG), systemic oxygenation (e.g. pulse oximetry), cerebral oxygenation (e.g. cerebral oximetry) and systemic circulation (e.g. NIBP), typically sensed by means of chest electrodes 654, a finger sensor 656, a forehead/scalp sensor 658 and a blood pressure cuff 660 respectively, may also be sensed and measured by suitable instrumentation 662.

The outputs of the capnograph 652 and possibly of additional instrumentation 662 are preferably supplied to a suitably programmed automatic diagnostic and treatment computer 664, having an associated display 666 which typically analyzes the respiration parameter output of the capnograph 652 and possibly other parameters and provides an output which preferably contains a diagnostic statement alerting hospital staff to the possibility of occurrence of acute myocardial infarction. A typical such statement is "VITAL SIGNS CONSISTENT WITH HEART ATTACK. CONDITION CRITICAL". Following sublingual and/or intravenous administration of a medicament such as nitroglycerin and morphine, a patient status statement is preferably provided, here "GOOD RESPONSE TO TREATMENT. CONDITION IMPROVING".

Figure 42:
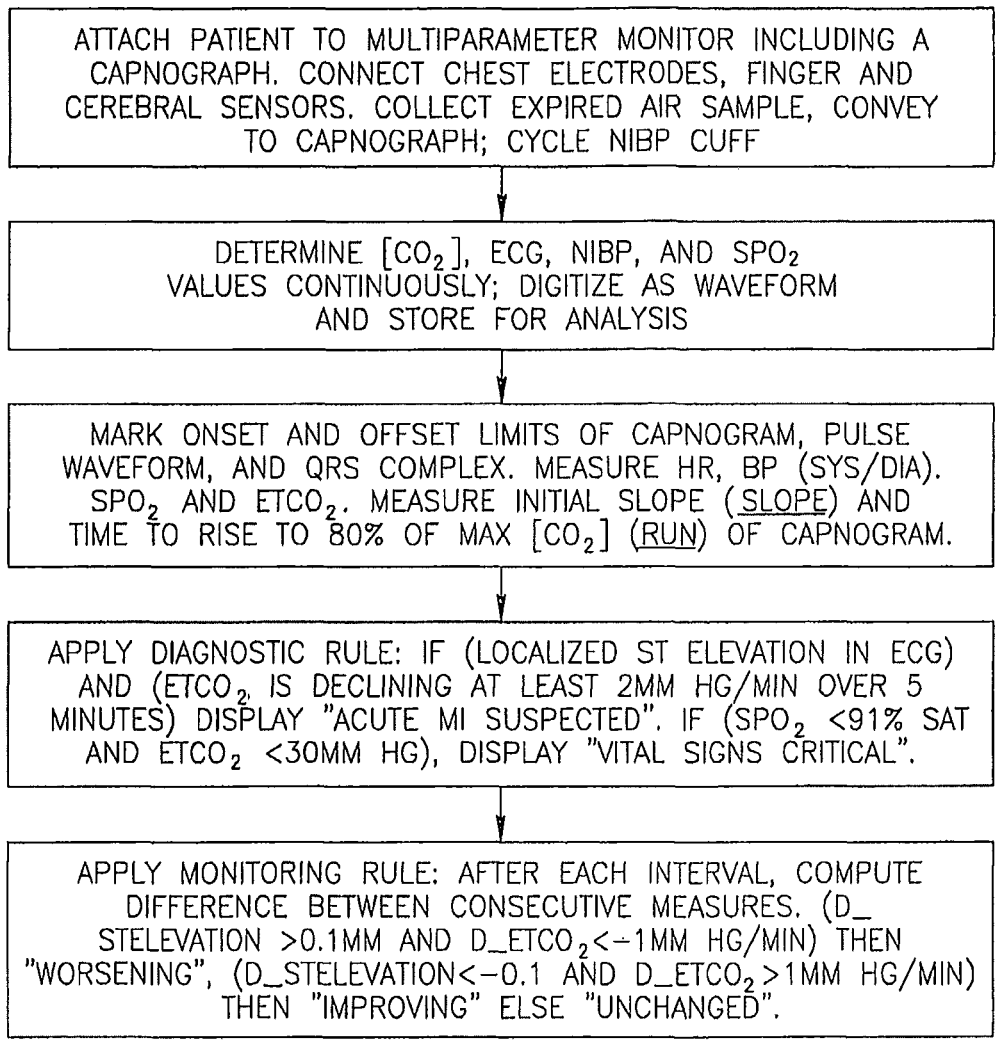
FIG. 42 is a flowchart illustrating operation of the embodiment of FIG. 41.

Reference is now made additionally to FIG. 42, which illustrates the operation of the system and methodology of the system of the present invention in the context of FIG. 41.

The patient, preferably attached to a multi-parameter monitor including capnograph 652 and suitable instrumentation 662, by means of cannula 650 and preferably also by means of chest electrodes 654, finger sensor 656, forehead/scalp sensor 658, and blood pressure cuff 660, is monitored continuously. The neurological status of the patient is acquired by any suitable technique. Values of $CO_2$ concentration, HR, BP (SYS/DIA) ECG, NIBP and $SPO_2$ are continuously measured, typically over a period of 30 seconds, and carbon dioxide waveforms are preferably digitized as a capnogram 667 and other waveforms and stored on computer 664.

Thereafter, the onset and offset limits of the capnogram, the pulse waveform and QRS onset and offset are determined by computer 664. The initial slope of the capnogram and the run are determined and stored in computer 664.

At various intervals, the differences between consecutive measurements of the various patient parameters are evaluated by computer 664. After each treatment, in a diagnostic rule application step, the following diagnostic rules are preferably applied to the measured parameters by computer 664:

1) If:
a) there is a localized elevation in the ST segment in the ECG; and
b) the $ETCO_2$ is declining at least by 2 mm Hg/min over five minutes;
then,
display 666 shows the message "ACUTE MYOCARDIAL INFARCTION (MI) SUSPECTED".

2) If:
a) the $SPO_2$ value is less than 91% SAT; and
b) the $ETCO_2$ value is less than 30 mm Hg;
then,
display 666 shows the message "VITAL SIGNS CRITICAL".

After each time interval, the difference between consecutive measures of each parameter are calculated by computer 664: Thereafter, the following monitoring rules are preferably applied to the measured parameters by computer 664.

1) If:
a) the difference in the ST elevation in the ECG is greater than 0.1 mm and
b) the difference in the $ETCO_2$ slope is less than −1 mm Hg/min;
then,
computer 664 displays on display 666 "PATIENT STATUS: WORSENING".

2) If:
a) the difference in the ST elevation in the ECG is less than −0.1 mm and
b) the difference in the ETCO$_2$ is more than 1 mm Hg/min;
then,
computer 664 displays on display 666 "PATIENT STATUS: IMPROVING".
3) If:
a) the difference in the ST elevation in the ECG is more than or equal to −0.1 mm but less than or equal to 0.1 mm; or
b) the difference in the ETCO$_2$ is more than or equal to −1 mm Hg/min and is less than or equal to 1 mm Hg/min;
then,
computer 664 displays on display 666 "PATIENT STATUS: UNCHANGED".

Figure 43:
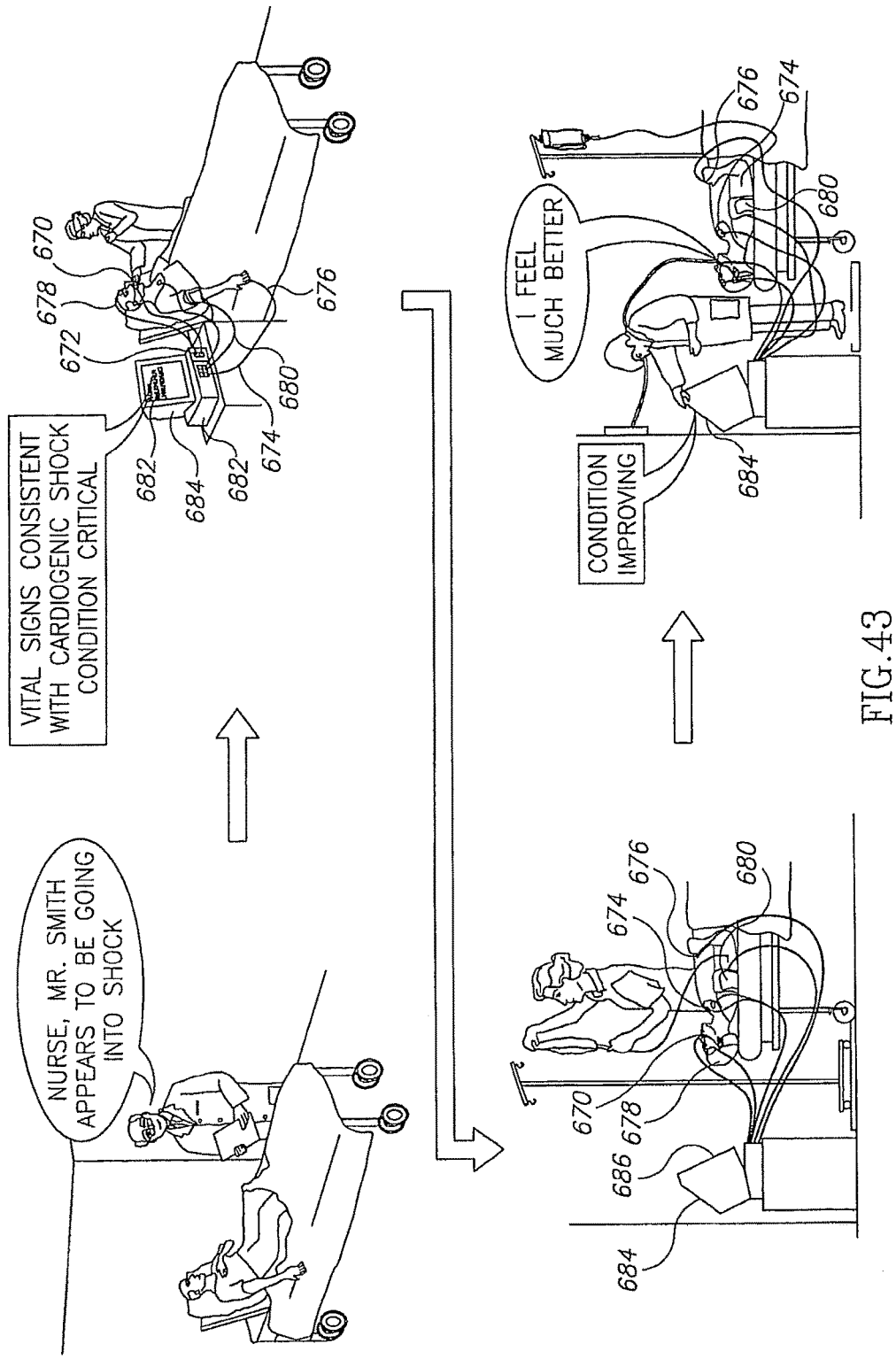
FIG. 43 is a simplified pictorial illustration of an automatic medical diagnostic and treatment system and methodology operative in a hospital environment for diagnosis and treatment of cardiogenic shock.

Reference is now made to FIG. 43, which is a simplified pictorial illustration of an automatic medical diagnostic and treatment system and methodology operative in a hospital environment for determining the presence of cardiogenic shock in a patient. As seen in FIG. 43, various patient physiologic activities are sensed and measured, including respiratory physiologic activities, preferably via an oral airway adapter and/or a nasal or nasal/oral cannula 670, such as a Model Nasal FilterLine Adult XS 04461, O$_2$/CO$_2$ Nasal. FilterLine Adult 007141, or Smart CapnoLine Adult (Oral/nasal FilterLine) 007414, commercially available from Oridion Ltd., of Jerusalem Israel, typically coupled with a capnograph 672, such as a Microcap, commercially available from Oridion Ltd., of Jerusalem Israel. Other patient physiologic activities relating to cardiac function (e.g. ECG), systemic oxygenation (e.g. pulse oximetry), cerebral oxygenation (e.g. cerebral oximetry) and systemic circulation (e.g. NIBP), typically sensed by means of chest-electrodes 674, a finger sensor 676, a forehead/scalp sensor 678 and a blood pressure cuff 680 respectively, may also be sensed and measured by suitable instrumentation 682.

The outputs of the capnograph 672 and possibly of additional instrumentation 682 are preferably supplied to a suitably programmed automatic diagnostic and treatment computer 684, having an associated display 686 which typically analyzes the respiration parameter output of the capnograph 672 and possibly other parameters and provides an output which preferably contains a diagnostic statement alerting hospital staff to the possibility of occurrence of cardiogenic shock. A typical such statement is "VITAL SIGNS CONSISTENT WITH CARDIOGENIC SHOCK. CONDITION CRITICAL". Following intravenous administration of a medicament such as dopamine dobutamine, a patient status statement is preferably provided, here "CONDITION IMPROVING".

Figure 44:
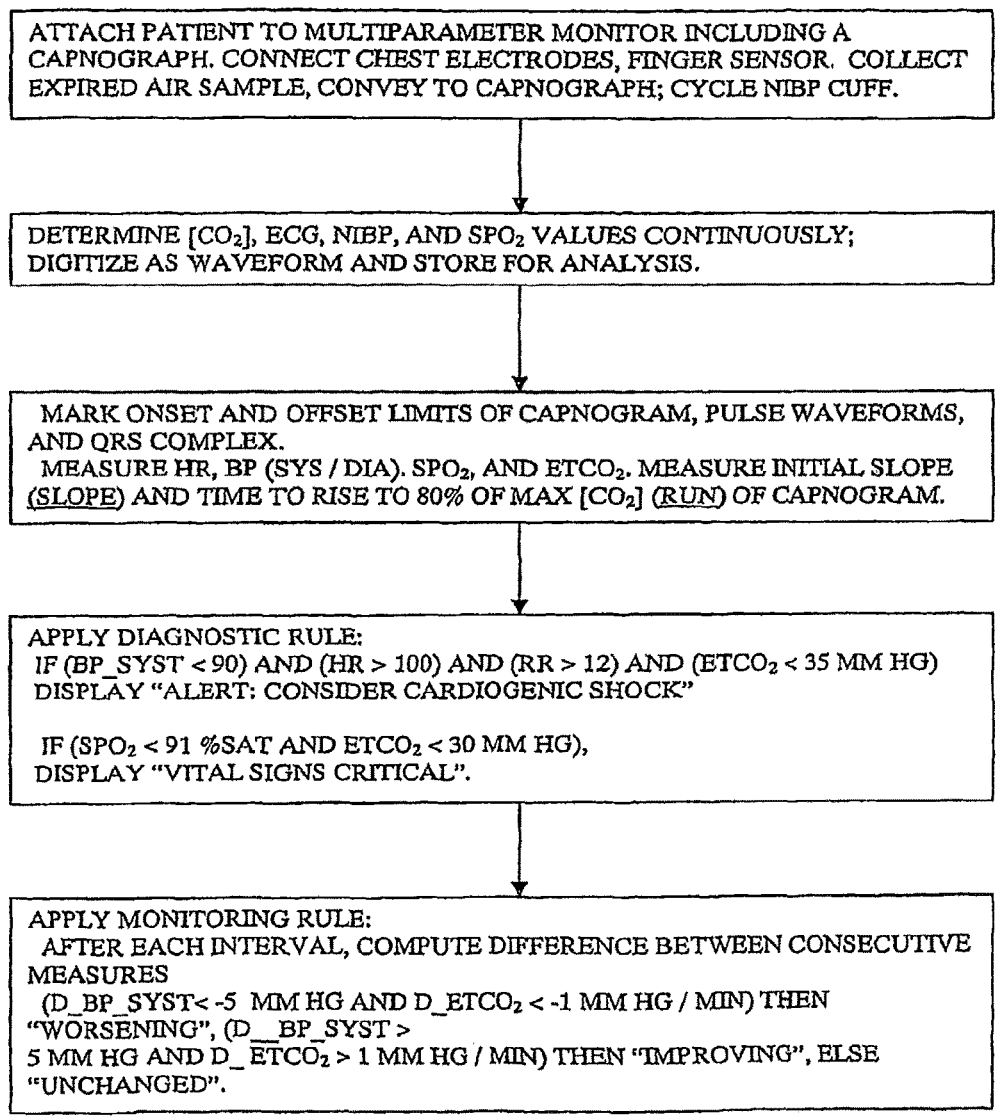
FIG. 44 is a flowchart illustrating operation of the embodiment of FIG. 43.

Reference is now made additionally to FIG. 44, which illustrates the operation of the system and methodology of the system of the present invention in the context of FIG. 43.

The patient, preferably attached to a multi-parameter monitor including capnograph 672 and suitable instrumentation 682, by means of cannula 670 and preferably also by means of chest electrodes 674, finger sensor 676, forehead/scalp sensor 678 and blood pressure cuff 680, is monitored continuously. The neurological status of the patient is acquired by any suitable technique. Values of CO$_2$ concentration, HR, BP (SYS/DIA) ECG, NIBP and SPO$_2$ are continuously measured, typically over a period of 30 seconds, and carbon dioxide waveforms are preferably digitized as a capnogram 667 and other waveforms and stored on computer 684.

Thereafter, the onset and offset limits of the capnogram, the pulse waveform and QRS onset and offset are determined by computer 684. The initial slope of the capnogram and the nm are determined and stored in computer 684.

At various intervals, the differences between consecutive measurements of the various patient parameters are evaluated by computer 684.

After each interval, in a diagnostic rule application step, the following diagnostic rules are preferably applied to the measured parameters by computer 684;
1) If:
a) the systolic blood pressure is less than 90 mm Hg;
b) the heart rate is more than 100/min;
c) the respiratory rate is more than 15/min; and
d) and the ETCO$_2$ is less than 35 mm Hg;
then,
display 686 shows the message "ALERT: CONSIDER CARDIOGENIC SHOCK".
2) If
a) the SPO$_2$ value is less than 91% SAT; and
b) the ETCO$_2$ value is less than 30 mm Hg;
then,
display 686 shows the message "VITAL SIGNS CRITICAL".

After each time interval, the difference between consecutive measures of each parameter are calculated by computer 684: Thereafter, the following monitoring rules are preferably applied to the measured parameters by computer 684.
1) If:
a) the difference in the systolic blood pressure is less than −5 mm Hg; and
b) the difference in the ETCO$_2$ is less than −1 mm Hg/min;
then,
computer 664 displays on display 666 "PATIENT STATUS:WORSENING".
2) If:
a) the difference in the systolic blood pressure is more than 5 mm Hg; and
b) the difference in the ETCO$_2$ is more than 1 mm Hg/min;
then,
computer 664 displays on display 666 "PATIENT STATUS:IMPROVING".
3) If:
a) the difference in the systolic blood pressure is more than or equal to −5 mm Hg and less than or equal to +5 mm Hg; and/or
b) the difference in the ETCO$_2$ is more than or equal to −1 mm Hg/min and is less than or equal to 1 mm Hg/min;
then,
computer 684 displays on display 686 "PATIENT STATUS:UNCHANGED".

Figure 45:
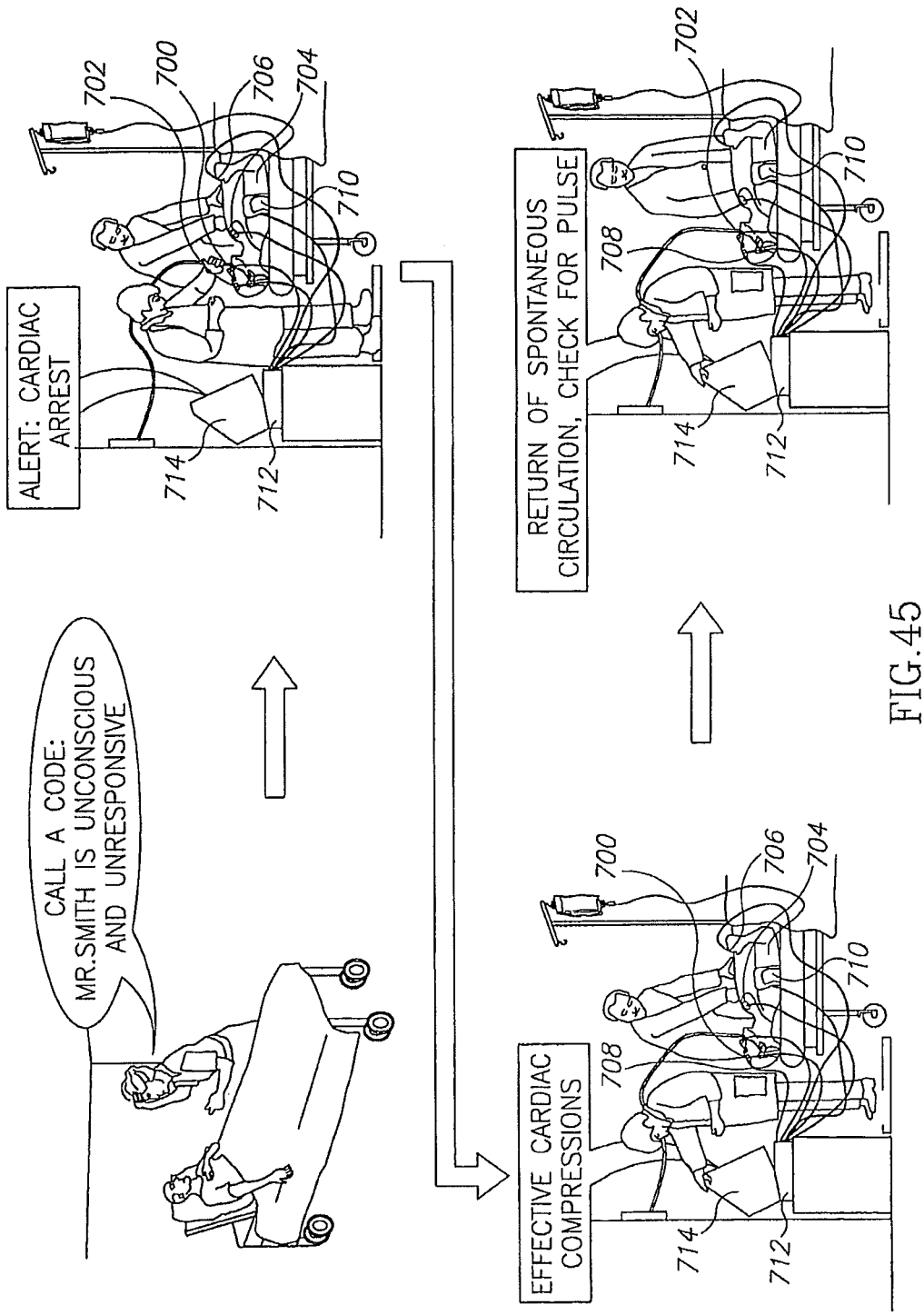
FIG. 45 is a simplified pictorial illustration of an automatic medical diagnostic and treatment system and methodology operative in a hospital environment for diagnosis and treatment of cardiac arrest.

Reference is now made to FIG. 45, which is a simplified pictorial illustration of an automatic medical diagnostic and treatment system and methodology operative in a hospital environment for determining the presence of cardiac arrest in a patient. As seen in FIG. 45, a patient who is found to be unconscious and unresponsive is subsequently connected to the system of the present invention. Various patient physiologic activities are sensed and measured, including respiratory physiologic activities, preferably via an oral airway adapter and/or a nasal or nasal/oral cannula 700, such as a Model Nasal FilterLine Adult XS 04461, O$_2$/CO$_2$ Nasal FilterLine Adult 007141, or Smart CapnoLine Adult (Oral/nasal FilterLine) 007414, commercially available from Oridion Ltd., of Jerusalem Israel, typically coupled with a capnograph 702, such as a Microcap, commercially available from Oridion Ltd., of Jerusalem Israel. Other patient physiologic activities relating to cardiac function (e.g. ECG), systemic oxygenation (e.g. pulse oximetry), cerebral oxygenation (e.g. cerebral oximetry) and systemic circulation (e.g. NIBP), typically sensed by means of chest electrodes 704, a finger sensor 706, a forehead/scalp sensor 708 and a blood pressure cuff 710 respectively, may also be sensed and measured by suitable instrumentation 712.

The outputs of the capnograph 702 and possibly of additional instrumentation 712 are preferably supplied to a suitably programmed automatic diagnostic and treatment computer 714, having an associated display 716 which typically analyzes the respiration parameter output of the capnograph 702 and possibly other parameters and provides an output which preferably contains a diagnostic statement alerting hospital staff to the possibility of occurrence of cardiac arrest. A typical such statement is "ALERT: CARDIAC ARREST". Following treatment, typically including intubation and intravenous administration of a medicament such as adrenaline, during extel cardiac massage, a patient status statement, indicating the effectiveness of the treatment is preferably provided, here "EFFECTIVE CARDIAC COMPRESSIONS." The system also preferably diagnoses the return of spontaneous circulation and prompts the caregiver to check for the presence of a pulse, here by means of a diagnostic statement and a treatment recommendation such as "RETURN OF SPONTANEOUS CIRCULATION. CHECK FOR PULSE".

Figure 46:
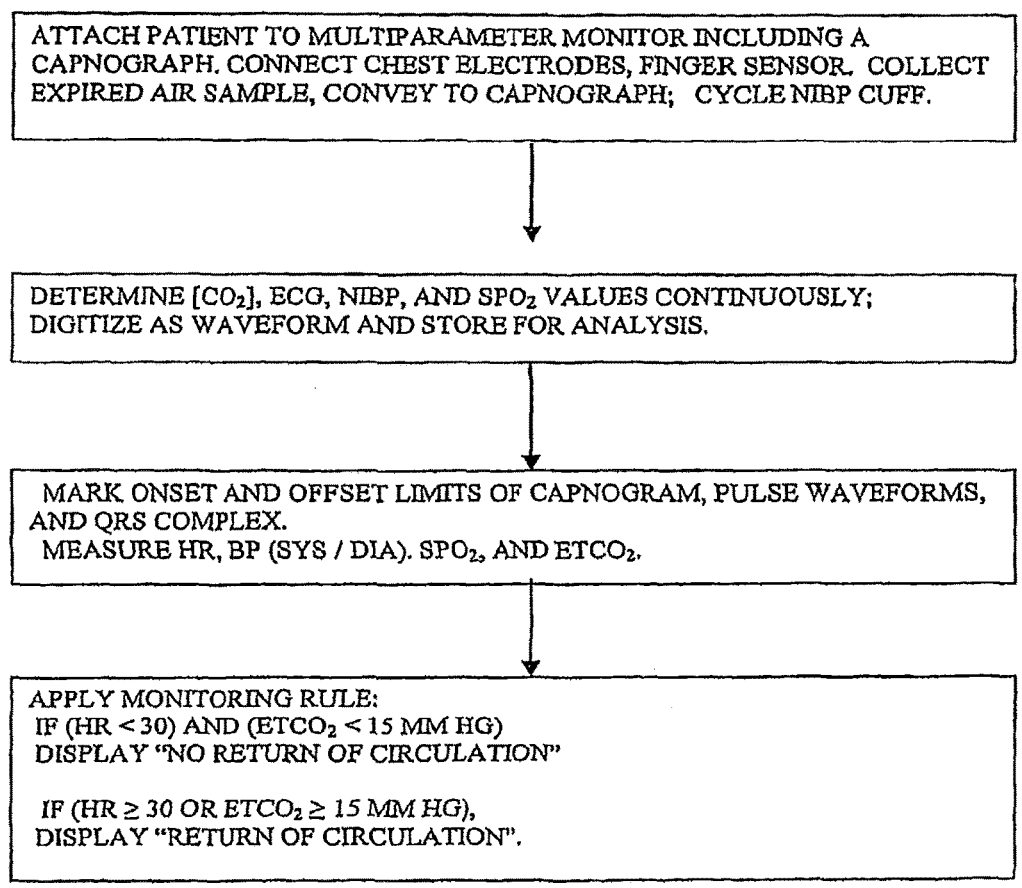
FIG. 46 is a flowchart illustrating operation of the embodiment of FIG. 45.

Reference is now made additionally to FIG. 46, which illustrates the operation of the system and methodology of the system of the present invention in the context of FIG. 45.

The patient, preferably attached to a multi-parameter monitor including capnograph 702 and suitable instrumentation 712, by means of cannula 700 and preferably also by means of chest electrodes 704, finger sensor 706, forehead/scalp sensor 708' and blood pressure cuff 710, is monitored continuously. The neurological status of the patient is acquired by any suitable technique. Values of $CO_2$ concentration, HR, BP (SYS/DIA) ECG, NIBP and $SPO_2$ are continuously measured, typically over a period of 30 seconds, and carbon dioxide waveforms are preferably digitized as a capnogram 717, and is stored on computer 714 together with other waveforms.

Thereafter, the onset and offset limits of the capnogram, the pulse waveform and QRS onset and offset are determined by computer 714. The initial slope of the capnogram and the run are determined and stored in computer 714.

At various intervals, the differences between consecutive measurements of the various patient parameters are evaluated by computer 714.

After each time interval, the difference between consecutive measures of each parameter are calculated by computer 714: Thereafter, the following monitoring rules are preferably applied to the measured parameters by computer 714.

1) If
  a) the heart rate is less than 30/min; and
  b) the $ETCO_2$ value is less than 15 mm Hg;
  then,
  computer 714 displays on display 716 "NO RETURN OF CIRCULATION".

2) If:
  a) the heart rate is more than or equal to 30/min; and
  b) the $ETCO_2$ value is more than or equal to 15 mm Hg;
  then,
  computer 714 displays on display 716 "RETURN OF CIRCULATION".

Figure 47:
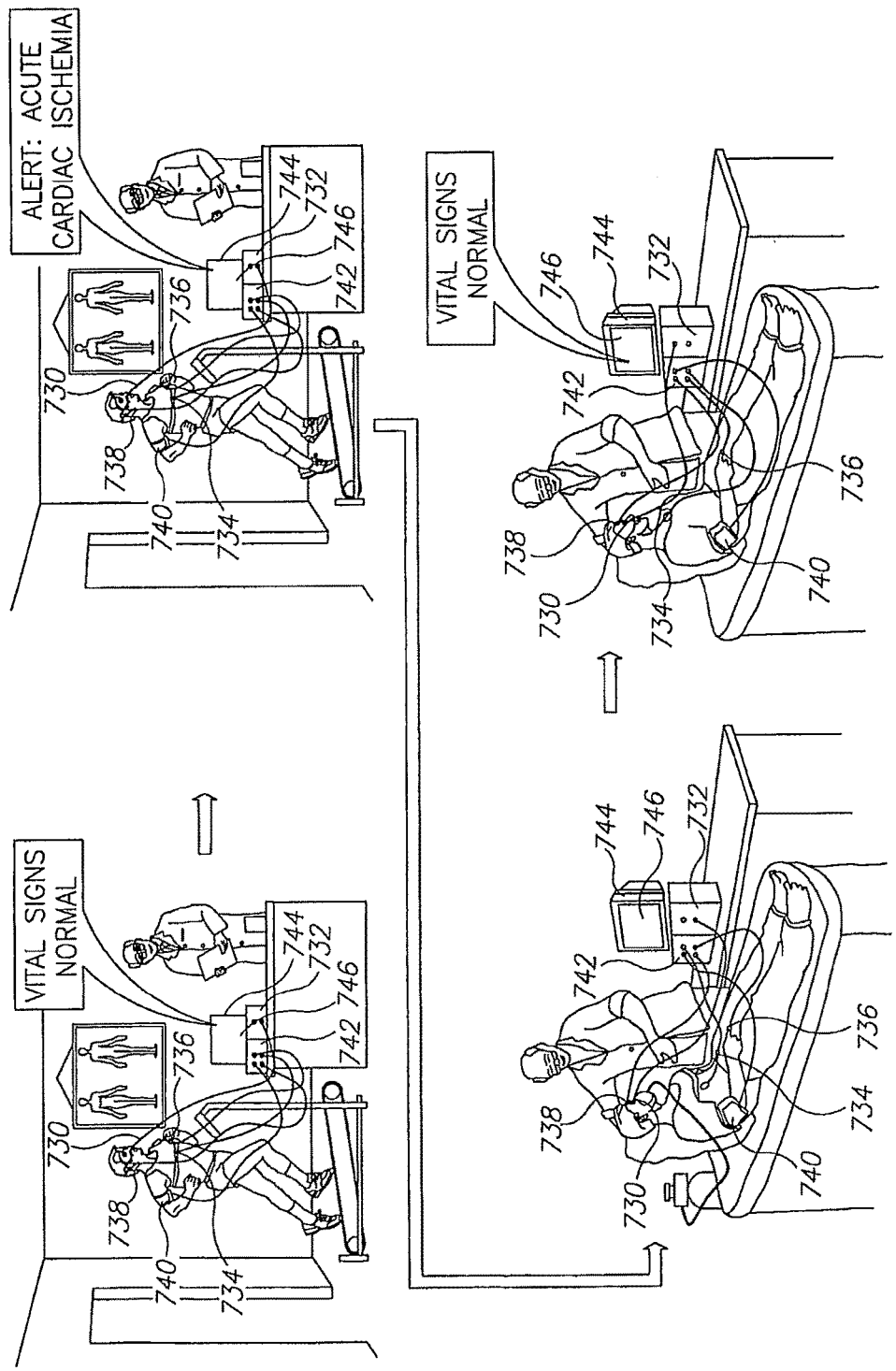
FIG. 47 is a simplified pictorial illustration of an automatic medical diagnostic and treatment system and methodology operative in a hospital environment for diagnosis and treatment of cardiac ischemia.

Reference is now made to FIG. 47, which is a simplified pictorial illustration of an automatic medical diagnostic and treatment system and methodology operative in a out of hospital environment for determining the presence of acute cardiac ischemia in a patient.

As seen in FIG. 47, while a patient, undergoes treadmill testing in a doctor's office, various patient physiologic activities are sensed and measured, including respiratory physiologic activities, preferably via an oral airway adapter and/or a nasal or nasal/oral cannula 730, such as a Model Nasal FilterLine Adult XS 04461, $O_2/CO_2$ Nasal FilterLine Adult 007141, or Smart CapnoLine Adult (Oral/nasal FilterLine) 007414, commercially available from Oridion Ltd., of Jerusalem Israel, typically coupled with a capnograph 732, such as a Microcap, commercially available from Oridion Ltd., of Jerusalem Israel. Other patient physiologic activities relating to cardiac function (e.g. ECG), systemic oxygenation (e.g. pulse oximetry), cerebral oxygenation (e.g. cerebral oximetry) and systemic circulation (e.g. NIBP), typically sensed by means of chest electrodes 734, a finger sensor 736, a forehead/scalp sensor 738 and a blood pressure cuff 740 respectively, may also be sensed and measured by suitable instrumentation 742.

The outputs of the capnograph 732 and possibly of additional instrumentation 742 are preferably supplied to a suitably programmed automatic diagnostic and treatment computer 744, having an associated display 746 which typically analyzes the respiration parameter output of the capnograph 732 and possibly other parameters and provides an output which preferably contains a diagnostic statement, here "VITAL SIGNS NORMAL", which indicates normal patient condition. At some point thereafter, a further diagnostic statement appears, here, "ALERT: ACUTE CARDIAC ISCHEMIA". :Upon noticing this statement, the physician causes the patient to lie down and administers oxygen treatment to the patient. The system assesses the patient's response to the treatment and provides a patient status message, here "VITAL SIGNS NORMAL".

Figure 48:
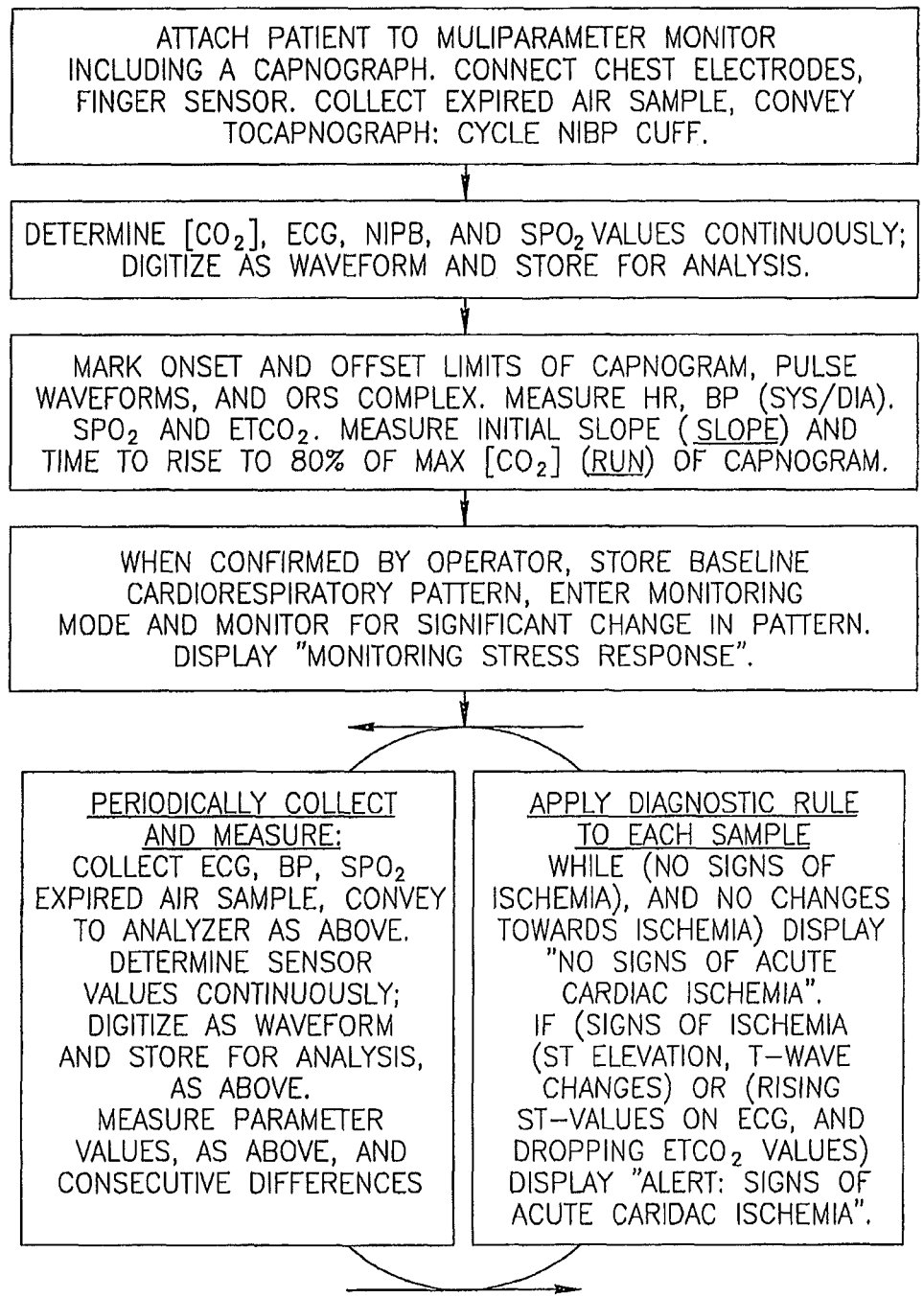
FIG. 48 is a flowchart illustrating operation of the embodiment of FIG. 47.

Reference is now made additionally to FIG. 48, which illustrates the operation of the system and methodology of the system of the present invention in the context of FIG. 47.

The patient, preferably attached to a multi-parameter monitor including capnograph 732 and suitable instrumentation 742, by means of cannula 730 and preferably also by means of chest electrodes 734, finger sensor 736, forehead/scalp sensor 738 and blood pressure cuff 740, is monitored continuously. The neurological status of the patient is acquired by any suitable technique. Values of $CO_2$ concentration, HR, BP (SYS/DIA) ECG, NIBP and $SPO_2$ are continuously measured, typically over a period of 30 seconds, and carbon dioxide waveforms are preferably digitized as a capnogram 747, and is stored on computer 744 together with other waveforms.

Thereafter, the onset and offset limits of the capnogram, the pulse waveform and QRS onset and offset are determined by computer 744. The initial slope of the capnogram and the run are determined and stored in computer 744.

In the next step, when the monitoring has been verified by the operator, that it is functioning correctly, the baseline cardiorespiratory pattern is stored in computer 744.

Thereafter, computer 744 and/or the operator activates capnograph 732 in a monitoring mode. The patient is monitored continuously by capnograph 732 for any significant change in the cardiorespiratory pattern.

The following monitoring rule is preferably applied to capnogram 747 by computer 744.

1) If:
   a) a significant change in the cardiorespiratory pattern is apparent;
   then,
   computer 744 displays "MONITORING STRESS RESPONSE" on display 746.

Thereafter, a cycle of alteting I) sampling step (data collection and measurement) and II) diagnostic rule application to the previous sample step I) is initiated.

I) Sampling Step
   a) A sample of expired air is taken and conveyed from cannula 400 to capnograph 732.
   b) The carbon dioxide concentration is measured continuously by capnograph 744 as a capnogram 747.
   c) The capnogram is digitized as waveform and store for analysis by computer 744.
   d) Computer 744 marks onset and offset limits of the capnogram.
   e) The waveform quality of the capnogram is assessed by employing the criteria that an acceptable quality is defined by:
      i) the root mean square (rms) of the noise of the waveform must be less than 2 mm Hg; and
      ii) the breath-to-breath correlation must be greater than 0.85.
   f) The slope and the run are determined by computer 744.

II) Diagnostic Rule Application Step

In a diagnostic rule application step, the following diagnostic rules are preferably applied to the measured parameters of each sample in I) Sampling step by computer 744:

1) If:
   a) there are no signs of ischemia (no elevation from baseline in the ECG ST segment; and no changes from baseline in the T-waves;
   b) there are no changes towards ischemia (rising ST-segment values on ECG from baseline, and dropping $ETCO_2$ values >5 mm Hg from baseline);
   then,
   Computer 744 displays on display 746 "NO SIGNS OF ACUTE CARDIAC ISCHEMIA".

2) If:
   a) a) there are signs of ischemia; or
   b) there are changes towards ischemia; then,
   Computer 744 displays on display 746 "ALERT: SIGNS OF ACUTE CARDIAC ISCHEMIA".

Figure 49:
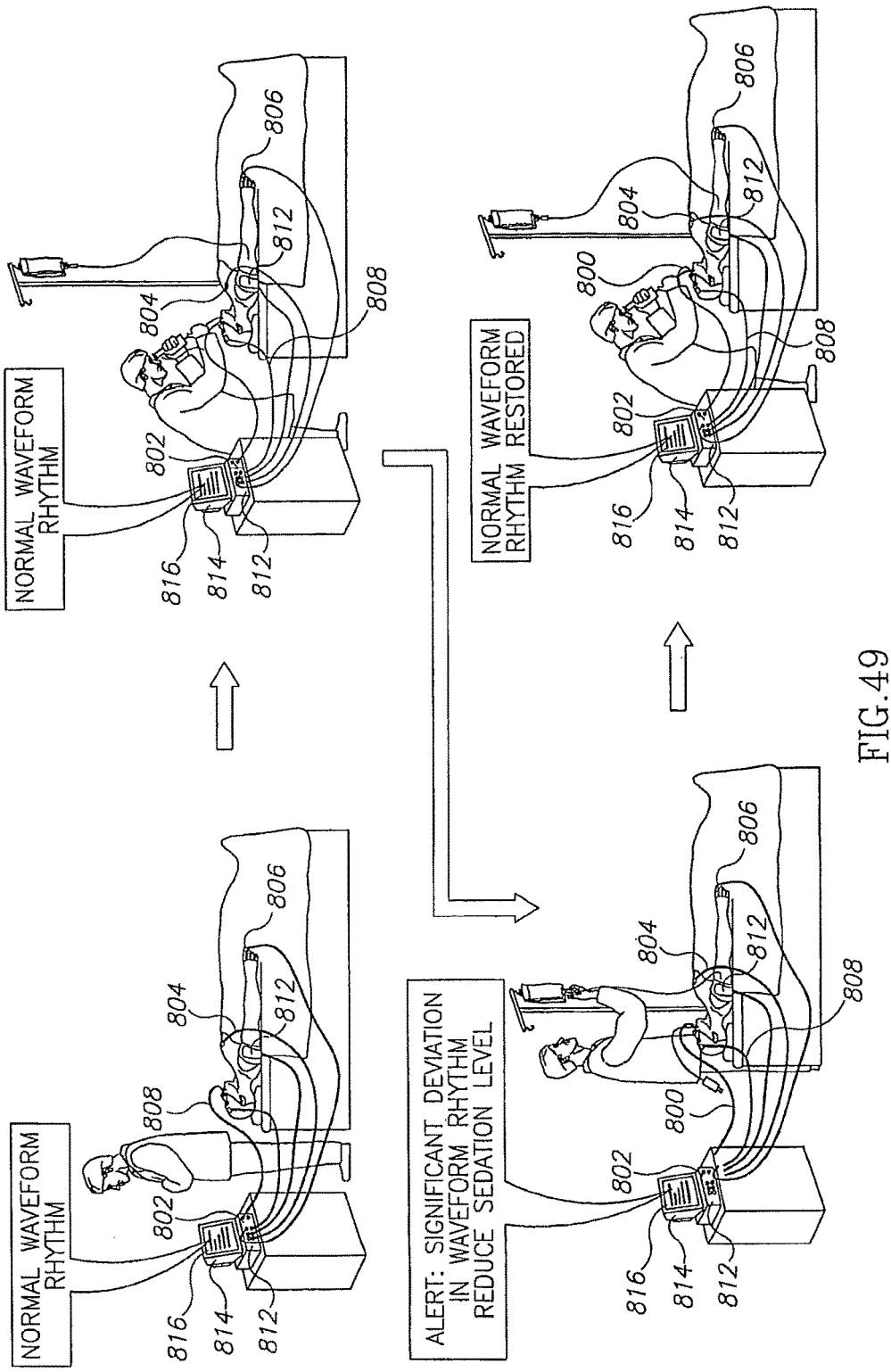
FIG. 49 is a simplified pictorial illustration of an automatic medical diagnostic and treatment system and methodology operative in a hospital environment for monitoring sedation.

Reference is now made to FIG. 49, which is a simplified pictorial illustration of an automatic medical diagnostic and treatment system and methodology operative in a hospital or outpatient environment for sedation and/or anesthesia monitoring. As seen in FIG. 49, while a patient is under sedation and/or anesthesia, typically in the course of a medical procedure, various patient physiologic activities are sensed and measured, including respiratory physiologic activities, preferably via an oral airway adapter and/or a nasal or nasal/oral cannula 800, such as a Model Nasal FilterLine Adult XS 04461, $O_2/CO_2$ Nasal FilterLine Adult 007141, or Smart CapnoLine Adult (Oral/nasal FilterLine) 007414, commercially available from Oridion Ltd., of Jerusalem Israel, typically coupled with a capnograph 802, such as a Microcap, commercially available from Oridion Ltd., of Jerusalem Israel. Other patient physiologic activities relating to cardiac function (e.g. ECG), systemic oxygenation (e.g. pulse oximetry), cerebral oxygenation (e.g. cerebral oximetry) and systemic circulation (e.g. NIBP), typically sensed by means of chest electrodes 804, a finger sensor 806, a forehead/scalp sensor 808 and a blood pressure cuff 810 respectively, may also be sensed and measured by suitable instrumentation 812.

The outputs of the capnograph 802 and possibly of additional instrumentation 812 are preferably supplied to a suitably programmed automatic diagnostic and treatment computer 814, having an associated display 816 which typically analyzes the respiration parameter output of the capnograph 802 and possibly other parameters and provides an output which preferably contains a diagnostic statement confirming proper respiration, here "NORMAL WAVEFORM RHYTHM".

If at a later stage during the medical procedure, a deviation from the patient's normal $CO_2$ waveform rhythm is sensed, a further diagnostic statement is provided, here "ALERT: SIGNIFICANT DEVIATION IN WAVEFORM RHYTHM". This statement is preferably accompanied by a treatment recommendation, here "REDUCE SEDATION LEVEL". Following reduction in the sedation level, a diagnostic statement which indicates the patient status is preferably presented, here "NORMAL WAVEFORM RHYTHM RESTORED".

Figure 50:
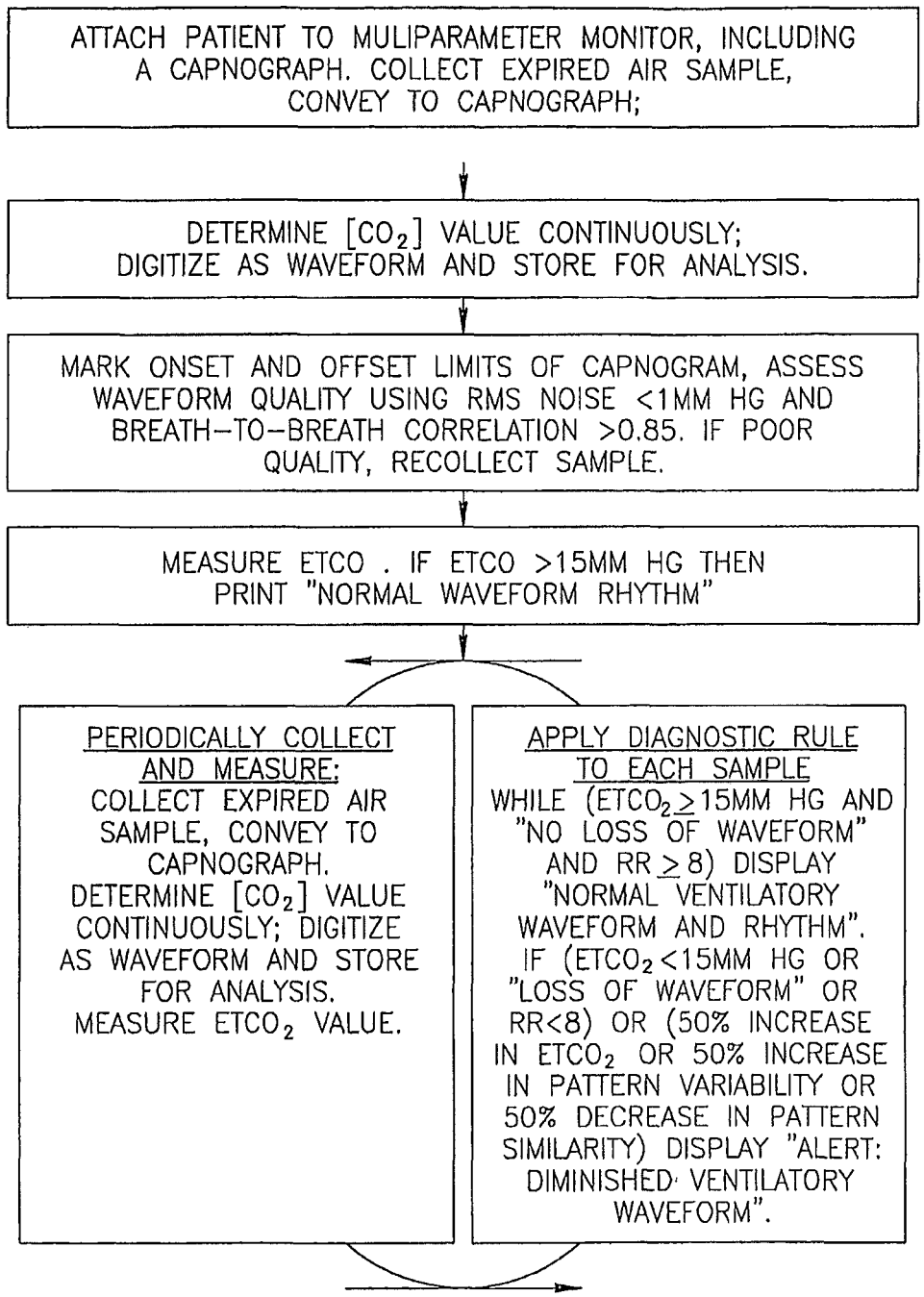
FIG. 50 is a flowchart illustrating operation of the embodiment of FIG. 49.

Reference is now made additionally to FIG. 50, which illustrates the operation of the system and methodology of the system of the present invention in the context of FIG. 49.

The patient, preferably attached to a multi-parameter monitor including capnograph 802, is typically monitored continuously for at least 30 seconds. Additionally or altetively, the patient may be monitored for shorter or longer durations. Expired air is collected via cannula 800 and is conveyed to the capnograph 802.

Values of the $CO_2$ concentration are continuously measured, typically over a period of 30 seconds, and carbon dioxide waveforms are preferably digitized as a capnogram 817 and, together with other waveforms, is stored on computer 814.

The onset and offset limits of the patient's capnogram from capnograph 802 are delineated by computer 814.

The waveform quality of the capnogram 817 is assessed by employing the criteria that an acceptable quality is defined by:
   i) the root mean square (rms) of the noise of the waveform must be less than 1 mm Hg; and
   ii) the breath-to-breath correlation must be greater than 0.85.

If the quality is unacceptable, further samples are collected until a sample of acceptable quality, according to the above two criteria, is taken.

The next step entails a checking procedure, wherein the $ETCO_2$ value is measured by capnograph 632. The slope and run values of the capnogram from capnograph 632 are determined by computer 644.

The following checking rule is preferably applied.
1) If
   a) the $ETCO_2$ value is more than 15 mm Hg;
   then,
   a display is provided by computer 814 stating NORMAL WAVEFORM RHYTHM".

After the waveform rhythm has been confirmed by an operator, the capnograph is entered into its monitoring mode, either by the operator or by computer 814. Capnograph 802 then monitors for any changes in the breathing pattern of the patient.

Thereafter, computer 814 displays "MONITORING SEDATION" on display 646.

The next step entails a cycle of alteting I) sampling step (data collection and measurement) and II) diagnostic rule application to the previous sample step I) is initiated.

I) Sampling Step

In this sampling step, an exhaled air sample from cannula 800 is periodically collected, conveyed and measured by capnograph 802. The carbon dioxide concentration value is determined continuously by capnograph 802. Computer 814 digitizes the capnograph signals as a waveform and store the waveform for analysis.

Thereafter, the $ETCO_2$ value is determined.

II) Diagnostic Rule Application Step.

The following diagnostic rules are applied to each sample:

1) If:
 a) The value of $ETCO_2$ is greater than or equal to 15 mm Hg; and
 b) There is no loss in the waveform from capnograph 802; and
 c) The respiratory rate is greater than or equal to 12/min; then,
 computer 814 displays "NORMAL VENTILATORY WAVEFORM AND RHYTHM" on display 816.

2) If:
 a) The value of $ETCO_2$ is less than 15 mm Hg; or
 b) There is a loss in the waveform from capnograph 802; or
 c) The respiratory rate is less than 10/min; or
 d) There is a decline in $ETCO_2$ of 50%; or
 e) There is a 50% increase in the pattern variability; or
 f) There is a 50% decrease in the pattern similarity; then,
 computer 814 displays "ALERT: DIMINISHED VENTILATORY WAVEFORM" on display 816.

This cycle typically proceeds until the patient monitoring is halted by the medical team or operator.

Figure 51:
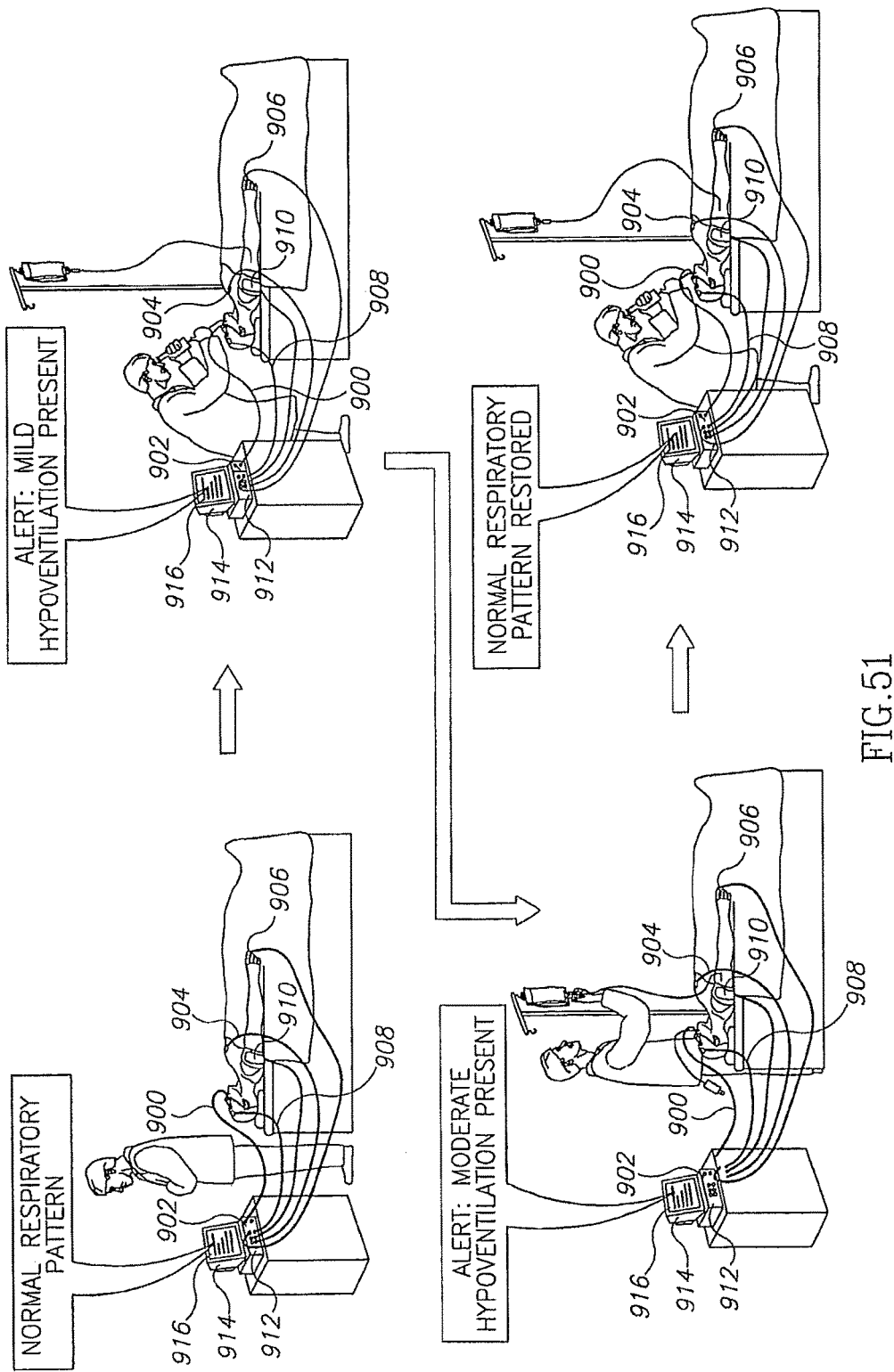
FIG. 51 is a simplified pictorial illustration of an automatic medical diagnostic and treatment system and methodology operative in a hospital environment for drug titration during sedation.

Reference is now made to FIG. 51, which is a simplified pictorial illustration of an automatic medical diagnostic and treatment system and methodology operative in a hospital or outpatient environment for sedation and/or anesthesia titration. As seen in FIG. 51, when a patient is being sedated prior to carrying out of a medical procedure, various patient physiologic activities are sensed and measured, including respiratory physiologic activities, preferably via an oral airway adapter and/or a nasal or nasal/oral cannula 900, such as a Model Nasal FilterLine Adult XS 04461, $O_2/CO_2$ Nasal FilterLine Adult 007141, or Smart CapnoLine Adult (Oral/nasal FilterLine) 007414, commercially available from Oridion Ltd., of Jerusalem Israel, typically coupled with a capnograph 902, such as a Microcap, commercially available from Oridion Ltd., of Jerusalem Israel. Other patient physiologic activities relating to cardiac function (e.g. ECG), systemic oxygenation (e.g. pulse oximetry), cerebral oxygenation (e.g. cerebral oximetry) and systemic circulation (e.g. NIBP), typically sensed by means of chest electrodes 904, a finger sensor 906, a forehead/scalp sensor 908 and a blood pressure cuff 910 respectively, may also be sensed and measured by suitable instrumentation 912.

The outputs of the capnograph 902 and possibly of additional instrumentation 912 are preferably supplied to a suitably programmed automatic diagnostic and treatment computer 914, having an associated display 916 which typically analyzes the respiration parameter output of the capnograph 902 and possibly other parameters and provides an output which preferably contains a patient status statement confirming proper respiration, here "NORMAL RESPIRATORY PATTERN". Following the administration of additional medication, a deviation from the patient's normal $CO_2$ waveform shape, amplitude or periodicity is sensed, a further status statement is provided, here "ALERT: MILD HYPOVENTILATION PRESENT". Following the administration of additional medication which increases the sedation level, an additional diagnostic statement which indicates the patient status is preferably presented, here "ALERT MODERATE HYPOVENTILATION PRESENT". This alert indicates that at this point, titration of medication is complete and the medical procedure may be commenced. Following completion of the medical procedure, monitoring continues until a further status statement, here "NORMAL RESPIRATORY PATTERN RESTORED" indicates normal respiration and that the patient may be safely discharged.

Figure 52:
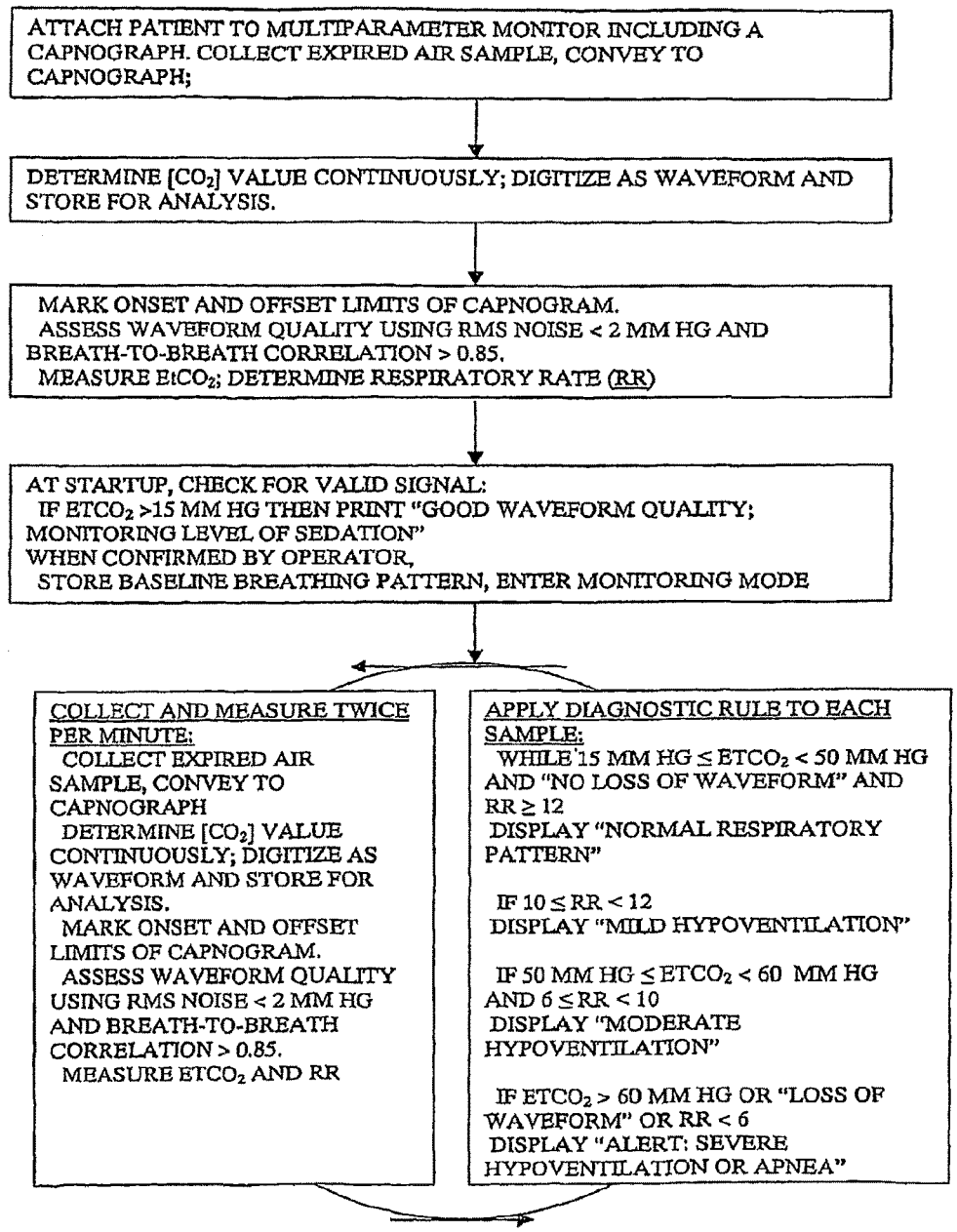
FIG. 52 is a flowchart illustrating operation of the embodiment of FIG. 51.

Reference is now made additionally to FIG. 52, which illustrates the operation of the system and methodology of the system of the present invention in the context of FIG. 51.

The patient, preferably attached to a multi-parameter monitor including capnograph 902, is monitored continuously for at least 30 seconds. Expired air is collected via cannula 900 and is conveyed to the capnograph 902.

Values of the $CO_2$ concentration is continuously measured, typically over a period of 30 seconds, and carbon dioxide waveforms are preferably digitized as a capnogram 917 and, together with other waveforms, is stored on computer 914.

The onset and offset limits of the patient's capnogram from capnograph 902 are delineated by computer 914.

The waveform quality of the capnogram 917 is assessed by employing the criteria that an acceptable quality is defined by:
 i) the root mean square (rms) of the noise of the waveform must be less than 2 mm Hg; and
 ii) the breath-to-breath correlation must be greater than 0.85.

If the quality is unacceptable, further samples are collected until a sample of acceptable quality, according to the above two criteria, is taken.

Thereafter, the $ETCO_2$ value and the respiratory rate are determined.

At startup a checking procedure is performed, wherein the $ETCO_2$ value is measured by capnograph 902. The slope and run values of the capnogram from capnograph 902 are determined by computer 914.

The following checking rule is preferably applied.

1) If
 a) the $ETCO_2$ value is more than 15 mm Hg; then,
 a display is provided by computer 914 stating "GOOD WAVEFORM QUALITY; MONITORING LEVEL OF SEDATION.

After the waveform rhythm has been confirmed by an operator, the baseline breathing pattern is stored in computer 914. Capnograph 902 is entered into its monitoring mode, either by the operator or by computer 914. Capnograph 902 then monitors for any changes in the breathing pattern of the patient.

The next step entails a cycle of alteting I) sampling step (data collection and measurement) twice per minute and II) diagnostic rule application to the previous sample step I) is initiated.

I) Sampling Step

In this sampling step, an exhaled air sample from cannula 900 is periodically collected, conveyed and measured by capnograph 902. The carbon dioxide concentration value is determined continuously by capnograph 902. Computer 914 digitizes the capnograph signals as a waveform and computer 914 stores the waveform for analysis. Computer 914 marks onset and offset limits of the capnogram.

The waveform quality of the capnogram is assessed by employing the criteria that an acceptable quality is defined by:

i) the root mean square (rms) of the noise of the waveform must be less than 2 mm Hg; and ii) the breath-to-breath correlation must be greater than 0.85.

Thereafter $ETCO_2$ and the respiratory rate are measured, and the results stored on computer 914.

II) Diagnostic Rule Application Step.

The following diagnostic rules are applied to each sample:

1) If a) The value of $ETCO_2$ is greater than or equal to 15 mm Hg, but less than 50 mm Hg;

b) There is no loss in the waveform from capnograph 902; and c) The respiratory rate is greater than 12/min;

then, computer 914 displays "NORMAL RESPIRATORY PATTERN" on display 916.

2) If:

a) The respiratory rate is more than or equal to 10/min, but less than 12/min;

then, computer 914 displays "MILD HYPOVENTILATION" on display 916.

3) If:

a) The value of $ETCO_2$ is greater than or equal to 50 mm Hg, but less than 60 mm Hg; and b) The respiratory rate is more than or equal to 6/min, but less than 10/min; then, computer 914 displays "MODERATE HYPOVENTILATION" on display 916.

4) If:

The value of $ETCO_2$ is greater or equal to 60 mm Hg; or b) There is a loss in the waveform; or c) The respiratory rate is less than 6/min;

then, computer 914 displays "ALERT: SEVERE HYPOVENTILATION OR APNEA" on display 916.

It should be understood that the rules, such as monitoring- and diagnostic rules exemplified hereinabove are not meant to be limiting only to those and the numerical values therein that have been shown herein, and that these rules could be applied using similar or different numerical values and could incorporate further rules applied to other parameters. The rules provided herein may be provided as continuous or discontinuous rules, and may additionally or altetively be applied in other combinations of continuity or discontinuity. Furthermore, it should be understood that the term "time interval" may include the time required for a treatment to be effective in a patient, and the word "treatment" may also be used to denote the time required for the treatment to be effective, such as in the phrase "after each treatment".

It will be appreciated by persons skilled in the art that the present invention is not limited by what has been particularly shown and described hereinabove. Rather the scope of the present invention includes both combinations and sub-combinations of the features described hereinabove as well as modifications and variations thereof which would occur to a person of skill in the art upon reading the foregoing description and which are not in the prior art.

What is claimed is:

1. A monitor for patient monitoring, comprising:

a transmitter communicatively coupled to one or more sensors disposed on a patient, wherein the transmitter is configured to transmit a plurality of physiological characteristics indicative of a status of a patient from the one or more sensors to a receiver via a wireless communication link, the plurality of physiological characteristics comprising at least data indicative of an electrocardiogram (ECG) waveform, data indicative of heart rate, data indicative of blood oxygen saturation, data indicative of exhaled carbon dioxide, and data indicative of respiration rate, and wherein the one or more sensors comprises a capnograph, a blood oxygenation sensor, a blood pressure sensor, chest electrodes, or a combination thereof; and a medical parameter interpretation processor comprising a computer-readable medium storing instructions, that when executed by the medical parameter interpretation processor, perform steps comprising:

monitoring at least one of the plurality of physiological characteristics;

generating at least one output indication based on a comparison of at least one of the plurality of physiological characteristics to one or more patient specific limits, the output indication relating to a type and severity of a medical condition; and activating an intubation monitoring mode of the capnograph based on the severity of the medical condition in response to an input confirming the severity of the medical condition.

2. The monitor of claim 1, wherein the at least one output indication comprises a pattern variability indication.

3. The monitor of claim 1, wherein the at least one output indication comprises a diagnostic statement indicative of a possibility of bronchospasm.

4. The monitor of claim 1, wherein the wireless communication link is a radio link.

5. The monitor of claim 1, wherein the wireless communication link is a cellular link.

6. The monitor of claim 1, wherein the medical parameter interpretation processor is further configured to monitor at least one of the plurality of physiological characteristics over a specific time period.

7. The monitor of claim 1, wherein the instructions are configured to activate the intubation monitoring mode of the capnograph when the medical condition is a critical respiratory condition.

8. The monitor of claim 1, wherein the intubation monitoring mode monitors a position of a tracheal tube within the patient's airway.

* * * * *